US007816139B2

(12) United States Patent
Slade et al.

(10) Patent No.: US 7,816,139 B2
(45) Date of Patent: Oct. 19, 2010

(54) COMPOSITIONS AND METHOD FOR MODULATION OF PLANT CELL DIVISION

(75) Inventors: Ann Slade, Kenmore, WA (US); Linda Madisen, Seattle, WA (US); Luca Comai, Seattle, WA (US)

(73) Assignee: University of Washington, Seattle, WA (US)

( * ) Notice: Subject to any disclaimer, the term of this patent is extended or adjusted under 35 U.S.C. 154(b) by 392 days.

(21) Appl. No.: 11/440,877

(22) Filed: May 25, 2006

(65) Prior Publication Data
US 2006/0218676 A1 Sep. 28, 2006

Related U.S. Application Data

(63) Continuation of application No. 10/129,912, filed as application No. PCT/US00/30794 on Nov. 10, 2000, now Pat. No. 7,056,739.

(60) Provisional application No. 60/164,587, filed on Nov. 10, 1999.

(51) Int. Cl.
*A01H 5/00* (2006.01)
*C12N 15/82* (2006.01)
(52) U.S. Cl. ...................... 435/419; 800/298
(58) Field of Classification Search .................. None
See application file for complete search history.

(56) References Cited
U.S. PATENT DOCUMENTS
7,056,739 B1 * 6/2006 Slade et al. ................ 435/419

FOREIGN PATENT DOCUMENTS
WO  WO-97/29123  8/1997

OTHER PUBLICATIONS

Whisstock J.C. et al. Prediction of protein function from protein sequence and structure. Q Rev Biophys. Aug. 2003;36(3):307-40. Review.*
Prigge M.J. et al. Class III homeodomain-leucine zipper gene family members have overlapping, antagonistic, and distinct roles in *Arabidopisis* develpment. Plant Cell. Jan. 2005;1(1):61-76. Epub Dec. 14, 2004.*
GenBank Accession No. AB005246 (*Arabidopsis thaliana* genomic DNA, chromosome 5, P1 clone: MUP24), Feb. 5, 1999.
Zhong, R. et al, "Disruption of Interfascicular Fiber Differentiation in an *Arabidopsis* Mutant", Plant Cell, vol. 9, No. 12, Dec. 1997, pp. 2159-2170.
Rose, T. M. et al, "Consensus-degenerate hybrid oligonucleotide primers for amplification of distantly related sequences", Nucleic Acids Research, Oxford University Press, vol. 26, No. 7, 1998, pp. 1628-1635.
Bell, C. J. et al, "Assignment of 30 microsatellite loci to the linkage map of *Arabidopsis*", Genomics, vol. 19, No. 1, 1994, pp. 137-144.

Katagiri, F, et al, "Plant Transcription Factors Present Knowledge and Future Challenges" Trends in Genetics, vol. 8, No. 1, 1992, pp. 22-27.
Ramachandran, S. et al, "Transcription factors in plant growth and development", Current Opinion in Genetics and Development, vol. 4, No. 5, 1994, pp. 642-646.
Peng, J. et al., "'Green revolution' genes encode mutant gibberellin response modulators", Nature, vol. 400, No. 6741, Jul. 15, 1999, pp. 256-261.
Peng J. et al, "The *Arabidopsis* GAI gene defines a signaling pathway that negatively regulates gibberellin responses", Genes and Developments, vol. 11, No. 23, Dec. 1, 1997, pp. 3194-3205.
Zhong, R. et al, "IFL1, a gene regulating interfascicular fiber differentiation in *Arabidopsis*, encodes a homeodomain-leucine zipper protein", Plant Cell, vol. 11, No. 11, Nov. 11, 1999.
Gen Bank Accession No. AAF 15262 and Sequence Revision History, Oct. 28, 2002.
Gen Bank Accession No. AF188994 and Sequence Revision History, Oct. 28, 2002.
Sato, S. et al, DNA Reserach 4:215-219 (1997).
Printed pages of archived kazusa.or.jp database on Jan. 29, 1998 from the internet web site web.archive.org (printed on Jun. 7, 2005).
Gen Bank Accession No. AB005246 Sequence Revision History and AB005246 from Feb. 5, 1999.
Chen, C. et al., "The *Arabidopsis* Filamentous Flower gene is required for flower formation", Development, vol. 126, pp. 2715-2726 (1999).
Meyerowitz, E. M., "Genetic control of cell division patterns in developing plants", Cell. 07, Feb. 1997, vol. 88, pp. 229-308.
Okamoto, M. et al., "Enhanced Expression of an Antimicrobial Peptide Sarcotoxin IA by GUS Fusion in Transgenic Tobacco Plants", Physiol. 39 (1); 57-63 (1998).
Otsuga et al., "Revoluta regulates meristem initiation at lateral positions", The Plant Journal, 2001, vol. 25, No. 2, pp. 223-236.
Ruberti, I. et al., "A novel class of plant proteins containing a homeodomain with a closely linked leucine zipper motif", The EMBO Journal, vol. 10, No. 7, pp. 1787-1791 (1991).
Schena M. et al., "HD-Zip proteins: Members of an *Arabidopsis* homeodomain protein superfamily", Proc. Natl. Acad. Science, vol. 89, pp. 3894-3898, (1992).
Schena M. et al., "The HAT4 gene of *Arabidopsis* encodes a developmental regulator", Genes & Development 7, pp. 367-379, (1993).
Steindler et al., "Shade avoidance responses are mediated by the ATHB-2- HD-Zip protein, a negative regulator of gene expression", Development 126, pp. 4235-4245 (1999).

(Continued)

*Primary Examiner*—Cynthia Collins
(74) *Attorney, Agent, or Firm*—Cooley LLP

(57) ABSTRACT

The present invention provides compositions and methods for modulating cell division in plants. In particular, the present invention provides polynucleotides that encode REVOLUTA. In addition, REVOLUTA vectors and transformed plants are provided wherein plant cell division is modulated by expression of a REVOLUTA transgene as compared to a control population of untransformed plants. The present invention also provides methods for the isolation and identification of REVOLUTA genes from higher plants.

10 Claims, 14 Drawing Sheets

OTHER PUBLICATIONS

Talbert et al., "The Revoluta gene is necessary for apical meristem development and for limiting cell division in the leaves and stems of *Arabidopsis thaliana*", Development, 1995, vol. 121, pp. 2723-2735.

Sessa, G. et al., "The *Arabidopsis* Athb-8, -9 and -14 genes are members of a small family coding for highly related HD-Zip proteins", Plant Molecular Biology, vol. 38, pp. 609-622 (1998).

GenBank Accession No. AF233592 and Sequence Revision History.

Ratcliffe et al. "*Interfascicular Fiberless1* is the Same Gene as *REVOLUTA*", The Plant Cell, Mar. 2000, 12:315-317.

European Patent Application Examination Report based on EP Application No. 00977104.9 (Apr. 30, 2010).

* cited by examiner

REVOLUTA Protein and rev mutants

```
                        Homeodomain
MEMAVANHRBSSDSMNRHL DSSGKYVRYT AEQVEA[LEAVYQRSSVNPKQKEREEL
              Homeodomain           L-zipper
[ARKEASRLLAMAWVSGIKTPEEVKRLEAENIR]QKQVSQLYC
ENGYMKQQLT TVVNDPSCES VVTTPQHSLR DANSPAGLLS IAEETLAEFL SKATGTAVDW
VQMPGMKPGP DSVGIFAISQ RCNGVAARAC GLVSLEPMKI AEILKDRPSW FRDCRSLEVF
                        rev-5
TMFPAGNGGT IELVYMQTYA PTTLAPARDF WTLRYTTSLD NGSFVVCERS LSGSGAGPNA
                                            rev-6
ASASQFVRAE MLSSGYLIRP CDGGGSIHI VDHLNLEAWS VPDVLRPLYE SSKVVAQKMT
rev-2,4
ISALRYIRQL AQESNGEVVY GLGRQPAVLR TFSQRLSRGF NDAVNGFGDD GVSTMHCDGA
RCGISGN*
        rev-1
EDIIVAINST KHLNNISNSL SFLGGVLCAK ASMLLQNVPP AVLIRFLREH RSEWADFNVD
AYSAATLKAG SFAYPGMRPT RFTGSQIIMP LGHTEHEEM LEVVRLEGHS LAQEDAFMSR
DVHLLQICTG IDENAVGACS ELIFAPINEM FPDDAPLYPS GFRVIPVDAK TGDVQDLLTA
       rev-3
NHRTLDTSS LEVGSPENA SGNSFESSSSS RCILTIAFQF PFENNLQENV AGMACQYVRS
VISSVQRVAM AISPSGISPS LGSKLSPGSP EAVTLAQWIS QSYSHHLGSE LLTIDSLGSD
DSVLKLLWDH QDAILCCSLK QPVFMFANQ AGLDMLETTL VALQDITLEK IFDESGRKAI
CSDFAKLMQQ GFACLPSGIC VSTMGRIIVSY EQAVAWKVFA ASEENNNNLH CLAFSFVNWSFV
```

*Fig.5A.*
  
*Fig.5B.*     *Fig.5C.*     *Fig.5D.*
  
*Fig.5E.*     *Fig.5F.*     *Fig.5G.*

  
*Fig. 7I.*      *Fig. 7J.*      *Fig. 7K.*
  
*Fig. 7L.*      *Fig. 7M.*      *Fig. 7N.*
 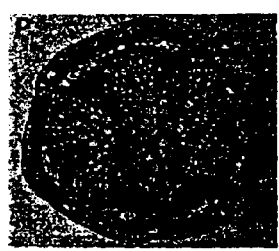
*Fig. 7O.*      *Fig. 7P.*
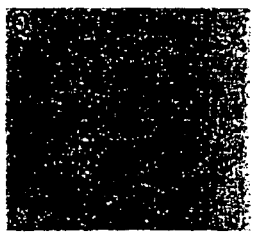 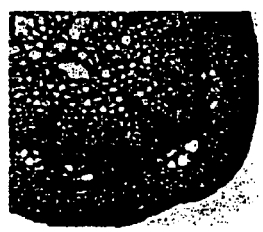 
*Fig. 7Q.*      *Fig. 7R.*      *Fig. 7S.*

SEQUENCE LISTING

<160> NUMBER OF SEQ ID NOS: 250

<210> SEQ ID NO 1
<211> LENGTH: 7747
<212> TYPE: DNA
<213> ORGANISM: Arabidopsis thaliana

<400> SEQUENCE: 1

```
gggaacactt aaagtatagt gcaattgtat tcaaactgac aaattaatca ttaattgtat      60
tagaaaatga tatattgtca tcgtgactaa tttgtctttt gaattcaatt gtaactacta     120
actactggtt ttcattttc agattatttc tcggttctta aaagaagaa aacacatacc       180
taatatcgtg tgtatcaaaa agccatgtgc gagcaaccat cttcctttgt aaatttgacc     240
cttttgtgta tcatttatat cgagtgtttg taattgttgg ttgattttgt gttatttgag     300
aggctagtca tttacgcaat ttctaaattt atcttttagt acgtatcaag atgttggagc     360
aactgtgtcc aacatacatg acatgtgaaa ttataattgt taaaacaaaa ggacatgtga     420
aattactatc tacttaaaga aaaaaaccag aaagaaaaaa aggtattaaa tttggaacta     480
aaagaaggtt aaaaagttt ttacagaaag taattacact tgcagatgaa agaaaaaagg      540
cagcatcatg atatgtaaaa aattgtcgaa gaggtttagt cgtatcactt tgtttgactg     600
atcactgtct tctgattcat ttttcagttt ttctttttca aattgtagct cacaacatta     660
aagttattca ctgctttaat cagatagttt aatactagta actagctcat ttaggcttta     720
aacacctctt tctgattact agcccactct ttggtggttc ttacatatca cacctaacta     780
tactgtgtat ccttgaagtg aaaatcaaat ttaccattcg tatcttactt acatacacta     840
ttatttttcc ttttttttt cactcaaggt cctactcttt gataccatag ctataatttg      900
gaataacta tttacagtgt attaattata cctaaacagt ttaatctgga ctaaatattt      960
agatagatgt tacaaatttg gttcgtctaa taatgaaga caagacatgc taacaaataa     1020
aacactacca caagggata gtgagagaat gtgttttgca acaagacata actttgattg      1080
cttgatgtgt taaaatgatt atgtcagaga cagagagcga tcataggctt tctttatttc     1140
taataacgtc gatttcttc ttcttttctg gcgttcaata atgtcgaatt ttaattcttg      1200
attttttgcaa ctctaaatat ccttaacgac attgaagcat ggtgcatgtc gatcgttaat    1260
aataaagttg aacaaaaatc ttgttgaatt aattacaagc acagcttcaa tagcataact    1320
ttacgagacg accagatctt atagacgagt ttcgctttta cttttttaat gattaaaact    1380
ttcatcggag aacataagtc ttcctcttaa ttaaaattac tacccgtgca taacttcatt    1440
ttttaaaaca tcaataatta atatacgatt acaaccctaa aaattagtca ccctatagta    1500
cataacaatg atgatagttt tttcttttg gtgtaatgtt aaaataaaat gttagccata     1560
ttaaacgata gttcttttaa cttagccatt gtaagatatt tcttacttta gtttttccgt    1620
agaagatatt cattatggta tggatagtat ataccttaac tgagtttaaa tattggatca    1680
ataccatcta ataacacata tctgatgttc aatacttaat aattttgcat aaatgttaag    1740
cgtgacaact taaaaaaaaa cacatcaaca gagtaaaaac atatctgtta aataagaaaa    1800
atgtcatttt tataacactt aaaaaaaaat gcatgaagcg tttcatagtt ttttttttt    1860
tcaaagtaat gtaggcgtta gatatttctt acaattttt gaaaatatt tttatgttg      1920
tgattggctg atatcaggta actaaaact ctttaaagaa ttgaagaaaa tttgaaaagt     1980
aaatagatgg attcctatat tgtcatttca gaaaaacagt agggacaact tcgtaaatga    2040
```

```
tagccgtatt attaaacaaa taaatttaaa ttagaaaaaa ggaaaaaaac gcaccacttt     2100 tcttttcgc tgatgcacag cttgtcggtt tgcgtgcaaa tcctctgttt cacaattttt      2160
tcttcttctc tttctctctc ttcctctttt attcctctgt tccaaagttc agcagaagca     2220
aacacacaca tcacttacta tctctctctc cttcttcact ttctcacata accaaactct     2280
ctctttctct cttttttttg aagtctcctt tgaaactata attgcccttt agtgttgttc     2340
gttcagagtc ttcaaaactt tgcagcttc aattgtacct gggtttcttc ttcattgttc      2400
ctaaggtttc tgtgtccttc aattcttctg atataatgct tctttaagag agttgacatc     2460
atcactttct tggggtactc ttctctgttt ctccccagaa aatccaactc tgtaattttg     2520 ggtcttatt ctgtttttct ctttgaagaa tctttaaaat tctcagatct tctgaatctc      2580
tcttctttaa aacttttttt aactttattt tttgtactcg cttctttgcc ttcattttc      2640 tcgtatccac atgtcgttgg tctttcgcta caagccacga ccgtagaatc ttcttttgtc     2700
tgaaaagaat tacaatttac gtttctctta cgatacgacg gactttccga agaaattaat     2760
ttaaagagaa aagaagaaga agccaaagaa gaagaagaag ctagaagaaa cagtaaagtt     2820
tgagactttt tttgagggtc gagctaaaat ggagatggcg gtggctaacc accgtgagag     2880
aagcagtgac agtatgaata gacatttaga tagtagcggt aagtacgtta ggtacacagc     2940
tgagcaagtc gaggctcttg agcgtgtcta cgctgagtgt cctaagccta gctctctccg     3000
tcgacaacaa ttgatccgtg aatgttccat tttggccaat attgagccta agcagatcaa     3060
agtctggttt cagaaccgca ggtattgctt ctcttaata tggccaggat taattttaa      3120 ttaaggattt tgaatttgat tctattggat ttagtgtgtt atattcaatg gatatgaagg     3180 accactttg ttgttatttc aagatttgat gcttcaattc aattctccga cacaatttcc      3240
tgtttttaca aagggttcc tttgaatctg tctggtagat ttggttattc aatagcttgg      3300
tgtaactgtt cttgtgacga tatggttact gtctgatctg gtgtctaatc ttaggagttt     3360
tgttgattcg ttttgttgtg tggtttcagg tgtcgagata agcagaggaa agaggcgtcg     3420
aggctccaga gcgtaaaccg gaagctctct gcgatgaata aactgttgat ggaggagaat     3480
gataggttgc agaagcaggt ttctcagctt gtctgcgaaa atggatatat gaaacagcag     3540
ctaactactg ttgtatgtaa cttaacattt ccttttgtca aatgtgttct taagaatca     3600 tttgttactc ctatcagttc aacatgtagc ttgagttata agttactga cttgttgttt      3660 taacttcagg ttaacgatcc aagctgtgaa tctgtggtca caactcctca gcattcgctt     3720
agagatgcga atagtcctgc tgggtaaagt ttcattttg gttttgaagt aaccttttc      3780 taatcttttt tctttgccta attgcttggt tttggtctta gattgctctc aatcgcagag     3840
gagactttgg cagagttcct atccaaggct acaggaactg ctgttgattg ggttcagatg     3900
cctgggatga aggttatacg catctcgtat cattacttaa gtgttatttt atctgttgat     3960
atctatggca atatgtgaaa tattgaaatg ttgtgtgttg tagcctggtc cggattcggt     4020
tggcatcttt gccatttcgc aaagatgcaa tggagtggca gctcgagcct gtggtcttgt     4080
tagcttagaa cctatgaagg taagaaaggg acactctttt cgttgctaaa gatacaagtc     4140
ataatgtttc attttcaacc agtttgggtt ttttgtgttc ttacagattg cagagatcct     4200
caaagatcgg ccatcttggt tccgtgactg taggagcctt gaagttttca ctatgttccc     4260
ggctggtaat ggtggcacaa tcgagcttgt ttatatgcag gtgaatcctt tagcctcttc     4320
tggtttagtt ttctatctct aacacttgaa gatgaatgaa taaagttgtg acatttgttc     4380
```

```
agacgtatgc accaacgact ctggctcctg cccgcgattt ctggaccctg agatacacaa    4440
cgagcctcga caatgggagt tttgtggtat gcagctctca taatgtctag tgtttacaga    4500
aaaactctgg gatcttgatg tttttcatat gtctttaaaa ggtttgtgag aggtcgctat    4560
ctggctctgg agctgggcct aatgctgctt cagcttctca gtttgtgaga gcagaaatgc    4620
tttctagtgg gtatttaata aggccttgtg atggtggtgg ttctattatt cacattgtcg    4680
atcaccttaa tcttgaggta cttaaatctt cacatgtggc attttgtgtg tgttttcagg    4740
aatttctaga agaattgatt ataaacattt gttcttgcat tgtaggcttg gagtgttccg    4800
gatgtgcttc gaccccttta tgagtcatcc aaagtcgttg cacaaaaaat gaccatttcc    4860
gtgagtgtat acatataata accttaagct ttgattgatt catataacat atctaacggt    4920
tggaggtgct tcatgtttta ggcgttgcgg tatatcaggc aattagccca agagtctaat    4980
ggtgaagtag tgtatggatt aggaaggcag cctgctgttc ttagaacctt tagccaaaga    5040
ttaagcaggt acttcgatct tgagctaaaa cctaattgtt ctttgctctg tttgctcatt    5100
gtcatttttt ctgttcttgg ttttcttgaa ggggcttcaa tgatgcggtt aatgggtttg    5160
gtgacgacgg gtggtctacg atgcattgtg atggagcgga agatattatc gttgctatta    5220
actctacaaa gcatttgaat aatatttcta attctctttc gttccttgga ggcgtgctct    5280
gtgccaaggc ttcaatgctt ctccaagtaa gttagtgtgt ccagtattgg tactttgtgt    5340
tcttttgaca gttttctatg gctgaaattt gtgttatcta ttgtcttctg tagaatgttc    5400
ctcctgcggt tttgatccgg ttccttagag agcatcgatc tgagtgggct gatttcaatg    5460
ttgatgcata ttccgctgct acacttaaag ctggtagctt tgcttatccg ggaatgagac    5520
caacaagatt cactgggagt cagatcataa tgccactagg acatacaatt gaacacgaag    5580
aagtaaggct tcaaagtctt tacctgccga caaaacatca ttttttatgtc tctctcttac    5640 atatatattt ggttttgtta tgtttagatg ctagaagttg ttagactgga aggtcattct    5700
cttgctcaag aagatgcatt tatgtcacgg gatgtccatc tccttcaggt atatcacttc    5760
taagttctaa cccaatggat cttgaaattt ttaccatttc aaagttaaaa ttgaccttaa    5820
tgatttatgg tagatttgta ccgggattga cgagaatgcc gttggagctt gttctgaact    5880
gatatttgct ccgattaatg agatgttccc ggatgatgct ccacttgttc cctctggatt    5940
ccgagtcata cccgttgatg ctaaaacggg actcttcttt gctgtaccac tgattttttct    6000 tttacttaga gatggtttgt ttcaaggctc atttttttctt actcatacag ggagatgtac    6060
aagatctgtt aaccgctaat caccgtacac tagacttaac ttctagcctt gaagtcggtc    6120
catcacctga gaatgcttct ggaaactctt tttctagctc aagctcgaga tgtattctca    6180
ctatcgcgtt tcaattccct tttgaaaaca acttgcaaga aaatgttgct ggtatggctt    6240
gtcagtatgt gaggagcgtg atctcatcag ttcaacgtgt tgcaatggcg atctcaccgt    6300
ctgggataag cccgagtctg ggctccaaat tgtccccagg atctcctgaa gctgttactc    6360
ttgctcagtg gatctctcaa agttacaggt gggggtgtaa atgtttactc tcgtctcttt    6420
cttataatcc tcgaacttat cgatgatgcc ttatgctgat atgtttgttt ttccagtcat    6480
cacttaggct cggagttgct gacgattgat tcacttggaa gcgacgactc ggtactaaaa    6540
cttctatggg atcaccaaga tgccatcctg tgttgctcat taaaggtatg tgtcctacac    6600
caaacaaaaa gcagaataca cctgtagttt tagacgtata atatggtctg gatatgttgc    6660
agccacagcc agtgttcatg tttgcgaacc aagctggtct agacatgcta gagacaacac    6720
ttgtagcctt acaagatata acactcgaaa agatattcga tgaatcgggt cgtaaggcta    6780
```

-continued

```
tctgttcgga cttcgccaag ctaatgcaac aggtaaagaa ccaaaacaaa aacatctgca    6840
gataaatggt tttgattcat ttgtctgaga actatctttg cgtctacagg gatttgcttg    6900
cttgccttca ggaatctgtg tgtcaacgat gggaagacat gtgagttatg aacaagctgt    6960
tgcttggaaa gtgtttgctg catctgaaga aaacaacaac aatctgcatt gtcttgcctt    7020
ctcctttgta aactggtctt ttgtgtgatt cgattgacag aaaagactaa atttaaattt    7080
acgttagaga actcaaattt ttggttgttg tttaggtgtc tctgttttgt ttttaaaat     7140 tattttgatc aaatgttact cactttcttc tttcacaacg tatttggttt taatgttttg    7200
gggaaaaaag cagagttgat caatctctat atataaaggg aatgatgtga taattttgtt    7260
aaaactaagc ttacaacatt ttttctatcg catttgacag tttcattttc acatctctcg    7320
ctatatatta gtaatataaa ctatttcaaa aaacaaagaa tcaacaagaa tccacagatg    7380
taagaaagaa aaatcacagc caaataactt ttttatttat ttggccgtta gataaaacta    7440
ccttcagaat ttcatgcatc tagccggtaa acctgtctga tgattgacgg cgacaatctc    7500
agagacattg ttgcaacgaa gaacatcttg accaagctta gctcctgcag ctttaagacc    7560
tttaagcgaa accggcatgt tgaagagatt gagtgatgga agcttagaaa gcggagggag    7620
tttctggttc ggtaagaagt ttctgaaatc atccataagc aatggaactt cgaaatcggt    7680
tttgttgtgt ttcaccacat tgtctttagc tgcgatgtga gctcctggtt ccatgtggtt    7740
ggttgag                                                              7747
```

<210> SEQ ID NO 2
<211> LENGTH: 842
<212> TYPE: PRT
<213> ORGANISM: Arabidopsis thaliana

<400> SEQUENCE: 2

```
Met Glu Met Ala Val Ala Asn His Arg Glu Arg Ser Ser Asp Ser Met
1               5                   10                  15

Asn Arg His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Ser Ile Leu Ala Asn
    50                  55                  60

Ile Glu Pro Lys Gln Ile Lys Val Trp Phe Gln Asn Arg Arg Cys Arg
65                  70                  75                  80

Asp Lys Gln Arg Lys Glu Ala Ser Arg Leu Gln Ser Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Tyr Met Lys Gln Gln
        115                 120                 125

Leu Thr Thr Val Val Asn Asp Pro Ser Cys Glu Ser Val Val Thr Thr
    130                 135                 140

Pro Gln His Ser Leu Arg Asp Ala Asn Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Asp Trp Val Gln Met Pro Gly Met Lys Pro Gly Pro Asp Ser
            180                 185                 190
```

-continued

```
Val Gly Ile Phe Ala Ile Ser Gln Arg Cys Asn Gly Val Ala Ala Arg
        195                 200                 205

Ala Cys Gly Leu Val Ser Leu Glu Pro Met Lys Ile Ala Glu Ile Leu
210                 215                 220

Lys Asp Arg Pro Ser Trp Phe Arg Asp Cys Arg Ser Leu Glu Val Phe
225                 230                 235                 240

Thr Met Phe Pro Ala Gly Asn Gly Gly Thr Ile Glu Leu Val Tyr Met
                245                 250                 255

Gln Thr Tyr Ala Pro Thr Thr Leu Ala Pro Ala Arg Asp Phe Trp Thr
        260                 265                 270

Leu Arg Tyr Thr Thr Ser Leu Asp Asn Gly Ser Phe Val Cys Glu
        275                 280                 285

Arg Ser Leu Ser Gly Ser Gly Ala Gly Pro Asn Ala Ala Ser Ala Ser
290                 295                 300

Gln Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Leu Asn Leu
                325                 330                 335

Glu Ala Trp Ser Val Pro Asp Val Leu Arg Pro Leu Tyr Glu Ser Ser
        340                 345                 350

Lys Val Val Ala Gln Lys Met Thr Ile Ser Ala Leu Arg Tyr Ile Arg
        355                 360                 365

Gln Leu Ala Gln Glu Ser Asn Gly Glu Val Val Tyr Gly Leu Gly Arg
        370                 375                 380

Gln Pro Ala Val Leu Arg Thr Phe Ser Gln Arg Leu Ser Arg Gly Phe
385                 390                 395                 400

Asn Asp Ala Val Asn Gly Phe Gly Asp Asp Gly Trp Ser Thr Met His
                405                 410                 415

Cys Asp Gly Ala Glu Asp Ile Ile Val Ala Ile Asn Ser Thr Lys His
                420                 425                 430

Leu Asn Asn Ile Ser Asn Ser Leu Ser Phe Leu Gly Gly Val Leu Cys
        435                 440                 445

Ala Lys Ala Ser Met Leu Leu Gln Asn Val Pro Pro Ala Val Leu Ile
450                 455                 460

Arg Phe Leu Arg Glu His Arg Ser Glu Trp Ala Asp Phe Asn Val Asp
465                 470                 475                 480

Ala Tyr Ser Ala Ala Thr Leu Lys Ala Gly Ser Phe Ala Tyr Pro Gly
                485                 490                 495

Met Arg Pro Thr Arg Phe Thr Gly Ser Gln Ile Ile Met Pro Leu Gly
        500                 505                 510

His Thr Ile Glu His Glu Glu Met Leu Glu Val Val Arg Leu Glu Gly
        515                 520                 525

His Ser Leu Ala Gln Glu Asp Ala Phe Met Ser Arg Asp Val His Leu
530                 535                 540

Leu Gln Ile Cys Thr Gly Ile Asp Glu Asn Ala Val Gly Ala Cys Ser
545                 550                 555                 560

Glu Leu Ile Phe Ala Pro Ile Asn Glu Met Phe Pro Asp Asp Ala Pro
                565                 570                 575

Leu Val Pro Ser Gly Phe Arg Val Ile Pro Val Asp Ala Lys Thr Gly
        580                 585                 590

Asp Val Gln Asp Leu Leu Thr Ala Asn His Arg Thr Leu Asp Leu Thr
        595                 600                 605

Ser Ser Leu Glu Val Gly Pro Ser Pro Glu Asn Ala Ser Gly Asn Ser
```

|  |  |  |  |  |
|---|---|---|---|---|
| Phe<br>625 | Ser | Ser | Ser | Ser<br>630 | Arg | Cys | Ile | Leu<br>635 | Thr | Ile | Ala | Phe | Gln<br>640 | Phe |

```
                    610                 615                 620
Phe Ser Ser Ser Ser Arg Cys Ile Leu Thr Ile Ala Phe Gln Phe
625                 630                 635                 640

Pro Phe Glu Asn Asn Leu Gln Glu Asn Val Ala Gly Met Ala Cys Gln
                645                 650                 655

Tyr Val Arg Ser Val Ile Ser Ser Val Gln Arg Val Ala Met Ala Ile
                660                 665                 670

Ser Pro Ser Gly Ile Ser Pro Ser Leu Gly Ser Lys Leu Ser Pro Gly
                675                 680                 685

Ser Pro Glu Ala Val Thr Leu Ala Gln Trp Ile Ser Gln Ser Tyr Ser
690                 695                 700

His His Leu Gly Ser Glu Leu Leu Thr Ile Asp Ser Leu Gly Ser Asp
705                 710                 715                 720

Asp Ser Val Leu Lys Leu Leu Trp Asp His Gln Asp Ala Ile Leu Cys
                725                 730                 735

Cys Ser Leu Lys Pro Gln Pro Val Phe Met Phe Ala Asn Gln Ala Gly
                740                 745                 750

Leu Asp Met Leu Glu Thr Thr Leu Val Ala Leu Gln Asp Ile Thr Leu
                755                 760                 765

Glu Lys Ile Phe Asp Glu Ser Gly Arg Lys Ala Ile Cys Ser Asp Phe
770                 775                 780

Ala Lys Leu Met Gln Gln Gly Phe Ala Cys Leu Pro Ser Gly Ile Cys
785                 790                 795                 800

Val Ser Thr Met Gly Arg His Val Ser Tyr Glu Gln Ala Val Ala Trp
                805                 810                 815

Lys Val Phe Ala Ala Ser Glu Glu Asn Asn Asn Asn Leu His Cys Leu
                820                 825                 830

Ala Phe Ser Phe Val Asn Trp Ser Phe Val
                835                 840
```

<210> SEQ ID NO 3
<211> LENGTH: 4197
<212> TYPE: DNA
<213> ORGANISM: Arabidopsis thaliana

<400> SEQUENCE: 3

| | |
|---|---|
| atggagatgg cggtggctaa ccaccgtgag agaagcagtg acagtatgaa tagacattta | 60 |
| gatagtagcg gtaagtacgt taggtacaca gctgagcaag tcgaggctct tgagcgtgtc | 120 |
| tacgctgagt gtcctaagcc tagctctctc cgtcgacaac aattgatccg tgaatgttcc | 180 |
| attttggcca atattgagcc taagcagatc aaagtctggt tcagaaccga caggtattgc | 240 |
| ttctctttaa tatggccagg attaattttt aattaaggat tttgaatttg attctattgg | 300 |
| atttagtgtg ttatattcaa tggatatgaa ggaccacttt tgttgttatt tcaagatttg | 360 |
| atgcttcaat tcaattctcc gacacaattt cctgttttta caaagggtt cctttgaatc | 420 |
| tgtctggtag atttggttat tcaatagctt ggtgtaactg ttcttgtgac gatatggtaa | 480 |
| ctgtctgatc tggtgtctaa tcttaggagt tttgttgatt cgttttgttg tgtggtttca | 540 |
| ggtgtcgaga taagcagagg aaagaggcgt cgaggctcca gagcgtaaac cggaagctct | 600 |
| ctgcgatgaa taaactgttg atggaggaga atgataggtt gcagaagcag gtttctcagc | 660 |
| ttgtctgcga aatggatat atgaaacagc agctaactac tgttgtatgt aacttaacat | 720 |
| tccttttgt caaatgtgtt cttaaagaat catttgttac tcctatcagt tcaacatgta | 780 |
| gcttgagtta taaagttact gacttgttgt tttaacttca ggttaacgat ccaagctgtg | 840 |

```
aatctgtggt cacaactcct cagcattcgc ttagagatgc gaatagtcct gctgggtaaa      900
gtttcatttt tggttttgaa gtaacctttt tctaatcttt tttctttgcc taattgcttg      960
gttttggtct tagattgctc tcaatcgcag aggagacttt ggcagagttc ctatccaagg     1020
ctacaggaac tgctgttgat tgggttcaga tgcctgggat gaaggttata cgcatctcgt     1080
atcattactt aagtgttatt ttatctgttg atatctatgg caatatgtga atatattgaaa    1140
tgttgtgtgt tgtagcctgg tccggattcg gttggcatct ttgccatttc gcaaagatgc     1200
aatggagtgg cagctcgagc ctgtggtctt gttagcttag aacctatgaa ggtaagaaag     1260
ggacactctt ttcgttgcta aagatacaag tcataatgtt tcattttcaa ccagtttggg     1320
ttttttgtgt tcttacagat tgcagagatc ctcaaagatc ggccatcttg gttccgtgac     1380
tgtaggagcc ttgaagtttt cactatgttc ccggctggta atggtggcac aatcgagctt     1440
gtttatatgc aggtgaatcc tttagcctct tctggtttag ttttctatct ctaacacttg     1500
aagatgaatg aataaagttg tgacatttgt tcagacgtat gcaccaacga ctctggctcc     1560
tgcccgcgat ttctggaccc tgagatacac aacgagcctc gacaatggga gttttgtggt     1620
atgcagctct cataatgtct agtgtttaca gaaaaactct gggatcttga tgttttcat      1680
atgtctttaa aaggtttgtg agaggtcgct atctggctct ggagctgggc ctaatgctgc     1740
ttcagcttct cagtttgtga gagcagaaat gctttctagt gggtatttaa taaggccttg     1800
tgatggtggt ggttctatta ttcacattgt cgatcacctt aatcttgagg tacttaaatc     1860
ttcacatgtg gcattttgtg tgtgttttca ggaatttcta aagaattga ttataaacat      1920
ttgttcttgc attgtaggct tggagtgttc cggatgtgct tcgacccctt tatgagtcat     1980
ccaaagtcgt tgcacaaaaa atgaccattt ccgtgagtgt atacatataa taaccttaag    2040
ctttgattga ttcatataac atatctaacg gttggaggtg cttcatgttt taggcgttgc    2100
ggtatatcag gcaattagcc caagagtcta atggtgaagt agtgtatgga ttaggaaggc    2160
agcctgctgt tcttagaacc tttagccaaa gattaagcag gtacttcgat cttgagctaa    2220
aacctaattg ttctttgctc tgtttgctca ttgtcatttt ttctgttctt ggttttcttg    2280
aaggggcttc aatgatgcgg ttaatgggtt tggtgacgac gggtggtcta cgatgcattg    2340
tgatggagcg gaagatatta tcgttgctat taactctaca aagcatttga ataatatttc    2400
taattctctt tcgttccttg gaggcgtgct ctgtgccaag gcttcaatgc ttctccaagt    2460
aagtagtgt gtccagtatt ggtactttgt gttcttttga cagttttcta tggctgaaat    2520
ttgtgttatc tattgtcttc tgtagaatgt tcctcctgcg gttttgatcc ggttccttag    2580
agagcatcga tctgagtggg ctgatttcaa tgttgatgca tattccgctg ctacacttaa    2640
agctggtagc tttgcttatc cgggaatgag accaacaaga ttcactggga gtcagatcat    2700
aatgccacta ggacatacaa ttgaacacga agaagtaagg cttcaaagtc tttacctgcc    2760
gacaaaacat cattttatg tctctctctt acatatatat ttggttttgt tatgtttaaa     2820
tgctagaagt tgttagactg gaaggtcatt tccttgctca agaagatgca tttatgtcac    2880
gggatgtcca tctccttcag gtatatcact tctaagttct aacccaatgg atcttgaaat    2940
ttttaccatt tcaaagttaa aattgacctt aatgatttat ggtagatttg taccgggatt    3000
gacgagaatg ccgttggagc ttgttctgaa ctgatatttg ctccgattaa tgagatgttc    3060
ccggatgatg ctccacttgt tccctctgga ttccgagtca tacccgttga tgctaaaacg    3120
gtactcttct ttgctgtacc actgatttt ctttttactta gagatggttt gtttcaaggc    3180
```

```
tcatttttc  ttactcatac  agggagatgt  acaagatctg  ttaaccgcta  atcaccgtac    3240
actagactta  acttctagcc  ttgaagtcgg  tccatcacct  gagaatgctt  ctggaaactc    3300
tttttctagc  tcaagctcga  gatgtattct  cactatcgcg  tttcaattcc  cttttgaaaa    3360
caacttgcaa  gaaaatgttg  ctggtatggc  ttgtcagtat  gtgaggagcg  tgatctcatc    3420
agttcaacgt  gttgcaatgg  cgatctcacc  gtctgggata  agcccgagtc  tgggctccaa    3480
attgtcccca  ggatctcctg  aagctgttac  tcttgctcag  tggatctctc  aaagttacag    3540 gtggggtgt   aaatgtttac  tctcgtctct  ttcttataat  cctcgaactt  atcgatgatg    3600
ccttatgctg  atatgtttgt  ttttccagtc  atcacttagg  ctcggagttg  ctgacgattg    3660
attcacttgg  aagcgacgac  tcggtactaa  aacttctatg  ggatcaccaa  gatgccatcc    3720
tgtgttgctc  attaaaggta  tgtgtcctac  accaaacaaa  aagcagaata  cacctgtagt    3780
tttagacgta  taatatggtc  tggatatgtt  gcagccacag  ccagtgttca  tgtttgcgaa    3840
ccaagctggt  ctagacatgc  tagagacaac  acttgtagcc  ttacaagata  taacactcga    3900
aaagatattc  gatgaatcgg  gtcgtaaggc  tatctgttcg  gacttcgcca  agctaatgca    3960
acaggtaaag  aaccaaaaca  aaaacatctg  cagataaatg  gttttgattc  atttgtctga    4020
gaactatctt  tgcgtctaca  gggatttgct  tgcttgcctt  caggaatctg  tgtgtcaacg    4080
atgggaagac  atgtgagtta  tgaacaagct  gttgcttgga  aagtgtttgc  tgcatctgaa    4140
gaaaacaaca  acaatctgca  ttgtcttgcc  ttctcctttg  taaactggtc  ttttgtg      4197
```

<210> SEQ ID NO 4
<211> LENGTH: 20
<212> TYPE: DNA
<213> ORGANISM: Artificial
<220> FEATURE:
<223> OTHER INFORMATION: primer

<400> SEQUENCE: 4
gtragtgccc catacttgct                                                      20

<210> SEQ ID NO 5
<211> LENGTH: 4197
<212> TYPE: DNA
<213> ORGANISM: Arabidopsis thaliana

<400> SEQUENCE: 5

```
atggagatgg  cggtggctaa  ccaccgtgag  agaagcagtg  acagtatgaa  tagacattta     60
gatagtagcg  gtaagtacgt  taggtacaca  gctgagcaag  tcgaggctct  tgagcgtgtc    120
tacgctgagt  gtcctaagcc  tagctctctc  cgtcgacaac  aattgatccg  tgaatgttcc    180 atttggcca   atattgagcc  taagcagatc  aaagtctggt  ttcagaaccg  caggtattgc    240
ttctctttaa  tatggccagg  attaattttt  aattaaggat  tttgaatttg  attctattgg    300
atttagtgtg  ttatattcaa  tggatatgaa  ggaccacttt  tgttgttatt  tcaagatttg    360
atgcttcaat  tcaattctcc  gacacaattt  cctgttttta  caaaagggtt  cctttgaatc    420
tgtctggtag  atttggttat  tcaatagctt  ggtgtaactg  ttcttgtgac  gatatggtta    480
ctgtctgatc  tggtgtctaa  tcttaggagt  tttgttgatt  cgttttgttg  tgtggtttca    540
ggtgtcgaga  taagcagagg  aaagaggcgt  cgaggctcca  gagcgtaaac  cggaagctct    600
ctgcgatgaa  taaactgttg  atggaggaga  atgataggtt  gcagaagcag  gtttctcagc    660
ttgtctgcga  aaatggatat  atgaaacagc  agctaactac  tgttgtatgt  aacttaacat    720 ttcctttgt   caaatgtgtt  cttaaagaat  catttgttac  tcctatcagt  tcaacatgta    780
```

```
gcttgagtta taaagttact gacttgttgt tttaacttca ggttaacgat ccaagctgtg    840
aatctgtggt cacaactcct cagcattcgc ttagagatgc gaatagtcct gctgggtaaa    900
gtttcatttt tggttttgaa gtaaccttt tctaatcttt tttctttgcc taattgcttg     960
gttttggtct tagattgctc tcaatcgcag aggagacttt ggcagagttc ctatccaagg   1020
ctacaggaac tgctgttgat tgggttcaga tgcctgggat gaaggttata cgcatctcgt   1080
atcattactt aagtgttatt ttatctgttg atatctatgg caatatgtga atattgaaa    1140
tgttgtgtgt tgtagcctgg tccggattcg gttggcatct ttgccatttc gcaaagatgc   1200
aatggagtgg cagctcgagc ctgtggtctt gttagcttag aacctatgaa ggtaagaaag   1260
ggacactctt tcgttgcta aagatacaag tcataatgtt tcattttcaa ccagtttggg    1320
ttttttgtgt tcttacagat tgcagagatc ctcaaagatc ggccatcttg gttccgtgac   1380
tgtaggagcc ttgaagtttt cactatgttc ccggctggta atggtggcac aatcgagctt   1440
gtttatatgc aggtgaatcc tttagcctct tctggtttag ttttctatct ctaacacttg   1500
aagatgaatg aataaagttg tgacatttgt tcagacgtat gcaccaacga ctctggctcc   1560
tgcccgcgat ttctggaccc tgagatacac aacgagcctc gacaatggga gttttgtggt   1620
atgcagctct cataatgtct agtgtttaca gaaaaactct gggatcttga tgttttcat    1680
atgtctttaa aaggtttgtg agaggtcgct atctggctct ggagctgggc ctaatgctgc   1740
ttcagcttct cagtttgtga gagcagaaat gctttctagt gggtatttaa taaggccttg   1800
tgatggtggt ggttctatta ttcacattgt cgatcacctt aatcttgagg tacttaaatc   1860
ttcacatgtg gcattttgtg tgtgttttca ggaatttcta aagaattga ttataaacat    1920
ttgttcttgc attgtaggct tggagtgttc cggatgtgct tcgaccccttt tatgagtcat   1980
ccaaagtcgt tgcacaaaaa atgaccattt ccgtgagtgt atacatataa taaccttaag   2040
cttttgattga ttcatataac atatctaacg gttggaggtg cttcatgttt taggcgttgc   2100
ggtatatcag gcaattagcc caagagtcta atggtgaagt agtgtatgga ttaggaaggc   2160
agcctgctgt tcttagaacc tttagccaaa gattaagcag gtacttcgat cttgagctaa   2220
aacctaattg ttctttgctc tgtttgctca ttgtcatttt ttctgttctt ggttttcttg   2280
aaggggcttc aatgatgcgg ttaatgggtt tggtgacgac gggtggtcta cgatgcattg   2340
tgatggagcg gaagatatta tcgttgctat taactctaca aagcatttga ataatatttc   2400
taattctctt tcgttccttg gaggcgtgct ctgtgccaag gcttcaatgc ttctccaagt   2460
aagttagtgt gtccagtatt ggtactttgt gttcttttga cagttttcta tggctgaaat   2520
ttgtgttatc tattgtcttc tgtagaatgt tcctcctgcg gttttgatcc ggttccttag   2580
agagcatcga tctgagtggg ctgatttcaa tgttgatgca tattccgctg ctacacttaa   2640
agctggtagc tttgcttatc cgggaatgag accaacaaga ttcactggga gtcagatcat   2700
aatgccacta ggacatacaa ttgaacacga agaagtaagg cttcaaagtc tttacctgcc   2760
gacaaaacat catttttatg tctctctctt acatatatat ttggttttgt tatgtttaga   2820
tgctagaagt tgttagactg gaaggtcatt ctcttgctca agaagatgca tttatgtcac   2880
gggatgtcca tctccttcag gtatatcact tctaagttct aacccaatgg atcttgaaat   2940
ttttaccatt tcaaagttaa aattgacctt aatgattat ggtagatttg taccgggatt    3000
gacgagaatg ccgttggagc ttgttctgaa ctgatatttg ctccgattaa tgagatgttc   3060
ccggatgatg ctccacttgt tccctctgga ttccgagtca tacccgttga tgctaaaacg   3120
```

-continued

```
gtactcttct tgctgtacc actgattttt cttttactta gagatggttt gtttcaaggc    3180
tcattttttc ttactcatac agggagatgt acaagatctg ttaaccgcta atcaccgtac    3240
actagactta atttctagcc ttgaagtcgg tccatcacct gagaatgctt ctggaaactc    3300
tttttctagc tcaagctcga gatgtattct cactatcgcg tttcaattcc cttttgaaaa    3360
caacttgcaa gaaatgttg ctggtatggc ttgtcagtat gtgaggagcg tgatctcatc    3420
agttcaacgt gttgcaatgg cgatctcacc gtctgggata agcccgagtc tgggctccaa    3480
attgtcccca ggatctcctg aagctgttac tcttgctcag tggatctctc aaagttacag    3540
gtgggggtgt aaatgtttac tctcgtctct ttcttataat cctcgaactt atcgatgatg    3600
ccttatgctg atatgtttgt ttttccagtc atcacttagg ctcggagttg ctgacgattg    3660
attcacttgg aagcgacgac tcggtactaa aacttctatg ggatcaccaa gatgccatcc    3720
tgtgttgctc attaaaggta tgtgtcctac accaaacaaa aagcagaata cacctgtagt    3780
tttagacgta taatatggtc tggatatgtt gcagccacag ccagtgttca tgtttgcgaa    3840
ccaagctggt ctagacatgc tagagacaac acttgtagcc ttacaagata taacactcga    3900
aaagatattc gatgaatcgg gtcgtaaggc tatctgttcg gacttcgcca agctaatgca    3960
acaggtaaag aaccaaaaca aaaacatctg cagataaatg gttttgattc atttgtctga    4020
gaactatctt tgcgtctaca gggatttgct tgcttgcctt caggaatctg tgtgtcaacg    4080
atgggaagac atgtgagtta tgaacaagct gttgcttgga aagtgtttgc tgcatctgaa    4140
gaaaacaaca acaatctgca ttgtcttgcc ttctcctttg taaactggtc ttttgtg      4197
```

<210> SEQ ID NO 6
<211> LENGTH: 842
<212> TYPE: PRT
<213> ORGANISM: Arabidopsis thaliana

<400> SEQUENCE: 6

```
Met Glu Met Ala Val Ala Asn His Arg Glu Arg Ser Ser Asp Ser Met
1               5                   10                  15

Asn Arg His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Ser Ile Leu Ala Asn
    50                  55                  60

Ile Glu Pro Lys Gln Ile Lys Val Trp Phe Gln Asn Arg Arg Cys Arg
65                  70                  75                  80

Asp Lys Gln Arg Lys Glu Ala Ser Arg Leu Gln Ser Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Tyr Met Lys Gln Gln
        115                 120                 125

Leu Thr Thr Val Val Asn Asp Pro Ser Cys Glu Ser Val Val Thr Thr
    130                 135                 140

Pro Gln His Ser Leu Arg Asp Ala Asn Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Asp Trp Val Gln Met Pro Gly Met Lys Pro Gly Pro Asp Ser
            180                 185                 190
```

-continued

```
Val Gly Ile Phe Ala Ile Ser Gln Arg Cys Asn Gly Val Ala Arg
        195                 200                 205
Ala Cys Gly Leu Val Ser Leu Glu Pro Met Lys Ile Ala Glu Ile Leu
    210                 215                 220
Lys Asp Arg Pro Ser Trp Phe Arg Asp Cys Arg Ser Leu Glu Val Phe
225                 230                 235                 240
Thr Met Phe Pro Ala Gly Asn Gly Gly Thr Ile Glu Leu Val Tyr Met
                245                 250                 255
Gln Thr Tyr Ala Pro Thr Thr Leu Ala Pro Ala Arg Asp Phe Trp Thr
            260                 265                 270
Leu Arg Tyr Thr Thr Ser Leu Asp Asn Gly Ser Phe Val Cys Glu
        275                 280                 285
Arg Ser Leu Ser Gly Ser Gly Ala Gly Pro Asn Ala Ala Ser Ala Ser
    290                 295                 300
Gln Phe Val Arg Ala Glu Met Leu Ser Ser Gly Tyr Leu Ile Arg Pro
305                 310                 315                 320
Cys Asp Gly Gly Gly Ser Ile Ile His Ile Val Asp His Leu Asn Leu
                325                 330                 335
Glu Ala Trp Ser Val Pro Asp Val Leu Arg Pro Leu Tyr Glu Ser Ser
            340                 345                 350
Lys Val Val Ala Gln Lys Met Thr Ile Ser Ala Leu Arg Tyr Ile Arg
        355                 360                 365
Gln Leu Ala Gln Glu Ser Asn Gly Glu Val Val Tyr Gly Leu Gly Arg
    370                 375                 380
Gln Pro Ala Val Leu Arg Thr Phe Ser Gln Arg Leu Ser Arg Gly Phe
385                 390                 395                 400
Asn Asp Ala Val Asn Gly Phe Gly Asp Asp Gly Trp Ser Thr Met His
                405                 410                 415
Cys Asp Gly Ala Glu Asp Ile Ile Val Ala Ile Asn Ser Thr Lys His
            420                 425                 430
Leu Asn Asn Ile Ser Asn Ser Leu Ser Phe Leu Gly Gly Val Leu Cys
        435                 440                 445
Ala Lys Ala Ser Met Leu Leu Gln Asn Val Pro Pro Ala Val Leu Ile
    450                 455                 460
Arg Phe Leu Arg Glu His Arg Ser Glu Trp Ala Asp Phe Asn Val Asp
465                 470                 475                 480
Ala Tyr Ser Ala Ala Thr Leu Lys Ala Gly Ser Phe Ala Tyr Pro Gly
                485                 490                 495
Met Arg Pro Thr Arg Phe Thr Gly Ser Gln Ile Ile Met Pro Leu Gly
            500                 505                 510
His Thr Ile Glu His Glu Glu Met Leu Glu Val Val Arg Leu Glu Gly
        515                 520                 525
His Ser Leu Ala Gln Glu Asp Ala Phe Met Ser Arg Asp Val His Leu
    530                 535                 540
Leu Gln Ile Cys Thr Gly Ile Asp Glu Asn Ala Val Gly Ala Cys Ser
545                 550                 555                 560
Glu Leu Ile Phe Ala Pro Ile Asn Glu Met Phe Pro Asp Asp Ala Pro
                565                 570                 575
Leu Val Pro Ser Gly Phe Arg Val Ile Pro Val Asp Ala Lys Thr Gly
            580                 585                 590
Asp Val Gln Asp Leu Leu Thr Ala Asn His Arg Thr Leu Asp Leu Ile
        595                 600                 605
```

```
Ser Ser Leu Glu Val Gly Pro Ser Pro Glu Asn Ala Ser Gly Asn Ser
    610                 615                 620

Phe Ser Ser Ser Ser Arg Cys Ile Leu Thr Ile Ala Phe Gln Phe
625                 630                 635                 640

Pro Phe Glu Asn Asn Leu Gln Glu Asn Val Ala Gly Met Ala Cys Gln
                645                 650                 655

Tyr Val Arg Ser Val Ile Ser Ser Val Gln Arg Val Ala Met Ala Ile
            660                 665                 670

Ser Pro Ser Gly Ile Ser Pro Ser Leu Gly Ser Lys Leu Ser Pro Gly
        675                 680                 685

Ser Pro Glu Ala Val Thr Leu Ala Gln Trp Ile Ser Gln Ser Tyr Ser
    690                 695                 700

His His Leu Gly Ser Glu Leu Leu Thr Ile Asp Ser Leu Gly Ser Asp
705                 710                 715                 720

Asp Ser Val Leu Lys Leu Leu Trp Asp His Gln Asp Ala Ile Leu Cys
                725                 730                 735

Cys Ser Leu Lys Pro Gln Pro Val Phe Met Phe Ala Asn Gln Ala Gly
            740                 745                 750

Leu Asp Met Leu Glu Thr Thr Leu Val Ala Leu Gln Asp Ile Thr Leu
        755                 760                 765

Glu Lys Ile Phe Asp Glu Ser Gly Arg Lys Ala Ile Cys Ser Asp Phe
    770                 775                 780

Ala Lys Leu Met Gln Gln Gly Phe Ala Cys Leu Pro Ser Gly Ile Cys
785                 790                 795                 800

Val Ser Thr Met Gly Arg His Val Ser Tyr Glu Gln Ala Val Ala Trp
                805                 810                 815

Lys Val Phe Ala Ala Ser Glu Glu Asn Asn Asn Leu His Cys Leu
            820                 825                 830

Ala Phe Ser Phe Val Asn Trp Ser Phe Val
        835                 840

<210> SEQ ID NO 7
<211> LENGTH: 4197
<212> TYPE: DNA
<213> ORGANISM: Arabidopsis thaliana

<400> SEQUENCE: 7
atggagatgg cggtggctaa ccaccgtgag agaagcagtg acagtatgaa tagacattta     60
gatagtagcg gtaagtacgt taggtacaca gctgagcaag tcgaggctct tgagcgtgtc    120
tacgctgagt gtcctaagcc tagctctctc cgtcgacaac aattgatccg tgaatgttcc    180
attttggcca atattgagcc taagcagatc aaagtctggt tcagaaccga caggtattgc    240
ttctctttaa tatggccagg attaattttt aattaaggat tttgaatttg attctattgg    300
atttagtgtg ttatattcaa tggatatgaa ggaccacttt tgttgttatt tcaagatttg    360
atgcttcaat tcaattctcc gacacaattt cctgttttta caaagggtt cctttgaatc     420 tgtctggtag atttggttat tcaatagctt ggtgtaactg ttcttgtgac gatatggtta    480
ctgtctgatc tggtgtctaa tcttaggagt tttgttgatt cgttttgttg tgtggtttca    540
ggtgtcgaga taagcagagg aaagaggcgt cgaggctcca gagcgtaaac cggaagctct    600
ctgcgatgaa taaactgttg atggaggaga atgataggt gcagaagcag gtttctcagc     660
ttgtctgcga aatggatat atgaaacagc agctaactac tgttgtatgt aacttaacat     720 ttcctttgt caaatgtgtt cttaaagaat catttgttac tcctatcagt tcaacatgta    780
```

```
gcttgagtta taaagttact gacttgttgt tttaacttca ggttaacgat ccaagctgtg    840
aatctgtggt cacaactcct cagcattcgc ttagagatgc gaatagtcct gctgggtaaa    900
gtttcatttt tggttttgaa gtaaccttt tctaatcttt tttctttgcc taattgcttg    960
gttttggtct tagattgctc tcaatcgcag aggagacttt ggcagagttc ctatccaagg   1020
ctacaggaac tgctgttgat tgggttcaga tgcctgggat gaaggttata cgcatctcgt   1080
atcattactt aagtgttatt ttatctgttg atatctatgg caatatgtga atatattgaaa  1140 tgttgtgtgt tgtagcctgg tccggattcg gttggcatct ttgccatttc gcaaagatgc   1200 aatgagtgg cagctcgagc ctgtggtctt gttagcttag aacctatgaa ggtaagaaag    1260
ggacactctt ttcgttgcta aagatacaag tcataatgtt tcattttcaa ccagtttggg   1320 tttttttgtgt tcttacagat tgcagagatc ctcaaagatc ggccatcttg gttccgtgac  1380
tgtaggagcc ttgaagtttt cactatgttc ccggctggta atggtggcac aatcgagctt   1440
gtttatatgc aggtgaatcc tttagcctct tctggtttag ttttctatct ctaacacttg   1500
aagatgaatg aataaagttg tgacatttgt tcagacgtat gcaccaacga ctctggctcc   1560
tgcccgcgat ttctggaccc tgagatacac aacgagcctc gacaatggga gttttgtggt   1620
atgcagctct cataatgtct agtgtttaca gaaaaactct gggatcttga tgttttttcat 1680 atgtctttaa aaggtttgtg agaggtcgct atctggctct ggagctgggc ctaatgctgc   1740
ttcagcttct cagtttgtga gagcagaaat gctttctagt gggtatttaa taaggccttg   1800
tgatggtggt ggttctatta ttcacattgt cgatcacctt aatcttgagg tacttaaatc   1860
ttcacatgtg gcattttgtg tgtgttttca ggaatttcta gaagaattga ttataaacat   1920
ttgttcttgc attgtaggct tggagtgttc cggatgtgct tcgaccccctt tatgagtcat  1980 ccaaagtcgt tgcacaaaaa atgaccattt ccgtgagtgt atacatataa taaccttaag   2040
ctttgattga ttcatataac atatctaacg gttggaggtg cttcatgttt taagcgttgc   2100
ggtatatcag gcaattagcc caagagtcta atggtgaagt agtgtatgga ttaggaaggc   2160
agcctgctgt tcttagaacc tttagccaaa gattaagcag gtacttcgat cttgagctaa   2220
aacctaattg ttctttgctc tgtttgctca ttgtcatttt ttctgttctt ggttttcttg   2280
aaggggcttc aatgatgcgg ttaatgggtt tggtgacgac gggtggtcta cgatgcattg   2340
tgatggagcg gaagatatta tcgttgctat taactctaca aagcatttga ataatatttc   2400
taattctctt tcgttccttg gaggcgtgct ctgtgccaag gcttcaatgc ttctccaagt   2460
aagttagtgt gtccagtatt ggtactttgt gttcttttga cagttttcta tggctgaaat   2520
ttgtgttatc tattgtcttc tgtagaatgt tcctcctgcg gttttgatcc ggttccttag   2580
agagcatcga tctgagtggg ctgatttcaa tgttgatgca tattccgctg ctacacttaa   2640
agctggtagc tttgcttatc cgggaatgag accaacaaga ttcactggga gtcagatcat   2700
aatgccacta ggacatacaa ttgaacacga agaagtaagg cttcaaagtc tttacctgcc   2760
gacaaaacat catttttatg tctctctctt acatatatat ttggttttgt tatgtttaga   2820
tgctagaagt tgttagactg gaaggtcatt ctccttgctca agaagatgca tttatgtcac   2880
gggatgtcca tctccttcag gtatatcact tctaagttct aacccaatgg atcttgaaat   2940
ttttaccatt tcaaagttaa aattgacctt aatgattat ggtagatttg taccgggatt    3000
gacgagaatg ccgttggagc ttgttctgaa ctgatatttg ctccgattaa tgagatgttc   3060
ccggatgatg ctccacttgt tccctctgga ttccgagtca tacccgttga tgctaaaacg   3120
gtactcttct ttgctgtacc actgattttt cttttactta gagatggttt gtttcaaggc   3180
```

-continued

```
tcatttttc ttactcatac agggagatgt acaagatctg ttaaccgcta atcaccgtac    3240
actagactta acttctagcc ttgaagtcgg tccatcacct gagaatgctt ctggaaactc    3300
tttttctagc tcaagctcga gatgtattct cactatcgcg tttcaattcc cttttgaaaa    3360
caacttgcaa gaaatgttg ctggtatggc ttgtcagtat gtgaggagcg tgatctcatc    3420
agttcaacgt gttgcaatgg cgatctcacc gtctgggata agcccgagtc tgggctccaa    3480
attgtcccca ggatctcctg aagctgttac tcttgctcag tggatctctc aaagttacag    3540 gtggggtgt aaatgtttac tctcgtctct tcttataat cctcgaactt atcgatgatg    3600
ccttatgctg atatgtttgt ttttccagtc atcacttagg ctcggagttg ctgacgattg    3660
attcacttgg aagcgacgac tcggtactaa aacttctatg ggatcaccaa gatgccatcc    3720
tgtgttgctc attaaaggta tgtgtcctac accaaacaaa aagcagaata cacctgtagt    3780
tttagacgta taatatggtc tggatatgtt gcagccacag ccagtgttca tgtttgcgaa    3840
ccaagctggt ctagacatgc tagagacaac acttgtagcc ttacaagata taacactcga    3900
aaagatattc gatgaatcgg gtcgtaaggc tatctgttcg gacttcgcca agctaatgca    3960
acaggtaaag aaccaaaaca aaaacatctg cagataaatg gttttgattc atttgtctga    4020
gaactatctt tgcgtctaca gggatttgct tgcttgcctt caggaatctg tgtgtcaacg    4080
atgggaagac atgtgagtta tgaacaagct gttgcttgga aagtgtttgc tgcatctgaa    4140
gaaaacaaca caatctgca ttgtcttgcc ttctcctttg taaactggtc ttttgtg     4197
```

<210> SEQ ID NO 8
<211> LENGTH: 369
<212> TYPE: PRT
<213> ORGANISM: Arabidopsis thaliana

<400> SEQUENCE: 8

```
Met Glu Met Ala Val Ala Asn His Arg Glu Arg Ser Ser Asp Ser Met
1               5                   10                  15

Asn Arg His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Ser Ile Leu Ala Asn
    50                  55                  60

Ile Glu Pro Lys Gln Ile Lys Val Trp Phe Gln Asn Arg Arg Cys Arg
65                  70                  75                  80

Asp Lys Gln Arg Lys Glu Ala Ser Arg Leu Gln Ser Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Tyr Met Lys Gln Gln
        115                 120                 125

Leu Thr Thr Val Val Asn Asp Pro Ser Cys Glu Ser Val Val Thr Thr
    130                 135                 140

Pro Gln His Ser Leu Arg Asp Ala Asn Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Asp Trp Val Gln Met Pro Gly Met Lys Pro Gly Pro Asp Ser
            180                 185                 190
```

Val Gly Ile Phe Ala Ile Ser Gln Arg Cys Asn Gly Val Ala Ala Arg
        195                 200                 205

Ala Cys Gly Leu Val Ser Leu Glu Pro Met Lys Ile Ala Glu Ile Leu
    210                 215                 220

Lys Asp Arg Pro Ser Trp Phe Arg Asp Cys Arg Ser Leu Glu Val Phe
225                 230                 235                 240

Thr Met Phe Pro Ala Gly Asn Gly Gly Thr Ile Glu Leu Val Tyr Met
                245                 250                 255

Gln Thr Tyr Ala Pro Thr Thr Leu Ala Pro Ala Arg Asp Phe Trp Thr
            260                 265                 270

Leu Arg Tyr Thr Thr Ser Leu Asp Asn Gly Ser Phe Val Cys Glu
        275                 280                 285

Arg Ser Leu Ser Gly Ser Gly Ala Gly Pro Asn Ala Ala Ser Ala Ser
    290                 295                 300

Gln Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Leu Asn Leu
                325                 330                 335

Glu Ala Trp Ser Val Pro Asp Val Leu Arg Pro Leu Tyr Glu Ser Ser
            340                 345                 350

Lys Val Val Ala Gln Lys Met Thr Ile Ser Arg Cys Gly Ile Ser Gly
        355                 360                 365

Asn

<210> SEQ ID NO 9
<211> LENGTH: 4197
<212> TYPE: DNA
<213> ORGANISM: Arabidopsis thaliana

<400> SEQUENCE: 9

```
atggagatgg cggtggctaa ccaccgtgag agaagcagtg acagtatgaa tagacattta      60
gatagtagcg gtaagtacgt taggtacaca gctgagcaag tcgaggctct tgagcgtgtc     120
tacgctgagt gtcctaagcc tagctctctc cgtcgacaac aattgatccg tgaatgttcc     180
attttggcca atattgagcc taagcagatc aaagtctggt ttcagaaccg caggtattgc     240
ttctctttaa tatggccagg attaattttt aattaaggat tttgaatttg attctattgg     300
atttagtgtg ttatattcaa tggatatgaa ggaccacttt tgttgttatt tcaagatttg     360
atgcttcaat tcaattctcc gacacaattt cctgttttta caaagggtt cctttgaatc      420
tgtctggtag atttggttat tcaatagctt ggtgtaactg ttcttgtgac gatatggtta     480
ctgtctgatc tggtgtctaa tcttaggagt tttgttgatt cgttttgttg tgtggtttca     540
ggtgtcgaga taagcagagg aaagaggcgt cgaggctcca gagcgtaaac cggaagctct     600
ctgcgatgaa taaactgttg atggaggaga atgataggtt gcagaagcag gtttctcagc     660
ttgtctgcga aatggatat atgaaacagc agctaactac tgttgtatgt aacttaacat      720
tccttttgt caaatgtgtt cttaaagaat catttgttac tcctatcagt tcaacatgta      780
gcttgagtta taagttact gacttgttgt tttaacttca ggttaacgat ccaagctgtg      840
aatctgtggt cacaactcct cagcattcgc ttagagatgc gaatagtcct gctgggtaaa     900
gtttcatttt tggttttgaa gtaacctttt tctaatcttt tttctttgcc taattgcttg     960
gttttggtct tagattgctc tcaatcgcag aggagacttt ggcagagttc ctatccaagg    1020
ctacaggaac tgctgttgat tgggttcaga tgcctgggat gaaggttata cgcatctcgt    1080
```

```
atcattactt aagtgttatt ttatctgttg atatctatgg caatatgtga aatattgaaa    1140
tgttgtgtgt tgtagcctgg tccggattcg gttggcatct ttgccatttc gcaaagatgc    1200
aatggagtgg cagctcgagc ctgtggtctt gttagcttag aacctatgaa ggtaagaaag    1260
ggacactctt ttcgttgcta aagatacaag tcataatgtt tcattttcaa ccagtttggg    1320
ttttttgtgt tcttacagat tgcagagatc ctcaaagatc ggccatcttg gttccgtgac    1380
tgtaggagcc ttgaagtttt cactatgttc ccggctggta atggtggcac aatcgagctt    1440
gtttatatgc aggtgaatcc tttagcctct tctggtttag ttttctatct ctaacacttg    1500
aagatgaatg aataaagttg tgacatttgt tcagacgtat gcaccaacga ctctggctcc    1560
tgcccgcgat ttctggaccc tgagatacac aacgagcctc gacaatggga gttttgtggt    1620
atgcagctct cataatgtct agtgtttaca gaaaaactct gggatcttga tgtttttcat    1680
atgtctttaa aaggtttgtg agaggtcgct atctggctct ggagctgggc ctaatgctgc    1740
ttcagcttct cagtttgtga gagcagaaat gctttctagt gggtatttaa taaggccttg    1800
tgatggtggt ggttctatta ttcacattgt cgatcacctt aatcttgagg tacttaaatc    1860
ttcacatgtg gcattttgtg tgtgttttca ggaatttcta aagaattga ttataaacat    1920 ttgttcttgc attgtaggct tggagtgttc cggatgtgct tcgaccccctt tatgagtcat    1980 ccaaagtcgt tgcacaaaaa atgaccattt ccgtgagtgt atacatataa taaccttaag    2040
ctttgattga ttcatataac atatctaacg gttggaggtg cttcatgttt taggcgttgc    2100
ggtatatcag gcaattagcc caagagtcta atggtgaagt agtgtatgga ttaggaaggc    2160
agcctgctgt tcttagaacc tttagccaaa gattaagcag gtacttcgat cttgagctaa    2220
aacctaattg ttccttgctc tgtttgctca ttgtcatttt ttctgttctt ggttttcttg    2280
aaggggcttc aatgatgcgg ttaatgggtt tggtgacgac gggtggtcta cgatgcattg    2340
tgatggagcg gaagatatta tcgttgctat taactctaca aagcatttga ataatatttc    2400
taattctctt tcgttccttg gaggcgtgct ctgtgccaag gcttcaatgc ttctccaagt    2460
aagttagtgt gtccagtatt ggtactttgt gttcttttga cagttttcta tggctgaaat    2520
ttgtgttatc tattgtcttc tgtagaatgt tcctcctgcg gttttgatcc ggttccttag    2580
agagcatcga tctgagtggg ctgatttcaa tgttgatgca tattccgctg ctacacttaa    2640
agctggtagc cttgcttatc cgggaatgag accaacaaga ttcactggga gtcagatcat    2700
aatgccacta ggacatacaa ttgaacacga agaagtaagg cttcaaagtc tttacctgcc    2760
gacaaaacat cattttttatg tctctctctt acatatatat ttggttttgt tatgtttaga    2820
tgctagaagt tgttagactg gaaggtcatt ctcttgctca agaagatgca tttatgtcac    2880
gggatgtcca tctccttcag gtatatcact tctaagttcc aacccaatgg atcttgaaat    2940
ttttaccatt tcaaagttaa aattgacctt aatgatttat ggtagatttg taccgggatt    3000
gacgagaatg ccgttggagc ttgttctgaa ctgatatttg ctccgattaa tgagatgttc    3060
ccggatgatg ctccacttgt tccctctgga ttccgagtca tacccgttga tgctaaaacg    3120
gtactcttct ttgctgtacc actgattttt cttttactta gagatggttt gtttcaaggc    3180 tcatttttc ttactcatac agggagatgt acaagatctg ttaaccgcta atcaccgtac    3240
actagactta acttctagcc ttgaagtcgg tccatcacct gagaatgctt ctggaaactc    3300
tttttctagc tcaagctcga gatgtattct cactatcgcg tttcaattcc cttttgaaaa    3360
caacttgcaa gaaaatgttg ctggtatggc ttgtcagtat gtgaggagcg tgatctcatc    3420
agttcaacgt gttgcaatgg cgatctcacc gtctgggata agcccgagtc tgggctccaa    3480
```

```
attgtcccca ggatctcctg aagctgttac tcttgctcag tggatctctc aaagttacag    3540
gtgggggtgt aaatgtttac tctcgtctct ttcttataat cctcgaactt atcgatgatg    3600
ccttatgctg atatgtttgt ttttccagtc atcacttagg ctcggagttg ctgacgattg    3660
attcacttgg aagcgacgac tcggtactaa aacttctatg ggatcaccaa gatgccatcc    3720
tgtgttgctc attaaaggta tgtgtcctac accaaacaaa agcagaata cacctgtagt     3780 tttagacgta taatatggtc tggatatgtt gcagccacag ccagtgttca tgtttgcgaa    3840
ccaagctggt ctagacatgc tagagacaac acttgtagcc ttacaagata taacactcga    3900
aaagatattc gatgaatcgg tcgtaaggc tatctgttcg gacttcgcca agctaatgca     3960
acaggtaaag aaccaaaaca aaacatctg cagataaatg gttttgattc atttgtctga     4020
gaactatctt tgcgtctaca gggatttgct tgcttgcctt caggaatctg tgtgtcaacg    4080
atgggaagac atgtgagtta tgaacaagct gttgcttgga agtgtttgc tgcatctgaa     4140 gaaaacaaca acaatctgca ttgtcttgcc ttctcctttg taaactggtc ttttgtg       4197
```

<210> SEQ ID NO 10
<211> LENGTH: 842
<212> TYPE: PRT
<213> ORGANISM: Arabidopsis thaliana

<400> SEQUENCE: 10

```
Met Glu Met Ala Val Ala Asn His Arg Glu Arg Ser Ser Asp Ser Met
1               5                   10                  15

Asn Arg His Leu Asp Ser Ser Gly Lys Tyr Val Arg Tyr Thr Ala Glu
                20                  25                  30

Gln Val Glu Ala Leu Glu Arg Val Tyr Ala Glu Cys Pro Lys Pro Ser
            35                  40                  45

Ser Leu Arg Arg Gln Gln Leu Ile Arg Glu Cys Ser Ile Leu Ala Asn
        50                  55                  60

Ile Glu Pro Lys Gln Ile Lys Val Trp Phe Gln Asn Arg Arg Cys Arg
65                  70                  75                  80

Asp Lys Gln Arg Lys Glu Ala Ser Arg Leu Gln Ser Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Tyr Met Lys Gln Gln
        115                 120                 125

Leu Thr Thr Val Val Asn Asp Pro Ser Cys Glu Ser Val Val Thr Thr
    130                 135                 140

Pro Gln His Ser Leu Arg Asp Ala Asn Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Asp Trp Val Gln Met Pro Gly Met Lys Pro Gly Pro Asp Ser
            180                 185                 190

Val Gly Ile Phe Ala Ile Ser Gln Arg Cys Asn Gly Val Ala Ala Arg
        195                 200                 205

Ala Cys Gly Leu Val Ser Leu Glu Pro Met Lys Ile Ala Glu Ile Leu
    210                 215                 220

Lys Asp Arg Pro Ser Trp Phe Arg Asp Cys Arg Ser Leu Glu Val Phe
225                 230                 235                 240

Thr Met Phe Pro Ala Gly Asn Gly Gly Thr Ile Glu Leu Val Tyr Met
```

-continued

```
                245                 250                 255
Gln Thr Tyr Val Pro Thr Thr Leu Ala Pro Ala Arg Asp Phe Trp Thr
                260                 265                 270
Leu Arg Tyr Thr Thr Ser Leu Asp Asn Gly Ser Phe Val Cys Glu
            275                 280                 285
Arg Ser Leu Ser Gly Ser Gly Ala Gly Pro Asn Ala Ala Ser Ala Ser
            290                 295                 300
Gln Phe Val Arg Ala Glu Met Leu Ser Ser Gly Tyr Leu Ile Arg Pro
305                 310                 315                 320
Cys Asp Gly Gly Gly Ser Ile Ile His Ile Val Asp His Leu Asn Leu
                325                 330                 335
Glu Ala Trp Ser Val Pro Asp Val Leu Arg Pro Leu Tyr Glu Ser Ser
            340                 345                 350
Lys Val Val Ala Gln Lys Met Thr Ile Ser Ala Leu Arg Tyr Ile Arg
            355                 360                 365
Gln Leu Ala Gln Glu Ser Asn Gly Glu Val Val Tyr Gly Leu Gly Arg
            370                 375                 380
Gln Pro Ala Val Leu Arg Thr Phe Ser Gln Arg Leu Ser Arg Gly Phe
385                 390                 395                 400
Asn Asp Ala Val Asn Gly Phe Gly Asp Asp Gly Trp Ser Thr Met His
                405                 410                 415
Cys Asp Gly Ala Glu Asp Ile Ile Val Ala Ile Asn Ser Thr Lys His
                420                 425                 430
Leu Asn Asn Ile Ser Asn Ser Leu Ser Phe Leu Gly Gly Val Leu Cys
            435                 440                 445
Ala Lys Ala Ser Met Leu Leu Gln Asn Val Pro Pro Ala Val Leu Ile
            450                 455                 460
Arg Phe Leu Arg Glu His Arg Ser Glu Trp Ala Asp Phe Asn Val Asp
465                 470                 475                 480
Ala Tyr Ser Ala Ala Thr Leu Lys Ala Gly Ser Phe Ala Tyr Pro Gly
                485                 490                 495
Met Arg Pro Thr Arg Phe Thr Gly Ser Gln Ile Ile Met Pro Leu Gly
                500                 505                 510
His Thr Ile Glu His Glu Glu Met Leu Glu Val Val Arg Leu Glu Gly
            515                 520                 525
His Ser Leu Ala Gln Glu Asp Ala Phe Met Ser Arg Asp Val His Leu
            530                 535                 540
Leu Gln Ile Cys Thr Gly Ile Asp Glu Asn Ala Val Gly Ala Cys Ser
545                 550                 555                 560
Glu Leu Ile Phe Ala Pro Ile Asn Glu Met Phe Pro Asp Asp Ala Pro
                565                 570                 575
Leu Val Pro Ser Gly Phe Arg Val Ile Pro Val Asp Ala Lys Thr Gly
                580                 585                 590
Asp Val Gln Asp Leu Leu Thr Ala Asn His Arg Thr Leu Asp Leu Thr
            595                 600                 605
Ser Ser Leu Glu Val Gly Pro Ser Pro Glu Asn Ala Ser Gly Asn Ser
            610                 615                 620
Phe Ser Ser Ser Ser Arg Cys Ile Leu Thr Ile Ala Phe Gln Phe
625                 630                 635                 640
Pro Phe Glu Asn Asn Leu Gln Glu Asn Val Ala Gly Met Ala Cys Gln
                645                 650                 655
Tyr Val Arg Ser Val Ile Ser Ser Val Gln Arg Val Ala Met Ala Ile
                660                 665                 670
```

```
Ser Pro Ser Gly Ile Ser Pro Ser Leu Gly Ser Lys Leu Ser Pro Gly
        675                 680                 685

Ser Pro Glu Ala Val Thr Leu Ala Gln Trp Ile Ser Gln Ser Tyr Ser
    690                 695                 700

His His Leu Gly Ser Glu Leu Leu Thr Ile Asp Ser Leu Gly Ser Asp
705                 710                 715                 720

Asp Ser Val Leu Lys Leu Leu Trp Asp His Gln Asp Ala Ile Leu Cys
                725                 730                 735

Cys Ser Leu Lys Pro Gln Pro Val Phe Met Phe Ala Asn Gln Ala Gly
            740                 745                 750

Leu Asp Met Leu Glu Thr Thr Leu Val Ala Leu Gln Asp Ile Thr Leu
        755                 760                 765

Glu Lys Ile Phe Asp Glu Ser Gly Arg Lys Ala Ile Cys Ser Asp Phe
    770                 775                 780

Ala Lys Leu Met Gln Gln Gly Phe Ala Cys Leu Pro Ser Gly Ile Cys
785                 790                 795                 800

Val Ser Thr Met Gly Arg His Val Ser Tyr Glu Gln Ala Val Ala Trp
                805                 810                 815

Lys Val Phe Ala Ala Ser Glu Glu Asn Asn Asn Leu His Cys Leu
            820                 825                 830

Ala Phe Ser Phe Val Asn Trp Ser Phe Val
        835                 840

<210> SEQ ID NO 11
<211> LENGTH: 4197
<212> TYPE: DNA
<213> ORGANISM: Arabidopsis thaliana

<400> SEQUENCE: 11
atggagatgg cggtggctaa ccaccgtgag agaagcagtg acagtatgaa tagacattta      60
gatagtagcg gtaagtacgt taggtacaca gctgagcaag tcgaggctct tgagcgtgtc     120
tacgctgagt gtcctaagcc tagctctctc cgtcgacaac aattgatccg tgaatgttcc     180
attttggcca atattgagcc taagcagatc aaagtctggt tcagaaccg caggtattgc     240 ttctctttaa tatggccagg attaattttt aattaaggat tttgaatttg attctattgg     300
atttagtgtg ttatattcaa tggatatgaa ggaccacttt tgttgttatt tcaagatttg     360
atgcttcaat tcaattctcc gacacaattt cctgtttta caaaagggtt cctttgaatc     420
tgtctggtag atttggttat tcaatagctt ggtgtaactg ttcttgtgac gatatggtta     480
ctgtctgatc tggtgtctaa tcttaggagt tttgttgatt cgttttgttg tgtggtttca     540
ggtgtcgaga taagcagagg aaagaggcgt cgaggctcca gagcgtaaac cggaagctct     600
ctgcgatgaa taaactgttg atggaggaga atgataggtt gcagaagcag gtttctcagc     660
ttgtctgcga aaatggatat atgaaacagc agctaactac tgttgtatgt aacttaacat     720 ttcctttgt caaatgtgtt cttaaagaat catttgttac tcctatcagt caacatgta      780 gcttgagtta taagttact gacttgttgt tttaacttca ggttaacgat ccaagctgtg     840
aatctgtggt cacaactcct cagcattcgc ttagagatgc gaatagtcct gctgggtaaa     900
gtttcatttt tggttttgaa gtaacctttt tctaatcttt tttctttgcc taattgcttg     960
gttttggtct tagattgctc tcaatcgcag aggagacttt ggcagagttc ctatccaagg    1020
ctacaggaac tgctgttgat tgggttcaga tgcctgggat gaaggttata cgcatctcgt    1080
atcattactt aagtgttatt ttatctgttg atatctatgg caatatgtga aatattgaaa    1140
```

```
tgttgtgtgt tgtagcctgg tccggattcg gttggcatct ttgccatttc gcaaagatgc    1200
aatggagtgg cagctcgagc ctgtggtctt gttagcttag aacctatgaa ggtaagaaag    1260
ggacactctt ttcgttgcta aagatacaag tcataatgtt tcattttcaa ccagtttggg    1320
ttttttgtgt tcttacagat tgcagagatc ctcaaagatc ggccatcttg gttccgtgac    1380
tgtaggagcc ttgaagtttt cactatgttc ccggctggta atggtggcac aatcgagctt    1440
gtttatatgc aggtgaatcc tttagcctct tctggtttag ttttctatct ctaacacttg    1500
aagatgaatg aataaagttg tgacatttgt tcagacgtat gcaccaacga ctctggctcc    1560
tgcccgcgat ttctggaccc tgagatacac aacgagcctc gacaatggga gttttgtggt    1620
atgcagctct cataatgtct agtgtttaca gaaaaactct gggatcttga tgttttcat    1680 atgtctttaa aaggtttgtg agaggtcgct atctggctct ggagctgggc ctaatgctgc    1740
ttcagcttct cagtttgtga gagcagaaat gctttctagt gggtatttaa taaggccttg    1800
tgatggtggt ggttctatta ttcacattgt cgatcacctt aatcttgagg tacttaaatc    1860
ttcacatgtg gcattttgtg tgtgttttca ggaatttcta gaagaattga ttataaacat    1920
ttgttcttgc attgtaggct tggagtgttc cggatgtgct ttgaccccctt tatgagtcat    1980 ccaaagtcgt tgcacaaaaa atgaccattt ccgtgagtgt atacatataa taaccttaag    2040
ctttgattga ttcatataac atatctaacg gttggaggtg cttcatgttt taggcgttgc    2100
ggtatatcag gcaattagcc caagagtcta atggtgaagt agtgtatgga ttaggaaggc    2160
agcctgctgt tcttagaacc tttagccaaa gattaagcag gtacttcgat cttgagctaa    2220
aacctaattg ttctttgctc tgtttgctca ttgtcatttt ttctgttctt ggttttcttg    2280
aaggggcttc aatgatgcgg ttaatgggtt tggtgacgac gggtggtcta cgatgcattg    2340
tgatggagcg gaagatatta tcgttgctat taactctaca aagcatttga ataatatttc    2400
taattctctt tcgttccttg gaggcgtgct ctgtgccaag gcttcaatgc ttctccaagt    2460
aagttagtgt gtccagtatt ggtactttgt gttctttgta cagttttcta tggctgaaat    2520
ttgtgttatc tattgtcttc tgtagaatgt tcctcctgcg gttttgatcc ggttccttag    2580
agagcatcga tctgagtggg ctgatttcaa tgttgatgca tattccgctg ctacacttaa    2640
agctggtagc tttgcttatc cgggaatgag accaacaaga ttcactggga gtcagatcat    2700
aatgccacta ggacatacaa ttgaacacga agaagtaagg cttcaaagtc tttacctgcc    2760
gacaaaacat cattttatg tctctctctt acatatatat ttggttttgt tatgtttaga    2820
tgctagaagt tgttagactg gaaggtcatt ctcttgctca agaagatgca tttatgtcac    2880
gggatgtcca tctccttcag gtatatcact tctaagttct aacccaatgg atcttgaaat    2940
ttttaccatt tcaaagttaa aattgacctt aatgattat ggtagatttg taccgggatt    3000
gacgagaatg ccgttggagc ttgttctgaa ctgatatttg ctccgattaa tgagatgttc    3060
ccggatgatg ctccacttgt tccctctgga ttccgagtca tacccgttga tgctaaaacg    3120
gtactcttct ttgctgtacc actgattttt cttttactta gagatggttt gtttcaaggc    3180
tcattttttc ttactcatac agggagatgt acaagatctg ttaaccgcta atcaccgtac    3240
actagactta acttctagcc ttgaagtcgg tccatcacct gagaatgctt ctggaaactc    3300
tttttctagc tcaagctcga gatgtattct cactatcgcg tttcaattcc cttttgaaaa    3360
caacttgcaa gaaaatgttg ctggtatggc ttgtcagtat gtgaggagcg tgatctcatc    3420
agttcaacgt gttgcaatgg cgatctcacc gtctgggata agcccgagtc tgggctccaa    3480
```

```
attgtcccca ggatctcctg aagctgttac tcttgctcag tggatctctc aaagttacag    3540
gtgggggtgt aaatgtttac tctcgtctct ttcttataat cctcgaactt atcgatgatg    3600
ccttatgctg atatgtttgt ttttccagtc atcacttagg ctcggagttg ctgacgattg    3660
attcacttgg aagcgacgac tcggtactaa aacttctatg ggatcaccaa gatgccatcc    3720
tgtgttgctc attaaaggta tgtgtcctac accaaacaaa aagcagaata cacctgtagt    3780
tttagacgta taatatggtc tggatatgtt gcagccacag ccagtgttca tgtttgcgaa    3840
ccaagctggt ctagacatgc tagagacaac acttgtagcc ttacaagata taacactcga    3900
aaagatattc gatgaatcgg gtcgtaaggc tatctgttcg gacttcgcca agctaatgca    3960
acaggtaaag aaccaaaaca aaaacatctg cagataaatg gttttgattc atttgtctga    4020
gaactatctt tgcgtctaca gggatttgct tgcttgcctt caggaatctg tgtgtcaacg    4080
atgggaagac atgtgagtta tgaacaagct gttgcttgga aagtgtttgc tgcatctgaa    4140
gaaaacaaca acaatctgca ttgtcttgcc ttctcctttg taaactggtc ttttgtg       4197
```

<210> SEQ ID NO 12
<211> LENGTH: 345
<212> TYPE: PRT
<213> ORGANISM: Arabidopsis thaliana

<400> SEQUENCE: 12

```
Met Glu Met Ala Val Ala Asn His Arg Glu Arg Ser Ser Asp Ser Met
1               5                   10                  15

Asn Arg His Leu Asp Ser Ser Gly Lys Tyr Val Arg Tyr Thr Ala Glu
            20                  25                  30

Gln Val Glu Ala Leu Glu Arg Val Tyr Ala Glu Cys Pro Lys Pro Ser
        35                  40                  45

Ser Leu Arg Arg Gln Gln Leu Ile Arg Glu Cys Ser Ile Leu Ala Asn
    50                  55                  60

Ile Glu Pro Lys Gln Ile Lys Val Trp Phe Gln Asn Arg Arg Cys Arg
65                  70                  75                  80

Asp Lys Gln Arg Lys Glu Ala Ser Arg Leu Gln Ser Val Asn Arg Lys
                85                  90                  95

Leu Ser Ala Met Asn Lys Leu Leu Met Glu Glu Asn Asp Arg Leu Gln
            100                 105                 110

Lys Gln Val Ser Gln Leu Val Cys Glu Asn Gly Tyr Met Lys Gln Gln
        115                 120                 125

Leu Thr Thr Val Val Asn Asp Pro Ser Cys Glu Ser Val Val Thr Thr
    130                 135                 140

Pro Gln His Ser Leu Arg Asp Ala Asn Ser Pro Ala Gly Leu Leu Ser
145                 150                 155                 160

Ile Ala Glu Glu Thr Leu Ala Glu Phe Leu Ser Lys Ala Thr Gly Thr
                165                 170                 175

Ala Val Asp Trp Val Gln Met Pro Gly Met Lys Pro Gly Pro Asp Ser
            180                 185                 190

Val Gly Ile Phe Ala Ile Ser Gln Arg Cys Asn Gly Val Ala Ala Arg
        195                 200                 205

Ala Cys Gly Leu Val Ser Leu Glu Pro Met Lys Ile Ala Glu Ile Leu
    210                 215                 220

Lys Asp Arg Pro Ser Trp Phe Arg Asp Cys Arg Ser Leu Glu Val Phe
225                 230                 235                 240

Thr Met Phe Pro Ala Gly Asn Gly Gly Thr Ile Glu Leu Val Tyr Met
                245                 250                 255
```

-continued

```
Gln Thr Tyr Ala Pro Thr Thr Leu Ala Pro Ala Arg Asp Phe Trp Thr
            260                 265                 270

Leu Arg Tyr Thr Thr Ser Leu Asp Asn Gly Ser Phe Val Val Cys Glu
        275                 280                 285

Arg Ser Leu Ser Gly Ser Gly Ala Gly Pro Asn Ala Ala Ser Ala Ser
    290                 295                 300

Gln Phe Val Arg Ala Glu Met Leu Ser Ser Gly Tyr Leu Ile Arg Pro
305                 310                 315                 320

Cys Asp Gly Gly Gly Ser Ile Ile His Ile Val Asp His Leu Asn Leu
                325                 330                 335

Glu Ala Trp Ser Val Pro Asp Val Leu
            340                 345

<210> SEQ ID NO 13
<211> LENGTH: 22
<212> TYPE: DNA
<213> ORGANISM: Arabidopsis thaliana

<400> SEQUENCE: 13
tcaggaggaa ctaaagtgag gg                                            22

<210> SEQ ID NO 14
<211> LENGTH: 22
<212> TYPE: DNA
<213> ORGANISM: Arabidopsis thaliana

<400> SEQUENCE: 14
cacactgaag atggtcttga gg                                            22

<210> SEQ ID NO 15
<211> LENGTH: 20
<212> TYPE: DNA
<213> ORGANISM: Arabidopsis thaliana

<400> SEQUENCE: 15
atcactgttg tttaccatta                                               20

<210> SEQ ID NO 16
<211> LENGTH: 18
<212> TYPE: DNA
<213> ORGANISM: Arabidopsis thaliana

<400> SEQUENCE: 16
gagcatttca cagagacg                                                 18

<210> SEQ ID NO 17
<211> LENGTH: 20
<212> TYPE: DNA
<213> ORGANISM: Arabidopsis thaliana

<400> SEQUENCE: 17
ctccctcctt tccagacaca                                               20

<210> SEQ ID NO 18
<211> LENGTH: 20
<212> TYPE: DNA
<213> ORGANISM: Arabidopsis thaliana

<400> SEQUENCE: 18
ttccaccaat tcactcacca                                               20
```

```
<210> SEQ ID NO 19
<211> LENGTH: 21
<212> TYPE: DNA
<213> ORGANISM: Arabidopsis thaliana

<400> SEQUENCE: 19
cgtaaaacgt cgtcgttcat t                                      21

<210> SEQ ID NO 20
<211> LENGTH: 20
<212> TYPE: DNA
<213> ORGANISM: Arabidopsis thaliana

<400> SEQUENCE: 20
atcgctggat tgttttggac                                        20

<210> SEQ ID NO 21
<211> LENGTH: 26
<212> TYPE: DNA
<213> ORGANISM: Arabidopsis thaliana

<400> SEQUENCE: 21
ttctaagaat gttttacca ccaaaa                                  26

<210> SEQ ID NO 22
<211> LENGTH: 20
<212> TYPE: DNA
<213> ORGANISM: Arabidopsis thaliana

<400> SEQUENCE: 22
ccaactgcga ctgccagata                                        20

<210> SEQ ID NO 23
<211> LENGTH: 21
<212> TYPE: DNA
<213> ORGANISM: Arabidopsis thaliana

<400> SEQUENCE: 23
tccgattggt ctaaagtacg a                                      21

<210> SEQ ID NO 24
<211> LENGTH: 20
<212> TYPE: DNA
<213> ORGANISM: Arabidopsis thaliana

<400> SEQUENCE: 24
tgaccaaggc caaacatact                                        20

<210> SEQ ID NO 25
<211> LENGTH: 20
<212> TYPE: DNA
<213> ORGANISM: Arabidopsis thaliana

<400> SEQUENCE: 25
gaaatctcac cggacaccat                                        20

<210> SEQ ID NO 26
<211> LENGTH: 20
<212> TYPE: DNA
<213> ORGANISM: Arabidopsis thaliana

<400> SEQUENCE: 26
cgaatcccca ttcgtcatag                                        20
```

<210> SEQ ID NO 27
<211> LENGTH: 23
<212> TYPE: DNA
<213> ORGANISM: Arabidopsis thaliana

<400> SEQUENCE: 27
tttccaacaa caaaagaata tgg                                    23

<210> SEQ ID NO 28
<211> LENGTH: 21
<212> TYPE: DNA
<213> ORGANISM: Arabidopsis thaliana

<400> SEQUENCE: 28
tggtatgcgg atatgatctt t                                      21

<210> SEQ ID NO 29
<211> LENGTH: 20
<212> TYPE: DNA
<213> ORGANISM: Arabidopsis thaliana

<400> SEQUENCE: 29
cactcgtagc atccatgtcg                                        20

<210> SEQ ID NO 30
<211> LENGTH: 22
<212> TYPE: DNA
<213> ORGANISM: Arabidopsis thaliana

<400> SEQUENCE: 30
tcagattcaa tcgaaaacga aa                                     22

<210> SEQ ID NO 31
<211> LENGTH: 20
<212> TYPE: DNA
<213> ORGANISM: Arabidopsis thaliana

<400> SEQUENCE: 31
ccgtggaggc tctactgaag                                        20

<210> SEQ ID NO 32
<211> LENGTH: 20
<212> TYPE: DNA
<213> ORGANISM: Arabidopsis thaliana

<400> SEQUENCE: 32
cgttaccttt tgggtggaaa                                        20

<210> SEQ ID NO 33
<211> LENGTH: 24
<212> TYPE: DNA
<213> ORGANISM: Artificial
<220> FEATURE:
<223> OTHER INFORMATION: PCR primer

<400> SEQUENCE: 33
aaaatggaga tggcggtggc taac                                   24

<210> SEQ ID NO 34
<211> LENGTH: 26
<212> TYPE: DNA
<213> ORGANISM: Artificial
<220> FEATURE:

<223> OTHER INFORMATION: PCR primer

<400> SEQUENCE: 34
tgtcaatcga atcacacaaa agacca                                    26

<210> SEQ ID NO 35
<211> LENGTH: 23
<212> TYPE: DNA
<213> ORGANISM: Artificial
<220> FEATURE:
<223> OTHER INFORMATION: Sequence primer

<400> SEQUENCE: 35
cagactttga tctgcttagg atc                                       23

<210> SEQ ID NO 36
<211> LENGTH: 22
<212> TYPE: DNA
<213> ORGANISM: Artificial
<220> FEATURE:
<223> OTHER INFORMATION: Sequence primer

<400> SEQUENCE: 36
tgagcctaag cagatcaaag tc                                        22

<210> SEQ ID NO 37
<211> LENGTH: 20
<212> TYPE: DNA
<213> ORGANISM: Artificial
<220> FEATURE:
<223> OTHER INFORMATION: Sequence primer

<400> SEQUENCE: 37
accggaagct ctctgcgatg                                           20

<210> SEQ ID NO 38
<211> LENGTH: 21
<212> TYPE: DNA
<213> ORGANISM: Artificial
<220> FEATURE:
<223> OTHER INFORMATION: Sequence primer

<400> SEQUENCE: 38
tcgcagagga gactttggca g                                         21

<210> SEQ ID NO 39
<211> LENGTH: 23
<212> TYPE: DNA
<213> ORGANISM: Artificial
<220> FEATURE:
<223> OTHER INFORMATION: Sequence primer

<400> SEQUENCE: 39
ggagccttga agttttcact atg                                       23

<210> SEQ ID NO 40
<211> LENGTH: 24
<212> TYPE: DNA
<213> ORGANISM: Artificial
<220> FEATURE:
<223> OTHER INFORMATION: Sequence primer

<400> SEQUENCE: 40
ggtatttaat aaggccttgt gatg                                      24

```
<210> SEQ ID NO 41
<211> LENGTH: 24
<212> TYPE: DNA
<213> ORGANISM: Artificial
<220> FEATURE:
<223> OTHER INFORMATION: Sequence primer

<400> SEQUENCE: 41
agaaccttta gccaaagatt aagc                                              24

<210> SEQ ID NO 42
<211> LENGTH: 21
<212> TYPE: DNA
<213> ORGANISM: Artificial
<220> FEATURE:
<223> OTHER INFORMATION: Sequence primer

<400> SEQUENCE: 42
agcatcgatc tgagtgggct g                                                 21

<210> SEQ ID NO 43
<211> LENGTH: 21
<212> TYPE: DNA
<213> ORGANISM: Artificial
<220> FEATURE:
<223> OTHER INFORMATION: Sequence primer

<400> SEQUENCE: 43
gtaccgggat tgacgagaat g                                                 21

<210> SEQ ID NO 44
<211> LENGTH: 21
<212> TYPE: DNA
<213> ORGANISM: Artificial
<220> FEATURE:
<223> OTHER INFORMATION: Sequence primer

<400> SEQUENCE: 44
tgaggagcgt gatctcatca g                                                 21

<210> SEQ ID NO 45
<211> LENGTH: 22
<212> TYPE: DNA
<213> ORGANISM: Artificial
<220> FEATURE:
<223> OTHER INFORMATION: Sequence primer

<400> SEQUENCE: 45
gccagtgttc atgtttgcga ac                                                22

<210> SEQ ID NO 46
<211> LENGTH: 24
<212> TYPE: DNA
<213> ORGANISM: Artificial
<220> FEATURE:
<223> OTHER INFORMATION: Sequence primer

<400> SEQUENCE: 46
atggcggtgg ctaaccaccg tgag                                              24

<210> SEQ ID NO 47
<211> LENGTH: 16
<212> TYPE: DNA
<213> ORGANISM: Artificial
<220> FEATURE:
<223> OTHER INFORMATION: Sequence primer
```

```
<400> SEQUENCE: 47
gtaaaacgac ggccag                                                    16

<210> SEQ ID NO 48
<211> LENGTH: 17
<212> TYPE: DNA
<213> ORGANISM: Artificial
<220> FEATURE:
<223> OTHER INFORMATION: Sequence primer

<400> SEQUENCE: 48
caggaaacag ctatgac                                                   17

<210> SEQ ID NO 49
<211> LENGTH: 35
<212> TYPE: DNA
<213> ORGANISM: Artificial
<220> FEATURE:
<223> OTHER INFORMATION: PCR primer

<400> SEQUENCE: 49
ttggatccgg gaacacttaa agtatagtgc aattg                               35

<210> SEQ ID NO 50
<211> LENGTH: 23
<212> TYPE: DNA
<213> ORGANISM: Artificial
<220> FEATURE:
<223> OTHER INFORMATION: PCR primer

<400> SEQUENCE: 50
cagactttga tctgcttagg ctc                                            23

<210> SEQ ID NO 51
<211> LENGTH: 36
<212> TYPE: DNA
<213> ORGANISM: Artificial
<220> FEATURE:
<223> OTHER INFORMATION: Primer

<400> SEQUENCE: 51
ttgcggccgc ttcgattgac agaaaaagac taattt                              36

<210> SEQ ID NO 52
<211> LENGTH: 33
<212> TYPE: DNA
<213> ORGANISM: Artificial
<220> FEATURE:
<223> OTHER INFORMATION: Primer

<400> SEQUENCE: 52
ttgggcccgg taccctcaac caaccacatg gac                                 33

<210> SEQ ID NO 53
<211> LENGTH: 28
<212> TYPE: DNA
<213> ORGANISM: Artificial
<220> FEATURE:
<223> OTHER INFORMATION: Primer

<400> SEQUENCE: 53
aaggtaccaa gttcgacgga gaaggtga                                       28

<210> SEQ ID NO 54
<211> LENGTH: 33
```

```
<212> TYPE: DNA
<213> ORGANISM: Artificial
<220> FEATURE:
<223> OTHER INFORMATION: Primer

<400> SEQUENCE: 54
aaggatcctg tagagagaga ctggtgattt cag                                33

<210> SEQ ID NO 55
<211> LENGTH: 43
<212> TYPE: PRT
<213> ORGANISM: Arabidopsis thaliana

<400> SEQUENCE: 55

Gly Lys Tyr Val Arg Tyr Thr Pro Glu Gln Val Glu Ala Leu Glu Arg
1               5                   10                  15

Val Tyr Thr Glu Cys Pro Lys Pro Ser Ser Leu Arg Arg Gln Gln Leu
            20                  25                  30

Ile Arg Glu Cys Pro Ile Leu Ser Asn Ile Glu
        35                  40

<210> SEQ ID NO 56
<211> LENGTH: 43
<212> TYPE: PRT
<213> ORGANISM: Arabidopsis thaliana

<400> SEQUENCE: 56

Gly Lys Tyr Val Arg Tyr Thr Pro Glu Gln Val Glu Ala Leu Glu Arg
1               5                   10                  15

Leu Tyr Asn Asp Cys Pro Lys Pro Ser Ser Met Arg Arg Gln Gln Leu
            20                  25                  30

Ile Arg Glu Cys Pro Ile Leu Ser Asn Ile Glu
        35                  40

<210> SEQ ID NO 57
<211> LENGTH: 43
<212> TYPE: PRT
<213> ORGANISM: Arabidopsis thaliana

<400> SEQUENCE: 57

Gly Lys Tyr Val Arg Tyr Thr Pro Glu Gln Val Glu Ala Leu Glu Arg
1               5                   10                  15

Val Tyr Ala Glu Cys Pro Lys Pro Ser Ser Leu Arg Arg Gln Gln Leu
            20                  25                  30

Ile Arg Glu Cys Pro Ile Leu Cys Asn Ile Glu
        35                  40

<210> SEQ ID NO 58
<211> LENGTH: 43
<212> TYPE: PRT
<213> ORGANISM: Arabidopsis thaliana

<400> SEQUENCE: 58

Gly Lys Tyr Val Arg Tyr Thr Ser Glu Gln Val Gln Ala Leu Glu Lys
1               5                   10                  15

Leu Tyr Cys Glu Cys Pro Lys Pro Thr Leu Leu Gln Arg Gln Gln Leu
            20                  25                  30

Ile Arg Glu Cys Ser Ile Leu Arg Asn Val Asp
        35                  40

<210> SEQ ID NO 59
```

```
<211> LENGTH: 43
<212> TYPE: PRT
<213> ORGANISM: Arabidopsis thaliana

<400> SEQUENCE: 59

Gly Lys Tyr Val Arg Tyr Thr Pro Glu Gln Val Glu Ala Leu Glu Arg
1               5                   10                  15
Leu Tyr His Asp Cys Pro Lys Pro Ser Ser Ile Arg Arg Gln Gln Leu
            20                  25                  30
Ile Arg Glu Cys Pro Ile Leu Ser Asn Ile Glu
        35                  40

<210> SEQ ID NO 60
<211> LENGTH: 25
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (20)..(20)
<223> OTHER INFORMATION: n is a, c, g, or t

<400> SEQUENCE: 60
ggcggcagca gctgathmgn gartg                                     25

<210> SEQ ID NO 61
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (25)..(25)
<223> OTHER INFORMATION: n is a, c, g, or t

<400> SEQUENCE: 61
ggagagggtg tactgcgagt gyccnaarcc                                30

<210> SEQ ID NO 62
<211> LENGTH: 25
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (23)..(23)
<223> OTHER INFORMATION: n is a, c, g, or t

<400> SEQUENCE: 62
tgcggtacac ccccgarcar gtnsa                                     25

<210> SEQ ID NO 63
<211> LENGTH: 27
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (23)..(23)
<223> OTHER INFORMATION: n is a, c, g, or t

<400> SEQUENCE: 63
tgcggtacac ccccgarcar gtnsarg                                   27
```

```
<210> SEQ ID NO 64
<211> LENGTH: 26
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (21)..(21)
<223> OTHER INFORMATION: n is a, c, g, or t

<400> SEQUENCE: 64
cggtacaccc ccgagcargt nsargc                                    26

<210> SEQ ID NO 65
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 65
tggagagggt gtactgcgan tgyccnaa                                  28

<210> SEQ ID NO 66
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (26)..(26)
<223> OTHER INFORMATION: n is a, c, g, or t

<400> SEQUENCE: 66
tggagagggt gtactgcgan tgyccnaarc                                30

<210> SEQ ID NO 67
<211> LENGTH: 26
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t

<400> SEQUENCE: 67
ccgacctcca tgcggmgnca rcaryt                                    26

<210> SEQ ID NO 68
<211> LENGTH: 22
<212> TYPE: DNA
<213> ORGANISM: Artificial
<220> FEATURE:
<223> OTHER INFORMATION: PCR primer
```

```
<220> FEATURE:
<221> NAME/KEY: misc_feature
<222> LOCATION: (20)..(20)
<223> OTHER INFORMATION: n is a, c, g, or t

<400> SEQUENCE: 68
ccatgcggcg gcarcarytn at                                              22

<210> SEQ ID NO 69
<211> LENGTH: 25
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (23)..(23)
<223> OTHER INFORMATION: n is a, c, g, or t

<400> SEQUENCE: 69 cggggtgta ccgcacrtay ttncc                                            25

<210> SEQ ID NO 70
<211> LENGTH: 27
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (19)..(19)
<223> OTHER INFORMATION: n is a, c, g, or t

<400> SEQUENCE: 70
ctgctcgggg gtgtacckna crtaytt                                         27

<210> SEQ ID NO 71
<211> LENGTH: 26
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 71
acctgctcgg gggtgtanck nacrta                                          26

<210> SEQ ID NO 72
<211> LENGTH: 25
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 72
```

-continued ccacctgctc gggggtrtan cknac 25

<210> SEQ ID NO 73
<211> LENGTH: 27
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (19)..(19)
<223> OTHER INFORMATION: n is a, c, g, or t

<400> SEQUENCE: 73
caccctctcc agggcctsna cytgytc 27

<210> SEQ ID NO 74
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (24)..(24)
<223> OTHER INFORMATION: n is a, c, g, or t

<400> SEQUENCE: 74
cagtacaccc tctccagggc ytsnacytgy t 31

<210> SEQ ID NO 75
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (24)..(24)
<223> OTHER INFORMATION: n is a, c, g, or t

<400> SEQUENCE: 75
cagtacaccc tctccagggc ytsnacytg 29

<210> SEQ ID NO 76
<211> LENGTH: 28
<212> TYPE: DNA
<213> ORGANISM: Artificial
<220> FEATURE:
<223> OTHER INFORMATION: PCR primer

<400> SEQUENCE: 76
ccatgaacaa gatgctgatg gargaraa 28

<210> SEQ ID NO 77
<211> LENGTH: 26
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (21)..(21)
<223> OTHER INFORMATION: n is a, c, g, or t

<400> SEQUENCE: 77
cggctgcaga ccgtgaayvg naaryt 26

```
<210> SEQ ID NO 78
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (22)..(22)
<223> OTHER INFORMATION: n is a, c, g, or t

<400> SEQUENCE: 78
gaccgccatg aacaagatgy tnatggarga                                      30

<210> SEQ ID NO 79
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (20)..(20)
<223> OTHER INFORMATION: n is a, c, g, or t

<400> SEQUENCE: 79
ccgccatgaa caagatgctn atggargara                                      30

<210> SEQ ID NO 80
<211> LENGTH: 30
<212> TYPE: DNA
<213> ORGANISM: Artificial
<220> FEATURE:
<223> OTHER INFORMATION: PCR primer

<400> SEQUENCE: 80
ccatgaacaa gatgctgatg gargaraayg                                      30

<210> SEQ ID NO 81
<211> LENGTH: 23
<212> TYPE: DNA
<213> ORGANISM: Artificial
<220> FEATURE:
<223> OTHER INFORMATION: PCR primer

<400> SEQUENCE: 81
cggcaccgcc ggttytgraa cca                                             23

<210> SEQ ID NO 82
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (24)..(24)
<223> OTHER INFORMATION: n is a, c, g, or t

<400> SEQUENCE: 82
atctggttca tggcggtcar yttncbrtt                                       29

<210> SEQ ID NO 83
<211> LENGTH: 23
<212> TYPE: DNA
<213> ORGANISM: Artificial
<220> FEATURE:
<223> OTHER INFORMATION: PCR primer
<220> FEATURE:
```

```
<221> NAME/KEY: misc_feature
<222> LOCATION: (18)..(18)
<223> OTHER INFORMATION: n is a, c, g, or t

<400> SEQUENCE: 83
cgccggttct ggaaccanac ytt                                              23

<210> SEQ ID NO 84
<211> LENGTH: 24
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (22)..(22)
<223> OTHER INFORMATION: n is a, c, g, or t

<400> SEQUENCE: 84
gcaccgccgg ttctgraacc anac                                             24

<210> SEQ ID NO 85
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (20)..(20)
<223> OTHER INFORMATION: n is a, c, g, or t

<400> SEQUENCE: 85
ccaaggccac catgctgytn carmaygt                                         28

<210> SEQ ID NO 86
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (27)..(27)
<223> OTHER INFORMATION: n is a, c, g, or t

<400> SEQUENCE: 86
aaggccacca tgctgctnca rmaygtnc                                         28

<210> SEQ ID NO 87
<211> LENGTH: 25
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (23)..(23)
<223> OTHER INFORMATION: n is a, c, g, or t

<400> SEQUENCE: 87
ccaccatgct gctgcarmay gtncc                                            25

<210> SEQ ID NO 88
<211> LENGTH: 26
```

```
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (21)..(21)
<223> OTHER INFORMATION: n is a, c, g, or t
<220> FEATURE:
<221> NAME/KEY: misc_feature
<222> LOCATION: (24)..(24)
<223> OTHER INFORMATION: n is a, c, g, or t

<400> SEQUENCE: 88
cccgtctgca tccggttyyt nmgnga                                  26

<210> SEQ ID NO 89
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (20)..(20)
<223> OTHER INFORMATION: n is a, c, g, or t
<220> FEATURE:
<221> NAME/KEY: misc_feature
<222> LOCATION: (23)..(23)
<223> OTHER INFORMATION: n is a, c, g, or t

<400> SEQUENCE: 89
ccgtctgcat ccggttcytn mgngarca                                28

<210> SEQ ID NO 90
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (21)..(21)
<223> OTHER INFORMATION: n is a, c, g, or t

<400> SEQUENCE: 90
gtctgcatcc ggttcctgmg ngarcaymg                               29

<210> SEQ ID NO 91
<211> LENGTH: 25
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (15)..(15)
<223> OTHER INFORMATION: n is a, c, g, or t
<220> FEATURE:
<221> NAME/KEY: misc_feature
<222> LOCATION: (17)..(17)
<223> OTHER INFORMATION: n is a, c, g, or t

<400> SEQUENCE: 91
tgcgggagca ccggnvngar tgggc                                   25

<210> SEQ ID NO 92
<211> LENGTH: 26
<212> TYPE: DNA
<213> ORGANISM: Artificial
<220> FEATURE:
```

<223> OTHER INFORMATION: PCR primer
<220> FEATURE:
<221> NAME/KEY: misc_feature
<222> LOCATION: (16)..(16)
<223> OTHER INFORMATION: n is a, c, g, or t
<220> FEATURE:
<221> NAME/KEY: misc_feature
<222> LOCATION: (25)..(25)
<223> OTHER INFORMATION: n is a, c, g, or t

<400> SEQUENCE: 92
gcgggagcac cggtcngart gggcng                                              26

<210> SEQ ID NO 93
<211> LENGTH: 24
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (22)..(22)
<223> OTHER INFORMATION: n is a, c, g, or t

<400> SEQUENCE: 93
ggagcaccgg tcggartggg cnga                                                24

<210> SEQ ID NO 94
<211> LENGTH: 21
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (13)..(13)
<223> OTHER INFORMATION: n is a, c, g, or t

<400> SEQUENCE: 94
gacgggcggc ggnacrtkyt g                                                   21

<210> SEQ ID NO 95
<211> LENGTH: 23
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (22)..(22)
<223> OTHER INFORMATION: n is a, c, g, or t

<400> SEQUENCE: 95
gacgggcggc ggnacrtkyt gna                                                 23

<210> SEQ ID NO 96
<211> LENGTH: 26
<212> TYPE: DNA
<213> ORGANISM: Artificial
<220> FEATURE:
<223> OTHER INFORMATION: PCR primer
<220> FEATURE:
<221> NAME/KEY: misc_feature
<222> LOCATION: (18)..(18)
<223> OTHER INFORMATION: n is a, c, g, or t
<220> FEATURE:
<221> NAME/KEY: misc_feature
<222> LOCATION: (21)..(21)
<223> OTHER INFORMATION: n is a, c, g, or t

<400> SEQUENCE: 96
cactccgacc ggtgctcnck narraa                                  26

<210> SEQ ID NO 97
<211> LENGTH: 213
<212> TYPE: DNA
<213> ORGANISM: Hordeum vulgare

<400> SEQUENCE: 97
agctctatcc accgtcagca gttgatcaga gagtgtccta ttctctccaa cattgagcct    60
aaacagatca agtatggtt tcagaaccga aggtaatgat gatgctaaca ctccttataa    120
tgcagtttta gtgattcttt gatcaaaatc tttttataaa aattcagatg cagagagaag   180
caaaggaaag aggcttcacg gcttcaagcg gtg                                213

<210> SEQ ID NO 98
<211> LENGTH: 46
<212> TYPE: PRT
<213> ORGANISM: Hordeum vulgare

<400> SEQUENCE: 98

Ser Ser Ile His Arg Gln Gln Leu Ile Arg Glu Cys Pro Ile Leu Ser
1               5                   10                  15

Asn Ile Glu Pro Lys Gln Ile Lys Val Trp Phe Gln Asn Arg Arg Cys
            20                  25                  30

Arg Glu Lys Gln Arg Lys Glu Ala Ser Arg Leu Gln Ala Val
        35                  40                  45

<210> SEQ ID NO 99
<211> LENGTH: 213
<212> TYPE: DNA
<213> ORGANISM: Hordeum vulgare

<400> SEQUENCE: 99
agctctatcc gccgtcagca gttgatcaga gagtgtccta ttctctccaa cattgagcct    60
aaacagatca agtatggtt tcagaaccga aggtaatgat gatgctaaca ctccttataa    120
tgcagtttta gtgattcttt gatcaaaatc tttttataaa aattcagatg cagagagaag   180
caaaggaaag aggcttcacg gcttcgagcg gtg                                213

<210> SEQ ID NO 100
<211> LENGTH: 46
<212> TYPE: PRT
<213> ORGANISM: Hordeum vulgare

<400> SEQUENCE: 100

Ser Ser Ile Arg Arg Gln Gln Leu Ile Arg Glu Cys Pro Ile Leu Ser
1               5                   10                  15

Asn Ile Glu Pro Lys Gln Ile Lys Val Trp Phe Gln Asn Arg Arg Cys
            20                  25                  30

Arg Glu Lys Gln Arg Lys Glu Ala Ser Arg Leu Arg Ala Val
        35                  40                  45

<210> SEQ ID NO 101
<211> LENGTH: 213
<212> TYPE: DNA
<213> ORGANISM: Hordeum vulgare

```
<400> SEQUENCE: 101
agctctatcc gccgtcagca gttgatcaga gagtgtccta ttctctccaa cattgagcct        60
aaacagatca agtatggtt tcagaaccga aggtaatgat gatgctaaca ctccttataa        120
tgcagtttta gtgattcttt gatcaaaatc tttttataaa aattcagatg cagagagaag       180
caaaggaaag aggcttcacg gcttcaagcg gtg                                    213

<210> SEQ ID NO 102
<211> LENGTH: 46
<212> TYPE: PRT
<213> ORGANISM: Hordeum vulgare

<400> SEQUENCE: 102

Ser Ser Ile Arg Arg Gln Gln Leu Ile Arg Glu Cys Pro Ile Leu Ser
1               5                   10                  15

Asn Ile Glu Pro Lys Gln Ile Lys Val Trp Phe Gln Asn Arg Arg Cys
            20                  25                  30

Arg Glu Lys Gln Arg Lys Glu Ala Ser Arg Leu Gln Ala Val
        35                  40                  45

<210> SEQ ID NO 103
<211> LENGTH: 75
<212> TYPE: DNA
<213> ORGANISM: Zea mays

<400> SEQUENCE: 103
agctccgcgc gcaggcagca gctgctacgc gagtgcccca tcctctcaaa catcgaggcc        60
aagcagatta aagtc                                                        75

<210> SEQ ID NO 104
<211> LENGTH: 25
<212> TYPE: PRT
<213> ORGANISM: Zea mays

<400> SEQUENCE: 104

Ser Ser Ala Arg Arg Gln Gln Leu Leu Arg Glu Cys Pro Ile Leu Ser
1               5                   10                  15

Asn Ile Glu Ala Lys Gln Ile Lys Val
            20                  25

<210> SEQ ID NO 105
<211> LENGTH: 75
<212> TYPE: DNA
<213> ORGANISM: Zea mays

<400> SEQUENCE: 105
agctccgcgc gcaggcagca gctgctacgc gagtgcccca tcctctcaaa catcgaggcc        60
aagcagatta aagtc                                                        75

<210> SEQ ID NO 106
<211> LENGTH: 25
<212> TYPE: PRT
<213> ORGANISM: Zea mays

<400> SEQUENCE: 106

Ser Ser Ala Arg Arg Gln Gln Leu Leu Arg Glu Cys Pro Ile Leu Ser
1               5                   10                  15

Asn Ile Glu Ala Lys Gln Ile Lys Val
            20                  25
```

```
<210> SEQ ID NO 107
<211> LENGTH: 75
<212> TYPE: DNA
<213> ORGANISM: Zea mays

<400> SEQUENCE: 107
acctcctccc gcaggcagca attgctgcgt gagtgcccca cacttgctaa cattgagccc      60
aagcagatca aggtc                                                       75

<210> SEQ ID NO 108
<211> LENGTH: 25
<212> TYPE: PRT
<213> ORGANISM: Zea mays

<400> SEQUENCE: 108

Thr Ser Ser Arg Arg Gln Gln Leu Leu Arg Glu Cys Pro Thr Leu Ala
1               5                   10                  15

Asn Ile Glu Pro Lys Gln Ile Lys Val
            20                  25

<210> SEQ ID NO 109
<211> LENGTH: 75
<212> TYPE: DNA
<213> ORGANISM: Zea mays

<400> SEQUENCE: 109
agctccgcgc gcaggcagca gctgctacgc gagtgcccca tcctctcaaa catcgaggcc      60
aagcagatta aagtc                                                       75

<210> SEQ ID NO 110
<211> LENGTH: 25
<212> TYPE: PRT
<213> ORGANISM: Zea mays

<400> SEQUENCE: 110

Ser Ser Ala Arg Arg Gln Gln Leu Leu Arg Glu Cys Pro Ile Leu Ser
1               5                   10                  15

Asn Ile Glu Ala Lys Gln Ile Lys Val
            20                  25

<210> SEQ ID NO 111
<211> LENGTH: 75
<212> TYPE: DNA
<213> ORGANISM: Zea mays

<400> SEQUENCE: 111
agctccgcgc gcaggcagca gctgctacgc gagtgcccca tcctctcaaa catcgaggcc      60
aagcagatta aagtc                                                       75

<210> SEQ ID NO 112
<211> LENGTH: 25
<212> TYPE: PRT
<213> ORGANISM: Zea mays

<400> SEQUENCE: 112

Ser Ser Ala Arg Arg Gln Gln Leu Leu Arg Glu Cys Pro Ile Leu Ser
1               5                   10                  15

Asn Ile Glu Ala Lys Gln Ile Lys Val
            20                  25
```

<210> SEQ ID NO 113
<211> LENGTH: 75
<212> TYPE: DNA
<213> ORGANISM: Zea mays

<400> SEQUENCE: 113
agctccgcgc gcaggcagca gctgctacgc gagtgcccca tcctctcaaa catcgaggcc    60
aagcagatta aagtc    75

<210> SEQ ID NO 114
<211> LENGTH: 25
<212> TYPE: PRT
<213> ORGANISM: Zea mays

<400> SEQUENCE: 114

Ser Ser Ala Arg Arg Gln Gln Leu Leu Arg Glu Cys Pro Ile Leu Ser
1               5                   10                  15

Asn Ile Glu Ala Lys Gln Ile Lys Val
            20                  25

<210> SEQ ID NO 115
<211> LENGTH: 138
<212> TYPE: DNA
<213> ORGANISM: Oryza sativa

<400> SEQUENCE: 115
agctcgctgc ggcggcagca gctggtgcgg gagtgcccgg cgctggcgaa cgtggacccg    60
aagcagatca aggtgtggtt ccagaaccgc cggtgccggg agaagcagcg caaggagtcg   120
tcgcggctgc aggcgctc    138

<210> SEQ ID NO 116
<211> LENGTH: 46
<212> TYPE: PRT
<213> ORGANISM: Oryza sativa

<400> SEQUENCE: 116

Ser Ser Leu Arg Arg Gln Gln Leu Val Arg Glu Cys Pro Ala Leu Ala
1               5                   10                  15

Asn Val Asp Pro Lys Gln Ile Lys Val Trp Phe Gln Asn Arg Arg Cys
            20                  25                  30

Arg Glu Lys Gln Arg Lys Glu Ser Ser Arg Leu Gln Ala Leu
        35                  40                  45

<210> SEQ ID NO 117
<211> LENGTH: 138
<212> TYPE: DNA
<213> ORGANISM: Oryza sativa

<400> SEQUENCE: 117
agctcgctgc ggcggcagca gctggtgcgg gagtgcccgg cgctggcgaa cgtggacccg    60
aagcagatca aggtgtggtt ccagaaccgc cggtgccggg agaagcagcg caaggagtcg   120
tcgcggctgc aggcgctc    138

<210> SEQ ID NO 118
<211> LENGTH: 46
<212> TYPE: PRT
<213> ORGANISM: Oryza sativa

<400> SEQUENCE: 118

Ser Ser Leu Arg Arg Gln Gln Leu Val Arg Glu Cys Pro Ala Leu Ala

```
1               5                   10                  15
Asn Val Asp Pro Lys Gln Ile Lys Val Trp Phe Gln Asn Arg Arg Cys
            20                  25                  30

Arg Glu Lys Gln Arg Lys Glu Ser Ser Arg Leu Gln Ala Leu
        35                  40                  45

<210> SEQ ID NO 119
<211> LENGTH: 138
<212> TYPE: DNA
<213> ORGANISM: Oryza sativa

<400> SEQUENCE: 119
agctcgctgc ggcggcagca gctggtgcgg gagtgcccgg cgctggcgaa cgtggacccg      60
aagcagatca aggtgtggtt ccagaaccgc cggtgccggg agaagcagcg caaggagtcg     120
tcgcggctgc aggcgctc                                                    138

<210> SEQ ID NO 120
<211> LENGTH: 46
<212> TYPE: PRT
<213> ORGANISM: Oryza sativa

<400> SEQUENCE: 120

Ser Ser Leu Arg Arg Gln Gln Leu Val Arg Glu Cys Pro Ala Leu Ala
1               5                   10                  15

Asn Val Asp Pro Lys Gln Ile Lys Val Trp Phe Gln Asn Arg Arg Cys
            20                  25                  30

Arg Glu Lys Gln Arg Lys Glu Ser Ser Arg Leu Gln Ala Leu
        35                  40                  45

<210> SEQ ID NO 121
<211> LENGTH: 135
<212> TYPE: DNA
<213> ORGANISM: Oryza sativa

<400> SEQUENCE: 121
tcctcccgca ggcagcaatt gctgcgtgag tgccccatac ttgctaacat tgagcccaag      60
cagatcaagg tctggttcca gaacagaaag tgccgggata agcagcggaa ggagtcttca     120
cggcttcagg ctgtc                                                       135

<210> SEQ ID NO 122
<211> LENGTH: 45
<212> TYPE: PRT
<213> ORGANISM: Oryza sativa

<400> SEQUENCE: 122

Ser Ser Arg Arg Gln Gln Leu Leu Arg Glu Cys Pro Ile Leu Ala Asn
1               5                   10                  15

Ile Glu Pro Lys Gln Ile Lys Val Trp Phe Gln Asn Arg Lys Cys Arg
            20                  25                  30

Asp Lys Gln Arg Lys Glu Ser Ser Arg Leu Gln Ala Val
        35                  40                  45

<210> SEQ ID NO 123
<211> LENGTH: 135
<212> TYPE: DNA
<213> ORGANISM: Oryza sativa

<400> SEQUENCE: 123
tcctcccgca ggcagcaatt gctgcgtaag tgccccatac ttgctaacat tgagcccaag      60
```

```
cagatcaagg tctggttcca gaacagaagg tgccgggata agcagcggaa ggagtcttca    120
cggcttcagg ctgtc                                                     135

<210> SEQ ID NO 124
<211> LENGTH: 45
<212> TYPE: PRT
<213> ORGANISM: Oryza sativa

<400> SEQUENCE: 124

Ser Ser Arg Arg Gln Gln Leu Leu Arg Lys Cys Pro Ile Leu Ala Asn
1               5                   10                  15

Ile Glu Pro Lys Gln Ile Lys Val Trp Phe Gln Asn Arg Arg Cys Arg
            20                  25                  30

Asp Lys Gln Arg Lys Glu Ser Ser Arg Leu Gln Ala Val
        35                  40                  45

<210> SEQ ID NO 125
<211> LENGTH: 135
<212> TYPE: DNA
<213> ORGANISM: Oryza sativa

<400> SEQUENCE: 125
tcctcccgca ggcagcaatt gctgcgtaag tgccccatac ttgctaacat tgagcccaag    60
cagatcaagg tctggttcca gaacagaagg tgccgggata agcagcggaa ggagtcttca    120
cggcttcagg ctgtc                                                     135

<210> SEQ ID NO 126
<211> LENGTH: 45
<212> TYPE: PRT
<213> ORGANISM: Oryza sativa

<400> SEQUENCE: 126

Ser Ser Arg Arg Gln Gln Leu Leu Arg Lys Cys Pro Ile Leu Ala Asn
1               5                   10                  15

Ile Glu Pro Lys Gln Ile Lys Val Trp Phe Gln Asn Arg Arg Cys Arg
            20                  25                  30

Asp Lys Gln Arg Lys Glu Ser Ser Arg Leu Gln Ala Val
        35                  40                  45

<210> SEQ ID NO 127
<211> LENGTH: 138
<212> TYPE: DNA
<213> ORGANISM: Hordeum vulgare

<400> SEQUENCE: 127
agctctatcc accgtcagca gttgatcaga gagtgtccta ttctctccaa cattgagcct    60
aaacagatca agtatggtt tcagaaccga agatgcagag agaagcaaag gaaagaggct    120
tcacggcttc aagcggtg                                                  138

<210> SEQ ID NO 128
<211> LENGTH: 138
<212> TYPE: DNA
<213> ORGANISM: Hordeum vulgare

<400> SEQUENCE: 128
agctctatcc gccgtcagca gttgatcaga gagtgtccta ttctctccaa cattgagcct    60
aaacagatca agtatggtt tcagaaccga agatgcagag agaagcaaag gaaagaggct    120
```

-continued

```
tcacggcttc gagcggtg                                              138

<210> SEQ ID NO 129
<211> LENGTH: 137
<212> TYPE: DNA
<213> ORGANISM: Hordeum vulgare

<400> SEQUENCE: 129
agctctatcc gccgtcagca gttgatcaga gagtgtccta ttctctccaa cattgagcct    60
aaacagatca agtatggtt tcagaaccga agatgcagag agaagcaaag gaaagggctt   120
cacggcttca agcggtg                                                  137

<210> SEQ ID NO 130
<211> LENGTH: 24
<212> TYPE: PRT
<213> ORGANISM: Arabidopsis thaliana

<400> SEQUENCE: 130

Gly Tyr Met Lys Gln Gln Leu Thr Thr Val Val Asn Asp Pro Ser Cys
1               5                   10                  15

Glu Ser Val Val Thr Thr Pro Gln
            20

<210> SEQ ID NO 131
<211> LENGTH: 24
<212> TYPE: PRT
<213> ORGANISM: Lycopersicon esculentum

<400> SEQUENCE: 131

Gly Tyr Met Arg Gln Gln Leu Gln Ser Val Thr Thr Asp Val Ser Cys
1               5                   10                  15

Glu Ser Gly Val Thr Thr Pro Gln
            20

<210> SEQ ID NO 132
<211> LENGTH: 26
<212> TYPE: PRT
<213> ORGANISM: Oryza sativa

<400> SEQUENCE: 132

Ala His Met Arg Gln Gln Leu Gln Asn Thr Pro Leu Ala Asn Asp Thr
1               5                   10                  15

Ser Cys Glu Ser Asn Val Thr Thr Pro Gln
            20                  25

<210> SEQ ID NO 133
<211> LENGTH: 26
<212> TYPE: PRT
<213> ORGANISM: Oryza sativa
<220> FEATURE:
<221> NAME/KEY: misc_feature
<222> LOCATION: (11)..(11)
<223> OTHER INFORMATION: Xaa can be any naturally occurring amino acid
<220> FEATURE:
<221> NAME/KEY: misc_feature
<222> LOCATION: (18)..(18)
<223> OTHER INFORMATION: Xaa can be any naturally occurring amino acid

<400> SEQUENCE: 133

Ala Tyr Met Lys Gln Gln Leu Gln Asn Pro Xaa Leu Gly Asn Asp Thr
1               5                   10                  15

Ser Xaa Glu Ser Asn Val Thr Thr Pro Gln
            20                  25
```

<210> SEQ ID NO 134
<211> LENGTH: 13
<212> TYPE: PRT
<213> ORGANISM: Arabidopsis thaliana

<400> SEQUENCE: 134

Cys Arg Ser Leu Glu Val Phe Thr Met Phe Pro Ala Gly
1               5                   10

<210> SEQ ID NO 135
<211> LENGTH: 13
<212> TYPE: PRT
<213> ORGANISM: Lycopersicon esculentum

<400> SEQUENCE: 135

Cys Arg Asn Val Glu Val Ile Thr Met Phe Pro Ala Gly
1               5                   10

<210> SEQ ID NO 136
<211> LENGTH: 13
<212> TYPE: PRT
<213> ORGANISM: Oryza sativa

<400> SEQUENCE: 136

Cys Arg Asn Leu Glu Val Phe Thr Met Ile Pro Ala Gly
1               5                   10

<210> SEQ ID NO 137
<211> LENGTH: 13
<212> TYPE: PRT
<213> ORGANISM: Oryza sativa

<400> SEQUENCE: 137

Cys Arg Ser Leu Glu Val Phe Thr Met Phe Pro Ala Gly
1               5                   10

<210> SEQ ID NO 138
<211> LENGTH: 28
<212> TYPE: DNA
<213> ORGANISM: Artificial
<220> FEATURE:
<223> OTHER INFORMATION: PCR primer

<400> SEQUENCE: 138
ttatcgatag ctttgcttat ccgggaat                                    28

<210> SEQ ID NO 139
<211> LENGTH: 30
<212> TYPE: DNA
<213> ORGANISM: Artificial
<220> FEATURE:
<223> OTHER INFORMATION: PCR primer

<400> SEQUENCE: 139
ttgcggccgc ctgacaagcc ataccagcaa                                  30

<210> SEQ ID NO 140
<211> LENGTH: 30
<212> TYPE: DNA
<213> ORGANISM: Artificial
<220> FEATURE:
<223> OTHER INFORMATION: PCR primer

<400> SEQUENCE: 140

```
ttgcggccgc agttcaacgt gttgcaatgg                                    30
```

<210> SEQ ID NO 141
<211> LENGTH: 34
<212> TYPE: DNA
<213> ORGANISM: Artificial
<220> FEATURE:
<223> OTHER INFORMATION: PCR primer

<400> SEQUENCE: 141

```
ttgcatgcgc tagcgtcgtc gcttccaagt gaat                               34
```

<210> SEQ ID NO 142
<211> LENGTH: 34
<212> TYPE: DNA
<213> ORGANISM: Artificial
<220> FEATURE:
<223> OTHER INFORMATION: PCR primer

<400> SEQUENCE: 142

```
ttgtcgaccc gcggagcttt gcttatccgg gaat                               34
```

<210> SEQ ID NO 143
<211> LENGTH: 33
<212> TYPE: DNA
<213> ORGANISM: Artificial
<220> FEATURE:
<223> OTHER INFORMATION: PCR primer

<400> SEQUENCE: 143

```
ttgatgcgct agcctgacaa gccataccag caa                                33
```

<210> SEQ ID NO 144
<211> LENGTH: 1193
<212> TYPE: DNA
<213> ORGANISM: Artificial
<220> FEATURE:
<223> OTHER INFORMATION: Complete IR-construct At

<400> SEQUENCE: 144

```
atcgatagct tgcttatcc gggaatgaga ccaacaagat tcactgggag tcagatcata    60
atgccactag gacatacaat tgaacacgaa gaaatgctag aagttgttag actggaaggt   120
cattctcttg ctcaagaaga tgcatttatg tcacgggatg tccatctcct tcagatttgt   180
accgggattg acgagaatgc cgttggagct tgttctgaac tgatatttgc tccgattaat   240
gagatgttcc cggatgatgc tccacttgtt ccctctggaa tccgagtcat acccgttgat   300
gctaaaacgg gagatgtaca agatctgtta accgctaatc accgtacact agacttaact   360
tctagccttg aagtcggtcc atcacctgag aatgcttctg gaaactcttt ttctagctca   420
agctcgagat gtattctcac tatcgcgttt caattccctt ttgaaaacaa cttgcaagaa   480
aatgttgctg gtatggcttg cgcggccgca gttcaacgtg ttgcaatggc gatctcaccg   540
tctgggataa gcccgagtct gggctccaaa ttgtccccag gatctcctga agctgttact   600
cttgctcagt ggatctctca aagttacagt catcacttag gctcggagtt gctgacgatt   660
gattcacttg gaagcgacga cgctagcgca tgccaagcca taccagcaac attttcttgc   720
aagttgtttt caaagggaa ttgaaacgcg atagtgagaa tacatctcga gcttgagcta   780
gaaaaagagt ttccagaagc attctcaggt gatggaccga cttcaaggct agaagttaag   840
tctagtgtac ggtgattagc ggttaacaga tcttgtacat ctcccgtttt agcatcaacg   900
ggtatgactc ggaatccaga gggaacaagt ggagcatcat ccgggaacat ctcattaatc   960
```

```
ggagcaaata tcagttcaga acaagctcca acggcattct cgtcaatccc ggtacaaatc    1020
tgaaggagat ggacatcccg tgacataaat gcatcttctt gagcaagaga atgaccttcc    1080
agtctaacaa cttctagcat tcttcgtgt tcaattgtat gtcctagtgg cattatgatc     1140
tgactcccag tgaatcttgt tggtctcatt cccggataag caaagctccg cgg           1193

<210> SEQ ID NO 145
<211> LENGTH: 474
<212> TYPE: DNA
<213> ORGANISM: Artificial
<220> FEATURE:
<223> OTHER INFORMATION: IR- construct At

<400> SEQUENCE: 145
atcgatgtta acgatccaag ctgtgaatct gtggtcacaa ctcctcagca ttcgcttaga      60
gatgcgaata gtcctgctgg attgctctca atcgcagagg agactttggc agagttccta    120
tccaaggcta caggaactgc tgttgattgg gttcagatgc ctgggatgaa gcctggtccg    180
gattcggttg gcatctttgc catttcgcaa agatgcaatg gagtggcagc tcgagcctgt    240
ggtcttgtta gcttagaacc tatgaagatt gcagagatcc tcaaagatcg gccatcttgg    300
ttccgtgact gtaggagcct tgaagttttc actatgttcc cggctggtaa tggtggcaca    360
atcgagcttg tttatatgca gacgtatgca ccaacgactc tggctcctgc ccgcgatttc    420
tggaccctga gatacacaac gagcctcgac aatgggagtt ttgtgcgcgg ccgc           474

<210> SEQ ID NO 146
<211> LENGTH: 418
<212> TYPE: DNA
<213> ORGANISM: Artificial
<220> FEATURE:
<223> OTHER INFORMATION: IR linker AT

<400> SEQUENCE: 146
ggagatgtac aagatctgtt aaccgctaat caccgtacac tagacttaac ttctagcctt      60
gaagtcggtc catcacctga gaatgcttct ggaaactctt tttctagctc aagctcgaga    120
tgtattctca ctatcgcgtt tcaattccct tttgaaaaca acttgcaaga aaatgttgct    180
ggtatggctt gtcagtatgt gaggagcgtg atctcatcag ttcaacgtgt tgcaatggcg    240
atctcaccgt ctgggataag cccgagtctg gctccaaat tgtccccagg atctcctgaa     300
gctgttactc ttgctcagtg gatctctcaa agttacaggc tagcgcatgc ctgcccgcga    360
tttctggacc ctgagataca caacgagcct cgacaatggg agttttgtgc gcggccgc      418

<210> SEQ ID NO 147
<211> LENGTH: 465
<212> TYPE: DNA
<213> ORGANISM: Artificial
<220> FEATURE:
<223> OTHER INFORMATION: IR construct At

<400> SEQUENCE: 147
cacaaaactc ccattgtcga ggctcgttgt gtatctcagg gtccagaaat cgcgggcagg      60
agccagagtc gttggtgcat acgtctgcat ataaacaagc tcgattgtgc caccattacc    120
agccgggaac atagtgaaaa cttcaaggct cctacagtca cggaaccaag atggccgatc    180
tttgaggatc tctgcaatct tcataggttc taagctaaca agaccacagg ctcgagctgc    240
cactccattg catctttgcg aaatggcaaa gatgccaacc gaatccggac caggcttcat    300
```

```
cccaggcatc tgaacccaat caacagcagt tcctgtagcc ttggatagga actctgccaa    360
agtctcctct gcgattgaga gcaatccagc aggactattc gcatctctaa gcgaatgctg    420
aggagttgtg accacagatt cacagcttgg atcgttaacc cgcgg                    465
```

<210> SEQ ID NO 148
<211> LENGTH: 489
<212> TYPE: DNA
<213> ORGANISM: Artificial
<220> FEATURE:
<223> OTHER INFORMATION: IR construct tomato

<400> SEQUENCE: 148

```
atcgatattg ctgatatcct caaagatcga ccttcttggt tccgcgactg ccggaatgtt     60
gaagttatca caatgtttcc tgctggaaat ggtggtacag ttgagctttt gtatacccag    120
atatatgctc ccacaactct ggctcccgcg cgtgattttt ggacgctgag atacacaaca    180
accctagaca atggtagtct cgtggtttgt gaaagatccc tatctggtaa tgggcctggc    240
ccaaatccta ctgctgcttc ccagtttgta agagctcaaa tgcttccatc tggatatctg    300
atccgaccgt gtgatggtgg aggatcaatc atacatattg ttgatcacct gaatcttgag    360
gcatggagtg cccctgagat tttgcgtcca ctctatgaat cgtcgaaagt tgtggcacag    420
aaaatgacta ttgcagcact gcgatatgca aggcaactag ctcaagagac tagcggcgag    480
cgcggccgc                                                            489
```

<210> SEQ ID NO 149
<211> LENGTH: 312
<212> TYPE: DNA
<213> ORGANISM: Artificial
<220> FEATURE:
<223> OTHER INFORMATION: IR linker

<400> SEQUENCE: 149

```
gtagtatatg gtctaggaag gcaacctgct gttcctcgaa cattcagcca gagattatgc     60
agagggttca atgatgccat caatggattc ggtgacgatg gctggtcaat gttaagttca    120
gatggtgctg aagatgtcat agttgctgtc aattcaagga agaacctcgc aaccacctcc    180
attcctcttt ccccgcttgg tggcgtcctt tgtaccaaag catcaatgct actccagaat    240
gtcccccctg ccgtactggt tcggtttctg agggagcacc gttcagaatg ggccgattat    300
gctagcgcat gc                                                        312
```

<210> SEQ ID NO 150
<211> LENGTH: 480
<212> TYPE: DNA
<213> ORGANISM: Artificial
<220> FEATURE:
<223> OTHER INFORMATION: IR construct tomato

<400> SEQUENCE: 150

```
ctcgccgcta gtctcttgag ctagttgcct tgcatatcgc agtgctgcaa tagtcatttt     60
ctgtgccaca actttcgacg attcatagag tggacgcaaa atctcagggg cactccatgc    120
ctcaagattc aggtgatcaa caatatgtat gattgatcct ccaccatcac acggtcggat    180
cagatatcca gatggaagca tttgagctct tacaaactgg aagcagcag taggatttgg    240 gccaggccca ttaccagata gggatctttc acaaaccacg agactaccat tgtctagggt    300
tgttgtgtat ctcagcgtcc aaaaatcacg cgcgggagcc agagttgtgg gagcatatat    360
ctgggtatac aaaagctcaa ctgtaccacc atttccagca ggaaacattg tgataacttc    420
```

```
aacattccgg cagtcgcgga accaagaagg tcgatctttg aggatatcag caatccgcgg        480

<210> SEQ ID NO 151
<211> LENGTH: 470
<212> TYPE: DNA
<213> ORGANISM: Artificial
<220> FEATURE:
<223> OTHER INFORMATION: IR construct rice

<400> SEQUENCE: 151
atcgattggt tcatgagaat gcccacatgc gacagcagct gcagaatact ccgctggcaa        60
atgatacaag ctgtgaatca aatgtgacta cccctcaaaa ccctttaagg gatgcaagta       120 accccctctgg gctcctttca attgcagagg agaccttgac agagttcctc tcaaaggcta      180
ctggtacagc tattgattgg gtccagatgc ctgggatgaa gcctggtccg gattcggttg       240
gtattgtggc catttcacat ggttgcccgt ggtgttgctg ccgtgcctgt ggtttggtga       300
acctagaacc aacaaaagtg gtagagatat tgaaagatcg tccatcttgg ttccgtgatt       360
gtcgaaacct ggaagtcttt acaatgattc cagcaggaaa tggaggaacg gttgaacttg       420
tctacacaca gttgtatgct ccaacaactt tagttcctgc acgcggccgc                  470

<210> SEQ ID NO 152
<211> LENGTH: 212
<212> TYPE: DNA
<213> ORGANISM: Artificial
<220> FEATURE:
<223> OTHER INFORMATION: IR construct rice

<400> SEQUENCE: 152
atgctaggga gtagcagtga tggaggtggc tatgataagg tttccgggat ggactccggt        60
aaatatgtgc gctacacgcc tgagcaggtg gaggcgcttg agcgggtgta cgccgattgc       120
cccaagccaa cctcctcccg caggcagcaa ttgctgcgtg agtgccccat acttgctaac       180
attgagccca agcagatcaa gctagcgcat gc                                     212

<210> SEQ ID NO 153
<211> LENGTH: 461
<212> TYPE: DNA
<213> ORGANISM: Artificial
<220> FEATURE:
<223> OTHER INFORMATION: IR construct rice

<400> SEQUENCE: 153
tgcaggaact aaagttgttg gagcatacaa ctgtgtgtag acaagttcaa ccgttcctcc        60
atttcctgct ggaatcattg taaagacttc caggtttcga caatcacgga accaagatgg       120
acgatctttc aatatctcta ccacttttgt tggttctagg ttcaccaaac cacaggcacg       180
gcagcaacac cacgggcaac catgtgaaat ggccacaata ccaaccgaat ccggaccagg       240
cttcatccca ggcatctgga cccaatcaat agctgtacca gtagcctttg agaggaactc       300
tgtcaaggtc tcctctgcaa ttgaaaggag cccagagggg ttacttgcat cccttaaagg       360
gttttgaggg gtagtcacat ttgattcaca gcttgtatca tttgccagcg gagtattctg       420
cagctgctgt cgcatgtggg cattctcatg aaccaccgcg g                           461

<210> SEQ ID NO 154
<211> LENGTH: 465
<212> TYPE: DNA
<213> ORGANISM: Artificial
<220> FEATURE:
```

<223> OTHER INFORMATION: IR construct rice

<400> SEQUENCE: 154

| atcgatgaat caaatgtgac cactcctcag aaccctctga gagatgcaag taacccgtct | 60 |
| ggactcctta caattgcgga ggagaccctg acagagttcc tctccaaggc tacagggact | 120 |
| gctgttgatt gggtgccaat gcctgggatg aagcctggtc cggattcgtt tggtattgtg | 180 |
| gccgtttcac atggttgccg tggtgttgct gcccgtgcct gtggtttggt gaatctagaa | 240 |
| ccaacaaaga tcgtggagat cttaaaagac cgcccatctt ggttccgtga ttgtcgaagt | 300 |
| cttgaagtct tcacaatgtt ccagctgga atggtggca cgatcgaact tgtttacatg | 360 |
| cagatgtatg ctcctactac tttggttcct gcacgagatt tttggacact tagatacaca | 420 |
| actacaatgg atgatggcag ccttgtggtc tgtgagcgcg gccgc | 465 |

<210> SEQ ID NO 155
<211> LENGTH: 196
<212> TYPE: DNA
<213> ORGANISM: Artificial
<220> FEATURE:
<223> OTHER INFORMATION: IR construct rice

<400> SEQUENCE: 155

| ccgcacagca atttgtaaga gctgagatgc ttcctagcgg ctatctagtg cgcccatgcg | 60 |
| agggtggtgg ctccgtcgtg catattgtgg accatctgga tcttgaggct tggagtgttc | 120 |
| cagaagtgct tcggccactc tacgagtcat ctagggtagt tgctcagaaa atgactgctg | 180 |
| cagcgctagc gcatgc | 196 |

<210> SEQ ID NO 156
<211> LENGTH: 456
<212> TYPE: DNA
<213> ORGANISM: Artificial
<220> FEATURE:
<223> OTHER INFORMATION: IR construct rice

<400> SEQUENCE: 156

| ctcacagacc acaaggctgc catcatccat tgtagttgtg tatctaagtg tccaaaaatc | 60 |
| tcgtgcagga accaaagtag taggagcata catctgcatg taaacaagtt cgatcgtgcc | 120 |
| accatttcca gctggaaaca ttgtgaagac ttcaagactt cgacaatcac ggaaccaaga | 180 |
| tgggcggtct tttaagatct ccacgatctt tgttggttct agattcacca aaccacaggc | 240 |
| acgggcagca acaccacggc aaccatgtga aacggccaca ataccaaacg aatccggacc | 300 |
| aggcttcatc ccaggcattg gcacccaatc aacagcagtc cctgtagcct tggagaggaa | 360 |
| ctctgtcagg gtctcctccg caattgtaag gagtccagac gggttacttg catctctcag | 420 |
| agggttctga ggagtggtca catttgattc ccgcgg | 456 |

<210> SEQ ID NO 157
<211> LENGTH: 1323
<212> TYPE: DNA
<213> ORGANISM: Oryza sativa
<220> FEATURE:
<221> NAME/KEY: misc_feature
<222> LOCATION: (1311)..(1311)
<223> OTHER INFORMATION: n is a, c, g, or t
<220> FEATURE:
<221> NAME/KEY: misc_feature
<222> LOCATION: (1313)..(1313)
<223> OTHER INFORMATION: n is a, c, g, or t

<400> SEQUENCE: 157

-continued

```
atgctaggga gtagcagtga tggaggtggc tatgataagg tttccgggat ggactccggt      60
aaatatgtgc gctacacgcc tgagcaggtg gaggcgcttg agcgggtgta cgccgattgc     120
cccaagccaa cctcctcccg caggcagcaa ttgctgcgtg agtgccccat acttgctaac     180
attgagccca agcagatcaa ggtctggttc cagaacagaa ggtgccggga taagcagcgg     240
aaggagtctt cacggcttca ggctgtcaac aggaaattga cggcaatgaa caagctactt     300
atggaagaga atgagcgact ccagaagcag gtctcccaat tggttcatga aatgcccac     360
atgcgacagc agctgcagaa tactccgctg gcaaatgata caagctgtga atcaaatgtg     420
actacccctc aaaacccttt aagggatgca agtaacccct ctgggctcct ttcaattgca     480
gaggagacct tgacagagtt cctctcaaag gctactggta cagctattga ttgggtccag     540
atgcctggga tgaagcctgg tccggattcg gttggtattg tggccatttc acatggttgc     600
ccgtggtgtt gctgccgtgc ctgtggtttg gtgaacctag aaccaacaaa agtggtagag     660
atattgaaag atcgtccatc ttggttccgt gattgtcgaa acctggaagt ctttacaatg     720
attccagcag gaaatggagg aacggttgaa cttgtctaca cacagttgta tgctccaaca     780
actttagttc ctgcacgaga tttttggacg ttacggtaca caaccacaat ggaagatggc     840
agtcttgtgg tctgtgagag atctttaagt ggttcagggg gcggtccaag tgctgcctct     900
gctcagcaat atgtgagagc ggaaatgctt ccaagtggat acctggttcg cccatgtgaa     960
ggtgggggat caattgtgca catagtggac catctggatc ttgaggcatg gagtgttcct    1020
gaggtgcttc ggccactcta tgaatcttca agggtagtcg ctcagaaaat gactactgcg    1080
gcactccggc acatcagaca aattgctcaa gaaacaagtg gggaagtggt gtatgccttg    1140
gggaggcaac cagcagtgct acggactttt agtcaaaggc tgagcagagg ctttaacgat    1200
gccattagtg gtttcaatga tgatgggtgg tctataatgg gtggagacgg tgttgaagat    1260
gtagttattg cttgcaactc aactaagaaa gttaggagta gcagcaatgc ngncatcgcc    1320
ttt                                                                   1323
```

<210> SEQ ID NO 158
<211> LENGTH: 1201
<212> TYPE: DNA
<213> ORGANISM: Oryza sativa
<220> FEATURE:
<221> NAME/KEY: misc_feature
<222> LOCATION: (32)..(32)
<223> OTHER INFORMATION: n is a, c, g, or t
<220> FEATURE:
<221> NAME/KEY: misc_feature
<222> LOCATION: (40)..(40)
<223> OTHER INFORMATION: n is a, c, g, or t
<220> FEATURE:
<221> NAME/KEY: misc_feature
<222> LOCATION: (147)..(147)
<223> OTHER INFORMATION: n is a, c, g, or t
<220> FEATURE:
<221> NAME/KEY: misc_feature
<222> LOCATION: (179)..(179)
<223> OTHER INFORMATION: n is a, c, g, or t
<220> FEATURE:
<221> NAME/KEY: misc_feature
<222> LOCATION: (213)..(213)
<223> OTHER INFORMATION: n is a, c, g, or t
<220> FEATURE:
<221> NAME/KEY: misc_feature
<222> LOCATION: (266)..(266)
<223> OTHER INFORMATION: n is a, c, g, or t
<220> FEATURE:
<221> NAME/KEY: misc_feature
<222> LOCATION: (289)..(289)

```
<223> OTHER INFORMATION: n is a, c, g, or t
<220> FEATURE:
<221> NAME/KEY: misc_feature
<222> LOCATION: (767)..(767)
<223> OTHER INFORMATION: n is a, c, g, or t
<220> FEATURE:
<221> NAME/KEY: misc_feature
<222> LOCATION: (773)..(773)
<223> OTHER INFORMATION: n is a, c, g, or t
<220> FEATURE:
<221> NAME/KEY: misc_feature
<222> LOCATION: (964)..(964)
<223> OTHER INFORMATION: n is a, c, g, or t
<220> FEATURE:
<221> NAME/KEY: misc_feature
<222> LOCATION: (1184)..(1184)
<223> OTHER INFORMATION: n is a, c, g, or t

<400> SEQUENCE: 158
cccaaaaccc agctcctccc gccgccagca gntgctccgn gactgcccca tcctcgccaa      60
catcgagccc aagcagatca aggtctggtt ccagaacaga aggtgccgag ataagcagcg     120
gaaggaggca tcaaggcttc aggccgngaa ccgaaaattg acggcgatga ataagctttnt   180
catggaggag aatgagcgtc ttcagaagca ggnctcccag ctggtccatg agaacgcgta    240
catgaagcag caacttcaga atccgncatt gggcaatgat acaagctgng aatcaaatgt    300
gaccactcct cagaaccctc tgagagatgc aagtaacccg tctggactcc ttacaattgc    360
ggaggagacc ctgacagagt tcctctccaa ggctacaggg actgctgttg attgggtgcc    420
aatgcctggg atgaagcctg gtccggattc gtttggtatt gtggccgttt cacatggttg    480
ccgtggtgtt gctgcccgtg cctgtggttt ggtgaatcta gaaccaacaa agatcgtgga    540
gatcttaaaa gaccgcccat cttggttccg tgattgtcga agtcttgaag tcttcacaat    600
gtttccagct ggaaatggtg gcacgatcga acttgtttac atgcagatgt atgctcctac    660
tactttggtt cctgcacgag atttttggac acttagatac acaactacaa tggatgatgg    720
cagccttgtg gtctgtgaga gatcattgag tggttctgga ggtggtncaa gtncagcctc    780
cgcacagcaa tttgtaagag ctgagatgct tcctagcggc tatctagtgc gcccatgcga    840
gggtggtggc tccgtcgtgc atattgtgga ccatctggat cttgaggctt ggagtgttcc    900
agaagtgctt cggccactct acgagtcatc tagggtagtt gctcagaaaa tgactgctgc    960
agcngtgcgg cacatcagac aaattgctca agagacaagc ggggaggttg tatacgcttt   1020
ggggaggcaa cctgctgttt tgcggacatt tagtcagagg ttgagtagag gcttcaatga   1080
tgctattagt ggtttcaacg atgatggttg gtctgtcatg ggtggggatg gcatcgaaga   1140
tgtgatcatt gcttgcaatg caaagagggt taggaatact agcncttcgg ccaatgcttt   1200
t                                                                  1201

<210> SEQ ID NO 159
<211> LENGTH: 454
<212> TYPE: PRT
<213> ORGANISM: Oryza sativa
<220> FEATURE:
<221> NAME/KEY: misc_feature
<222> LOCATION: (444)..(444)
<223> OTHER INFORMATION: Xaa can be any naturally occurring amino acid

<400> SEQUENCE: 159

Met Ala Ala Ala Val Ala Met Leu Gly Ser Ser Ser Asp Gly Gly Gly
1               5                   10                  15

Tyr Asp Lys Val Ser Gly Met Asp Ser Gly Lys Tyr Val Arg Tyr Thr
            20                  25                  30
```

```
Pro Glu Gln Val Glu Ala Leu Glu Arg Val Tyr Ala Asp Cys Pro Lys
             35                  40                  45

Pro Thr Ser Ser Arg Arg Gln Gln Leu Leu Arg Glu Cys Pro Ile Leu
         50                  55                  60

Ala Asn Ile Glu Pro Lys Gln Ile Lys Val Trp Phe Gln Asn Arg Arg
 65                  70                  75                  80

Cys Arg Asp Lys Gln Arg Lys Glu Ser Ser Arg Leu Gln Ala Val Asn
                 85                  90                  95

Arg Lys Leu Thr Ala Met Asn Lys Leu Leu Met Glu Glu Asn Glu Arg
                100                 105                 110

Leu Gln Lys Gln Val Ser Gln Leu Val His Glu Asn Ala His Met Arg
            115                 120                 125

Gln Gln Leu Gln Asn Thr Pro Leu Ala Asn Asp Thr Ser Cys Glu Ser
        130                 135                 140

Asn Val Thr Thr Pro Gln Asn Pro Leu Arg Asp Ala Ser Asn Pro Ser
145                 150                 155                 160

Gly Leu Leu Ser Ile Ala Glu Glu Thr Leu Thr Glu Phe Leu Ser Lys
                165                 170                 175

Ala Thr Gly Thr Ala Ile Asp Trp Val Gln Met Pro Gly Met Lys Pro
            180                 185                 190

Gly Pro Asp Ser Val Gly Ile Val Ala Ile Ser His Gly Cys Pro Trp
        195                 200                 205

Cys Cys Cys Arg Ala Cys Gly Leu Val Asn Leu Glu Pro Thr Lys Val
    210                 215                 220

Val Glu Ile Leu Lys Asp Arg Pro Ser Trp Phe Arg Asp Cys Arg Asn
225                 230                 235                 240

Leu Glu Val Phe Thr Met Ile Pro Ala Gly Asn Gly Gly Thr Val Glu
                245                 250                 255

Leu Val Tyr Thr Gln Leu Tyr Ala Pro Thr Thr Leu Val Pro Ala Arg
            260                 265                 270

Asp Phe Trp Thr Leu Arg Tyr Thr Thr Thr Met Glu Asp Gly Ser Leu
        275                 280                 285

Val Val Cys Glu Arg Ser Leu Ser Gly Ser Gly Gly Pro Ser Ala
    290                 295                 300

Ala Ser Ala Gln Gln Tyr Val Arg Ala Glu Met Leu Pro Ser Gly Tyr
305                 310                 315                 320

Leu Val Arg Pro Cys Glu Gly Gly Ser Ile Val His Ile Val Asp
                325                 330                 335

His Leu Asp Leu Glu Ala Trp Ser Val Pro Glu Val Leu Arg Pro Leu
            340                 345                 350

Tyr Glu Ser Ser Arg Val Val Ala Gln Lys Met Thr Thr Ala Ala Leu
        355                 360                 365

Arg His Ile Arg Gln Ile Ala Gln Glu Thr Ser Gly Glu Val Val Tyr
    370                 375                 380

Ala Leu Gly Arg Gln Pro Ala Val Leu Arg Thr Phe Ser Gln Arg Leu
385                 390                 395                 400

Ser Arg Gly Phe Asn Asp Ala Ile Ser Gly Phe Asn Asp Asp Gly Trp
                405                 410                 415

Ser Ile Met Gly Gly Asp Gly Val Glu Asp Val Val Ile Ala Cys Asn
            420                 425                 430

Ser Thr Lys Lys Val Arg Ser Ser Ser Asn Ala Xaa Ile Ala Phe Gly
        435                 440                 445
```

```
Ala Pro Gly Gly Ile Ile
    450

<210> SEQ ID NO 160
<211> LENGTH: 414
<212> TYPE: PRT
<213> ORGANISM: Oryza sativa
<220> FEATURE:
<221> NAME/KEY: misc_feature
<222> LOCATION: (18)..(18)
<223> OTHER INFORMATION: Xaa can be any naturally occurring amino acid
<220> FEATURE:
<221> NAME/KEY: misc_feature
<222> LOCATION: (56)..(56)
<223> OTHER INFORMATION: Xaa can be any naturally occurring amino acid
<220> FEATURE:
<221> NAME/KEY: misc_feature
<222> LOCATION: (67)..(67)
<223> OTHER INFORMATION: Xaa can be any naturally occurring amino acid
<220> FEATURE:
<221> NAME/KEY: misc_feature
<222> LOCATION: (78)..(78)
<223> OTHER INFORMATION: Xaa can be any naturally occurring amino acid
<220> FEATURE:
<221> NAME/KEY: misc_feature
<222> LOCATION: (96)..(96)
<223> OTHER INFORMATION: Xaa can be any naturally occurring amino acid
<220> FEATURE:
<221> NAME/KEY: misc_feature
<222> LOCATION: (103)..(103)
<223> OTHER INFORMATION: Xaa can be any naturally occurring amino acid
<220> FEATURE:
<221> NAME/KEY: misc_feature
<222> LOCATION: (263)..(263)
<223> OTHER INFORMATION: Xaa can be any naturally occurring amino acid
<220> FEATURE:
<221> NAME/KEY: misc_feature
<222> LOCATION: (265)..(265)
<223> OTHER INFORMATION: Xaa can be any naturally occurring amino acid
<220> FEATURE:
<221> NAME/KEY: misc_feature
<222> LOCATION: (402)..(402)
<223> OTHER INFORMATION: Xaa can be any naturally occurring amino acid

<400> SEQUENCE: 160

Glu Arg Val Tyr Cys Glu Cys Pro Lys Pro Ser Ser Ser Arg Arg Gln
1               5                   10                  15

Gln Xaa Leu Arg Asp Cys Pro Ile Leu Ala Asn Ile Glu Pro Lys Gln
            20                  25                  30

Ile Lys Val Trp Phe Gln Asn Arg Arg Cys Arg Asp Lys Gln Arg Lys
        35                  40                  45

Glu Ala Ser Arg Leu Gln Ala Xaa Asn Arg Lys Leu Thr Ala Met Asn
    50                  55                  60

Lys Leu Xaa Met Glu Glu Asn Glu Arg Leu Gln Lys Gln Xaa Ser Gln
65                  70                  75                  80

Leu Val His Glu Asn Ala Tyr Met Lys Gln Gln Leu Gln Asn Pro Xaa
                85                  90                  95

Leu Gly Asn Asp Thr Ser Xaa Glu Ser Asn Val Thr Thr Pro Gln Asn
            100                 105                 110

Pro Leu Arg Asp Ala Ser Asn Pro Ser Gly Leu Leu Thr Ile Ala Glu
        115                 120                 125

Glu Thr Leu Thr Glu Phe Leu Ser Lys Ala Thr Gly Thr Ala Val Asp
    130                 135                 140

Trp Val Pro Met Pro Gly Met Lys Pro Gly Pro Asp Ser Phe Gly Ile
145                 150                 155                 160

Val Ala Val Ser His Gly Cys Arg Gly Val Ala Arg Ala Cys Gly
                165                 170                 175
```

-continued

```
Leu Val Asn Leu Glu Pro Thr Lys Ile Val Glu Ile Leu Lys Asp Arg
            180                 185                 190

Pro Ser Trp Phe Arg Asp Cys Arg Ser Leu Glu Val Phe Thr Met Phe
        195                 200                 205

Pro Ala Gly Asn Gly Gly Thr Ile Glu Leu Val Tyr Met Gln Met Tyr
    210                 215                 220

Ala Pro Thr Thr Leu Val Pro Ala Arg Asp Phe Trp Thr Leu Arg Tyr
225                 230                 235                 240

Thr Thr Thr Met Asp Asp Gly Ser Leu Val Val Cys Glu Arg Ser Leu
                245                 250                 255

Ser Gly Ser Gly Gly Gly Xaa Ser Xaa Ala Ser Ala Gln Gln Phe Val
            260                 265                 270

Arg Ala Glu Met Leu Pro Ser Gly Tyr Leu Val Arg Pro Cys Glu Gly
            275                 280                 285

Gly Gly Ser Val Val His Ile Val Asp His Leu Asp Leu Glu Ala Trp
        290                 295                 300

Ser Val Pro Glu Val Leu Arg Pro Leu Tyr Glu Ser Ser Arg Val Val
305                 310                 315                 320

Ala Gln Lys Met Thr Ala Ala Val Arg His Ile Arg Gln Ile Ala
                325                 330                 335

Gln Glu Thr Ser Gly Glu Val Val Tyr Ala Leu Gly Arg Gln Pro Ala
            340                 345                 350

Val Leu Arg Thr Phe Ser Gln Arg Leu Ser Arg Gly Phe Asn Asp Ala
            355                 360                 365

Ile Ser Gly Phe Asn Asp Asp Gly Trp Ser Val Met Gly Gly Asp Gly
        370                 375                 380

Ile Glu Asp Val Ile Ile Ala Cys Asn Ala Lys Arg Val Arg Asn Thr
385                 390                 395                 400

Ser Xaa Ser Ala Asn Ala Phe Val Thr Pro Gly Gly Val Ile
                405                 410
```

<210> SEQ ID NO 161
<211> LENGTH: 25
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (20)..(20)
<223> OTHER INFORMATION: n is a, c, g, or t

<400> SEQUENCE: 161
gcagcagcat ggaggcyttn gcrca                                    25

<210> SEQ ID NO 162
<211> LENGTH: 36
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (29)..(29)
<223> OTHER INFORMATION: n is a, c, g, or t

<400> SEQUENCE: 162
cagcagaata agcatcaaca ttataatcng cccayt                        36

<210> SEQ ID NO 163
<211> LENGTH: 3308
<212> TYPE: DNA
<213> ORGANISM: Lycopersicon esculentum

<400> SEQUENCE: 163

| | | | | | |
|---|---|---|---|---|---|
| agctcgttgc | gtcgacagca | attgatccgt | gaatgtcata | ttctgtcgaa | tatcgagcct | 60 |
| aagcagatca | aagtttggtt | tcagaacaga | aggtatactt | ccattgttca | attttgccca | 120 |
| aattttggtt | tatgttttgt | tgttaattgc | atacattttt | atatgtctat | tgtgtacgat | 180 |
| tgatctgcac | tttactttgt | ttagtactgc | tcgaatcttg | tattagttag | atcagtgatg | 240 |
| ataaactgaa | tgtatcactg | tagttctcct | tgcctaggct | tgttggttga | gtggtagggt | 300 |
| atgtgttaac | cttaggtgat | tgggaaattg | agcttagagt | ttggtatgga | gggtaaacgt | 360 |
| tgtatcattt | caggtgtcga | gagaagcaaa | ggaaagagtc | ttctcgattg | cagactgtga | 420 |
| acagaaagtt | gtctgcgatg | aataaactgt | tgatggagga | gaatgaccgc | ttgcagaaac | 480 |
| aagtctcgca | gcttgtatgt | gaaaatggct | atatgcggca | acaattgcaa | aatgtaagct | 540 |
| aacttaactc | ttcgtttatt | ttttatgtcc | aaaagctcca | tgtgttgctt | actatatagt | 600 |
| agattaatgt | caaacatatc | ttgtcttttt | tgttcacttg | atctatgctg | ctgaaatggc | 660 |
| tactcactgt | gtagtctaga | ttatacaata | ttccaccgct | attgagtcca | tgattttaat | 720 |
| cagtcagtct | tataattctg | gaatgcgtta | ctttatatat | gggactaaat | tggcatggca | 780 |
| ttattttgt | gtagtagtac | aagaaacatt | taaggtcctg | tgacttcaaa | attgtaagat | 840 |
| gacagatatc | accagtcatt | tgtggatcaa | gaggacttaa | tttaagctta | cttaagactc | 900 |
| taattgtgtt | tgctgcaggt | atcggcggcc | actactgatg | taagttgtga | atcaggggta | 960 |
| accactcctc | agcattccct | tagagatgct | aacaaccctg | ctgggtaata | atttaaaaca | 1020 |
| gctatttctt | tcactcctta | cttatatgat | gttaattcta | aaacgtgttc | atactgtatc | 1080 |
| tttggaggaa | gtaaatagca | aatttcacaa | tttaagggac | tgattattta | tctctaagtc | 1140 |
| atgtttattc | tctatgcaga | ctactaccaa | ttgcagaaga | aaccttggca | gagttccttt | 1200 |
| ctaaggctac | aggaactgct | gtcgattggg | tcccgatgcc | tgggatgaag | gttgaactct | 1260 |
| agtcaatcac | ctttattttt | ttaaaattca | gtatttccat | ctgtatcatt | gaccagacgg | 1320 |
| ctaaaaggca | atattatcat | tcaattgtca | gcctggtccg | gattcagttg | gattttttgc | 1380 |
| catctcacac | agttgcagtg | gagtggcagc | ccgagcatgt | ggtcttgtta | gtttagagcc | 1440 |
| aacaaaggta | aacaattgga | agtctattca | gaaatattac | tgctgctcca | ttgctagttt | 1500 |
| tagtccatta | atgattgtag | atgttgtcag | cttttttctta | ctaaaacatt | ttacagattg | 1560 |
| ctgatatcct | caaagatcga | ccttcttggt | tccgcgactg | ccggaatgtt | gaagttatca | 1620 |
| caatgtttcc | tgctggaaat | ggtggtacag | ttgagctttt | gtatacccag | gtgaataccct | 1680 |
| tctcctcaat | ctctatgtac | acttctgatt | tgattagata | cagcattgag | gggatcaatg | 1740 |
| aatcatttct | ttcagatata | tgctcccaca | actctggctc | ccgcgcgtga | tttttggacg | 1800 |
| ctgagataca | caacaaccct | agacaatggt | agtctcgtgg | taagcaatcc | ttcacattta | 1860 |
| agtgagcttg | tgttggcgac | ctggccactt | ttatacttag | ttctggcatt | ccctggttta | 1920 |
| actagtcttt | taacatctca | acctttcaat | ccttggattg | aacagaagtc | ctgaaatgta | 1980 |
| atattttgg | gtcatatttta | accaaatgct | gcattataat | ccccgtctag | acctttgagt | 2040 |
| atcttgctac | ttcagtataa | tacttggctc | cattatttgt | gattcttaat | agtgaattct | 2100 |
| attagctgcg | tcatttggta | gatgttgctc | acagtttctt | tttgtgtggc | atcaatttat | 2160 |

-continued

```
cctcctcacc aaggtttgtg aaagatccct atctggtaat gggcctggcc caaatcctac       2220
tgctgcttcc cagtttgtaa gagctcaaat gcttccatct ggatatctga tccgaccgtg       2280
tgatggtgga ggatcaatca tacatattgt tgatcacctg aatcttgagg taagattttg       2340
taaagtactg cttacctttg tcatgaacct gttttgcatg gtagctgcaa ttcacttcat       2400
atatttttca ggcatggagt gcccctgaga ttttgcgtcc actctatgaa tcgtcgaaag       2460
ttgtggcaca gaaaatgact attgcagtga gttcaaccct tcgttatcat ttaatacggc       2520
atatagattt atatgtttgt caggtttaaa gtacttgtgc agtatcacac ttcccatagc       2580
ttactgccac agaagaagaa ccatgatttc atgctttact ttcttttctg tgaaggcact       2640
gcgatatgca aggcaactag ctcaagagac tagcggcgag gtagtatatg gtctaggaag       2700
gcaacctgct gttcctcgaa cattcagcca gagattatgc aggtgatgct tatttctgat       2760
ttttgttatg tggctttgag atgatgaaaa tttatgcact tctgagatgc caattctgaa       2820
gtacatatac aagtacctta ttaggccatt tctatattgc agagggttca atgatgccat       2880
caatggattc ggtgacgatg gctggtcaat gttaagttca gatggtgctg aagatgtcat       2940
agttgctgtc aattcaagga agaacctcgc aaccacctcc attcctcttt cccgcttgg       3000 tggcgtcctt tgtaccaaag catcaatgct actccaggtg aatagtggat ctttcttgaa       3060
ctgaatagaa tttttcattc gacaactacc ttgctcttgt taatacacaa caaacagaag       3120
ttcacaagtt catatttgca tcctcttttta cgataccaac tgagagactg gtccatatca       3180
gcaatagatg gagttaattg ttaagacaag tgtaactgga taaatgagaa taatttgact       3240
cttttgtttc ctggcagaat gtccccctg ccgtactggt tcggtttctg agggagcacc       3300
gttcagaa                                                                3308
```

<210> SEQ ID NO 164
<211> LENGTH: 1290
<212> TYPE: DNA
<213> ORGANISM: Lycopersicon esculentum

<400> SEQUENCE: 164

```
agctcgttgc gtcgacagca attgatccgt gaatgtcata ttctgtcgaa tatcgagcct        60
aagcagatca aagtttggtt tcagaacaga aggtgtcgag agaagcaaag gaaagagtct       120
tctcgattgc agactgtgaa cagaaagttg tctgcgatga ataaactgtt gatggaggag       180
aatgaccgct tgcagaaaca agtctcgcag cttgtatgtg aaaatggcta tatgcggcaa       240
caattgcaaa atgtatcggc ggccactact gatgtaagtt gtgaatcagg ggtaaccact       300
cctcagcatt cccttagaga tgctaacaac cctgctggac tactaccaat tgcagaagaa       360
accttggcag agttcctttc taaggctaca ggaactgctg tcgattgggt cccgatgcct       420
gggatgaagc ctggtccgga ttcagttggg attttttgcca tctcacacag ttgcagtgga       480
gtggcagccc gagcatgtgg tcttgttagt ttagagccaa caaagattgc tgatatcctc       540
aaagatcgac cttcttggtt ccgcgactgc cggaatgttg aagttatcac aatgtttcct       600
gctggaaatg gtgtacagt tgagcttttg tatacccaga tatatgctcc cacaactctg       660
gctcccgcgc gtgatttttg gacgctgaga tacacaacaa ccctagacaa tggtagtctc       720
gtggtttgtg aaagatccct atctggtaat gggcctggcc caaatcctac tgctgcttcc       780
cagtttgtaa gagctcaaat gcttccatct ggatatctga tccgaccgtg tgatggtgga       840
ggatcaatca tacatattgt tgatcacctg aatcttgagg catggagtgc ccctgagatt       900
ttgcgtccac tctatgaatc gtcgaaagtt gtggcacaga aaatgactat tgcagcactg       960
```

```
cgatatgcaa ggcaactagc tcaagagact agcggcgagg tagtatatgg tctaggaagg    1020
caacctgctg ttcctcgaac attcagccag agattatgca gagggttcaa tgatgccatc    1080
aatggattcg gtgacgatgg ctggtcaatg ttaagttcag atggtgctga agatgtcata    1140
gttgctgtca attcaaggaa gaacctcgca accacctcca ttcctctttc ccgcttggt     1200 ggcgtccttt gtaccaaagc atcaatgcta ctccagcaga atgtcccccc tgccgtactg    1260
gttcggtttc tgagggagca ccgttcagaa                                     1290
```

<210> SEQ ID NO 165
<211> LENGTH: 430
<212> TYPE: PRT
<213> ORGANISM: Lycopersicon esculentum

<400> SEQUENCE: 165

```
Ser Ser Leu Arg Arg Gln Gln Leu Ile Arg Glu Cys His Ile Leu Ser
1               5                   10                  15

Asn Ile Glu Pro Lys Gln Ile Lys Val Trp Phe Gln Asn Arg Arg Cys
            20                  25                  30

Arg Glu Lys Gln Arg Lys Glu Ser Ser Arg Leu Gln Thr Val Asn Arg
        35                  40                  45

Lys Leu Ser Ala Met Asn Lys Leu Leu Met Glu Glu Asn Asp Arg Leu
    50                  55                  60

Gln Lys Gln Val Ser Gln Leu Val Cys Glu Asn Gly Tyr Met Arg Gln
65                  70                  75                  80

Gln Leu Gln Asn Val Ser Ala Ala Thr Thr Asp Val Ser Cys Glu Ser
                85                  90                  95

Gly Val Thr Thr Pro Gln His Ser Leu Arg Asp Ala Asn Asn Pro Ala
            100                 105                 110

Gly Leu Leu Pro Ile Ala Glu Glu Thr Leu Ala Glu Phe Leu Ser Lys
        115                 120                 125

Ala Thr Gly Thr Ala Val Asp Trp Val Pro Met Pro Gly Met Lys Pro
    130                 135                 140

Gly Pro Asp Ser Val Gly Ile Phe Ala Ile Ser His Ser Cys Ser Gly
145                 150                 155                 160

Val Ala Ala Arg Ala Cys Gly Leu Val Ser Leu Glu Pro Thr Lys Ile
                165                 170                 175

Ala Asp Ile Leu Lys Asp Arg Pro Ser Trp Phe Arg Asp Cys Arg Asn
            180                 185                 190

Val Glu Val Ile Thr Met Phe Pro Ala Gly Asn Gly Thr Val Glu
        195                 200                 205

Leu Leu Tyr Thr Gln Ile Tyr Ala Pro Thr Thr Leu Ala Pro Ala Arg
    210                 215                 220

Asp Phe Trp Thr Leu Arg Tyr Thr Thr Thr Leu Asp Asn Gly Ser Leu
225                 230                 235                 240

Val Val Cys Glu Arg Ser Leu Ser Gly Asn Gly Pro Gly Pro Asn Pro
                245                 250                 255

Thr Ala Ala Ser Gln Phe Val Arg Ala Gln Met Leu Pro Ser Gly Tyr
            260                 265                 270

Leu Ile Arg Pro Cys Asp Gly Gly Ser Ile His Ile Val Asp
        275                 280                 285

His Leu Asn Leu Glu Ala Trp Ser Ala Pro Glu Ile Leu Arg Pro Leu
    290                 295                 300

Tyr Glu Ser Ser Lys Val Val Ala Gln Lys Met Thr Ile Ala Ala Leu
```

```
                 305                 310                 315                 320
Arg Tyr Ala Arg Gln Leu Ala Gln Glu Thr Ser Gly Glu Val Val Tyr
                325                 330                 335
Gly Leu Gly Arg Gln Pro Ala Val Pro Arg Thr Phe Ser Gln Arg Leu
                340                 345                 350
Cys Arg Gly Phe Asn Asp Ala Ile Asn Gly Phe Gly Asp Asp Gly Trp
                355                 360                 365
Ser Met Leu Ser Ser Asp Gly Ala Glu Asp Val Ile Val Ala Val Asn
                370                 375                 380
Ser Arg Lys Asn Leu Ala Thr Thr Ser Ile Pro Leu Ser Pro Leu Gly
385                 390                 395                 400
Gly Val Leu Cys Thr Lys Ala Ser Met Leu Leu Gln Gln Asn Val Pro
                405                 410                 415
Pro Ala Val Leu Val Arg Phe Leu Arg Glu His Arg Ser Glu
                420                 425                 430

<210> SEQ ID NO 166
<211> LENGTH: 24
<212> TYPE: DNA
<213> ORGANISM: Artificial
<220> FEATURE:
<223> OTHER INFORMATION: primer
<220> FEATURE:
<221> NAME/KEY: misc_feature
<222> LOCATION: (22)..(22)
<223> OTHER INFORMATION: n is a, c, g, or t

<400> SEQUENCE: 166
gccgttcacg gcstcrttra ancc                                              24

<210> SEQ ID NO 167
<211> LENGTH: 23
<212> TYPE: DNA
<213> ORGANISM: Artificial
<220> FEATURE:
<223> OTHER INFORMATION: primer

<400> SEQUENCE: 167
cgacgactcc tggagtccgt cag                                               23

<210> SEQ ID NO 168
<211> LENGTH: 20
<212> TYPE: DNA
<213> ORGANISM: Artificial
<220> FEATURE:
<223> OTHER INFORMATION: primer

<400> SEQUENCE: 168
tgtatcattt gccagcggag                                                   20

<210> SEQ ID NO 169
<211> LENGTH: 3017
<212> TYPE: DNA
<213> ORGANISM: Oryza sativa
<220> FEATURE:
<221> NAME/KEY: misc_feature
<222> LOCATION: (359)..(359)
<223> OTHER INFORMATION: n is a, c, g, or t
<220> FEATURE:
<221> NAME/KEY: misc_feature
<222> LOCATION: (440)..(440)
<223> OTHER INFORMATION: n is a, c, g, or t
<220> FEATURE:
<221> NAME/KEY: misc_feature
<222> LOCATION: (915)..(915)
```

```
<223> OTHER INFORMATION: n is a, c, g, or t
<220> FEATURE:
<221> NAME/KEY: misc_feature
<222> LOCATION: (1298)..(1298)
<223> OTHER INFORMATION: n is a, c, g, or t
<220> FEATURE:
<221> NAME/KEY: misc_feature
<222> LOCATION: (1355)..(1355)
<223> OTHER INFORMATION: n is a, c, g, or t

<400> SEQUENCE: 169
```

| | | | | | |
|---|---|---|---|---|---|
| gtaagtgccc | catacttgct | aacattgagc | ccaagcagat | caaggtctgg | ttccagaaca | 60 |
| gaaggtaatg | ataatagaat | tgaatctttc | tacgtttgtt | ctctgtgaca | aaaacttgtt | 120 |
| atggcagttt | tccctgattg | tttcatctgt | cacctgaaat | aacatttcgt | tagtttcctt | 180 |
| ctggggaggc | tatggttcta | atatgctgcg | ttgttgttgt | gatgatgagc | ggtattttga | 240 |
| tatgagggga | gctgcaatgc | caattgttta | tcatttcatt | tgtttgcgca | ccagcaaaat | 300 |
| gtagtataat | tactttagct | gacggctctg | catgtatatg | atttttcgt | ttttcatgnt | 360 |
| cgctgaagtg | gatacttgtg | cttgtgttgc | tctaggtgcc | gggataagca | gcggaaggag | 420 |
| tcttcacggt | tcaggctgn | caacaggaaa | ttgacggcaa | tgaacaagct | acttatggaa | 480 |
| gagaatgagc | gactccagaa | gcaggtctcc | caattggttc | atgagaatgc | ccacatgcga | 540 |
| cagcagctgt | agaatgtaag | ctcttgatgt | gctggtgctg | atgttgtccc | ccatgcataa | 600 |
| acaygttctc | actgaaatgc | tatctattcy | ttgygcattt | tgttatacgc | atggcatgtc | 660 |
| cggggatgtg | ttgttctgta | ctgtatattg | tagattagta | taactttaaa | atttgatgta | 720 |
| tgtgtagcta | taccagctgg | ggccatatgc | gtcagttcct | ttagaattga | tatatgaatt | 780 |
| aatcctcaga | atgtccatga | gatcgctaga | tttcactgat | aacaccactt | gcttgggtgc | 840 |
| agactccgct | ggcaaatgat | acaagctgtg | aatcaaatgt | gactacccct | caaaacccctt | 900 |
| taagggatgc | aagtnacccc | tctgggtaag | taaatagttc | tgagtgactc | aggtagaatt | 960 |
| attgttggat | ggacktgctc | tttcgatatc | atgctatctt | aactgccttt | tatcttgytc | 1020 |
| taggctcctt | tcaattgcag | aggagaccctt | gacagagttc | ctctcaaagg | ctactggtac | 1080 |
| cagctattga | ttgggtccag | atgcctggga | tgaaggttcc | atgctagcac | tgtttgtttt | 1140 |
| tttgttctgt | gattcgtgct | aagaggtttt | tacttgaagt | gcttactacc | cttttgtttt | 1200 |
| catgatgtaa | gcctggtccg | gattcggttg | gtattgtggc | catttcacat | ggttgccgtg | 1260 |
| gtgttgctgc | ccgtgcctgt | ggttcggtga | acctagancc | aacaaaagta | agtgttgtag | 1320 |
| ctatttgggt | acatgggttt | ggtatttta | tgttncctca | gtattccctg | gtctgtatgt | 1380 |
| tttctgaagc | atctattttg | gggtgatagc | aagcctatcc | accagtcact | tagttttctt | 1440 |
| tgtgtgcaaa | tggttagaaa | cctactacct | ccatcccaaa | atatagccaa | aagttgctat | 1500 |
| atcaaaaatc | ctatcagaag | tggctcctga | acacattgct | gccgagtgtg | gaattaagac | 1560 |
| acactgtaat | tcactttaat | aaatactaaa | ctttgaagat | gtcactttag | aggtctaatg | 1620 |
| atttcatgtc | tgccaactgt | tatcatcaaa | tttaatcgtg | aagataagca | gatatcttgc | 1680 |
| ttttttttgtt | actttattca | ggagattttg | tgtctcatag | aactttgtta | cgtaggtggt | 1740 |
| agagatattg | aaagatcgtc | catcttggtt | ccgtgattgt | cgaaacctgg | aagtctttac | 1800 |
| aatgattcca | gcaggaaatg | gagggacggt | tgaacttgtc | tacacacagg | tgaacactgt | 1860 |
| ttcattttac | attgtataat | ggtatatcct | cagtcttctc | tatcaatgca | tgtgcttcat | 1920 |
| gccatgaaca | ttattacttg | tttttgctta | cagttgtatg | ctccaacaac | tttagttcct | 1980 |
| gcacgagatt | tttggacgtt | acggtacaca | accacaatgg | aagatggcag | tcttgtggta | 2040 |

| | |
|---|---|
| tgtatgaaca tgaacactgt tttcacccca caatgagtct caatgtgatg ttacccttgc | 2100 |
| taatattcct ccatctccaa ggtctgtgag agatctttaa gtggttcagg gggcggtcca | 2160 |
| agtgctgcct ctgctcagca atatgtgaga gcggaaatgc ttccaagtgg atacctggtt | 2220 |
| cgcccatgtg aaggtggggg atcaattgtg cacatagtgg accatctgga tcttgaggta | 2280 |
| tttttcacac ttttgtacag ttgaaccatg ttttttgtcc ctttgatgta ggaccatttt | 2340 |
| tgtatcctgt caaactaata atacaatttg gtttaatct tttcaggcat ggagtgttcc | 2400 |
| tgaggtgctt cggccactct atgaatcttc aagggtagtc gctcagaaaa tgactactgc | 2460 |
| ggtaagctgt cgtgaaatga tattcagctc aaatttcatt gatgtgatta caagttcatc | 2520 |
| atttcaagtg aaacttgttt ttaatgaact cttcaagttt cataacattg gatttttttt | 2580 |
| tagaaaaaat aaaataaaaa tccaatatta tgaaacttga agagttcaag ctaatgataa | 2640 |
| agtttgtgtt ttggataaag cttataatat tggatatgtg gtgaaaatga tttatatggg | 2700 |
| ttggtacaac taatgataaa atttgccttt tggatatgtt gaacagttca ttttctgcaa | 2760 |
| tctactttat actaaccttt tattgtctat cctatatatc aaggcactcc ggcacatcag | 2820 |
| acaaattgct caagaaacaa gtggggaagt ggtgtatgcc ttggggaggc aaccagcagt | 2880 |
| gctacggact tttagtcaaa ggctgagcag gtgattttt tataaattat tactcagcaa | 2940 |
| ttaatatttt tttcacctgt ttaatctaac accaatatta tgcttttctt agaggtttca | 3000 |
| acgacgccgt gaacggc | 3017 |

```
<210> SEQ ID NO 170
<211> LENGTH: 1581
<212> TYPE: DNA
<213> ORGANISM: Oryza sativa
<220> FEATURE:
<221> NAME/KEY: misc_feature
<222> LOCATION: (1548)..(1548)
<223> OTHER INFORMATION: n is a, c, g, or t
<220> FEATURE:
<221> NAME/KEY: misc_feature
<222> LOCATION: (1550)..(1550)
<223> OTHER INFORMATION: n is a, c, g, or t

<400> SEQUENCE: 170
```

| | |
|---|---|
| cggggccgtg gctgtggggt ggctgtgagg gtgccccccgg cggcgctccc ctccgcgcct | 60 |
| gccggcgagg gggctcggac tgaagggatc taggcgagct gaaaattgaa gygcaggcaa | 120 |
| ggagataaga gcagcgtcca aattgtgagt acttcattag caggaggtag tggttgtgct | 180 |
| tgcttggctc ctttgcaatt tggctttggc gaggtagcaa tggctgcggc agtggcaatg | 240 |
| ctagggagta gcagtgatgg aggtggctat gataaggttt ccgggatgga ctccggtaaa | 300 |
| tatgtgcgct acacgcctga gcaggtggag gcgcttgagc gggtgtacgc cgattgcccc | 360 |
| aagccaacct cctcccgcag gcagcaattg ctgcgtgagt gccccatact tgctaacatt | 420 |
| gagcccaagc agatcaaggt ctggttccag aacagaaggt gccgggataa gcagcggaag | 480 |
| gagtcttcac ggcttcaggc tgtcaacagg aaattgacgg caatgaacaa gctacttatg | 540 |
| gaagagaatg agcgactcca gaagcaggtc tcccaattgg ttcatgagaa tgcccacatg | 600 |
| cgacagcagc tgcagaatac tccgctggca atgatacaa gctgtgaatc aaatgtgact | 660 |
| accccctcaaa acccttttaag ggatgcaagt aacccctctg ggctcctttc aattgcagag | 720 |
| gagaccttga cagagttcct ctcaaaggct actggtacag ctattgattg ggtccagatg | 780 |
| cctgggatga agcctggtcc ggattcggtt ggtattgtgg ccatttcaca tggttgcccg | 840 |

-continued

```
tggtgttgct gccgtgcctg tggtttggtg aacctagaac caacaaaagt ggtagagata    900
ttgaaagatc gtccatcttg gttccgtgat tgtcgaaacc tggaagtctt tacaatgatt    960
ccagcaggaa atggaggaac ggttgaactt gtctacacac agttgtatgc tccaacaact   1020
ttagttcctg cacgagattt ttggacgtta cggtacacaa ccacaatgga agatggcagt   1080
cttgtggtct gtgagagatc tttaagtggt tcagggggcg gtccaagtgc tgcctctgct   1140
cagcaatatg tgagagcgga aatgcttcca agtggatacc tggttcgccc atgtgaaggt   1200
gggggatcaa ttgtgcacat agtggaccat ctggatcttg aggcatggag tgttcctgag   1260
gtgcttcggc cactctatga atcttcaagg gtagtcgctc agaaaatgac tactgcggca   1320
ctccggcaca tcagacaaat tgctcaagaa acaagtgggg aagtggtgta tgccttgggg   1380
aggcaaccag cagtgctacg gacttttagt caaaggctga gcagaggctt taacgatgcc   1440
attagtggtt tcaatgatga tgggtggtct ataatgggtg gagacggtgt tgaagatgta   1500
gttattgctt gcaactcaac taagaaagtt aggagtagca gcaatgcngn catcgccttt   1560
ggagcccccg gaggtattat a                                             1581
```

<210> SEQ ID NO 171
<211> LENGTH: 447
<212> TYPE: PRT
<213> ORGANISM: Oryza sativa
<220> FEATURE:
<221> NAME/KEY: misc_feature
<222> LOCATION: (444)..(444)
<223> OTHER INFORMATION: Xaa can be any naturally occurring amino acid

<400> SEQUENCE: 171

```
Met Ala Ala Ala Val Ala Met Leu Gly Ser Ser Asp Gly Gly
1               5                   10                  15

Tyr Asp Lys Val Ser Gly Met Asp Ser Gly Lys Tyr Val Arg Tyr Thr
                20                  25                  30

Pro Glu Gln Val Glu Ala Leu Glu Arg Val Tyr Ala Asp Cys Pro Lys
            35                  40                  45

Pro Thr Ser Ser Arg Arg Gln Gln Leu Leu Arg Glu Cys Pro Ile Leu
        50                  55                  60

Ala Asn Ile Glu Pro Lys Gln Ile Lys Val Trp Phe Gln Asn Arg Arg
65                  70                  75                  80

Cys Arg Asp Lys Gln Arg Lys Glu Ser Ser Arg Leu Gln Ala Val Asn
                85                  90                  95

Arg Lys Leu Thr Ala Met Asn Lys Leu Leu Met Glu Glu Asn Glu Arg
            100                 105                 110

Leu Gln Lys Gln Val Ser Gln Leu Val His Glu Asn Ala His Met Arg
        115                 120                 125

Gln Gln Leu Gln Asn Thr Pro Leu Ala Asn Asp Thr Ser Cys Glu Ser
    130                 135                 140

Asn Val Thr Thr Pro Gln Asn Pro Leu Arg Asp Ala Ser Asn Pro Ser
145                 150                 155                 160

Gly Leu Leu Ser Ile Ala Glu Glu Thr Leu Thr Glu Phe Leu Ser Lys
                165                 170                 175

Ala Thr Gly Thr Ala Ile Asp Trp Val Gln Met Pro Gly Met Lys Pro
            180                 185                 190

Gly Pro Asp Ser Val Gly Ile Val Ala Ile Ser His Gly Cys Pro Trp
        195                 200                 205

Cys Cys Cys Arg Ala Cys Gly Leu Val Asn Leu Glu Pro Thr Lys Val
    210                 215                 220
```

```
Val Glu Ile Leu Lys Asp Arg Pro Ser Trp Phe Arg Asp Cys Arg Asn
225                 230                 235                 240

Leu Glu Val Phe Thr Met Ile Pro Ala Gly Asn Gly Gly Thr Val Glu
            245                 250                 255

Leu Val Tyr Thr Gln Leu Tyr Ala Pro Thr Thr Leu Val Pro Ala Arg
            260                 265                 270

Asp Phe Trp Thr Leu Arg Tyr Thr Thr Thr Met Glu Asp Gly Ser Leu
            275                 280                 285

Val Val Cys Glu Arg Ser Leu Ser Gly Ser Gly Gly Pro Ser Ala
    290                 295                 300

Ala Ser Ala Gln Gln Tyr Val Arg Ala Glu Met Leu Pro Ser Gly Tyr
305                 310                 315                 320

Leu Val Arg Pro Cys Glu Gly Gly Gly Ser Ile Val His Ile Val Asp
            325                 330                 335

His Leu Asp Leu Glu Ala Trp Ser Val Pro Glu Val Leu Arg Pro Leu
            340                 345                 350

Tyr Glu Ser Ser Arg Val Val Ala Gln Lys Met Thr Thr Ala Ala Leu
            355                 360                 365

Arg His Ile Arg Gln Ile Ala Gln Glu Thr Ser Gly Glu Val Val Tyr
            370                 375                 380

Ala Leu Gly Arg Gln Pro Ala Val Leu Arg Thr Phe Ser Gln Arg Leu
385                 390                 395                 400

Ser Arg Gly Phe Asn Asp Ala Ile Ser Gly Phe Asn Asp Asp Gly Trp
            405                 410                 415

Ser Ile Met Gly Gly Asp Gly Val Glu Asp Val Val Ile Ala Cys Asn
            420                 425                 430

Ser Thr Lys Lys Val Arg Ser Ser Ser Asn Ala Xaa Ile Ala Phe
            435                 440                 445

<210> SEQ ID NO 172
<211> LENGTH: 1127
<212> TYPE: DNA
<213> ORGANISM: Oryza sativa
<220> FEATURE:
<221> NAME/KEY: misc_feature
<222> LOCATION: (107)..(107)
<223> OTHER INFORMATION: n is a, c, g, or t
<220> FEATURE:
<221> NAME/KEY: misc_feature
<222> LOCATION: (139)..(139)
<223> OTHER INFORMATION: n is a, c, g, or t
<220> FEATURE:
<221> NAME/KEY: misc_feature
<222> LOCATION: (173)..(173)
<223> OTHER INFORMATION: n is a, c, g, or t
<220> FEATURE:
<221> NAME/KEY: misc_feature
<222> LOCATION: (226)..(226)
<223> OTHER INFORMATION: n is a, c, g, or t
<220> FEATURE:
<221> NAME/KEY: misc_feature
<222> LOCATION: (249)..(249)
<223> OTHER INFORMATION: n is a, c, g, or t
<220> FEATURE:
<221> NAME/KEY: misc_feature
<222> LOCATION: (924)..(924)
<223> OTHER INFORMATION: n is a, c, g, or t

<400> SEQUENCE: 172
gactgcccca tcctcgccaa catcgagccc aagcagatca aggtctggtt ccagaacaga      60
aggtgccgag ataagcagcg gaaggaggca tcaaggcttc aggccgngaa ccgaaaattg     120
```

```
acggcgatga ataagcttnt catggaggag aatgagcgtc ttcagaagca ggnctcccag      180
ctggtccatg agaacgcgta catgaagcag caacttcaga atccgncatt gggcaatgat      240
acaagctgng aatcaaatgt gaccactcct cagaaccctc tgagagatgc aagtaacccg      300
tctggactcc ttacaattgc ggaggagacc ctgacagagt tcctctccaa ggctacaggg      360
actgctgttg attgggtgcc aatgcctggg atgaagcctg gtccggattc gtttggtatt      420
gtggccgttt cacatggttg ccgtggtgtt gctgcccgtg cctgtggttt ggtgaatcta      480
gaaccaacaa agatcgtgga gatcttaaaa gaccgcccat cttggttccg tgattgtcga      540
agtcttgaag tcttcacaat gtttccagct ggaaatggtg gcacgatcga acttgtttac      600
atgcagatgt atgctcctac tactttggtt cctgcacgag atttttggac acttagatac      660
acaactacaa tggaggatgg cagccttgtg gtctgtgaga gatcattgag tggttctgga      720
ggtggtccaa gtacagcctc cgcacagcaa tttgtaagag ctgagatgct tcctagcggc      780
tatctagtgc gcccatgcga gggtggtggc tccatcgtgc atattgtgga ccatctggat      840
cttgaggctt ggagtgttcc agaagtgctt cggccactct acgagtcatc tagggtagtt      900
gctcagaaaa tgactactgc agcngtgcgg cacatcagac aaattgctca agagacaagc      960
ggggaggttg tatacgcttt ggggaggcaa cctgctgttt tgcggacatt tagtcagagg     1020
ttgagtagag gcttcaatga tgctataagt ggtttcaatg atgatggttg gtctgtcatg     1080
ggtggggatg gcattgaaga tgtgatcatt gcttgcaatg caaagaa                   1127

<210> SEQ ID NO 173
<211> LENGTH: 375
<212> TYPE: PRT
<213> ORGANISM: Oryza sativa
<220> FEATURE:
<221> NAME/KEY: misc_feature
<222> LOCATION: (36)..(36)
<223> OTHER INFORMATION: Xaa can be any naturally occurring amino acid
<220> FEATURE:
<221> NAME/KEY: misc_feature
<222> LOCATION: (47)..(47)
<223> OTHER INFORMATION: Xaa can be any naturally occurring amino acid
<220> FEATURE:
<221> NAME/KEY: misc_feature
<222> LOCATION: (58)..(58)
<223> OTHER INFORMATION: Xaa can be any naturally occurring amino acid
<220> FEATURE:
<221> NAME/KEY: misc_feature
<222> LOCATION: (76)..(76)
<223> OTHER INFORMATION: Xaa can be any naturally occurring amino acid
<220> FEATURE:
<221> NAME/KEY: misc_feature
<222> LOCATION: (83)..(83)
<223> OTHER INFORMATION: Xaa can be any naturally occurring amino acid
<220> FEATURE:
<221> NAME/KEY: misc_feature
<222> LOCATION: (308)..(308)
<223> OTHER INFORMATION: Xaa can be any naturally occurring amino acid

<400> SEQUENCE: 173

Asp Cys Pro Ile Leu Ala Asn Ile Glu Pro Lys Gln Ile Lys Val Trp
1               5                   10                  15

Phe Gln Asn Arg Arg Cys Arg Asp Lys Gln Arg Lys Glu Ala Ser Arg
                20                  25                  30

Leu Gln Ala Xaa Asn Arg Lys Leu Thr Ala Met Asn Lys Leu Xaa Met
            35                  40                  45

Glu Glu Asn Glu Arg Leu Gln Lys Gln Xaa Ser Gln Leu Val His Glu
        50                  55                  60

Asn Ala Tyr Met Lys Gln Gln Leu Gln Asn Pro Xaa Leu Gly Asn Asp
```

```
                65                  70                  75                  80
Thr Ser Xaa Glu Ser Asn Val Thr Thr Pro Gln Asn Pro Leu Arg Asp
                85                  90                  95

Ala Ser Asn Pro Ser Gly Leu Leu Thr Ile Ala Glu Glu Thr Leu Thr
            100                 105                 110

Glu Phe Leu Ser Lys Ala Thr Gly Thr Ala Val Asp Trp Val Pro Met
        115                 120                 125

Pro Gly Met Lys Pro Gly Pro Asp Ser Phe Gly Ile Val Ala Val Ser
    130                 135                 140

His Gly Cys Arg Gly Val Ala Ala Arg Ala Cys Gly Leu Val Asn Leu
145                 150                 155                 160

Glu Pro Thr Lys Ile Val Glu Ile Leu Lys Asp Arg Pro Ser Trp Phe
                165                 170                 175

Arg Asp Cys Arg Ser Leu Glu Val Phe Thr Met Phe Pro Ala Gly Asn
            180                 185                 190

Gly Gly Thr Ile Glu Leu Val Tyr Met Gln Met Tyr Ala Pro Thr Thr
        195                 200                 205

Leu Val Pro Ala Arg Asp Phe Trp Thr Leu Arg Tyr Thr Thr Thr Met
    210                 215                 220

Glu Asp Gly Ser Leu Val Val Cys Glu Arg Ser Leu Ser Gly Ser Gly
225                 230                 235                 240

Gly Gly Pro Ser Thr Ala Ser Ala Gln Gln Phe Val Arg Ala Glu Met
                245                 250                 255

Leu Pro Ser Gly Tyr Leu Val Arg Pro Cys Glu Gly Gly Ser Ile
            260                 265                 270

Val His Ile Val Asp His Leu Asp Leu Glu Ala Trp Ser Val Pro Glu
        275                 280                 285

Val Leu Arg Pro Leu Tyr Glu Ser Ser Arg Val Val Ala Gln Lys Met
    290                 295                 300

Thr Thr Ala Xaa Val Arg His Ile Arg Gln Ile Ala Gln Glu Thr Ser
305                 310                 315                 320

Gly Glu Val Val Tyr Ala Leu Gly Arg Gln Pro Ala Val Leu Arg Thr
                325                 330                 335

Phe Ser Gln Arg Leu Ser Arg Gly Phe Asn Asp Ala Ile Ser Gly Phe
            340                 345                 350

Asn Asp Asp Gly Trp Ser Val Met Gly Gly Asp Gly Ile Glu Asp Val
        355                 360                 365

Ile Ile Ala Cys Asn Ala Lys
    370                 375

<210> SEQ ID NO 174
<211> LENGTH: 845
<212> TYPE: PRT
<213> ORGANISM: Artificial
<220> FEATURE:
<223> OTHER INFORMATION: Chimeric rice Rev1/Arabidopsis

<400> SEQUENCE: 174

Met Ala Ala Val Ala Met Leu Gly Ser Ser Ser Asp Gly Gly Gly
1               5                   10                  15

Tyr Asp Lys Val Ser Gly Met Asp Ser Gly Lys Tyr Val Arg Tyr Thr
            20                  25                  30

Pro Glu Gln Val Glu Ala Leu Glu Arg Val Tyr Ala Asp Cys Pro Lys
        35                  40                  45

Pro Thr Ser Ser Arg Arg Gln Gln Leu Leu Arg Glu Cys Pro Ile Leu
```

-continued

```
                 50                  55                  60
Ala Asn Ile Glu Pro Lys Gln Ile Lys Val Trp Phe Gln Asn Arg Arg
 65                  70                  75                  80

Cys Arg Asp Lys Gln Arg Lys Glu Ser Ser Arg Leu Gln Ala Val Asn
                     85                  90                  95

Arg Lys Leu Thr Ala Met Asn Lys Leu Leu Met Glu Glu Asn Glu Arg
                    100                 105                 110

Leu Gln Lys Gln Val Ser Gln Leu Val His Glu Asn Ala His Met Arg
                    115                 120                 125

Gln Gln Leu Gln Asn Thr Pro Leu Ala Asn Asp Thr Ser Cys Glu Ser
130                 135                 140

Asn Val Thr Thr Pro Gln Asn Pro Leu Arg Asp Ala Ser Asn Pro Ser
145                 150                 155                 160

Gly Leu Leu Ser Ile Ala Glu Glu Thr Leu Thr Glu Phe Leu Ser Lys
                    165                 170                 175

Ala Thr Gly Thr Ala Ile Asp Trp Val Gln Met Pro Gly Met Lys Pro
                    180                 185                 190

Gly Pro Asp Ser Val Gly Ile Val Ala Ile Ser His Gly Cys Pro Trp
                    195                 200                 205

Cys Cys Cys Arg Ala Cys Gly Leu Val Asn Leu Glu Pro Thr Lys Val
210                 215                 220

Val Glu Ile Leu Lys Asp Arg Pro Ser Trp Phe Arg Asp Cys Arg Asn
225                 230                 235                 240

Leu Glu Val Phe Thr Met Ile Pro Ala Gly Asn Gly Gly Thr Val Glu
                    245                 250                 255

Leu Val Tyr Thr Gln Leu Tyr Ala Pro Thr Thr Leu Val Pro Ala Arg
                    260                 265                 270

Asp Phe Trp Thr Leu Arg Tyr Thr Thr Thr Met Glu Asp Gly Ser Leu
                    275                 280                 285

Val Val Cys Glu Arg Ser Leu Ser Gly Ser Gly Gly Pro Ser Ala
                    290                 295                 300

Ala Ser Ala Gln Gln Tyr Val Arg Ala Glu Met Leu Pro Ser Gly Tyr
305                 310                 315                 320

Leu Val Arg Pro Cys Glu Gly Gly Ser Ile Val His Ile Val Asp
                    325                 330                 335

His Leu Asp Leu Glu Ala Trp Ser Val Pro Glu Val Leu Arg Pro Leu
                    340                 345                 350

Tyr Glu Ser Ser Arg Val Val Ala Gln Lys Met Thr Thr Ala Ala Leu
                    355                 360                 365

Arg His Ile Arg Gln Ile Ala Gln Glu Thr Ser Gly Glu Val Val Tyr
                    370                 375                 380

Ala Leu Gly Arg Gln Pro Ala Val Leu Arg Thr Phe Ser Gln Arg Leu
385                 390                 395                 400

Ser Arg Gly Phe Asn Asp Ala Ile Ser Gly Phe Asn Asp Asp Gly Trp
                    405                 410                 415

Ser Ile Met Gly Gly Asp Gly Val Glu Asp Val Val Ala Ile Asn Ser
                    420                 425                 430

Thr Lys His Leu Asn Asn Ile Ser Asn Ser Leu Ser Phe Leu Gly Gly
                    435                 440                 445

Val Leu Cys Ala Lys Ala Ser Met Leu Leu Gln Asn Val Pro Pro Ala
                    450                 455                 460

Val Leu Ile Arg Phe Leu Arg Glu His Arg Ser Glu Trp Ala Asp Phe
465                 470                 475                 480
```

Asn Val Asp Ala Tyr Ser Ala Ala Thr Leu Lys Ala Gly Ser Phe Ala
            485                 490                 495

Tyr Pro Gly Met Arg Pro Thr Arg Phe Thr Gly Ser Gln Ile Ile Met
            500                 505                 510

Pro Leu Gly His Thr Ile Glu His Glu Glu Met Leu Glu Val Val Arg
            515                 520                 525

Leu Glu Gly His Ser Leu Ala Gln Glu Asp Ala Phe Met Ser Arg Asp
            530                 535                 540

Val His Leu Leu Gln Ile Cys Thr Gly Ile Asp Glu Asn Ala Val Gly
545                 550                 555                 560

Ala Cys Ser Glu Leu Ile Phe Ala Pro Ile Asn Glu Met Phe Pro Asp
            565                 570                 575

Asp Ala Pro Leu Val Pro Ser Gly Phe Arg Val Ile Pro Val Asp Ala
            580                 585                 590

Lys Thr Gly Asp Val Gln Asp Leu Leu Thr Ala Asn His Arg Thr Leu
            595                 600                 605

Asp Leu Thr Ser Ser Leu Glu Val Gly Pro Ser Pro Glu Asn Ala Ser
            610                 615                 620

Gly Asn Ser Phe Ser Ser Ser Ser Arg Cys Ile Leu Thr Ile Ala
625                 630                 635                 640

Phe Gln Phe Pro Phe Glu Asn Asn Leu Gln Glu Asn Val Ala Gly Met
            645                 650                 655

Ala Cys Gln Tyr Val Arg Ser Val Ile Ser Ser Val Gln Arg Val Ala
            660                 665                 670

Met Ala Ile Ser Pro Ser Gly Ile Ser Pro Ser Leu Gly Ser Lys Leu
            675                 680                 685

Ser Pro Gly Ser Pro Glu Ala Val Thr Leu Ala Gln Trp Ile Ser Gln
            690                 695                 700

Ser Tyr Ser His His Leu Gly Ser Glu Leu Leu Thr Ile Asp Ser Leu
705                 710                 715                 720

Gly Ser Asp Asp Ser Val Leu Lys Leu Leu Trp Asp His Gln Asp Ala
            725                 730                 735

Ile Leu Cys Cys Ser Leu Lys Pro Gln Pro Val Phe Met Phe Ala Asn
            740                 745                 750

Gln Ala Gly Leu Asp Met Leu Glu Thr Thr Leu Val Ala Leu Gln Asp
            755                 760                 765

Ile Thr Leu Glu Lys Ile Phe Asp Glu Ser Gly Arg Lys Ala Ile Cys
            770                 775                 780

Ser Asp Phe Ala Lys Leu Met Gln Gln Gly Phe Ala Cys Leu Pro Ser
785                 790                 795                 800

Gly Ile Cys Val Ser Thr Met Gly Arg His Val Ser Tyr Glu Gln Ala
            805                 810                 815

Val Ala Trp Lys Val Phe Ala Ala Ser Glu Glu Asn Asn Asn Asn Leu
            820                 825                 830

His Cys Leu Ala Phe Ser Phe Val Asn Trp Ser Phe Val
            835                 840                 845

<210> SEQ ID NO 175
<211> LENGTH: 23
<212> TYPE: DNA
<213> ORGANISM: Artificial
<220> FEATURE:
<223> OTHER INFORMATION: primer

<400> SEQUENCE: 175

```
ggagccttga agttttcact atg                                    23
```

<210> SEQ ID NO 176
<211> LENGTH: 20
<212> TYPE: DNA
<213> ORGANISM: Artificial
<220> FEATURE:
<223> OTHER INFORMATION: primer

<400> SEQUENCE: 176

```
aggctgcctt cctaatccat                                        20
```

<210> SEQ ID NO 177
<211> LENGTH: 21
<212> TYPE: DNA
<213> ORGANISM: Artificial
<220> FEATURE:
<223> OTHER INFORMATION: primer

<400> SEQUENCE: 177

```
tgaggagcgt gatctcatca g                                      21
```

<210> SEQ ID NO 178
<211> LENGTH: 24
<212> TYPE: DNA
<213> ORGANISM: Artificial
<220> FEATURE:
<223> OTHER INFORMATION: primer

<400> SEQUENCE: 178

```
caaaattatc acatcattcc cttt                                   24
```

<210> SEQ ID NO 179
<211> LENGTH: 20
<212> TYPE: DNA
<213> ORGANISM: Artificial
<220> FEATURE:
<223> OTHER INFORMATION: primer

<400> SEQUENCE: 179

```
cgtctatgtc ctccccttcc                                        20
```

<210> SEQ ID NO 180
<211> LENGTH: 19
<212> TYPE: DNA
<213> ORGANISM: Artificial
<220> FEATURE:
<223> OTHER INFORMATION: primer

<400> SEQUENCE: 180

```
aacgttagca gctgcagga                                         19
```

<210> SEQ ID NO 181
<211> LENGTH: 20
<212> TYPE: DNA
<213> ORGANISM: Artificial
<220> FEATURE:
<223> OTHER INFORMATION: Histone H4 primer

<400> SEQUENCE: 181

```
tggaaaggga ggaaaaggtt                                        20
```

<210> SEQ ID NO 182
<211> LENGTH: 20
<212> TYPE: DNA

```
<213> ORGANISM: Artificial
<220> FEATURE:
<223> OTHER INFORMATION: Histone H4 primer

<400> SEQUENCE: 182
gccgaatccg taaagagtcc                                                     20

<210> SEQ ID NO 183
<211> LENGTH: 20
<212> TYPE: DNA
<213> ORGANISM: Artificial
<220> FEATURE:
<223> OTHER INFORMATION: primer

<400> SEQUENCE: 183
aacgagagca ttggttcaag                                                     20

<210> SEQ ID NO 184
<211> LENGTH: 20
<212> TYPE: DNA
<213> ORGANISM: Artificial
<220> FEATURE:
<223> OTHER INFORMATION: primer

<400> SEQUENCE: 184
caacgaaaga tatgagagag                                                     20

<210> SEQ ID NO 185
<211> LENGTH: 92
<212> TYPE: DNA
<213> ORGANISM: Lycopersicon esculentum

<400> SEQUENCE: 185
agctcgttgc gtcgacagca attgatccgt gaatgtcata ttctgtcgaa tatcgagcct         60
aagcagatca aagtttggtt tcagaacaga ag                                       92

<210> SEQ ID NO 186
<211> LENGTH: 160
<212> TYPE: DNA
<213> ORGANISM: Lycopersicon esculentum

<400> SEQUENCE: 186
gtgtcgagag aagcaaagga aagagtcttc tcgattgcag actgtgaaca gaaagttgtc         60
tgcgatgaat aaactgttga tggaggagaa tgaccgcttg cagaaacaag tctcgcagct        120
tgtatgtgaa aatggctata tgcggcaaca attgcaaaat                              160

<210> SEQ ID NO 187
<211> LENGTH: 86
<212> TYPE: DNA
<213> ORGANISM: Lycopersicon esculentum

<400> SEQUENCE: 187
gtatcggcgg ccactactga tgtaagttgt gaatcagggg taaccactcc tcagcattcc         60
cttagagatg ctaacaaccc tgctgg                                              86

<210> SEQ ID NO 188
<211> LENGTH: 91
<212> TYPE: DNA
<213> ORGANISM: Lycopersicon esculentum

<400> SEQUENCE: 188
actactacca attgcagaag aaaccttggc agagttcctt tctaaggcta caggaactgc         60
```
tgtcgattgg gtcccgatgc ctgggatgaa g					91

<210> SEQ ID NO 189
<211> LENGTH: 96
<212> TYPE: DNA
<213> ORGANISM: Lycopersicon esculentum

<400> SEQUENCE: 189
cctggtccgg attcagttgg gattttgcc atctcacaca gttgcagtgg agtggcagcc			60 cgagcatgtg gtcttgttag tttagagcca acaaag						96

<210> SEQ ID NO 190
<211> LENGTH: 114
<212> TYPE: DNA
<213> ORGANISM: Lycopersicon esculentum

<400> SEQUENCE: 190
attgctgata tcctcaaaga tcgaccttct tggttccgcg actgccggaa tgttgaagtt			60 atcacaatgt ttcctgctgg aaatggtggt acagttgagc ttttgtatac ccag			114

<210> SEQ ID NO 191
<211> LENGTH: 84
<212> TYPE: DNA
<213> ORGANISM: Lycopersicon esculentum

<400> SEQUENCE: 191
atatatgctc ccacaactct ggctcccgcg cgtgattttt ggacgctgag atacacaaca			60 accctagaca atggtagtct cgtg							84

<210> SEQ ID NO 192
<211> LENGTH: 156
<212> TYPE: DNA
<213> ORGANISM: Lycopersicon esculentum

<400> SEQUENCE: 192
gtttgtgaaa gatccctatc tggtaatggg cctggcccaa atcctactgc tgcttcccag			60 tttgtaagag ctcaaatgct tccatctgga tatctgatcc gaccgtgtga tggtggagga			120 tcaatcatac atattgttga tcacctgaat cttgag						156

<210> SEQ ID NO 193
<211> LENGTH: 75
<212> TYPE: DNA
<213> ORGANISM: Lycopersicon esculentum

<400> SEQUENCE: 193
gcatggagtg cccctgagat tttgcgtcca ctctatgaat cgtcgaaagt tgtggcacag			60 aaaatgacta ttgca								75

<210> SEQ ID NO 194
<211> LENGTH: 107
<212> TYPE: DNA
<213> ORGANISM: Lycopersicon esculentum

<400> SEQUENCE: 194
gcactgcgat atgcaaggca actagctcaa gagactagcg gcgaggtagt atatggtcta			60 ggaaggcaac ctgctgttcc tcgaacattc agccagagat tatgcag				107

<210> SEQ ID NO 195

```
<211> LENGTH: 175
<212> TYPE: DNA
<213> ORGANISM: Lycopersicon esculentum

<400> SEQUENCE: 195
agggttcaat gatgccatca atggattcgg tgacgatggc tggtcaatgt taagttcaga    60
tggtgctgaa gatgtcatag ttgctgtcaa ttcaaggaag aacctcgcaa ccacctccat   120
tcctctttcc ccgcttggtg gcgtcctttg taccaaagca tcaatgctac tccag        175

<210> SEQ ID NO 196
<211> LENGTH: 54
<212> TYPE: DNA
<213> ORGANISM: Lycopersicon esculentum

<400> SEQUENCE: 196
cagaatgtcc cccctgccgt actggttcgg tttctgaggg agcaccgttc agaa          54

<210> SEQ ID NO 197
<211> LENGTH: 42
<212> TYPE: PRT
<213> ORGANISM: Arabidopsis thaliana

<400> SEQUENCE: 197
```

Ile Lys Val Trp Phe Gln Asn Arg Arg Cys Arg Glu Lys Gln Arg Lys
1               5                  10                  15

Glu Ala Ala Arg Leu Gln Thr Val Asn Arg Lys Leu Asn Ala Met Asn
            20                  25                  30

Lys Leu Leu Met Glu Glu Asn Asp Arg Leu
        35                  40

```
<210> SEQ ID NO 198
<211> LENGTH: 42
<212> TYPE: PRT
<213> ORGANISM: Arabidopsis thaliana

<400> SEQUENCE: 198
```

Ile Lys Val Trp Phe Gln Asn Arg Arg Cys Arg Glu Lys Gln Arg Lys
1               5                  10                  15

Glu Ala Ser Arg Leu Gln Ala Val Asn Arg Lys Leu Thr Ala Met Asn
            20                  25                  30

Lys Leu Leu Met Glu Glu Asn Asp Arg Leu
        35                  40

```
<210> SEQ ID NO 199
<211> LENGTH: 42
<212> TYPE: PRT
<213> ORGANISM: Arabidopsis thaliana

<400> SEQUENCE: 199
```

Ile Lys Val Trp Phe Gln Asn Arg Arg Cys Arg Glu Lys Gln Arg Lys
1               5                  10                  15

Glu Ser Ala Arg Leu Gln Thr Val Asn Arg Lys Leu Ser Ala Met Asn
            20                  25                  30

Lys Leu Leu Met Glu Glu Asn Asp Arg Leu
        35                  40

```
<210> SEQ ID NO 200
<211> LENGTH: 42
<212> TYPE: PRT
<213> ORGANISM: plant
```

-continued

<400> SEQUENCE: 200

Ile Lys Val Trp Phe Gln Asn Arg Arg Cys Arg Glu Lys Gln Arg Lys
1               5                   10                  15

Glu Trp Cys Arg Leu Gln Ser Leu Asn Gly Lys Leu Thr Pro Ile Asn
            20                  25                  30

Thr Met Leu Met Glu Glu Asn Val Gln Leu
        35                  40

<210> SEQ ID NO 201
<211> LENGTH: 42
<212> TYPE: PRT
<213> ORGANISM: Arabidopsis thaliana

<400> SEQUENCE: 201

Ile Lys Val Trp Phe Gln Asn Arg Arg Cys Arg Glu Lys Gln Arg Lys
1               5                   10                  15

Glu Ala Ser Arg Leu Gln Ala Val Asn Arg Lys Leu Thr Ala Met Asn
            20                  25                  30

Lys Leu Leu Met Glu Glu Asn Asp Arg Leu
        35                  40

<210> SEQ ID NO 202
<211> LENGTH: 29
<212> TYPE: PRT
<213> ORGANISM: Arabidopsis thaliana

<400> SEQUENCE: 202

Asn Pro Ala Gly Leu Leu Ser Ile Ala Glu Glu Ala Leu Ala Glu Phe
1               5                   10                  15

Leu Ser Lys Ala Thr Gly Thr Ala Val Asp Trp Val Gln
            20                  25

<210> SEQ ID NO 203
<211> LENGTH: 29
<212> TYPE: PRT
<213> ORGANISM: Arabidopsis thaliana

<400> SEQUENCE: 203

Ser Pro Ala Gly Leu Leu Ser Ile Ala Asp Glu Thr Leu Thr Glu Phe
1               5                   10                  15

Ile Ser Lys Ala Thr Gly Thr Ala Val Glu Trp Val Gln
            20                  25

<210> SEQ ID NO 204
<211> LENGTH: 29
<212> TYPE: PRT
<213> ORGANISM: Arabidopsis thaliana

<400> SEQUENCE: 204

Asn Pro Ala Asn Leu Leu Ser Ile Ala Glu Glu Thr Leu Ala Glu Phe
1               5                   10                  15

Leu Cys Lys Ala Thr Gly Thr Ala Val Asp Trp Val Gln
            20                  25

<210> SEQ ID NO 205
<211> LENGTH: 29
<212> TYPE: PRT
<213> ORGANISM: plant

<400> SEQUENCE: 205

His Val Ala Gln Leu Val Thr Ile Asn His Ala Leu Arg Arg Gln Leu

```
                1               5                  10                  15
Ser Ser Thr Pro Ser His Phe Arg Phe Pro Thr Val Ser
            20                  25
```

<210> SEQ ID NO 206
<211> LENGTH: 29
<212> TYPE: PRT
<213> ORGANISM: Arabidopsis thaliana

<400> SEQUENCE: 206

```
Ser Pro Ala Gly Leu Leu Ser Ile Ala Glu Glu Thr Leu Ala Glu Phe
1               5                  10                  15
Leu Ser Lys Ala Thr Gly Thr Ala Val Glu Trp Val Gln
            20                  25
```

<210> SEQ ID NO 207
<211> LENGTH: 31
<212> TYPE: PRT
<213> ORGANISM: Arabidopsis thaliana

<400> SEQUENCE: 207

```
Val Leu Cys Ala Lys Ala Ser Met Leu Leu Gln Asn Val Pro Pro Ala
1               5                  10                  15
Val Leu Val Arg Phe Leu Arg Glu His Arg Ser Glu Trp Ala Asp
            20                  25                  30
```

<210> SEQ ID NO 208
<211> LENGTH: 31
<212> TYPE: PRT
<213> ORGANISM: Arabidopsis thaliana

<400> SEQUENCE: 208

```
Val Leu Cys Ala Lys Ala Ser Met Leu Leu Gln Asn Val Pro Pro Ser
1               5                  10                  15
Ile Leu Leu Arg Phe Leu Arg Glu His Arg Gln Glu Trp Ala Asp
            20                  25                  30
```

<210> SEQ ID NO 209
<211> LENGTH: 30
<212> TYPE: PRT
<213> ORGANISM: Arabidopsis thaliana

<400> SEQUENCE: 209

```
Val Leu Cys Ala Lys Ala Ser Met Leu Leu Gln Asn Val Pro Pro Leu
1               5                  10                  15
Val Leu Ile Arg Phe Leu Arg Glu His Arg Ala Glu Trp Ala
            20                  25                  30
```

<210> SEQ ID NO 210
<211> LENGTH: 31
<212> TYPE: PRT
<213> ORGANISM: plant
<220> FEATURE:
<221> NAME/KEY: misc_feature
<222> LOCATION: (21)..(31)
<223> OTHER INFORMATION: Xaa can be any naturally occurring amino acid

<400> SEQUENCE: 210

```
Leu Met Asn Ile Tyr Ala Ile Val Arg Leu Gln His Val Pro Ile Pro
1               5                  10                  15
Glu Cys Arg Ser Xaa Xaa Xaa Xaa Xaa Xaa Xaa Xaa Xaa Xaa Xaa
            20                  25                  30
```

<210> SEQ ID NO 211
<211> LENGTH: 31
<212> TYPE: PRT
<213> ORGANISM: Arabidopsis thaliana

<400> SEQUENCE: 211

Val Leu Cys Ala Lys Ala Ser Met Leu Leu Gln Asn Val Pro Pro Ala
1               5                   10                  15

Ile Leu Leu Arg Phe Leu Arg Glu His Arg Ser Glu Trp Ala Asp
            20                  25                  30

<210> SEQ ID NO 212
<211> LENGTH: 2588
<212> TYPE: DNA
<213> ORGANISM: Arabidopsis thaliana

<400> SEQUENCE: 212

```
atggagatgg cggtggctaa ccaccgtgag agaagcagtg acagtatgaa tagacattta      60
gatagtagcg gtaagtacgt taggtacaca gctgagcaag tcgaggctct tgagcgtgtc     120
tacgctgagt gtcctaagcc tagctctctc cgtcgacaac aattgatccg tgaatgttcc     180
attttggcca atattgagcc taagcagatc aaagtctggt ttcagaaccg caggtgtcga     240
gataagcaga ggaaagaggc gtcgaggctc cagagcgtaa accggaagct ctctgcgatg     300
aataaactgt tgatggagga gaatgatagg ttgcagaagc aggtttctca gcttgtctgc     360
gaaaatggat atatgaaaca gcagctaact actgttgtta acgatccaag ctgtgaatct     420
gtggtcacaa ctcctcagca ttcgcttaga gatgcgaata gtcctgctgg attgcttggt     480
tttggtctta gattgctctc aatcgcagag gagactttgg cagagttcct atccaaggct     540
acaggaactg ctgttgattg ggttcagatg cctgggatga agtgtgttgt agcctggtcc     600
ggattcggtt ggcatctttg ccatttcgca aagatgcaat ggagtggcag ctcgagcctg     660
tggtcttgtt agcttagaac ctatgaagat tgcagagatc ctcaaagatc ggccatcttg     720
gttccgtgac tgtaggagcc ttgaagtttt cactatgttc ccggctggta atggtggcac     780
aatcgagctt gtttatatgc agacgtatgc accaacgact ctggctcctg cccgcgattt     840
ctggaccctg agatacacaa cgagcctcga caatgggagt tttgtggttt gtgagaggtc     900
gctatctggc tctggagctg ggcctaatgc tgcttcagct tctcagtttg tgagagcaga     960
aatgctttct agtgggtatt taataaggcc ttgtgatggt ggtggttcta ttattcacat    1020
tgtcgatcac cttaatcttg aggcttggag tgttccggat gtgcttcgac cccttttatga    1080
gtcatccaaa gtcgttgcac aaaaaatgac catttccgcg ttgcggtata tcaggcaatt    1140
agcccaagag tctaatggtg aagtagtgta tggattagga aggcagcctg ctgttcttag    1200
aacctttagc caaagattaa gcaggggctt caatgatgcg gttaatgggt tggtgacgag    1260
cgggtggtct acgatgcatt gtgatggagc ggaagatatt atcgttgcta ttaactctac    1320
aaagcatttg aataatattt ctaattctct ttcgttcctt ggaggcgtgc tctgtgccaa    1380
ggcttcaatg cttctccaaa atgttcctcc tgccgttttg atccggttcc ttagagagca    1440
tcgatctgag tgggctgatt tcaatgttga tgcatattcc gctgctacac ttaaagctgg    1500
tagctttgct tatccgggaa tgagaccaac aagattcact gggagtcaga tcataatgcc    1560
actaggacat acaattgaac acgaagaaat gtttagatgc tagaagttgt tagactggaa    1620
ggtcattctc ttgctcaaga agatgcattt atgtcacggg atgtccatct ccttcagatt    1680
tgtaccggga ttgacgagaa tgccgttgga gcttgttctg aactgatatt tgctccgatt    1740
```

-continued

```
aatgagatgt tcccggatga tgctccactt gttccctctg gattccgagt catacccgtt    1800
gatgctaaaa cgggagatgt acaagatctg ttaaccgcta atcaccgtac actagactta    1860
acttctagcc ttgaagtcgg tccatcacct gagaatgctt ctggaaactc tttttctagc    1920
tcaagctcga gatgtattct cactatcgcg tttcaattcc cttttgaaaa caacttgcaa    1980
gaaaatgttg ctggtatggc ttgtcagtat gtgaggagcg tgatctcatc agttcaacgt    2040
gttgcaatgg cgatctcacc gtctgggata agcccgagtc tgggctccaa attgtcccca    2100
ggatctcctg aagctgttac tcttgctcag tggatctctc aaagttacag atgctgatat    2160
gtttgttttt ccagtcatca cttaggctcg gagttgctga cgattgattc acttggaagc    2220
gacgactcgg tactaaaact tctatgggat caccaagatg ccatcctgtg ttgctcatta    2280
aagccacagc cagtgttcat gtttgcgaac caagctggtc tagacatgct agagacaaca    2340
cttgtagcct tacaagatat aacactcgaa aagatattcg atgaatcggg tcgtaaggct    2400
atctgttcgg acttcgccaa gctaatgcaa caggatttgc ttgcttgcct tcaggaatct    2460
gtgtgtcaac gatgggaaga catgtgagtt atgaacaagc tgttgcttgg aaagtgtttg    2520
ctgcatctga agaaacaac aacaatctgc attgtcttgc cttctccttt gtaaactggt    2580
cttttgtg                                                             2588
```

<210> SEQ ID NO 213
<211> LENGTH: 8
<212> TYPE: PRT
<213> ORGANISM: Artificial
<220> FEATURE:
<223> OTHER INFORMATION: Amino acid sequence encoded by redundant primer

<400> SEQUENCE: 213

Arg Gln Gln Leu Ile Arg Glu Cys
1               5

<210> SEQ ID NO 214
<211> LENGTH: 10
<212> TYPE: PRT
<213> ORGANISM: Artificial
<220> FEATURE:
<223> OTHER INFORMATION: Amino acid sequence encoded by redundant primer

<400> SEQUENCE: 214

Glu Arg Val Tyr Cys Glu Cys Pro Lys Pro
1               5                   10

<210> SEQ ID NO 215
<211> LENGTH: 8
<212> TYPE: PRT
<213> ORGANISM: Artificial
<220> FEATURE:
<223> OTHER INFORMATION: Amino acid sequence encoded by redundant primer

<400> SEQUENCE: 215

Arg Tyr Thr Pro Glu Gln Val Glu
1               5

<210> SEQ ID NO 216
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 216

```
Arg Tyr Thr Pro Glu Gln Val Glu Ala
1               5

<210> SEQ ID NO 217
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 217

Glu Arg Val Tyr Cys Glu Cys Pro Lys
1               5

<210> SEQ ID NO 218
<211> LENGTH: 10
<212> TYPE: PRT
<213> ORGANISM: Artificial
<220> FEATURE:
<223> OTHER INFORMATION: Amino acid sequence encoded by redundant primer

<400> SEQUENCE: 218

Glu Arg Val Tyr Cys Glu Cys Pro Lys Pro
1               5                   10

<210> SEQ ID NO 219
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 219

Pro Ser Ser Leu Arg Arg Gln Gln Leu
1               5

<210> SEQ ID NO 220
<211> LENGTH: 7
<212> TYPE: PRT
<213> ORGANISM: Artificial
<220> FEATURE:
<223> OTHER INFORMATION: Amino acid sequence encoded by redundant primer

<400> SEQUENCE: 220

Leu Arg Arg Gln Gln Leu Ile
1               5

<210> SEQ ID NO 221
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 221

Gly Lys Tyr Val Arg Tyr Thr Pro Glu
1               5

<210> SEQ ID NO 222
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 222
```

```
Lys Tyr Val Arg Tyr Thr Pro Glu Gln
1               5
```

<210> SEQ ID NO 223
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 223

```
Tyr Val Arg Tyr Thr Pro Glu Gln Val
1               5
```

<210> SEQ ID NO 224
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 224

```
Val Arg Tyr Thr Pro Glu Gln Val Glu
1               5
```

<210> SEQ ID NO 225
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 225

```
Glu Gln Val Glu Ala Leu Glu Arg Val
1               5
```

<210> SEQ ID NO 226
<211> LENGTH: 10
<212> TYPE: PRT
<213> ORGANISM: Artificial
<220> FEATURE:
<223> OTHER INFORMATION: Amino acid sequence encoded by redundant primer

<400> SEQUENCE: 226

```
Gln Val Glu Ala Leu Glu Arg Val Tyr Cys
1               5                   10
```

<210> SEQ ID NO 227
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 227

```
Met Asn Lys Met Leu Met Glu Glu Asn
1               5
```

<210> SEQ ID NO 228
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 228

```
Arg Leu Gln Ser Val Asn Arg Lys Leu
```

<210> SEQ ID NO 229
<211> LENGTH: 10
<212> TYPE: PRT
<213> ORGANISM: Artificial
<220> FEATURE:
<223> OTHER INFORMATION: Amino acid sequence encoded by redundant primer

<400> SEQUENCE: 229

Thr Ala Met Asn Lys Met Leu Met Glu Glu
1               5                   10

<210> SEQ ID NO 230
<211> LENGTH: 10
<212> TYPE: PRT
<213> ORGANISM: Artificial
<220> FEATURE:
<223> OTHER INFORMATION: Amino acid sequence encoded by redundant primer

<400> SEQUENCE: 230

Ala Met Asn Lys Met Leu Met Glu Glu Asn
1               5                   10

<210> SEQ ID NO 231
<211> LENGTH: 12
<212> TYPE: PRT
<213> ORGANISM: Artificial
<220> FEATURE:
<223> OTHER INFORMATION: Amino acid sequence encoded by redundant primer

<400> SEQUENCE: 231

Met Asn Lys Met Leu Met Leu Met Glu Glu Asn Asp
1               5                   10

<210> SEQ ID NO 232
<211> LENGTH: 8
<212> TYPE: PRT
<213> ORGANISM: Artificial
<220> FEATURE:
<223> OTHER INFORMATION: Amino acid sequence encoded by redundant primer

<400> SEQUENCE: 232

Trp Phe Gln Asn Arg Arg Cys Arg
1               5

<210> SEQ ID NO 233
<211> LENGTH: 10
<212> TYPE: PRT
<213> ORGANISM: Artificial
<220> FEATURE:
<223> OTHER INFORMATION: Amino acid sequence encoded by redundant primer

<400> SEQUENCE: 233

Asn Arg Lys Leu Thr Ala Met Asn Lys Met
1               5                   10

<210> SEQ ID NO 234
<211> LENGTH: 8
<212> TYPE: PRT
<213> ORGANISM: Artificial
<220> FEATURE:
<223> OTHER INFORMATION: Amino acid sequence encoded by redundant primer

<400> SEQUENCE: 234

Lys Val Trp Phe Gln Asn Arg Arg
1               5

<210> SEQ ID NO 235
<211> LENGTH: 8
<212> TYPE: PRT
<213> ORGANISM: Artificial
<220> FEATURE:
<223> OTHER INFORMATION: Amino acid sequence encoded by redundant primer

<400> SEQUENCE: 235

Val Trp Phe Gln Asn Arg Arg Cys
1               5

<210> SEQ ID NO 236
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 236

Lys Ala Ser Met Leu Leu Gln Asn Val
1               5

<210> SEQ ID NO 237
<211> LENGTH: 10
<212> TYPE: PRT
<213> ORGANISM: Artificial
<220> FEATURE:
<223> OTHER INFORMATION: Amino acid sequence encoded by redundant primer

<400> SEQUENCE: 237

Lys Ala Ser Met Leu Leu Gln Asn Val Pro
1               5                   10

<210> SEQ ID NO 238
<211> LENGTH: 8
<212> TYPE: PRT
<213> ORGANISM: Artificial
<220> FEATURE:
<223> OTHER INFORMATION: Amino acid sequence encoded by redundant primer

<400> SEQUENCE: 238

Ser Met Leu Leu Gln Asn Val Pro
1               5

<210> SEQ ID NO 239
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 239

Ala Val Cys Ile Arg Phe Leu Arg Glu
1               5

<210> SEQ ID NO 240
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 240

Val Cys Ile Arg Phe Leu Arg Glu His
1               5

```
<210> SEQ ID NO 241
<211> LENGTH: 10
<212> TYPE: PRT
<213> ORGANISM: Artificial
<220> FEATURE:
<223> OTHER INFORMATION: Amino acid sequence encoded by redundant primer

<400> SEQUENCE: 241

Val Cys Ile Arg Phe Leu Arg Glu His Arg
1               5                   10

<210> SEQ ID NO 242
<211> LENGTH: 8
<212> TYPE: PRT
<213> ORGANISM: Artificial
<220> FEATURE:
<223> OTHER INFORMATION: Amino acid sequence encoded by redundant primer

<400> SEQUENCE: 242

Arg Glu His Arg Ser Glu Trp Ala
1               5

<210> SEQ ID NO 243
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 243

Arg Glu His Arg Ser Glu Trp Ala Asp
1               5

<210> SEQ ID NO 244
<211> LENGTH: 8
<212> TYPE: PRT
<213> ORGANISM: Artificial
<220> FEATURE:
<223> OTHER INFORMATION: Amino acid sequence encoded by redundant primer

<400> SEQUENCE: 244

Glu His Arg Ser Glu Trp Ala Asp
1               5

<210> SEQ ID NO 245
<211> LENGTH: 7
<212> TYPE: PRT
<213> ORGANISM: Artificial
<220> FEATURE:
<223> OTHER INFORMATION: Amino acid sequence encoded by redundant primer

<400> SEQUENCE: 245

Gln Asn Val Pro Pro Ala Val
1               5

<210> SEQ ID NO 246
<211> LENGTH: 9
<212> TYPE: PRT
<213> ORGANISM: Artificial
<220> FEATURE:
<223> OTHER INFORMATION: Amino acid sequence encoded by redundant primer

<400> SEQUENCE: 246

Phe Leu Arg Glu His Arg Ser Glu Trp
1               5
```

<210> SEQ ID NO 247
<211> LENGTH: 794
<212> TYPE: PRT
<213> ORGANISM: Arabidopsis thaliana

<400> SEQUENCE: 247

```
Met Ala Met Ser Cys Lys Asp Gly Lys Leu Gly Cys Leu Asp Asn Gly
1               5                   10                  15
Lys Tyr Val Arg Tyr Thr Pro Glu Gln Val Glu Ala Leu Glu Arg Leu
                20                  25                  30
Tyr His Asp Cys Pro Lys Pro Ser Ser Ile Arg Arg Gln Gln Leu Ile
            35                  40                  45
Arg Glu Cys Pro Ile Leu Ser Asn Ile Glu Pro Lys Gln Ile Lys Val
50                  55                  60
Trp Phe Gln Asn Arg Arg Cys Arg Glu Lys Gln Arg Lys Glu Ala Ser
65                  70                  75                  80
Arg Leu Gln Ala Val Asn Arg Lys Leu Thr Ala Met Asn Lys Leu Leu
                85                  90                  95
Met Glu Glu Asn Asp Arg Leu Gln Lys Gln Val Ser Gln Leu Val His
            100                 105                 110
Glu Asn Ser Tyr Phe Arg Gln His Thr Pro Asn Pro Ser Leu Pro Ala
        115                 120                 125
Lys Asp Thr Ser Cys Glu Ser Val Val Thr Ser Gly Gln His Gln Leu
130                 135                 140
Ala Ser Gln Asn Pro Gln Arg Asp Ala Ser Pro Ala Gly Leu Leu Ser
145                 150                 155                 160
Ile Ala Glu Glu Thr Leu Ala Glu Phe Leu Ser Lys Ala Thr Gly Thr
                165                 170                 175
Ala Val Glu Trp Val Gln Met Pro Gly Met Lys Pro Gly Pro Asp Ser
            180                 185                 190
Ile Gly Ile Ile Ala Ile Ser His Gly Cys Thr Gly Val Ala Ala Arg
        195                 200                 205
Ala Cys Gly Leu Val Gly Leu Glu Pro Thr Arg Val Ala Glu Ile Val
210                 215                 220
Lys Asp Arg Pro Ser Trp Phe Arg Glu Cys Arg Ala Val Glu Val Met
225                 230                 235                 240
Asn Val Leu Pro Thr Ala Asn Gly Gly Thr Val Glu Leu Leu Tyr Met
                245                 250                 255
Gln Leu Tyr Ala Pro Thr Thr Leu Ala Pro Pro Arg Asp Phe Trp Leu
            260                 265                 270
Leu Arg Tyr Thr Ser Val Leu Glu Asp Gly Ser Leu Val Val Cys Glu
        275                 280                 285
Arg Ser Leu Lys Ser Thr Gln Asn Gly Pro Ser Met Pro Leu Val Gln
290                 295                 300
Asn Phe Val Arg Ala Glu Met Leu Ser Ser Gly Tyr Leu Ile Arg Pro
305                 310                 315                 320
Cys Asp Gly Gly Gly Ser Ile Ile His Ile Val Asp His Met Asp Leu
                325                 330                 335
Glu Ala Cys Ser Val Pro Glu Val Leu Arg Pro Leu Tyr Glu Ser Pro
            340                 345                 350
Lys Val Leu Ala Gln Lys Thr Thr Met Ala Ala Leu Arg Gln Leu Lys
        355                 360                 365
Gln Ile Ala Gln Glu Val Thr Gln Thr Asn Ser Ser Val Asn Gly Trp
370                 375                 380
```

```
Gly Arg Arg Pro Ala Ala Leu Arg Ala Leu Ser Gln Arg Leu Ser Arg
385                 390                 395                 400

Gly Phe Asn Glu Ala Val Asn Gly Phe Thr Asp Glu Gly Trp Ser Val
            405                 410                 415

Ile Gly Asp Ser Met Asp Val Thr Ile Thr Val Asn Ser Ser Pro
                420                 425                 430

Asp Lys Leu Met Gly Leu Asn Leu Thr Phe Ala Asn Gly Phe Ala Pro
            435                 440                 445

Val Ser Asn Val Val Leu Cys Ala Lys Ala Ser Met Leu Leu Gln Asn
        450                 455                 460

Val Pro Pro Ala Ile Leu Leu Arg Phe Leu Arg Glu His Arg Ser Glu
465                 470                 475                 480

Trp Ala Asp Asn Asn Ile Asp Ala Tyr Leu Ala Ala Val Lys Val
                485                 490                 495

Gly Pro Cys Ser Ala Arg Val Gly Gly Phe Gly Gly Gln Val Ile Leu
                500                 505                 510

Pro Leu Ala His Thr Ile Glu His Glu Glu Phe Met Glu Val Ile Lys
            515                 520                 525

Leu Glu Gly Leu Gly His Ser Pro Glu Asp Ala Ile Val Pro Arg Asp
530                 535                 540

Ile Phe Leu Leu Gln Leu Cys Ser Gly Met Asp Glu Asn Ala Val Gly
545                 550                 555                 560

Thr Cys Ala Glu Leu Ile Phe Ala Pro Ile Asp Ala Ser Phe Ala Asp
                565                 570                 575

Asp Ala Pro Leu Leu Pro Ser Gly Phe Arg Ile Ile Pro Leu Asp Ser
            580                 585                 590

Ala Lys Glu Val Ser Ser Pro Asn Arg Thr Leu Asp Leu Ala Ser Ala
        595                 600                 605

Leu Glu Ile Gly Ser Ala Gly Thr Lys Ala Ser Thr Asp Gln Ser Gly
610                 615                 620

Asn Ser Thr Cys Ala Arg Ser Val Met Thr Ile Ala Phe Glu Phe Gly
625                 630                 635                 640

Ile Glu Ser His Met Gln Glu His Val Ala Ser Met Ala Arg Gln Tyr
                645                 650                 655

Val Arg Gly Ile Ile Ser Ser Val Gln Arg Val Ala Leu Ala Leu Ser
                660                 665                 670

Pro Ser His Ile Ser Ser Gln Val Gly Leu Arg Thr Pro Leu Gly Thr
            675                 680                 685

Pro Glu Ala Gln Thr Leu Ala Arg Trp Ile Cys Gln Ser Tyr Arg Gly
690                 695                 700

Tyr Met Gly Val Glu Leu Leu Lys Ser Asn Ser Asp Gly Asn Glu Ser
705                 710                 715                 720

Ile Leu Lys Asn Leu Trp His His Thr Asp Ala Ile Ile Cys Cys Ser
                725                 730                 735

Met Lys Ala Leu Pro Val Phe Thr Phe Ala Asn Gln Ala Gly Leu Asp
            740                 745                 750

Met Leu Glu Thr Thr Leu Val Ala Leu Gln Asp Ile Ser Leu Glu Lys
        755                 760                 765

Ile Phe Asp Asp Asn Gly Arg Lys Thr Leu Cys Ser Glu Phe Pro Gln
        770                 775                 780

Ile Met Gln Gln Val Leu Arg Asn Ile Phe
785                 790
```

-continued

<210> SEQ ID NO 248
<211> LENGTH: 833
<212> TYPE: PRT
<213> ORGANISM: Arabidopsis thaliana

<400> SEQUENCE: 248

```
Met Gly Gly Gly Ser Asn Asn Ser His Asn Met Asp Asn Gly Lys Tyr
1               5                   10                  15

Val Arg Tyr Thr Pro Glu Gln Val Glu Ala Leu Glu Arg Leu Tyr Asn
            20                  25                  30

Asp Cys Pro Lys Pro Ser Ser Met Arg Arg Gln Gln Leu Ile Arg Glu
        35                  40                  45

Cys Pro Ile Leu Ser Asn Ile Glu Pro Lys Gln Ile Lys Val Trp Phe
    50                  55                  60

Gln Asn Arg Arg Cys Arg Glu Lys Gln Arg Lys Glu Ala Ser Arg Leu
65                  70                  75                  80

Gln Ala Val Asn Arg Lys Leu Thr Ala Met Asn Lys Leu Leu Met Glu
                85                  90                  95

Glu Asn Asp Arg Leu Gln Lys Gln Val Ser His Leu Val Tyr Glu Asn
            100                 105                 110

Ser Tyr Phe Arg Gln His Pro Gln Asn Gln Gly Asn Leu Ala Thr Thr
        115                 120                 125

Asp Thr Ser Cys Glu Ser Val Val Thr Ser Gly Gln His His Leu Thr
    130                 135                 140

Pro Gln His Gln Pro Arg Asp Ala Ser Pro Ala Gly Leu Leu Ser Ile
145                 150                 155                 160

Ala Asp Glu Thr Leu Thr Glu Phe Ile Ser Lys Ala Thr Gly Thr Ala
                165                 170                 175

Val Glu Trp Val Gln Met Pro Gly Met Lys Pro Gly Pro Asp Ser Ile
            180                 185                 190

Gly Ile Val Ala Ile Ser His Gly Cys Thr Gly Ile Ala Ala Arg Ala
        195                 200                 205

Cys Gly Leu Val Gly Leu Asp Pro Thr Arg Val Ala Glu Ile Leu Lys
    210                 215                 220

Asp Lys Pro Cys Trp Leu Arg Asp Cys Arg Ser Leu Asp Ile Val Asn
225                 230                 235                 240

Val Leu Ser Thr Ala Asn Gly Gly Thr Leu Glu Leu Ile Tyr Met Gln
                245                 250                 255

Leu Tyr Ala Pro Thr Thr Leu Ala Pro Ala Arg Asp Phe Trp Met Leu
            260                 265                 270

Arg Tyr Thr Ser Val Met Glu Asp Gly Ser Leu Val Ile Cys Glu Arg
        275                 280                 285

Ser Leu Asn Asn Thr Gln Asn Gly Pro Ser Met Pro Pro Ser Pro His
    290                 295                 300

Phe Val Arg Ala Glu Ile Leu Pro Ser Gly Tyr Leu Ile Arg Pro Cys
305                 310                 315                 320

Glu Gly Gly Gly Ser Ile Leu His Ile Val Asp His Phe Asp Leu Glu
                325                 330                 335

Pro Trp Ser Val Pro Glu Val Leu Arg Ser Leu Tyr Glu Ser Ser Thr
            340                 345                 350

Leu Leu Ala Gln Arg Thr Met Ala Ala Leu Arg Tyr Leu Arg Gln
        355                 360                 365

Ile Ser Gln Glu Ile Ser Gln Pro Asn Val Thr Gly Trp Gly Arg Arg
    370                 375                 380
```

-continued

```
Pro Ala Leu Arg Ala Leu Ser Gln Arg Leu Ser Lys Gly Phe Asn
385                 390                 395                 400

Glu Ala Val Asn Gly Phe Ser Asp Glu Gly Trp Ser Ile Leu Glu Ser
                405                 410                 415

Asp Gly Ile Asp Asp Val Thr Leu Leu Val Asn Ser Ser Pro Thr Lys
            420                 425                 430

Met Met Met Thr Ser Ser Leu Pro Phe Ala Asn Gly Tyr Thr Ser Met
        435                 440                 445

Pro Ser Ala Val Leu Cys Ala Lys Ala Ser Met Leu Leu Gln Asn Val
    450                 455                 460

Pro Pro Ser Ile Leu Leu Arg Phe Leu Arg Glu His Arg Gln Glu Trp
465                 470                 475                 480

Ala Asp Asn Ser Ile Asp Ala Tyr Ser Ala Ala Ile Lys Ala Gly
                485                 490                 495

Pro Cys Ser Leu Pro Ile Pro Arg Pro Gly Ser Phe Gly Gly Gln Val
            500                 505                 510

Ile Leu Pro Leu Ala His Thr Ile Glu Asn Glu Glu Phe Met Glu Val
        515                 520                 525

Ile Lys Leu Glu Ser Leu Gly His Tyr Gln Glu Asp Met Met Met Pro
    530                 535                 540

Ala Asp Ile Phe Leu Leu Gln Met Cys Ser Gly Val Asp Glu Asn Ala
545                 550                 555                 560

Val Glu Ser Cys Ala Glu Leu Ile Phe Ala Pro Ile Asp Ala Ser Phe
                565                 570                 575

Ser Asp Asp Ala Pro Ile Ile Pro Ser Gly Phe Arg Ile Ile Pro Leu
            580                 585                 590

Asp Ser Lys Ser Glu Gly Leu Ser Pro Asn Arg Thr Leu Asp Leu Ala
        595                 600                 605

Ser Ala Leu Asp Val Gly Ser Arg Thr Ala Gly Asp Ser Cys Gly Ser
    610                 615                 620

Arg Gly Asn Ser Lys Ser Val Met Thr Ile Ala Phe Gln Leu Ala Phe
625                 630                 635                 640

Glu Met His Met Gln Glu Asn Val Ala Ser Met Ala Arg Gln Tyr Val
                645                 650                 655

Arg Ser Val Ile Ala Ser Val Gln Arg Val Ala Leu Ala Leu Ser Pro
            660                 665                 670

Ser Ser His Gln Leu Ser Gly Leu Arg Pro Pro Ala Ser Pro Glu
        675                 680                 685

Ala His Thr Leu Ala Arg Trp Ile Ser His Ser Tyr Arg Cys Tyr Leu
    690                 695                 700

Gly Val Asp Leu Leu Lys Pro His Gly Thr Asp Leu Leu Lys Ser Leu
705                 710                 715                 720

Trp His His Pro Asp Ala Val Met Cys Cys Ser Leu Lys Ala Leu Ser
                725                 730                 735

Pro Val Phe Thr Phe Ala Asn Gln Ala Gly Leu Asp Met Leu Glu Thr
            740                 745                 750

Thr Leu Val Ala Leu Gln Asp Ile Thr Leu Asp Lys Ile Phe Asp Asn
        755                 760                 765

Asn Asn Gly Lys Lys Thr Leu Ser Ser Glu Phe Pro Gln Ile Met Gln
    770                 775                 780

Gln Gly Phe Met Cys Met Asp Gly Gly Ile Cys Met Ser Ser Met Gly
785                 790                 795                 800

Arg Ala Val Thr Tyr Glu Lys Ala Val Gly Trp Lys Val Leu Asn Asp
```

-continued

```
                805                 810                 815
Asp Glu Asp Pro His Cys Ile Cys Phe Met Phe Leu Asn Trp Ser Phe
            820                 825                 830

Ile

<210> SEQ ID NO 249
<211> LENGTH: 841
<212> TYPE: PRT
<213> ORGANISM: Arabidopsis thaliana

<400> SEQUENCE: 249

Met Met Ala His His Ser Met Asp Asp Arg Asp Ser Pro Asp Lys Gly
1               5                   10                  15

Phe Asp Ser Gly Lys Tyr Val Arg Tyr Thr Pro Glu Gln Val Glu Ala
            20                  25                  30

Leu Glu Arg Val Tyr Ala Glu Cys Pro Lys Pro Ser Ser Leu Arg Arg
        35                  40                  45

Gln Gln Leu Ile Arg Glu Cys Pro Ile Leu Cys Asn Ile Glu Pro Arg
    50                  55                  60

Gln Ile Lys Val Trp Phe Gln Asn Arg Arg Cys Arg Glu Lys Gln Arg
65                  70                  75                  80

Lys Glu Ser Ala Arg Leu Gln Thr Val Asn Arg Lys Leu Ser Ala Met
                85                  90                  95

Asn Lys Leu Leu Met Glu Glu Asn Asp Arg Leu Gln Lys Gln Val Ser
            100                 105                 110

Asn Leu Val Tyr Glu Asn Gly Phe Met Lys His Arg Ile His Thr Ala
        115                 120                 125

Ser Gly Thr Thr Thr Asp Asn Ser Cys Glu Ser Val Val Val Ser Gly
    130                 135                 140

Gln Gln Arg Gln Gln Gln Asn Pro Thr His Gln His Pro Gln Arg Asp
145                 150                 155                 160

Val Asn Asn Pro Ala Asn Leu Leu Ser Ile Ala Glu Glu Thr Leu Ala
                165                 170                 175

Glu Phe Leu Cys Lys Ala Thr Gly Thr Ala Val Asp Trp Val Gln Met
            180                 185                 190

Ile Gly Met Lys Pro Gly Pro Asp Ser Ile Gly Ile Val Ala Val Ser
        195                 200                 205

Arg Asn Cys Ser Gly Ile Ala Ala Arg Ala Cys Gly Leu Val Ser Leu
    210                 215                 220

Glu Pro Met Lys Val Ala Glu Ile Leu Lys Asp Arg Pro Ser Trp Phe
225                 230                 235                 240

Arg Asp Cys Arg Cys Val Glu Thr Leu Asn Val Ile Pro Thr Gly Asn
                245                 250                 255

Gly Gly Thr Ile Glu Leu Val Asn Thr Gln Ile Tyr Ala Pro Thr Thr
            260                 265                 270

Leu Ala Ala Ala Arg Asp Phe Trp Thr Leu Arg Tyr Ser Thr Ser Leu
        275                 280                 285

Glu Asp Gly Ser Tyr Val Val Cys Glu Arg Ser Leu Thr Ser Ala Thr
    290                 295                 300

Gly Gly Pro Asn Gly Pro Leu Ser Ser Ser Phe Val Arg Ala Lys Met
305                 310                 315                 320

Leu Ser Ser Gly Phe Leu Ile Arg Pro Cys Asp Gly Gly Ser Ile
                325                 330                 335

Ile His Ile Val Asp His Val Asp Leu Asp Val Ser Ser Val Pro Glu
```

-continued

```
            340                 345                 350
Val Leu Arg Pro Leu Tyr Glu Ser Ser Lys Ile Leu Ala Gln Lys Met
            355                 360                 365
Thr Val Ala Ala Leu Arg His Val Arg Gln Ile Ala Gln Glu Thr Ser
            370                 375                 380
Gly Glu Val Gln Tyr Ser Gly Arg Gln Pro Ala Val Leu Arg Thr
385                 390                 395                 400
Phe Ser Gln Arg Leu Cys Arg Gly Phe Asn Asp Ala Val Asn Gly Phe
                    405                 410                 415
Val Asp Asp Gly Trp Ser Pro Met Ser Ser Asp Gly Gly Glu Asp Ile
                420                 425                 430
Thr Ile Met Ile Asn Ser Ser Ser Ala Lys Phe Ala Gly Ser Gln Tyr
            435                 440                 445
Gly Ser Ser Phe Leu Pro Ser Phe Gly Ser Gly Val Leu Cys Ala Lys
            450                 455                 460
Ala Ser Met Leu Leu Gln Asn Val Pro Pro Leu Val Leu Ile Arg Phe
465                 470                 475                 480
Leu Arg Glu His Arg Ala Glu Trp Ala Asp Tyr Gly Val Asp Ala Tyr
                    485                 490                 495
Ser Ala Ala Ser Leu Arg Ala Thr Pro Tyr Ala Val Pro Cys Val Arg
                500                 505                 510
Thr Gly Gly Phe Pro Ser Asn Gln Val Ile Leu Pro Leu Ala Gln Thr
            515                 520                 525
Leu Glu His Glu Glu Phe Leu Glu Val Val Arg Leu Gly Gly His Ala
            530                 535                 540
Tyr Ser Pro Glu Asp Met Gly Leu Ser Arg Asp Met Tyr Leu Leu Gln
545                 550                 555                 560
Leu Cys Ser Gly Val Asp Glu Asn Val Val Gly Gly Cys Ala Gln Leu
                    565                 570                 575
Val Phe Ala Pro Ile Asp Glu Ser Phe Ala Asp Ala Pro Leu Leu
                580                 585                 590
Pro Ser Gly Phe Arg Val Ile Pro Leu Asp Gln Lys Thr Asn Pro Asn
            595                 600                 605
Asp His Gln Ser Ala Ser Arg Thr Arg Asp Leu Ala Ser Ser Leu Asp
            610                 615                 620
Gly Ser Thr Lys Thr Asp Ser Glu Thr Asn Ser Arg Leu Val Leu Thr
625                 630                 635                 640
Ile Ala Phe Gln Phe Thr Phe Asp Asn His Ser Arg Asp Asn Val Ala
                    645                 650                 655
Thr Met Ala Arg Gln Tyr Val Arg Asn Val Val Gly Ser Ile Gln Arg
                660                 665                 670
Val Ala Leu Ala Ile Thr Pro Arg Pro Gly Ser Met Gln Leu Pro Thr
            675                 680                 685
Ser Pro Glu Ala Leu Thr Leu Val Arg Trp Ile Thr Arg Ser Tyr Ser
            690                 695                 700
Ile His Thr Gly Ala Asp Leu Phe Gly Ala Asp Ser Gln Ser Cys Gly
705                 710                 715                 720
Gly Asp Thr Leu Leu Lys Gln Leu Trp Asp His Ser Asp Ala Ile Leu
                    725                 730                 735
Cys Cys Ser Leu Lys Thr Asn Ala Ser Pro Val Phe Thr Phe Ala Asn
                740                 745                 750
Gln Ala Gly Leu Asp Met Leu Glu Thr Thr Leu Val Ala Leu Gln Asp
            755                 760                 765
```

```
Ile Met Leu Asp Lys Thr Leu Asp Asp Ser Gly Arg Arg Ala Leu Cys
    770                 775                 780

Ser Glu Phe Ala Lys Ile Met Gln Gln Gly Tyr Ala Asn Leu Pro Ala
785                 790                 795                 800

Gly Ile Cys Val Ser Ser Met Gly Arg Pro Val Ser Tyr Glu Gln Ala
                805                 810                 815

Thr Val Trp Lys Val Val Asp Asp Asn Glu Ser Asn His Cys Leu Ala
            820                 825                 830

Phe Thr Leu Val Ser Trp Ser Phe Val
            835                 840

<210> SEQ ID NO 250
<211> LENGTH: 852
<212> TYPE: PRT
<213> ORGANISM: Arabidopsis thaliana

<400> SEQUENCE: 250

Met Met Met Val His Ser Met Ser Arg Asp Met Met Asn Arg Glu Ser
1               5                   10                  15

Pro Asp Lys Gly Leu Asp Ser Gly Lys Tyr Val Arg Tyr Thr Pro Glu
            20                  25                  30

Gln Val Glu Ala Leu Glu Arg Val Tyr Thr Glu Cys Pro Lys Pro Ser
        35                  40                  45

Ser Leu Arg Arg Gln Gln Leu Ile Arg Glu Cys Pro Ile Leu Ser Asn
    50                  55                  60

Ile Glu Pro Lys Gln Ile Lys Val Trp Phe Gln Asn Arg Arg Cys Arg
65                  70                  75                  80

Glu Lys Gln Arg Lys Glu Ala Ala Arg Leu Gln Thr Val Asn Arg Lys
                85                  90                  95

Leu Asn Ala Met Asn Lys Leu Leu Met Glu Glu Asn Asp Arg Leu Gln
            100                 105                 110

Lys Gln Val Ser Asn Leu Val Tyr Glu Asn Gly His Met Lys His Gln
        115                 120                 125

Leu His Thr Ala Ser Gly Thr Thr Thr Asp Asn Ser Cys Glu Ser Val
    130                 135                 140

Val Val Ser Gly Gln Gln His Gln Gln Gln Asn Pro Asn Pro Gln His
145                 150                 155                 160

Gln Gln Arg Asp Ala Asn Asn Pro Ala Gly Leu Leu Ser Ile Ala Glu
                165                 170                 175

Glu Ala Leu Ala Glu Phe Leu Ser Lys Ala Thr Gly Thr Ala Val Asp
            180                 185                 190

Trp Val Gln Met Ile Gly Met Lys Pro Gly Pro Asp Ser Ile Gly Ile
        195                 200                 205

Val Ala Ile Ser Arg Asn Cys Ser Gly Ile Ala Ala Arg Ala Cys Gly
    210                 215                 220

Leu Val Ser Leu Glu Pro Met Lys Val Ala Glu Ile Leu Lys Asp Arg
225                 230                 235                 240

Pro Ser Trp Leu Arg Asp Cys Arg Ser Val Asp Thr Leu Ser Val Ile
                245                 250                 255

Pro Ala Gly Asn Gly Gly Thr Ile Glu Leu Ile Tyr Thr Gln Met Tyr
            260                 265                 270

Ala Pro Thr Thr Leu Ala Ala Ala Arg Asp Phe Trp Thr Leu Arg Tyr
        275                 280                 285

Ser Thr Cys Leu Glu Asp Gly Ser Tyr Val Val Cys Glu Arg Ser Leu
```

```
            290                 295                 300
Thr Ser Ala Thr Gly Gly Pro Thr Gly Pro Ser Ser Asn Phe Val
305                 310                 315                 320

Arg Ala Glu Met Lys Pro Ser Gly Phe Leu Ile Arg Pro Cys Asp Gly
                325                 330                 335

Gly Gly Ser Ile Leu His Ile Val Asp His Val Asp Leu Asp Ala Trp
                340                 345                 350

Ser Val Pro Glu Val Met Arg Pro Leu Tyr Glu Ser Ser Lys Ile Leu
                355                 360                 365

Ala Gln Lys Met Thr Val Ala Ala Leu Arg His Val Arg Gln Ile Ala
370                 375                 380

Gln Glu Thr Ser Gly Glu Val Gln Tyr Gly Gly Arg Gln Pro Ala
385                 390                 395                 400

Val Leu Arg Thr Phe Ser Gln Arg Leu Cys Arg Gly Phe Asn Asp Ala
                405                 410                 415

Val Asn Gly Phe Val Asp Asp Gly Trp Ser Pro Met Gly Ser Asp Gly
                420                 425                 430

Ala Glu Asp Val Thr Val Met Ile Asn Leu Ser Pro Gly Lys Phe Gly
                435                 440                 445

Gly Ser Gln Tyr Gly Asn Ser Phe Leu Pro Ser Phe Gly Ser Gly Val
                450                 455                 460

Leu Cys Ala Lys Ala Ser Met Leu Leu Gln Asn Val Pro Pro Ala Val
465                 470                 475                 480

Leu Val Arg Phe Leu Arg Glu His Arg Ser Glu Trp Ala Asp Tyr Gly
                485                 490                 495

Val Asp Ala Tyr Ala Ala Ala Ser Leu Arg Ala Ser Pro Phe Ala Val
                500                 505                 510

Pro Cys Ala Arg Ala Gly Gly Phe Pro Ser Asn Gln Val Ile Leu Pro
                515                 520                 525

Leu Ala Gln Thr Val Glu His Glu Glu Ser Leu Glu Val Val Arg Leu
                530                 535                 540

Glu Gly His Ala Tyr Ser Pro Glu Asp Met Gly Leu Ala Arg Asp Met
545                 550                 555                 560

Tyr Leu Leu Gln Leu Cys Ser Gly Val Asp Glu Asn Val Val Gly Gly
                565                 570                 575

Cys Ala Gln Leu Val Phe Ala Pro Ile Asp Glu Ser Phe Ala Asp Asp
                580                 585                 590

Ala Pro Leu Leu Pro Ser Gly Phe Arg Ile Ile Pro Leu Glu Gln Lys
                595                 600                 605

Ser Thr Pro Asn Gly Ala Ser Ala Asn Arg Thr Leu Asp Leu Ala Ser
                610                 615                 620

Ala Leu Glu Gly Ser Thr Arg Gln Ala Gly Glu Ala Asp Pro Asn Gly
625                 630                 635                 640

Cys Asn Phe Arg Ser Val Leu Thr Ile Ala Phe Gln Phe Thr Phe Asp
                645                 650                 655

Asn His Ser Arg Asp Ser Val Ala Ser Met Ala Arg Gln Tyr Val Arg
                660                 665                 670

Ser Ile Val Gly Ser Ile Gln Arg Val Ala Leu Ala Ile Ala Pro Arg
                675                 680                 685

Pro Gly Ser Asn Ile Ser Pro Ile Ser Val Pro Thr Ser Pro Glu Ala
                690                 695                 700

Leu Thr Leu Val Arg Trp Ile Ser Arg Ser Tyr Ser Leu His Thr Gly
705                 710                 715                 720
```

```
                            -continued

Ala Asp Leu Phe Gly Ser Asp Ser Gln Thr Ser Gly Asp Thr Leu Leu
                725             730             735

His Gln Leu Trp Asn His Ser Asp Ala Ile Leu Cys Cys Ser Leu Lys
            740             745             750

Thr Asn Ala Ser Pro Val Phe Thr Phe Ala Asn Gln Thr Gly Leu Asp
        755             760             765

Met Leu Glu Thr Thr Leu Val Ala Leu Gln Asp Ile Met Leu Asp Lys
    770             775             780

Thr Leu Asp Glu Pro Gly Arg Lys Ala Leu Cys Ser Glu Phe Pro Lys
785             790             795             800

Ile Met Gln Gln Gly Tyr Ala His Leu Pro Ala Gly Val Cys Ala Ser
                805             810             815

Ser Met Gly Arg Met Val Ser Tyr Glu Gln Ala Thr Val Trp Lys Val
            820             825             830

Leu Glu Asp Asp Glu Ser Asn His Cys Leu Ala Phe Met Phe Val Asn
        835             840             845

Trp Ser Phe Val
    850
```

COMPOSITIONS AND METHOD FOR MODULATION OF PLANT CELL DIVISION

CROSS-REFERENCE TO RELATED APPLICATIONS

The present application is a continuation of application Ser. No. 10/129,912, filed May 10, 2002, which is the National Stage of International Application No. PCT/US00/30794, filed Nov. 10, 2000, which claims the benefit of Provisional Application No. 60/164,587, filed Nov. 10, 1999.

INCORPORATION OF SEQUENCE LISTING

The contents of the following submission on compact discs are incorporated herein by reference in its entirety: two copies of the Sequence Listing (COPY 1 and COPY 2) and a computer-readable form of the Sequence Listing (CRF COPY), all on CD-ROMs, each containing: file name: 6769-14 Sequence Listing, date recorded: May 25, 2006, size: 158 KB.

FIELD OF THE INVENTION

The present invention relates generally to compositions and methods for modulating plant division and growth. More specifically, transgene vectors, cells, plants and methods for producing the same are provided that facilitate the production of plants having an increased or decreased number of cells.

BACKGROUND OF THE INVENTION

Elaboration of the plant body pattern depends primarily on the proper regulation of cell division versus cell differentiation at the growth sites called meristems. In seed plants, apical growth is carried out by the apical meristems. Although structurally identical, shoot apical meristems differ ontogenetically. A primary shoot apical meristem originates during embryogenesis and becomes the apex of the primary shoot. Secondary shoot apical meristems develop later-on the sides of the primary shoot and form lateral shoots. In many seed plants, radial growth of the shoot is conferred by the cambium, a cylindrical meristematic layer in the shoot body. Growth of lateral "leafy" organs (i.e., leaves, petals, etc.) occurs from transient meristems formed on the flank of the apical meristem. Root growth occurs from analogous apical and cambial meristems. Presently, very little of the regulation and interaction of these different types of meristems is understood.

The commercial value of a cultivated plant is directly related to yield, i.e. to the size and number of the harvested plant part, which in turn is determined by the number of cell divisions in the corresponding plant tissues. Although a genetic approach to the study of plant development has provided important information on pattern formation and organ morphogenesis (see, for example, Riechmann et al., 1997 *Biol. Chem.* 378:1079-1101; Barton, 1998 *Current Opin. Plant Biol.* 1:3742; Christensen et al., 1998 *Current Biol.* 8:643-645; Hudson, 1999 *Current Opin. Plant Biol.* 2:56-60; Irish, 1999 *Dev. Biol.* 209:211-220; Scheres et al., 1999 *Current Topics Dev. Biol.* 45:207-247). Very little has been learned about how and what regulates plant cell division, and, therefore the overall size of a plant organ. Therefore, the isolation and manipulation of genes controlling organ size via regulatory effects on cell division will have a large impact on the productivity of virtually every commercial plant species.

Hermerly et al. (1995 *EMBO J.* 14:3925-3936) studied the effects on tobacco plant growth and development using a dominant negative mutation of an *Arabidopsis thaliana* Cdc2 kinase gene. Cdc2 kinase activity is required in all eukaryotic organisms to properly progress through the cell cycle. Hermerly et al. showed that expression of the *Arabidopsis thaliana* gene encoding the dominant negative Cdc2 protein in tobacco plants resulted in plants that were morphologically normal, but were smaller in size due to a reduction in the frequency of cell division. Thus, the regulation of plant cell division can be at least partially uncoupled from plant development. However, in normal plant growth and development, Cdc2 kinase activity must be activated by other regulatory proteins in order to instigate plant cell division.

A large number of plant mutants have been isolated that display a wide variety of abnormal morphological and growth phenotypes (see, for example, Lenhard et al., 1999 *Current Opin. Plant Biol.* 2:4450). However, it is difficult to visually identify which plant morphology phenotypes are due to mutations in the putative key controller genes that determine whether a plant cell will grow and divide verses other genes that specify the developmental fate of a cell. Furthermore, even when such a putative plant growth mutant has been identified, a great deal of effort is required to identify which DNA segment encodes the mutant gene product that functions to regulate plant cell division.

For example, Talbert et al. (1995 *Development* 121:2723-2735), reported *Arabidopsis thaliana* mutants defective in a gene named revoluta (RET), that appear to display an abnormal regulation of cell division in meristematic regions of mutant plants. More specifically, the REV gene is required to promote the growth of apical meristems, including paraclade meristems, floral meristems and the primary shoot apical meristem. Simultaneously, the REV gene has an opposing effect on the meristems of leaves, floral organs and stems. That is, in leaf, floral organ and stem tissues REV acts to limit cell division, thereby, reducing both the rate of plant growth and final size of the tissue. Loss of functional REV protein in leaf, floral organ and stem tissues leads to an increase in the number of cells and the size of these tissues. In contrast, loss of functional REV protein in apical meristem cells leads to a reduction in cell division and reduced organ size. Talbert et al., (1995, incorporated herein by reference) reports the detailed morphological changes observed in homozygous revoluta plants. The aberrant morphologies recorded for revoluta mutants strongly suggest that the REV gene product has a role in regulating the relative growth of apical and non-apical meristems in *Arabidopsis*. The revoluta mutations were used to map the REV gene to the generally distal, but unspecified, portion of Chromosome 5 in *Arabidopsis*. However, prior to the present invention the REV gene sequence and methods for using polynucleotides encoding the REV protein to modulate cell division in transgenic plant cells were unknown.

In principle, mutations in a plant growth regulator gene could also be identified based upon their sequence similarity at the DNA or protein level as compared to animal or fungal genes that are known to play an important role in initiating the cell cycle (such as cyclins) or otherwise regulating growth. For example, homeobox (HB) genes are well know in animals as encoding proteins that act as master control genes that specify the body plan and otherwise regulate development of higher organisms (Gehring et al. 1994, *Annu. Rev. Biochem.* 63:487-526). The HB genes of animals encode an approximately 60 amino acid protein motif called a homeodomain (HD) that is involved in DNA binding, and the proteins that contain an HD are transcription factors which act as regulators of the expression of target genes. HD regions are highly conserved between both plants and animal. Plant homeobox genes were first identified based upon the isolation of a maize mutant called knotted1 (kn1) that had a dominant mutation that altered leaf development (Vollbrecht et al. 1991, *Nature* 350:241-243). Genes encoding proteins homologous to the maize Knotted protein have been identified and cloned from a wide variety of plant species based upon their sequence homology (for a review see Chan et al., 1998 *Biochim. et. Biophys. Acta* 1442:1-19). Hybridization studies indicate that there may be about 35 to 70 different HD-containing genes in *Arabidopsis* (Schena et al., 1992 *Proc. Natl. Acad. Sci. USA* 89:3894-3898).

A large number of plant HD-containing genes have been isolated using degenerate oligonucleotides made from conserved HD sequences as hybridization probes or PCR primers to identify and isolate cDNA clones (Ruberti et al., 1991 *EMBO J.* 10:1787-1791; Schena et al, 1992; Mattsson et al, 1992 *Plant Mol Biol.* 18:1019-1022; Carabelli et al., 1993 *Plant J.* 4:469-479; Schena et al., 1994 *Proc. Natl. Acad. Sci. USA* 91:8393-8397; Soderman et al., 1994 *Plant Mol Biol.* 26, 145-154; Kawahara et al., 1995 *Plant Molec. Biol.* 27:155-164; Meissner et al., 1995 *Planta* 195:541-547; Moon et al., 1996 *Mol. Cells* 6:366-373; Moon et al., 1996 *Mol. Cells* 6:697-703; Gonzalez et al., 1997 *Biochem. Biophys. Acta* 1351:137-149; Meijer et al., 1997 *Plant J.* 11:263-276; Sessa et al., 1998 *Plant Mol. Biol.* 38:609-622; Aso et al., 1999 *Mol. Biol. Evol.* 16:544-552). Analysis of these HD-containing genes revealed the presence of an additional large class of HD-containing genes in plants, known as HD-Zip genes because the proteins encoded by these genes contain a leucine zipper in association with the homeodomain. This class of HD genes are unique to plants (Schena et al., 1992). Based upon amino acid sequence similarity the proteins encoded by the HD-Zip genes have been divided into four HD-Zip subfamilies based upon the degree of amino acid similarity within the HD and leucine zipper protein domains (Sessa et al., 1994 In *Molecular-Genetic Analysis of Plant Development and Metabolism* [Puigdomenech, P. and Coruzzi, G., eds] Berlin: Springer Verlag, pp 411-426; Meijer et al., 1997). However, similar to the Knotted class of plant HD genes, the HD-Zip genes are also thought to encode proteins that function to regulate plant development (Chan et al., 1998). The presence of both HD and leucine zipper domains in the HD-Zip protein suggests very strongly that these proteins form multimeric structures via the leucine zipper domains, and then bind to specific DNA sequences via the HD regions to transcriptionally regulate target gene expression (Chan et al., 1998). This inference has been experimentally documented by in vitro experiments for many of the HD-Zip proteins (Sessa et al., 1993; Aoyama et al., 1995 *Plant Cell* 7:1773-1785; Ganzalez et al., 1997 *Biochim. Biophys. Acta* 1351:137-149; Meijer et al., 1997; Palena et al., 1999 *Biochem. J.* 341:81-87; Sessa et al., 1999), which publications are incorporated herein by reference.

Antisense and ectopic expression experiments have been performed with some HD-Zip subfamily I, II, III and IV genes to access the phenotypic consequences of shutting off HD-Zip gene expression and over producing HD-Zip protein throughout a plant (Schena et al., 1993; Aoyama et al., 1995; Tornero et al., 1996; Meijer et al., 1997; Altamura et al., 1998). Additional evidence regarding HD-Zip function has been inferred from in situ hybridization and Northern blot hybridization experiments to determine the temporal pattern of HD-Zip gene expression through plant development as well as to locate which specific plant cells or tissues exhibit HD-Zip gene expression (See Table 1). However, as demonstrated by the information compiled in Table 1, there is no clear pattern as to what regulatory roles HD-Zip proteins play in plant growth and development either as a super family or at the subfamily level. Furthermore, there has been no recognition that a HD-Zip gene product is involved in the regulation of plant cell division.

TABLE 1

HD-Zip Genes And Their Proposed Functions

| HD-Zip Subfamily and Gene | Expression Pattern | Proposed Function | Reference |
|---|---|---|---|
| Subfamily I | | | |
| Athb-1 | late plant development | activation of genes related to leaf development | Aoyama et al., 1995 |
| Athb-3 | root and stem cortex | ? | Soderman et al., 1994 |
| Athb-5 | leaf, root and flower | ? | Soderman et al., 1994 |
| Athb-6 | leaf, root and flower | ? | Soderman et al., 1994 |
| Athb-7 | low level throughout plant, induced by abscisic acid and water deficit | signal transduction pathway in response to water deficit | Soderman et al., 1994, 1996 |
| CHB1 | early embryogenesis | maintenance of indeterminant cell fate | Kawahara et al., 1995 |
| CHB2 | early embryogenesis | ? | Kawahara et al., 1995 |
| CHB3 | mature tissue | ? | Kawahara et al., 1995 |
| CHB4 | hypocotyl | ? | Kawahara et al., 1995 |
| CHB5 | hypocotyl and roots | ? | Kawahara et al., 1995 |
| CHB6 | late embryogenesis, mature tissue | ? | Kawahara et al., 1995 |
| Hahb-1 | stem | ? | Chan et al., 1994 |
| VAHOX-1 | phloem of adult plants | differentiation of cambium cells to phloem tissue | Tornero et al., 1996 |
| Subfamily II | | | |
| Athb-2 (HAT4) | vegetative and reproductive phases of plant, induced by far-red-rich light | involved in light perception and related responses in regulation of development | Schena et al., 1993; Carabelli et al, 1993; 1996; Steindler et al., 1999; |

TABLE 1-continued

HD-Zip Genes And Their Proposed Functions

| HD-Zip Subfamily and Gene | Expression Pattern | Proposed Function | Reference |
| --- | --- | --- | --- |
| Athb-4 | vegetative and reproductive phases of plant, induced by far-red-rich light | involved in light perception and related responses | Carabelli et al, 1993 |
| Hahb-10 | stems and roots | ? | Gonzalez et al., 1997 |
| Oshox 1 | embryos, shoots of seedlings and leaves of mature plants | leaf developmental regulator | Meijer et al., 1997 |
| Subfamily III | | | |
| Athb-8 | procambial cells of the embryo, induced by auxins | regulation of vascular development | Baima et al., 1995; Altamura et al., 1998; Sessa et al., 1998 |
| Athb-9 | mRNA slightly enriched in stem compared to leaf, root and flower | ? | Sessa et al., 1998 |
| Athb-14 | Strongly enriched in stem, root, slightly enriched in flower compared to leaf | ? | Sessa et al., 1998 |
| crhb1 | expressed only in gametophyte | ? | Aso et al., 1999 |
| Subfamily IV | | | |
| Athb-10 (G1-2) | trichome cells and non-hair root cells | positive regulator of epidermal cell development | Rerie et al., 1994; Di Cristina et al., 1996; Masucci et al., 1996 |
| ATML1 | Expressed in L1 layer of the shoot apical meristem | Regulation of epidermal cell fate and pattern formation | Lu et al., 1996 |
| Hahr1 | Expressed in dry seeds, hypocotyls and roots | Early plant development? | Valle et al., 1997 |

The results summarized in Table 1 show that the regulatory role of any one individual HD-Zip gene product can not be predicted based upon which HD-Zip subfamily a gene is placed. The HD-Zip subfamilies were determined by alignment and comparison of the amino acid sequences found in the HD and leucine zipper domains (See Aso et al. 1999, FIG. 2 for the most recent HD-Zip region alignments). Conservation of HD-Zip regulatory function can be expected in many cases to depend on the extent of amino acid sequence similarity found in conserved protein domains found outside of the HD-Zip regions. That is, HD-Zip gene products from different plant species that are functional homologues to each other (i.e., perform the same biological function) are expected to not only share conserved HD-Zip regions, but show more amino acid sequence similarity over the entire length of the protein compared to other HD-Zip proteins that perform different biological roles. Thus, it is not surprising that the data summarized in Table 1 shows that there is no consistent pattern as to the inferred biological functions for individual HD-Zip I, II, III and IV gene products. Nonetheless, there is still wide-spread speculation that the proteins of the HD-Zip super family play important roles in regulating plant development (See, for example, Chan et al. 1998).

Given the agronomic importance of plant growth, there is a strong need for transgene compositions containing gene sequences which when expressed in a transgenic plant allow the growth of the plant to be modulated. The compositions and methods of the present invention allow useful transgenic plants to be created wherein cell division is modulated due to expression of a REVOLUTA transgene. Compositions and methods, such as those provided by the present invention, allow for controlling (including increasing) plant size via the ability to control (e.g., increase) the number of cell divisions in specific plant tissues.

The inventive compositions and methods provide another way to meet the ever increasing need for food and plant fiber due to the continual increase in world population and the desire to improve the standard of living throughout the world. Despite the recent agricultural success in keeping food production abreast of population growth, there are over 800 million people in the world today who are chronically undernourished and 180 million children who are severely underweight for their age. 400 million women of childbearing age suffer from iron deficiency and the anemia it causes results in infant and maternal mortality. An extra 2 billion persons will have to be fed by the year 2020, and so many more that will be chronically undernourished. For example, in forest trees the cambium is responsible for girth growth. In tomato (and many other plants), the ovary walls are responsible, not only for mature fruit size but also for soluble solids content. In cereal crops, the endosperm contributes to seed size. In some cases, increased yield may be achieved by lengthening a fruit-bearing structure, such as maize where the ear is a modified stem whose length determines the number of kernels. Moreover, possible use of transgenic plants as a source of pharmaceuticals and industrial products may require control of organ specific growth modulation.

The potential of a designer growth-increasing or growth-decreasing technology in agriculture is very large. A yield increase as small as a few percent would be highly desirable in each crop. Conversely, in many fruit crops it is highly desirable to have seedless fruits. The present invention, in addition to being applicable to all existing plant varieties, could also change the way crops are bred. Plant breeding could concentrate on stress and pest resistance as well as nutritional and taste quality. The growth-conferring quality of the present invention could then be introduced in advanced elite lines to boost their yield potential.

SUMMARY OF THE INVENTION

The present invention provides compositions and methods for modulating plant cell division by altering the level of REVOLUTA protein within transgenic plants. In particular, the present invention relates to the use of REVOLUTA transgenes to increase or decrease the expression of biologically active REVOLUTA protein and thereby modulate plant cell division.

In one embodiment of the present invention, a DNA molecule comprising a polynucleotide sequence that encodes a REVOLUTA protein that is at least about 70% identical to the *Arabidopsis* REVOLUTA protein sequence [SEQ ID NO:2] is provided. According to certain embodiments, the protein is at least about 80% identical to SEQ ID NO:2. Preferably, the DNA molecule comprises a polynucleotide sequence that encodes a REVOLUTA protein that has the same biological activity as the *Arabidopsis* REVOLUTA protein, i.e. it modulates plant cell division. According to certain preferred embodiments, the protein encoded by the DNA molecule confers a REV phenotype.

According to certain preferred embodiments, the invention provides a polynucleotide at least 80% identical to at least one exon of the *Arabidopsis* REVOLUTA nucleic acid sequence, selected from exons 3-18 (nucleotides 3670-3743, 3822-3912, 4004-4099, 4187-4300, 4383-4466, 4542-4697, 4786-4860, 4942-5048, 5132-5306, 5394-5582, 5668-5748, 5834-5968, 6051-6388, 6477-6585, 6663-6812, and 6890-7045 of SEQ ID NO:1).

Similarly, the present invention provides an isolated DNA molecule comprising a polynucleotide sequence at least about 80% identical to at least one exon of the tomato Rev gene, or a polynucleotide, selected from the group consisting of SEQ ID NO:187, SEQ ID NO:188, SEQ ID NO:189, SEQ ID NO:190, SEQ ID NO:191, SEQ ID NO:192, SEQ ID NO:193, SEQ ID NO:194, SEQ ID NO:195, and SEQ ID NO:196.

According to other embodiments, the present invention provides an isolated DNA molecule comprising a polynucleotide sequence which encodes a protein comprised of an amino acid sequence at least about 95% identical to certain regions of a REV gene product, especially a sequence selected from the group consisting of SEQ ID NO:130; SEQ ID NO:131; SEQ ID NO:132; SEQ ID NO:133; SEQ ID NO:134; SEQ ID NO:135; SEQ ID NO: 136; and SEQ ID NO:137.

According to certain embodiments of the present invention, the encoded protein comprises an amino acid sequence selected from the group consisting of SEQ ID NO.:2, SEQ ID NO.:6, SEQ ID NO.:8, SEQ ID NO.:10, SEQ ID NO.:10, SEQ ID NO.:12, SEQ ID NO.:159, SEQ ID NO.:160, SEQ ID NO.:165, SEQ ID NO.:171 and SEQ ID NO.:173.

The present invention also provides embodiments where the polynucleotide sequence is selected from the group consisting of SEQ ID NO:1, SEQ ID NO:3, SEQ ID NO:5, SEQ ID NO:7, SEQ ID NO:9, SEQ ID NO:11, SEQ ID NO:157, SEQ ID NO:158, SEQ ID NO:163, SEQ ID NO:164, SEQ ID NO:169, SEQ ID NO:170, and SEQ ID NO:172.

Another embodiment of the present invention provides a polynucleotide sequence selected from the group consisting of SEQ ID NO:3, SEQ ID NO:5, SEQ ID NO:7, SEQ ID NO:9 and SEQ ID NO:11, wherein the polynucleotide sequence encodes a mutant revoluta protein that is defective in normal regulation of cell division as compared to the wild-type REV protein. The present invention also provides an isolated protein comprising an amino sequence selected from the group consisting of wild-type *Arabidopsis* REVOLUTA protein [SEQ ID NO:2], and revoluta mutant proteins designated rev-1, rev-2,4, rev-3, rev-5 and rev-6, as set forth in FIG. 3. Other inventive REVOLUTA proteins are provided that comprise amino acid sequences that are at least about 70% identical to the *Arabidopsis* REV amino acid sequence as set forth in SEQ ID NO:2.

In yet another embodiment of the present invention, transgenic vectors are provided that comprise a replicon and a REVOLUTA transgene comprising a nucleic acid sequence selected from the group consisting of SEQ ID NO:1, SEQ ID NO:3, SEQ ID NO:5, SEQ ID NO:7, SEQ ID NO:9 and SEQ ID NO:11. Preferably, the transgenic vectors of the present invention also include either a constitutive or a tissue specific promoter region that directs the expression of the REVOLUTA transgene, and a polyA addition region. The expression of the REVOLUTA transgene results in a modulation of cell division in plant cells transformed with the inventive transgenic vector. In another embodiment the transgene vectors of the present invention contain a polynucleotide sequence comprising a sequence that encodes a protein that is at least about 70% identical to the wild-type *Arabidopsis* REVOLUTA protein sequence [SEQ ID NO:2]. In yet another embodiment of the present invention, the polynucleotide sequence encodes a protein that has a peptide region that is at least about 70% identical to a region of wild-type *Arabidopsis* REVOLUTA protein that is defined by amino acid 114 up to and including amino acid 842 of the protein in SEQ ID NO:2.

In another aspect of the invention transgenic plants are provided that comprise at least one of the above described polynucleotides and REVOLUTA transgene vectors. In one aspect of the invention the transformed plants exhibit a modulation of cell division, as compared to untransformed plants, when the inventive REVOLUTA transgenes are expressed within the transformed cells. In particular, the present invention provides transgenic plants (genetically transformed with a nucleic acid sequence comprising a REVOLUTA transgene selected from the group consisting of a sense gene, an antisense gene, an inverted repeat gene or a ribozyme gene) that exhibit modulated cell division as compared to a control population of untransformed plants. The transgenic plants of the present invention can be further propagated to generate genetically true-breeding populations of plants possessing the modulated cell division trait. Further, the transgenic plants of the present invention can be crossed with other plant varieties, having one or more desirable phenotypic traits, such as for example, stress and pest resistance or nutritional and taste quality, to generate novel plants possessing the aforementioned desirable traits in combination with the transgenic trait that modulates cell division.

In another aspect, the present invention provides methods for modulating plant cell division comprising the steps of introducing a REVOLUTA transgene into at least one plant cell. The methods of the present invention include the further step of regenerating one or more plants from the cells transformed with the REVOLUTA transgene. Optionally, the regenerated plants may be screened to identify plants exhibiting modulated cell division as compared to untransformed plants. Transgenic plants having a modulated cell division have at least one plant organ or tissue that is larger or smaller in size (due to an increased or decreased number of cells) as compared to untransformed plants. The presently preferred REVOLUTA transgenes for practicing the inventive methods are the polynucleotide sequences previously described above. In addition, the inventive methods can be practiced with a REVOLUTA transgene that is selected from the group consisting of a sense gene, an anti-sense gene, an inverted repeat gene and a REVOLUTA ribozyme gene.

In yet another embodiment of the present invention, a method is provided for isolating a REVOLUTA gene from a plant. More specifically the inventive method comprises the steps of:

a) amplifying a plant polynucleotide sequence using a forward and a reverse oligonucleotide primer, said primers encoding an amino acid sequence that is at least about 50% identical to a corresponding amino acid sequence found in SEQ ID NO:2;

b) hybridizing said amplified plant polynucleotide to a library of recombinant plant DNA clones;

c) isolating a DNA molecule from a recombinant DNA clone that hybridizes to said amplified plant polynucleotide;

d) transforming with a vector comprising said amplified plant polynucleotide or said DNA molecule into a plant; and e) determining that cell division in the transformed plant is modulated by comparing the transformed plant with an untransformed plant.

Preferably, the DNA isolated by the inventive method encodes an amino acid sequence that is at least about 70% identical to an amino acid sequence within the REVOLUTA protein having the sequence of SEQ ID NO:2. In addition, modulation of cell division is preferably determined by comparing the size of a transgenic plant, tissue, or organ thereof with a corresponding untransformed plant, tissue or organ. An increase or decrease in the number of cells in the transgenic plant, tissue or organ as compared to the untransformed plant, tissue or organ indicates that the isolated DNA molecule encodes a REVOLUTA gene of the present invention.

The present invention also provides a plant comprising a chimeric plant gene having a promoter sequence that functions in plant cells; a coding sequence which causes the production of RNA encoding a fusion polypeptide or an RNA transcript that causes homologous gene suppression such that expression of the chimeric plant gene modulates plant growth, e.g. by modulating cell division; and a 3' non-translated region that encodes a polyadenylation signal which functions in plant cells to cause the addition of polyadenylate nucleotides to the 3' end of the RNA, where the promoter is heterologous with respect to the coding sequence and adapted to cause sufficient expression of the chimeric plant gene to modulate plant growth of a plant transformed with the chimeric gene.

BRIEF DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein:

FIG. 3 shows the complete protein sequence [SEQ ID NO:2] deduced from a REVOLUTA gene [SEQ ID NO:1] isolated from *Arabidopsis thaliana*. Open triangles indicate splice junctions between the exon and intron nucleotide sequences in the DNA sequence [SEQ ID NO:1] that encodes REVOLUTA. Conserved homeodomain and leucine zipper motifs are indicated in shaded boxes. The underlined amino acid region indicates a second potential leucine zipper motif. Intron-exon junctions are indicated by an inverted triangle. The rev-4 mutant amino acid C-terminal extension is indicated in bold under the wild-type sequence.

DETAILED DESCRIPTION OF THE PREFERRED EMBODIMENTS

Figure 1:
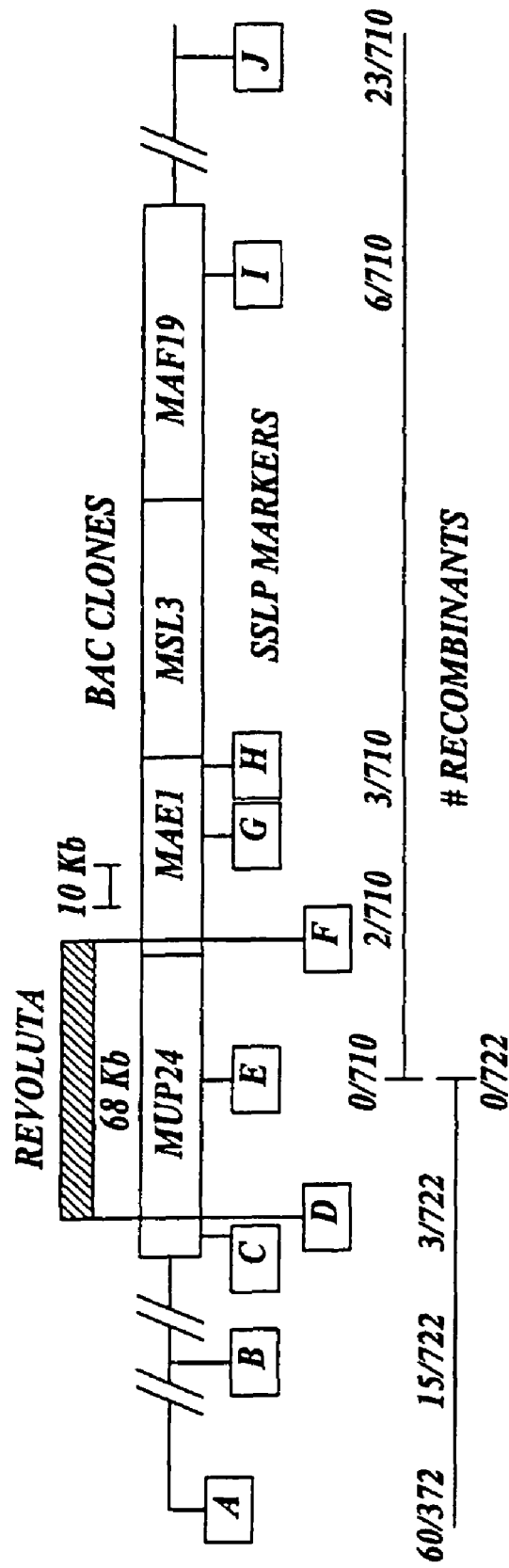
FIG. 1 presents a genetic map of a 1.95 Mb region of chromosome 5 from *Arabidopsis thaliana*.

As used herein, the terms "amino acid" and "amino acids" refer to all naturally occurring L-α-amino acids or their residues. The amino acids are identified by either the single-letter or three-letter designations:

| Asp | D | aspartic acid | Ile | I | isoleucine |
|-----|---|---------------|-----|---|------------|
| Thr | T | threonine | Leu | L | leucine |
| Ser | S | serine | Tyr | Y | tyrosine |
| Glu | E | glutamic acid | Phe | F | phenylalanine |
| Pro | P | proline | His | H | histidine |
| Gly | G | glycine | Lys | K | lysine |
| Ala | A | alanine | Arg | R | arginine |
| Cys | C | cysteine | Trp | W | tryptophan |
| Val | V | valine | Gln | Q | glutamine |
| Met | M | methionine | Asn | N | asparagine |

As used herein, the term "nucleotide" means a monomeric unit of DNA or RNA containing a sugar moiety (pentose), a phosphate and a nitrogenous heterocyclic base. The base is linked to the sugar moiety via the glycosidic carbon (1' carbon of pentose) and that combination of base and sugar is called a nucleoside. The base characterizes the nucleotide with the four bases of DNA being adenine ("A"), guanine ("G"), cytosine ("C") and thymine ("T"). Inosine ("I") is a synthetic base that can be used to substitute for any of the four, naturally-occurring bases (A, C, G or T). The four RNA bases are A, G, C and uracil ("U"). The nucleotide sequences described herein comprise a linear array of nucleotides connected by phosphodiester bonds between the 3' and 5' carbons of adjacent pentoses.

The terms "DNA sequence encoding," "DNA encoding" and "nucleic acid encoding" refer to the order or sequence of deoxyribonucleotides along a strand of deoxyribonucleic acid. The order of these deoxyribonucleotides determines the order of amino acids along the translated polypeptide chain. The DNA sequence thus codes for the amino acid sequence.

The term "recombinant DNA molecule" refers to any DNA molecule that has been created by the joining together of two or more DNA molecules in vitro into a recombinant molecule. A "library of recombinant DNA molecules" refers to any clone bank comprising a number of different recombinant DNA molecules wherein the recombinant DNA molecules comprise a replicable vector and DNA sequence derived from a source organism.

"Oligonucleotide" refers to short length single or double stranded sequences of deoxyribonucleotides linked via phosphodiester bonds. The oligonucleotides are chemically synthesized by known methods and purified, for example, on polyacrylamide gels.

The term "plant" includes whole plants, plant organs (e.g., leaves, stems, flowers, roots, etc.), seeds and plant cells (including tissue culture cells) and progeny of same. The class of plants which can be used in the method of the invention is generally as broad as the class of higher plants amenable to transformation techniques, including both monocotyledonous and dicotyledonous plants, as well as certain lower plants such as algae. It includes plants of a variety of ploidy levels, including polyploid, diploid and haploid.

A "heterologous sequence" is one that originates from a foreign species, or, if from the same species, is substantially modified from its original form. For example, a heterologous promoter operably linked to a structural gene is from a species different from that from which the structural gene was derived, or, if from the same species, is substantially modified from its original form.

The terms "REVOLUTA gene" or "REVOLUTA transgene" are used herein to mean any polynucleotide sequence that encodes or facilitates the expression and/or production of a REVOLUTA protein. Thus, the terms "REVOLUTA gene" and "REVOLUTA transgene" include sequences that flank the REVOLUTA protein encoding sequences. More specifically, the terms "REVOLUTA gene" and "REVOLUTA transgene" include the nucleotide sequences that are protein encoding sequences (exons), intervening sequences (introns), the flanking 5' and 3' DNA regions that contain sequences required for the normal expression of the REVOLUTA gene (i.e. the promoter and polyA addition regions, respectively, and any enhancer sequences).

The terms "REVOLUTA protein," "REVOLUTA homolog" or "REVOLUTA ortholog" are used herein to mean proteins having the ability to regulate plant cell division (when utilized in the practice of the methods of the present invention) and that have an amino acid sequence that is at least about 70% identical, more preferably at least about 75% identical, most preferably at least about 80% identical to amino acid residues 1 to 842, inclusive, of SEQ ID NO:2. A REVOLUTA protein of the present invention is also at least about 70% identical, more preferably at least about 75% identical, most preferably at least about 80% identical to an amino acid region defined by amino acids 114 to 842, inclusive, of SEQ ID NO:2. A REVOLUTA protein of the present invention is also identified as a protein that is at least about 70% identical, more preferably at least about 75% identical, most preferably at least about 80% identical to an amino acid region defined by amino acids 433 to 842, inclusive, of SEQ ID NO:2. A REVOLUTA protein of the present invention is also identified as a protein that is at least about 70% identical, more preferably at least about 75% identical, most preferably at least about 80% identical to an amino acid region defined by amino acids 611 to 745, inclusive, of SEQ ID NO:2.

Amino acid sequence identity can be determined, for example, in the following manner. The portion of the amino acid sequence of REVOLUTA (shown in FIG. 3) extending from amino acid 1 up to and including amino acid 842 is used to search a nucleic acid sequence database, such as the Genbank database, using the program BLASTP version 2.0.9 (Altschul et al., 1997 *Nucleic Acids Res.* 25:3389-3402). Alternatively, the search can be performed with a REVOLUTA protein sequence extending from amino acid 114 up to and including amino acid 842, or amino acid 433 up to and including amino acid 842 or amino acid 611 up to and including 745 of SEQ ID NO:2. The program is used in the default mode. Those retrieved sequences that yield identity scores of at least about 70% when compared to any of the above identified regions of SEQ ID NO:2, are considered to be REVOLUTA proteins.

Sequence comparisons between two (or more) polynucleotides or polypeptides are typically performed by comparing sequences of the two sequences over a "comparison window" to identify and compare local regions of sequence similarity. A "comparison window", as used herein, refers to a segment of at least about 20 contiguous positions, usually about 50 to about 200, more usually about 100 to about 150 in which a sequence may be compared to a reference sequence of the same number of contiguous positions after the two sequences are optimally aligned.

Optimal alignment of sequences for comparison may be conducted by local identity or similarity algorithms such as those described in Smith and Waterman, 1981 *Adv. Appl. Math.* 2:482, by the homology alignment algorithm of Needleman and Wunsch, 1970 *J. Mol. Biol.* 48:443, by the search for similarity method of Pearson and Lipman, 1988 *Proc. Natl. Acad Sci. (U.S.A)* 85:2444, by computerized implementations of these algorithms (GAP, BESTFIT, BLAST, BLASTP2.0.9, TBLASTN, FASTA, and TFASTA in the Wisconsin Genetics Software Package, Genetics Computer Group (GCG), 575 Science Dr., Madison, Wis.; Atdschul et al., 1997), or by inspection.

The term "percent identity" means the percentage of amino acids or nucleotides that occupy the same relative position when two amino acid sequences, or two nucleic acid sequences are aligned side by side using the BLASTP2.0.9 program. "Percent amino acid sequence identity," as used herein, is determined using the BLASTP2.0.9 program with the default matrix: BLOSUM62 (Open Gap=11, Gap extension penalty=1). The percentage is calculated by determining the number of positions at which the identical nucleic acid base of amino acid residue occurs in both sequences to yield the number of matched positions in the window of comparison and multiplying the result by 100 to yield the percentage of sequence identity. Neither N- or C-terminal extensions nor insertions shall be construed as reducing sequence identity.

The term "percent similarity" is a statistical measure of the degree of relatedness of two compared protein sequences. The percent similarity is calculated by a computer program that assigns a numerical value to each compared pair of amino acids based on chemical similarity (e.g., whether the compared amino acids are acidic, basic, hydrophobic, aromatic, etc.) and/or evolutionary distance as measured by the minimum number of base pair changes that would be required to convert a codon encoding one member of a pair of compared amino acids to a codon encoding the other member of the pair. Calculations are made after a best fit alignment of the two sequences have been made empirically by iterative comparison of all possible alignments. (Henikoff et al., 1992 *Proc. Natl. Acad. Sci. USA* 89:10915-10919).

The term "substantial identity" of polynucleotide sequences means that a polynucleotide comprises a sequence that has at least 60% sequence identity, preferably at least 70%, more preferably at least 80% and most preferably at least 90%, compared to a reference sequence using the programs described above (preferably BLAST2) using standard parameters. One of skill will recognize that these values can be appropriately adjusted to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, preferably at least 70%, more preferably at least 80%. Polypeptides which are "substantially similar" share sequences as noted above except that residue positions which are not identical may differ by conservative amino acid changes. Conservative amino acid substitutions refer to the interchangeability of residues having similar side chains. For example, a group of amino acids having aliphatic side chains is glycine, alanine, valine, leucine, and isoleucine; a group of amino acids having aliphatic-hydroxyl side chains is serine and threonine; a group of amino acids having amide-containing side chains is asparagine and glutamine; a group of amino acids having aromatic side chains is phenylalanine, tyrosine, and tryptophan; a group of amino acids having basic side chains is lysine, arginine, and histidine; and a group of amino acids having sulfur-containing side chains is cysteine and methionine. Preferred conservative amino acids substitution groups are: valine-leucine-isoleucine, phenylalanine-tyrosine, lysine-arginine, alanine-valine, and asparagine-glutamine.

Another indication that nucleotide sequences are substantially identical is if two molecules hybridize to each other, or a third nucleic acid, under stringent conditions. Stringent conditions are sequence dependent and will be different in different circumstances. Generally, stringent conditions are selected to be about 5° C. lower than the thermal melting point (Tm) for the specific sequence at a defined ionic strength and pH. The Tm is the temperature (under defined ionic strength and pH) at which 50% of the target sequence hybridizes to a perfectly matched probe. Typically, stringent conditions will be those in which the salt concentration is about 0.02 molar at pH 7 and the temperature is at least about 60° C. Moderately stringent conditions are more preferred when heterologous hybridizations are performed between polynucleotide sequences isolated from different species.

Exemplary high stringency hybridization and wash conditions useful for identifying (by Southern blotting) additional nucleic acid molecules encoding REVOLUTA-homologues are: hybridization at 68° C. in 0.25 M $Na_2HPO_4$ buffer (pH 7.2) containing 1 mM $Na_2EDTA$, 20% sodium dodecyl sulfate; washing (three washes of twenty minutes each at 65° C.) is conducted in 20 mM $Na_2HPO_4$ buffer (pH 7.2) containing 1 mM $Na_2EDTA$, 1% (w/v) sodium dodecyl sulfate.

Exemplary moderate stringency hybridization and wash conditions useful for identifying (by Southern blotting) additional nucleic acid molecules encoding REVOLUTA-homologues are: hybridization at 45° C. in 0.25 M $Na_2HPO_4$ buffer (pH 7.2) containing 1 mM $Na_2EDTA$, 20% sodium dodecyl sulfate; washing is conducted in 5×SSC, containing 0.1% (w/v) sodium dodecyl sulfate, at 55° C. to 65° C. The abbreviation "SSC" refers to a buffer used in nucleic acid hybridization solutions. One liter of the 20× (twenty times concentrate) stock SSC buffer solution (pH 7.0) contains 175.3 g sodium chloride and 88.2 g sodium citrate.

In the case of both expression of transgenes and inhibition of endogenous genes (e.g., by antisense, ribozyme, inverted repeat, sense suppression or transgene directed homologous recombination) one of skill will recognize that the inserted polynucleotide sequence need not be identical and may be "substantially identical" to a sequence of the gene from which it was derived. As explained below, these variants are specifically covered by this term.

In the case where the inserted polynucleotide sequence is transcribed and translated to produce a functional polypeptide, one of skill will recognize that because of codon degeneracy a number of polynucleotide sequences will encode the same polypeptide. These variants are specifically covered by the terms "REVOLUTA gene" and "REVOLUTA transgene." In addition, these terms specifically includes those full length sequences substantially identical (determined as described below) with a gene sequence and that encode a proteins that retain the function of the REVOLUTA gene product.

In the case of polynucleotides used to inhibit expression of an endogenous gene, the introduced sequence need not be perfectly identical to a sequence of the target endogenous gene. The introduced polynucleotide sequence will typically be at least substantially identical (as determined below) to the target endogenous sequence.

Two nucleic acid sequences or polypeptides are said to be "identical" if the sequence of nucleotides or amino acid residues, respectively, in the two sequences is the same when aligned for maximum correspondence as described above. The term "complementary to" is used herein to mean that the complementary sequence is identical to all or a portion of a reference polynucleotide sequence.

The term "modulation of cell division" means any change in the number of cell divisions that occur in a plant or any plant tissue or plant organ as compared to a control set of plants. For example, modulation of cell division in a transgenic plant of the present invention may result in leaf that is larger than a leaf on an untransformed plant due to an increased number of leaf cells. Modulation of cell division may occur in one plant tissue or organ cell type or through out the plant depending upon the promoter that is responsible for the expression of a REVOLUTA transgene. In addition, modulation of cell division by a REVOLUTA transgene may result in a transgenic plant or tissue that has arrested plant growth due to a cessation or diminution of cell division. Modulation of cell division can be determined by a variety of methods well known in the art of plant anatomy (see, for example, Esau, *Anatomy of Seed Plants* [2nd ed.] 1977 John Wiley & Sons, Inc. New York). For example, the overall mass of a transgenic plant may be determined or organ or tissue cell counts may be conducted whereby all of the cells in a representative tissue or organ cross-section are counted. Where the REVOLUTA transgene is expressed in the embryo, modulation of cell division may be also be determined by measuring the size of the seed containing the transgenic embryo as a measure of the number of cells within the embryo.

The terms "alteration", "amino acid sequence alteration", "variant" and "amino acid sequence variant" refer to REVOLUTA proteins with some differences in their amino acid sequences as compared to the corresponding, native, i.e., naturally-occurring, REVOLUTA protein. Ordinarily, the variants will possess at least about 67% identity with the corresponding native REVOLUTA protein, and preferably, they will be at least about 80% identical with the corresponding, native REVOLUTA protein. The amino acid sequence variants of the REVOLUTA protein falling within this invention possess substitutions, deletions, and/or insertions at certain positions. Sequence variants of REVOLUTA may be used to attain desired enhanced or reduced DNA binding, protein oligomerization, ability to engage in specific protein-protein interactions or modifications, transcriptional regulation activity, or modified ability to regulate plant cell division.

Substitutional REVOLUTA protein variants are those that have at least one amino acid residue in the native REVOLUTA protein sequence removed and a different amino acid inserted in its place at the same position. The substitutions may be single, where only one amino acid in the molecule has been substituted, or they may be multiple, where two or more amino acids have been substituted in the same molecule. Substantial changes in the activity of the REVOLUTA protein molecules of the present invention may be obtained by substituting an amino acid with another whose side chain is significantly different in charge and/or structure from that of the native amino acid. This type of substitution would be expected to affect the structure of the polypeptide backbone and/or the charge or hydrophobicity of the molecule in the area of the substitution.

Moderate changes in the functional activity of the REVOLUTA proteins of the present invention would be expected by substituting an amino acid with a side chain that is similar in charge and/or structure to that of the native molecule. This type of substitution, referred to as a conservative substitution, would not be expected to substantially alter either the structure of the polypeptide backbone or the charge or hydrophobicity of the molecule in the area of the substitution. However, it is predictable that even conservative amino acid substitutions may result in dramatic changes in protein function when such changes are made in amino acid positions that are critical for protein function.

Insertional REVOLUTA protein variants are those with one or more amino acids inserted immediately adjacent to an amino acid at a particular position in the native REVOLUTA protein molecule. Immediately adjacent to an amino acid means connected to either the α-carboxy or α-amino functional group of the amino acid The insertion may be one or more amino acids. Ordinarily, the insertion will consist of one or two conservative amino acids. Amino acids similar in charge and/or structure to the amino acids adjacent to the site of insertion are defined as conservative. Alternatively, this invention includes insertion of an amino acid with a charge and/or structure that is substantially different from the amino acids adjacent to the site of insertion.

Deletional variants are those where one or more amino acids in the native REVOLUTA protein molecules have been removed. Ordinarily, deletional variants will have one or two amino acids deleted in a particular region of the REVOLUTA protein molecule.

The terms "biological activity", "biologically active", "activity", "active" "biological function", "REV biological activity" and "functionality" refer to the ability of the REVOLUTA proteins of the present invention to dimerize (or otherwise assemble into protein oligomers), or the ability to modulate or otherwise effect the dimerization of native wild type (e.g., endogenous) REVOLUTA proteins. However the terms are also intended to encompass the ability of the REVOLUTA proteins of the present invention to bind and/or interact with other molecules and which binding and/or interaction event(s) mediate plant cell division and ultimately confer a REV phenotype, or the ability to modulate or otherwise effect the binding and/or interaction of other molecules with native wild type REVOLUTA proteins (e.g., endogenous) and which binding and/or interaction event(s) mediate plant cell division and ultimately confer a REV phenotype. Examples of such molecules include, for example, other members of the HD-Zip III family.

Biological activity as used herein in reference to a nucleic acid of the invention is intended to refer to the ability the nucleic acid to modulate or effect the transcription and/or translation of the nucleic acid and/or ultimately confer a REV phenotype. Biological activity as used herein in reference to a nucleic acid of the invention is also intended to encompass the ability the nucleic acid to modulate or affect the transcription and/or translation of a native wild type REVOLUTA (e.g., endogenous) nucleic acid and/or ultimately confer a Rev phenotype.

REV phenotype as used herein is intended to refer to a phenotype conferred by a REV nucleic acid or protein of the present invention and particularly encompasses the characteristic wherein an effect, relative to wild type, on organ or tissue size (e.g., increased size of seed, leaves, fruit, or root) is exhibited. Typically, a REV phenotype is determined by examination of the plant, where the number of cells contained in various tissues is compared to the number of cells in the corresponding tissues of a parental plant. Plants having a REV phenotype have a statistically significant change in the number of cells within a representative cross sectional area of the tissue.

The biological activities of REVOLUTA proteins of the present invention can be measured by a variety of methods well known in the art, such as: a transcription activity assay, a DNA binding assay, or a protein oligomerization assay. Such assays in the context of HD-Zip proteins, have been described in Sessa et al., 1993; 1997 *J. Mol. Biol.* 274:303-309; 1999; Gonzalez et al., 1997; and Palena et al., 1999 *Biochem. J.* 341:81-87 (contents of said publications incorporated herein by reference). Amino acid sequence variants of the REVOLUTA proteins of the present invention may have desirable altered biological activity including, for example, increased or decreased binding affinity to DNA target sites, increased or decreased ability to form homo- and/or heter-protein oligomers, and altered regulation of target genes.

The terms "vector", "expression vector", refer to a piece of DNA, usually double-stranded, which may have inserted into it a piece of foreign DNA. The vector or replicon may be for example, of plasmid or viral origin. Vectors contain "replicon" polynucleotide sequences that facilitate the autonomous replication of the vector in a host cell. The term "replicon" in the context of this disclosure also includes sequence regions that target or otherwise facilitate the recombination of vector sequences into a host chromosome. In addition, while the foreign DNA may be inserted initially into a DNA virus vector, transformation of the viral vector DNA into a host cell may result in conversion of the viral DNA into a viral RNA vector molecule. Foreign DNA is defined as heterologous DNA, which is DNA not naturally found in the host cell, which, for example, replicates the vector molecule, encodes a selectable or screenable marker or transgene. The vector is used to transport the foreign or heterologous DNA into a suitable host cell. Once in the host cell, the vector can replicate independently of or coincidental with the host chromosomal DNA, and several copies of the vector and its inserted (foreign) DNA may be generated. Alternatively, the vector may target insert of the foreign DNA into a host chromosome. In addition, the vector also contains the necessary elements that permit transcription of the foreign DNA into a mRNA molecule or otherwise cause replication of the foreign DNA into multiple copies of RNA. Some expression vectors additionally contain sequence elements adjacent to the inserted foreign DNA that allow translation of the mRNA into a protein molecule. Many molecules of the mRNA and polypeptide encoded by the foreign DNA can thus be rapidly synthesized.

The term "transgene vector" refers to a vector that contains an inserted segment of foreign DNA, the "transgene," that is transcribed into mRNA or replicated as a RNA within a host cell. The term "transgene" refers not only to that portion of foreign DNA that is converted into RNA, but also those portions of the vector that are necessary for the transcription or replication of the RNA. In addition, a transgene need not necessarily comprise a polynucleotide sequence that contains an open reading frame capable of producing a protein.

The terms "transformed host cell," "transformed" and "transformation" refer to the introduction of DNA into a cell. The cell is termed a "host cell", and it may be a prokaryotic or a eukaryotic cell. Typical prokaryotic host cells include various strains of *E. coli*. Typical eukaryotic host cells are plant cells, such as maize cells, yeast cells, insect cells or animal cells. The introduced DNA is usually in the form of a vector containing an inserted piece of DNA. The introduced DNA sequence may be from the same species as the host cell or from a different species from the host cell, or it may be a hybrid DNA sequence, containing some foreign DNA and some DNA derived from the host species.

In addition to the native REVOLUTA amino acid sequences, sequence variants produced by deletions, substitutions, mutations and/or insertions are intended to be within the scope of the invention except insofar as limited by the prior art. The REVOLUTA acid sequence variants of this invention may be constructed by mutating the DNA sequences that encode the wild-type REVOLUTA, such as by using techniques commonly referred to as site-directed mutagenesis. Nucleic acid molecules encoding the REVOLUTA proteins of the present invention can be mutated by a variety of polymerase chain reaction (PCR) techniques well known to one of ordinary skill in the art. See, e.g., "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, NY (1990).

By way of non-limiting example, the two primer system utilized in the Transformer Site-Directed Mutagenesis kit from Clontech, may be employed for introducing site-directed mutants into the REVOLUTA genes of the present invention. Following denaturation of the target plasmid in this system, two primers are simultaneously annealed to the plasmid; one of these primers contains the desired site-directed mutation, the other contains a mutation at another point in the plasmid resulting in elimination of a restriction site. Second strand synthesis is then carried out, tightly linking these two mutations, and the resulting plasmids are transformed into a mutS strain of *E. coli*. Plasmid DNA is isolated from the transformed bacteria, restricted with the relevant restriction enzyme (thereby linearizing the unmutated plasmids), and then retransformed into *E. coli*. This system allows for generation of mutations directly in an expression plasmid, without the necessity of subcloning or generation of single-stranded phagemids. The tight linkage of the two mutations and the subsequent linearization of unmutated plasmids results in high mutation efficiency and allows minimal screening. Following synthesis of the initial restriction site primer, this method requires the use of only one new primer type per mutation site. Rather than prepare each positional mutant separately, a set of "designed degenerate" oligonucleotide primers can be synthesized in order to introduce all of the desired mutations at a given site simultaneously. Transformants can be screened by sequencing the plasmid DNA through the mutagenized region to identify and sort mutant clones. Each mutant DNA can then be restricted and analyzed by electrophoresis on Mutation Detection Enhancement gel (J. T. Baker) to confirm that no other alterations in the sequence have occurred (by band shift comparison to the unmutagenized control). Alternatively, the entire DNA region can be sequenced to confirm that no additional mutational events have occurred outside of the targeted region.

The verified mutant duplexes in the pET (or other) overexpression vector can be employed to transform *E. coli* such as strain *E. coli* BL21(DE3)pLysS, for high level production of the mutant protein, and purification by standard protocols. The method of FAB-MS mapping can be employed to rapidly check the fidelity of mutant expression. This technique provides for sequencing segments throughout the whole protein and provides the necessary confidence in the sequence assignment. In a mapping experiment of this type, protein is digested with a protease (the choice will depend on the specific region to be modified since this segment is of prime interest and the remaining map should be identical to the map of unmutagenized protein). The set of cleavage fragments is fractionated by microbore HPLC (reversed phase or ion exchange, again depending on the specific region to be modified) to provide several peptides in each fraction, and the molecular weights of the peptides are determined by FAB-MS. The masses are then compared to the molecular weights of peptides expected from the digestion of the predicted sequence, and the correctness of the sequence quickly ascertained. Since this mutagenesis approach to protein modification is directed, sequencing of the altered peptide should not be necessary if the MS agrees with prediction. If necessary to verify a changed residue, CAD-tandem MS/MS can be employed to sequence the peptides of the mixture in question, or the target peptide purified for subtractive Edman degradation or carboxypeptidase Y digestion depending on the location of the modification.

In the design of a particular site directed mutagenesis, it is generally desirable to first make a non-conservative substitution (e.g., Ala for Cys, His or Glu) and determine if activity is greatly impaired as a consequence. The properties of the mutagenized protein are then examined with particular attention to DNA target site binding and HD-Zip protein oligomerization which may be deduced by comparison to the properties of the native REVOLUTA protein using assays previously described. If the residue is by this means demonstrated to be important by activity impairment, or knockout, then conservative substitutions can be made, such as Asp for Glu to alter side chain length, Ser for Cys, or Arg for His. For hydrophobic segments, it is largely size that is usefully altered, although aromatics can also be substituted for alkyl side chains. Changes in the DNA binding and protein multimerization process will reveal which properties of REVOLUTA have been altered by the mutation.

Other site directed mutagenesis techniques may also be employed with the nucleotide sequences of the invention. For example, restriction endonuclease digestion of DNA followed by ligation may be used to generate deletion variants of REVOLUTA, as described in section 15.3 of Sambrook et al. (*Molecular Cloning: A Laboratory Manual,* 2nd Ed., 1989 Cold Spring Harbor Laboratory Press, New York, N.Y.). A similar strategy may be used to construct insertion variants, as described in section 15.3 of Sambrook et al., supra. More recently Zhu et al. (1999, *Proc. Natl. Acad. Sci. USA* 96:8768-8713) have devised a method of targeting mutations to plant genes in vivo using chimeric RNA/DNA oligonucleotides.

Oligonucleotide-directed mutagenesis may also be employed for preparing substitution variants of this invention. It may also be used to conveniently prepare the deletion and insertion variants of this invention. This technique is well known in the art as described by Adelman et al. (1983 *DNA* 2:183); Sambrook et al., supra; "Current Protocols in Molecular Biology", 1991, Wiley (N.Y.), F. T. Ausubel, R. Brent, R. E. Kingston, D. D. Moore, J. D. Seidman, J. A. Smith and K Struhl, eds.

Generally, oligonucleotides of at least 25 nucleotides in length are used to insert, delete or substitute two or more nucleotides in the nucleic acid molecules encoding REVOLUTA proteins of the invention. An optimal oligonucleotide will have 12 to 15 perfectly matched nucleotides on either side of the nucleotides coding for the mutation. To mutagenize nucleic acids encoding wild-type REVOLUTA genes of the invention, the oligonucleotide is annealed to the single-stranded DNA template molecule under suitable hybridization conditions. A DNA polymerizing enzyme, usually the Klenow fragment of *E. coli* DNA polymerase I, is then added. This enzyme uses the oligonucleotide as a primer to complete the synthesis of the mutation-bearing strand of DNA. Thus, a heteroduplex molecule is formed such that one strand of DNA encodes the wild-type REVOLUTA inserted in the vector, and the second strand of DNA encodes the mutated form of the REVOLUTA inserted into the same vector. This heteroduplex molecule is then transformed into a suitable host cell.

Mutants with more than one amino acid substituted may be generated in one of several ways. If the amino acids are located close together in the polypeptide chain, they may be mutated simultaneously using one oligonucleotide that codes for all of the desired amino acid substitutions. If however, the amino acids are located some distance from each other (separated by more than ten amino acids, for example) it is more difficult to generate a single oligonucleotide that encodes all of the desired changes. Instead, one of two alternative methods may be employed. In the first method, a separate oligonucleotide is generated for each amino acid to be substituted. The oligonucleotides are then annealed to the single-stranded template DNA simultaneously, and the second strand of DNA that is synthesized from the template will encode all of the desired amino acid substitutions. An alternative method involves two or more rounds of mutagenesis to produce the desired mutant. The first round is as described for the single mutants: wild-type REVOLUTA DNA is used for the template, an oligonucleotide encoding the first desired amino acid substitution(s) is annealed to this template, and the heteroduplex DNA molecule is then generated. The second round of mutagenesis utilizes the mutated DNA produced in the first round of mutagenesis as the template. Thus, this template already contains one or more mutations. The oligonucleotide encoding the additional desired amino acid substitution(s) is then annealed to this template, and the resulting strand of DNA now encodes mutations from both the first and second rounds of mutagenesis. This resultant DNA can be used as a template in a third round of mutagenesis, and so on.

Transgenic Plants

Transgenic plants can be obtained, for example, by transferring transgenic vectors (e.g. plasmids, virus etc.) that encode REVOLUTA into a plant Preferably, when the vector is a plasmid the vector also includes a selectable marker gene, e.g., the kan gene encoding resistance to kanamycin. The most common method of plant transformation is performed by cloning a target transgene into a plant transformation vector that is then transformed into *Agrobacterium tumifaciens* containing a helper Ti-plasmid as described in Hoeckema et al., (1983 *Nature* 303:179-181). The *Agrobacterium* cells containing the transgene vector are incubated with leaf slices of the plant to be transformed as described by An et al., 1986 *Plant Physiology* 81:301-305 (See also Hooykaas, 1989 *Plant Mol. Biol.* 13:327-336). Transformation of cultured plant host cells is normally accomplished through *Agrobacterium tumifaciens*, as described above. Cultures of host cells that do not have rigid cell membrane barriers are usually transformed using the calcium phosphate method as originally described by Graham et al. (1978 *Virology* 52:546) and modified as described in sections 16.32-16.37 of Sambrook et al., supra. However, other methods for introducing DNA into cells such as Polybrene (Kawai et al., 1984 *Mol. Cell. Biol.* 4:1172), protoplast fusion (Schaffner, 1980 *Proc. Natl. Acad. Sci. USA* 77:2163), electroporation (Neumann et al., 1982 *EMBO J.* 1:841), and direct microinjection into nuclei (Capecchi, 1980 *Cell* 22:479) may also be used. Transformed plant calli may be selected through the selectable marker by growing the cells on a medium containing, e.g., kanamycin, and appropriate amounts of phytohormone such as naphthalene acetic acid and benzyladenine for callus and shoot induction. The plant cells may then be regenerated and the resulting plants transferred to soil using techniques well known to those skilled in the art.

In addition to the methods described above, a large number of methods are known in the art for transferring cloned DNA into a wide variety of plant species, including gymnosperms, angiosperms, monocots and dicots (see, e.g., Glick and Thompson, eds., 1993 *Methods in Plant Molecular Biology*, CRC Press, Boca Raton, Fla.; Vasil, 1994 *Plant Mol. Biol.* 25:925-937; and Komari et al., 1998 *Current Opinions Plant Biol.* 1:161-165 (general reviews); Loopstra et al., 1990 *Plant Mol. Biol.* 15:1-9 and Brasileiro et al., 1991 *Plant Mol. Biol.* 17:441-452 (transformation of trees); Eimert et al., 1992 *Plant Mol. Biol.* 19:485-490 (transformation of *Brassica*); Hiei et al., 1994 *Plant J.* 6:271-282; Hiei et al., 1997 *Plant Mol. Biol.* 35:205-218; Chan et al., 1993 *Plant Mol. Biol.* 22:491-506; U.S. Pat. Nos. 5,516,668 and 5,824,857 (rice transformation); and U.S. Pat. No. 5,955,362 (wheat transformation); U.S. Pat. No. 5,969,213 (monocot transformation); U.S. Pat. No. 5,780,798 (corn transformation); U.S. Pat. Nos. 5,959,179 and 5,914,451 (soybean transformation). Representative examples include electroporation-facilitated DNA uptake by protoplasts (Rhodes et al., 1988 *Science* 240(4849):204-207; Bates, 1999 *Methods Mol. Biol.* 111: 359-366; D'Halluin et al., 1999 *Methods Mol. Biol.* 111:367-373; U.S. Pat. No. 5,914,451); treatment of protoplasts with polyethylene glycol (Lyznik et al., 1989 *Plant Molecular Biology* 13:151-161; Datta et al., 1999 *Methods Mol. Biol.*, 111:335-34); and bombardment of cells with DNA laden microprojectiles (Klein et al., 1989 *Plant Physiol.* 91:440-444; Boynton et al., 1988 *Science* 240(4858):1534-1538; Register et al., 1994 *Plant Mol. Biol.* 25:951-961; Barcelo et al., 1994 *Plant J.* 5:583-592; Vasil et al., 1999 *Methods Mol. Biol.*, 111:349-358; Christou, 1997 *Plant Mol. Biol.* 35:197-203; Finer et al., 1999 *Curr. Top. Microbiol. Immunol.* 240: 59-80). Additionally, plant transformation strategies and techniques are reviewed in Birch, R. G., 1997 *Ann Rev Plant Phys Plant Mol Biol* 48:297; Forester et al., 1997 *Exp. Agric.* 33:15-33. Minor variations make these technologies applicable to a broad range of plant species.

In the case of monocot transformation, particle bombardment appears to be the method of choice for most commercial and university laboratories. However, monocots such as maize can also be transformed by using *Agrobacterium* transformation methods as described in U.S. Pat. No. 5,591,616 to Hiei et al, issued Jan. 7, 1997 "Method for transforming monocotyledons." Another method to effect corn transformation mixes cells from embryogenic suspension cultures with a suspension of fibers (5% w/v, Silar SC-9 whiskers) and plasmid DNA (1 µg/ul) and then placed either upright in a multiple sample head on a Vortex Genie II vortex mixer (Scientific Industries, Inc., Bohemia, N.Y., USA) or horizontally in the holder of a Mixomat dental amalgam mixer (Degussa Canada Ltd., Burlington, Ontario, Canada). Transformation is then carried out by mixing at full speed for 60 seconds (Vortex Genie II) or shaking at fixed speed for 1 second (Mixomat). This process results in the production of cell populations out of which stable transformants can be selected. Plants are regenerated from the stably transformed calluses and these plants and their progeny can be shown by Southern hybridization analysis to be transgenic. The principal advantages of the approach are its simplicity and low cost. Unlike particle bombardment, expensive equipment and supplies are not required. The use of whiskers for the transformation of plant cells, particularly maize, is described in U.S. Pat. No. 5,464,765 to Coffee et al, issued Nov. 7, 1995 "Transformation of plant cells."

U.S. Pat. No. 5,968,830 to Dan et al published Oct. 19, 1999 "Soybean transformation and regeneration methods" describes methods of transforming and regenerating soybean. U.S. Pat. No. 5,969,215 to Hall et al, issued Oct. 19, 1999, describes transformation techniques for producing transformed *Beta vulgaris* plants, such as the sugar beet.

Each of the above transformation techniques has advantages and disadvantages. In each of the techniques, DNA from a plasmid is genetically engineered such that it contains not only the gene of interest, but also selectable and screenable marker genes. A selectable marker gene is used to select only those cells that have integrated copies of the plasmid (the construction is such that the gene of interest and the selectable and screenable genes are transferred as a unit). The screenable gene provides another check for the successful culturing of only those cells carrying the genes of interest.

Traditional *Agrobacterium* transformation with antibiotic resistance selectable markers is problematical because of public opposition that such plants pose an undue risk of spreading antibiotic tolerance to animals and humans. Such antibiotic markers can be eliminated from plants by transforming plants using the *Agrobacterium* techniques similar to those described in U.S. Pat. No. 5,731,179 to Komari et al, issued Mar. 24, 1998 "Method for introducing two T-DNAS into plants and vectors therefor." Antibiotic resistance issues can also be effectively avoided by the use of bar or pat coding sequences, such as is described in U.S. Pat. No. 5,712,135, issued Jan. 27, 1998 "Process for transforming monocotyledonous plants." These preferred marker DNAs encode second proteins or polypeptides inhibiting or neutralizing the action of glutamine synthetase inhibitor herbicides phosphinothricin (glufosinate) and glufosinate ammonium salt (Basta, Ignite).

The plasmid containing one or more of these genes is introduced into either plant protoplasts or callus cells by any of the previously mentioned techniques. If the marker gene is a selectable gene, only those cells that have incorporated the DNA package survive under selection with the appropriate phytotoxic agent. Once the appropriate cells are identified and propagated, plants are regenerated. Progeny from the transformed plants must be tested to insure that the DNA package has been successfully integrated into the plant genome.

There are numerous factors which influence the success of transformation. The design and construction of the exogenous gene construct and its regulatory elements influence the integration of the exogenous sequence into the chromosomal DNA of the plant nucleus and the ability of the transgene to be expressed by the cell. A suitable method for introducing the exogenous gene construct into the plant cell nucleus in a non-lethal manner is essential. Importantly, the type of cell into which the construct is introduced must, if whole plants are to be recovered, be of a type which is amenable to regeneration, given an appropriate regeneration protocol.

Prokaryotes may also be used as host cells for the initial cloning steps of this invention. They are particularly useful for rapid production of large amounts of DNA, for production of single-stranded DNA templates used for site-directed mutagenesis, for screening many mutants simultaneously, and for DNA sequencing of the mutants generated. Suitable prokaryotic host cells include *E. coil* K12 strain 94 (ATCC. No. 31,446), *E. coil* strain W3110 (ATCC No. 27,325) *E. coil* X1776 (ATCC No. 31,537), and *E. coli* B; however many other strains of *E. coli*, such as HB101, JM101, NM522, NM538, NM539, and many other species and genera of prokaryotes including bacilli such as *Bacillus subtilis*, other enterobacteriaceae such as *Salmonella typhimurium* or *Serratia marcesans*, and various *Pseudomonas* species may all be used as hosts. Prokaryotic host cells or other host cells with rigid cell walls are preferably transformed using the calcium chloride method as described in section 1.82 of Sambrook et al., supra. Alternatively, electroporation may be used for transformation of these cells. Prokaryote transformation techniques are set forth in Dower, W. J., in Genetic Engineering, Principles and Methods, 12:275-296, Plenum Publishing Corp., 1990; Hanahan et al., 1991 *Meth. Enzymol.*, 204:63.

As will be apparent to those skilled in the art, any plasmid vector containing replicon and control sequences that are derived from species compatible with the host cell may also be used in the practice of the invention. The vector usually has a replication site, marker genes that provide phenotypic selection in transformed cells, one or more promoters, and a polylinker region containing several restriction sites for insertion of foreign DNA. Plasmids typically used for transformation of *E. coli* include pBR322, pUC18, pUC19, pUCI18, pUC119, and Bluescript M13, all of which are described in sections 1.12-1.20 of Sambrook et al., supra. However, many other suitable vectors are available as well. These vectors contain genes coding for ampicillin and/or tetracycline resistance which enables cells transformed with these vectors to grow in the presence of these antibiotics.

The promoters most commonly used in prokaryotic vectors include the β-lactamase (penicillinase) and lactose promoter systems (Chang et al. 1978 *Nature* 375:615; Itakura et al., 1977 *Science* 198:1056; Goeddel et al., 1979 *Nature* 281:544) and a tryptophan (trp) promoter system (Goeddel et al., 1980 *Nucl. Acids Res.* 8:4057; EPO Appl. Publ. No. 36,776), and the alkaline phosphatase systems. While these are the most commonly used, other microbial promoters have been utilized, and details concerning their nucleotide sequences have been published, enabling a skilled worker to ligate them functionally into plasmid vectors (see Siebenlist et al., 1980 *Cell* 20:269).

Many eukaryotic proteins normally secreted from the cell contain an endogenous secretion signal sequence as part of the amino acid sequence. Thus, proteins normally found in the cytoplasm can be targeted for secretion by linking a signal sequence to the protein. This is readily accomplished by ligating DNA encoding a signal sequence to the 5' end of the DNA encoding the protein and then expressing this fusion protein in an appropriate host cell. The DNA encoding the signal sequence may be obtained as a restriction fragment from any gene encoding a protein with a signal sequence. Thus, prokaryotic, yeast, and eukaryotic signal sequences may be used herein, depending on the type of host cell utilized to practice the invention. The DNA and amino acid sequence encoding the signal sequence portion of several eukaryotic genes including, for example, human growth hormone, proinsulin, and proalbumin are known (see Stryer, 1988 *Biochemistry* W. H. Freeman and Company, New York, N.Y., p. 769), and can be used as signal sequences in appropriate eukaryotic host cells. Yeast signal sequences, as for example acid phosphatase (Arima et al., 1983 *Nuc. Acids Res.* 11:1657), α-factor, alkaline phosphatase and invertase may be used to direct secretion from yeast host cells. Prokaryotic signal sequences from genes encoding, for example, LamB or OmpF (Wong et al., 1988 *Gene* 68:193), MalE, PhoA, or beta-lactamase, as well as other genes, may be used to target proteins expressed in prokaryotic cells into the culture medium.

The construction of suitable vectors containing DNA encoding replication sequences, regulatory sequences, phenotypic selection genes and the REVOLUTA DNA of interest are prepared using standard recombinant DNA procedures. Isolated plasmids, virus vectors and DNA fragments are cleaved, tailored, and ligated together in a specific order to generate the desired vectors, as is well known in the art (see, for example, Maniatis, supra, and Sambrook et al., supra).

As discussed above, REVOLUTA variants are produced by means of mutation(s) that are generated using the method of site-specific mutagenesis. This method requires the synthesis and use of specific oligonucleotides that encode both the sequence of the desired mutation and a sufficient number of adjacent nucleotides to allow the oligonucleotide to stably hybridize to the DNA template.

The present invention comprises compositions and methods for modulating plant cell division. A wide variety of transgenic vectors containing a REVOLUTA derived polynucleotide can be used to practice the present invention. When the REVOLUTA transgenes of the present invention are introduced into plants and expressed either a RNA or RNA and then protein, plant cell division is modulated. Provided below are examples of a number of different ways in which a REVOLUTA transgene may be used to increase or decrease the amount of REVOLUTA protein within a transgenic plant. The altered REVOLUTA protein levels may occur throughout the plant or in a tissue or organ specific manner depending upon the type of promoter sequence operably linked to the REVOLUTA transgene.

The present invention also provides a transgenic plant comprising a chimeric plant gene having a promoter sequence that functions in plant cells; a coding sequence which causes the production of RNA encoding a fusion polypeptide or an RNA that causes homologous gene suppression such that expression of the chimeric plant gene modulates plant growth. The chimeric plant gene also has a 3' non-translated region immediately adjacent to the 3' end of the gene that encodes a polyadenylation signal. The polyadenylation signal functions in plant cells to cause the addition of polyadenylate nucleotides to the 3' end of the RNA. The 5' promoter sequence used to transcriptionally activate the chimeric plant gene is a promoter that is heterologous with respect to the coding sequence and adapted to cause sufficient expression of the chimeric gene to modulate plant growth of a plant transformed with the gene.

Inhibition of REVOLUTA Gene Expression

A number of methods can be used to inhibit gene expression in plants. For instance, antisense RNA technology can be conveniently used. The successful implementation of antisense RNA in developmental systems to inhibit the expression of unwanted genes has previously been demonstrated (Van der Krol et al., 1990 *Plant Mol. Biol.* 14:457; Visser et al., 1991, *Mol. Gen. Genet.* 225:289; Hamilton et al., 1990, *Nature* 346:284; Stockhaus et al., 1990, *EMBO J.* 9:3013; Hudson et al., 1992, *Plant Physiol.* 98:294; U.S. Pat. Nos. 4,801,340, 5,773,692, 5,723,761, and 5,959,180). For example, polygalacturonase is responsible for fruit softening during the latter stages of ripening in tomato (Hiatt et al., 1989 in *Genetic Engineering*, Setlow, ed. p. 49; Sheehy et al., 1988, *Proc. Natl. Acad. Sci. USA* 85:8805; Smith et al., 1988, *Nature* 334:724). The integration of anti-sense constructs into the genome, under the control of the CaMV 35S promoter, has inhibited this softening. Examination of the polygalacturonase mRNA levels showed a 90% suppression of gene expression.

The anti-sense gene is a DNA sequence produced when a sense gene is inverted relative to its normal presentation for transcription. The "sense" gene refers to the gene which is being targeted for control using the anti-sense technology, in its normal orientation. An anti-sense gene may be constructed in a number of different ways provided that it is capable of interfering with the expression of a sense gene. Preferably, the anti-sense gene is constructed by inverting the coding region of the sense gene relative to its normal presentation for transcription to allow the transcription of its complement, hence the RNAs encoded by the anti-sense and sense gene are complementary. It is understood that a portion of the anti-sense gene incorporated into an anti-sense construct, of the present invention, may be sufficient to effectively interfere with the expression of a sense gene and thus the term "anti-sense gene" used herein encompasses any functional portion of the full length anti-sense gene. By the term "functional" it is meant to include a portion of the anti-sense gene which is effective in interfering with the expression of the sense gene.

The nucleic acid segment to be introduced generally will be substantially identical to at least a portion of the endogenous REVOLUTA gene or genes to be repressed. The sequence, however, need not be perfectly identical to inhibit expression. Generally, higher homology can be used to compensate for the use of a shorter REVOLUTA sequence. Furthermore, the introduced REVOLUTA sequence need not have the same intron or exon pattern, and homology of non-coding segments may be equally effective. Normally, a sequence of between about 25 or 40 nucleotides and about the full length REVOLUTA gene sequence should be used, though a sequence of at least about 100 nucleotides is preferred, a sequence of at least about 200 nucleotides is more preferred, and a sequence of at least about 500 nucleotides is especially preferred. The construct is then transformed into plants and the antisense strand of RNA is produced.

Catalytic RNA molecules or ribozymes can also be used to inhibit expression of REVOLUTA genes. It is possible to design ribozyme transgenes that encode RNA ribozymes that specifically pair with virtually any target RNA and cleave the phosphodiester backbone at a specific location, thereby functionally inactivating the target RNA. In carrying out this cleavage, the ribozyme is not itself altered, and is thus capable of recycling and cleaving other molecules, making it a true enzyme. The inclusion of ribozyme sequences within antisense RNAs confers RNA-cleaving activity upon them, thereby increasing the activity of the constructs.

One class of ribozymes is derived from a number of small circular RNAs which are capable of self-cleavage and replication in plants. The RNAs replicate either alone (viroid RNAs) or with a helper virus (satellite RNAs). Examples include RNAs from avocado sunblotch viroid and the satellite RNAs from tobacco ringspot virus, lucerne transient streak virus, velvet tobacco mottle virus, solanum nodiflorum mottle virus and subterranean clover mottle virus. The design and use of target RNA-specific ribozymes is described in Haseloff et al. (1988 *Nature*, 334:585-591) (see also U.S. Pat. No. 5,646,023). Tabler et al. (1991, *Gene* 108:175) have greatly simplified the construction of catalytic RNAs by combining the advantages of the anti-sense RNA and the ribozyme technologies in a single construct Smaller regions of homology are required for ribozyme catalysis, therefore this can promote the repression of different members of a large gene family if the cleavage sites are conserved. Together, these results point to the feasibility of utilizing anti-sense RNA and/or ribozymes as practical means of manipulating the composition of valuable crops.

Another method of suppressing REVOLUTA protein expression is sense suppression. Introduction of nucleic acid configured in the sense orientation has been recently shown to be an effective means by which to block the transcription of target genes. For an example of the use of this method to modulate expression of endogenous genes see, Napoli et al. (1990 *Plant Cell* 2:279-289), Hamilton et al. (1999 *Science* 286:950-952), and U.S. Pat. Nos. 5,034,323, 5,231,020, 5,283,184 and 5,942,657.

More recently, a new method of suppressing the expression of a target gene has been developed. This method involves the introduction into a host cell of an inverted repeat transgene that directs the production of a mRNA that self-anneal to form double stranded (ds) RNA structures (Vionnet et al., 1998 *Cell* 95:177-187; Waterhouse et al., 1998 *Proc. Natl. Acad. Sci. USA* 95:13959-13964; Misquitta et al., 1999 *Proc. Natl. Acad. Sci. USA* 96:1451-1456; Baulcombe, 1999 *Current Opinion Plant Biol.* 2:109-113; Sharp, 1999 *Genes and Develop.* 13:139-141). The ds RNA molecules, in a manner not understood, interfere with the post transcriptional expression of endogenous genes that are homologous to the dsRNA. It has been shown that the region of dsRNA homology must contain region that is homologous to an exon portion of the target gene. Thus, the dsRNA may include sequences that are homologous to noncoding portions of the target gene. Alternatively, gene suppressive dsRNA could also be produce by transform a cell with two different transgenes, one expressing a sense RNA and the other a complementary antisense RNA.

A construct containing an inverted repeat of a REVOLUTA transcribed sequence is made by following the general example of Waterhouse et al. (1998). The inverted repeat part of the construct comprises about 200 to 1500 bp of transcribed DNA repeated in a head to head or tail to tail arrangement. The repeats are separated by about 200 to 1500 bp of non-repeated DNA which can also be part of the transcribed REVOLUTA region, or can be from a different gene, and perhaps contain an intron. A suitable REVOLUTA suppressor transgene construct is made by attaching in the proper order: a plant promoter; a 3' region from a REVOLUTA cDNA oriented in a proper "sense" orientation; a 5' region from the cDNA; the same 3' region of REVOLUTA coding sequence from the cDNA but oriented in "anti-sense" orientation; and finally a polyA addition signal. Whatever the order chosen, the transcribed REVOLUTA RNA resulting from introduction of the inverted repeat transgene into a target plant will have the potential of forming an internal dsRNA region containing sequences from the REVOLUTA target gene that is to be suppressed. The dsRNA sequences are chosen to suppress a single or perhaps multiple REVOLUTA genes. In some cases, the sequences with the potential for dsRNA formation may originate from two or more REVOLUTA genes.

An additional strategy suitable for suppression of REVOLUTA activity entails the sense expression of a mutated or partially deleted form of REVOLUTA protein according to general criteria for the production of dominant negative mutations (Herskowitz 1, 1987, *Nature* 329:219-222). The REV protein is mutated in the DNA binding motif of the homeodomain, or in such a way to produce a truncated REV protein. Examples of strategies that produced dominant negative mutations are provided (Mizukami, 1996; Emmler, 1995; Sheen, 1998; and Paz-Ares, 1990).

Generally, where inhibition of expression is desired, some transcription of the introduced sequence occurs. The effect may occur where the introduced sequence contains no coding sequence per se, but only intron or untranslated sequences homologous to sequences present in the primary transcript of the endogenous sequence. The introduced sequence generally will be substantially identical to the endogenous sequence intended to be repressed. This minimal identity will typically be greater than about 65%, but a higher identity might exert a more effective repression of expression of the endogenous sequences. Substantially greater identity of more than about 80% is preferred, though about 95% to absolute identity would be most preferred. As with antisense regulation, the effect should apply to any other proteins within a similar family of genes exhibiting homology or substantial homology.

For sense suppression, the introduced sequence, needing less than absolute identity, also need not be full length, relative to either the primary transcription product or fully processed mRNA. This may be preferred to avoid concurrent production of some plants which are overexpressers. A higher identity in a shorter than full length sequence may compensate for a longer, less identical sequence. Furthermore, the introduced sequence need not have the same intron or exon pattern, and identity of non-coding segments will be equally effective. Normally, a sequence of the size ranges noted above for antisense regulation is used.

Wild-type REVOLUTA gene function can also be eliminated or diminished by using DNA regions flanking the REVOLUTA gene to target an insertional disruption of the REVOLUTA coding sequence (Miao et al., 1995; *Plant J.* 7:359-365; Kempin et al., 1997 *Nature* 389:802-803). The targeted gene replacement of REVOLUTA is mediated by homologous recombination between sequences in a transformation vector that are from DNA regions flanking the REV gene and the corresponding chromosomal sequences. A selectable marker, such as kanamycin, bar or pat, or a screenable marker, such as beta-glucuronidase (GUS), is included in between the REV flanking regions. These markers facilitate the identification of cells that have undergone REV gene replacement. Plants in which successful REVOLUTA gene replacement has occurred can also be identified because plant tissues have an altered number of cell.

Promoters

An illustrative example of a responsive promoter system that can be used in the practice of this invention is the glutathione-S-transferase (GST) system in maize. GSTs are a family of enzymes that can detoxify a number of hydrophobic electrophilic compounds that often are used as pre-emergent herbicides (Weigand et al., 1986 *Plant Molecular Biology* 7:235-243). Studies have shown that the GSTs are directly involved in causing this enhanced herbicide tolerance. This action is primarily mediated through a specific 1.1 kb mRNA transcription product. In short, maize has a naturally occurring quiescent gene already present that can respond to external stimuli and that can be induced to produce a gene product. This gene has previously been identified and cloned. Thus, in one embodiment of this invention, the promoter is removed from the GST responsive gene and attached to a REVOLUTA coding sequence. If the REVOLUTA gene is derived from a genomic DNA source than it is necessary to remove the native promoter during construction of the chimeric gene. This engineered gene is the combination of a promoter that responds to an external chemical stimulus and a gene responsible for successful production of REVOLUTA protein.

An inducible promoter is a promoter that is capable of directly or indirectly activating transcription of one or more DNA sequences or genes in response to an inducer. In the absence of an inducer the DNA sequences or genes will not be transcribed. Typically the protein factor, that binds specifically to an inducible promoter to activate transcription, is present in an inactive form which is then directly or indirectly converted to the active form by the inducer. The inducer can be a chemical agent such as a protein, metabolite, a growth regulator, herbicide or a phenolic compound or a physiological stress imposed directly by heat, cold, salt, or toxic elements or indirectly through the action of a pathogen or disease agent such as a virus. A plant cell containing an inducible promoter may be exposed to an inducer by externally applying the inducer to the cell or plant such as by spraying, watering, heating or similar methods. If it is desirable to activate the expression of the target gene to a particular time during plant development, the inducer can be so applied at that time.

Examples of such inducible promoters include heat shock promoters, such as the inducible 70 KD heat shock promoter of *Drosphilia melanogaster* (Freeling et al., *Ann. Rev. of Genetics,* 19:297-323); a cold inducible promoter, such as the cold inducible promoter from *B. napus* (White, et al., 1994 *Plant Physiol.* 106); and the alcohol dehydrogenase promoter which is induced by ethanol (Nagao, R. T. et al., Miflin, B. J., Ed. *Oxford Surveys of Plant Molecular and Cell Biology* 1986 Vol. 3, p 384-438, Oxford University Press, Oxford).

Alternatively, the REVOLUTA transgenes of the present invention can be expressed using a promoter such as is the BCE.4 (*B. campestris* embryo) promoter which has been shown to direct high levels of expression in very early seed development (i.e. is transcribed before the napin promoter). This is a period prior to storage product accumulation but of rapid pigment biosynthesis in the *Brassica* seed (derived from Johnson-Flanagan et al., 1989 *J. Plant Physiol.* 136:180; Johnson-Flanagan et al., 1991 *Physiol. Plant* 81:301). Seed storage protein promoters have also been shown to direct a high level of expression in a seed-specific manner (Voelker et al., 1989 *Plant Cell* 1:95; Altenbach et al., 1989 *Plant Mol. Biol.* 13:513; Lee et al., 1991, *Proc. Nat. Acad. Sci. USA* 99:6181; Russell et al., 1997 *Transgenic Res* 6:157-68). The napin promoter has been shown to direct oleosin gene expression in transgenic *Brassica*, such that oleosin accumulates to approximately 1% of the total seed protein (Lee et al., 1991 *Proc. Nat. Acad. Sci. USA* 99:6181). Table 2 lists other embryo specific promoters that can be used to practice the present invention.

TABLE 2

Embryo Specific Promoters

| Promoter | Embryo | Endosperm | Timing | Reference |
|---|---|---|---|---|
| oleosin from Arabidopsis | strong, uniform | none | traces at heart, higher early-to late-cotyledonary stage | Al et al. 1994 Plant Mol. Biol. 25: 193-205. |
| USP from Vicia faba | strong, uniform | none | early not known, strong in late cot., | Baumlein et al. 1991 Mol. Gen. Genet. 225: 459-467. |
| Legumin from Vicia faba | strong, preferential in cotyledons | aleurone layer (late) | early not known, strong in late cot., | Baumlein et al. 1991. |
| Napin from Brassica | | ? | late | Kohno-Murase 1994 Plant Mol. Biol. 26: 1115-1124 |
| Albumin S1 from Arabidopsis | in axis only | none | early-to late-cotyledonary stage | Guerche et al., 1990 Plant Cell 2: 469-478. |
| Albumin S2 | in axis and cotyledons | none | early-to late-cotyledonary stage | Guerche et al., 1990. |

In choosing a promoter, it may be desirable to use a tissue-specific or developmentally regulated promoter that allows suppression or overexpression of in certain tissues without affecting expression in other tissues. "Tissue specific promoters" refer to coding region that direct gene expression primarily in specific tissues such as roots, leaves, stems, pistils, anthers, flower petals, seed coat, seed nucellus or epidermal layers. Transcription stimulators, enhancers or activators may be integrated into tissue specific promoters to create a promoter with a high level of activity that retains tissue specificity. For instance, promoters utilized in overexpression will preferably be tissue-specific. Overexpression in the wrong tissue, such as leaves when attempting to overexpress in seed storage areas, could be deleterious. Preferred expression cassettes of the invention will generally include, but are not limited to, a seed-specific promoter. A seed specific promoter is used in order to ensure subsequent expression in the seeds only.

Examples of seed-specific promoters include the 5' regulatory regions of an *Arabidopsis* oleosin gene as described in U.S. Pat. No. 5,977,436 to Thomas et al issued Nov. 2, 1999 "Oleosin 5' regulatory region for the modification of plant seed lipid composition" (incorporated in its entirety by reference), which when operably linked to either the coding sequence of a heterologous gene or sequence complementary to a native plant gene, direct expression of the heterologous gene or complementary sequence in a plant seed.

Examples also include promoters of seed storage proteins which express these proteins in seeds in a highly regulated manner such as, for dicotyledonous plants, phaseolin (bean cotyledon) (Sengupta-Gopalan, et al., 1985 *Proc. Natl. Acad. Sci. U.S.A.* 82:3320-3324), a napin promoter, a conglycinin promoter, and a soybean lectin promoter, patatin (potato tubers) (Rocha-Sosa, et al., 1989 *EMBO J.* 8:23-29), convicilin, vicilin, and legumin (pea cotyledons) (Rerie, et al., 1991 *Mol. Gen. Genet.* 259:148-157; Newbigin, et al., 1990 *Planta* 180:461470; Higgins, et al., 1988 *Plant Mol. Biol.* 11:683-695), phytohemagglutinin (bean cotyledon) (Voelker, et al. 1987 *EMBO J.* 6:3571-3577), conglycinin and glycinin (soybean cotyledon) (Chen, et al. 1988 *EMBO J.* 7: 297-302), and sporamin (sweet potato tuberous root) (Hattori, et al., 1990 *Plant Mol. Biol.* 14:595-604). For monocotyledonous plants, promoters useful in the practice of the invention include, but are not limited to, maize zein promoters (Schernthaner, et al., (1988) *EMBO J.* 7:1249-1255), a zein promoter, a waxy promoter, a shrunken-1 promoter, a globulin 1 promoter, and the shrunken-2 promoter, glutelin (rice endosperm), hordein (barley endosperm) (Marris, et al. 1988 *Plant Mol. Biol.* 10:359-366), glutenin and gliadin (wheat endosperm) (U.S. Pat. No. 5,650,558). Differential screening techniques can be used to isolate promoters expressed at specific (developmental) times, such as during fruit development. However, other promoters useful in the practice of the invention are known to those of skill in the art.

Particularly preferred promoters are those that allow seed-specific expression. This may be especially useful since seeds are a primary organ of interest, and also since seed-specific expression will avoid any potential deleterious effect in non-seed tissues. Examples of seed-specific promoters include, but are not limited to, the promoters of seed storage proteins, which can represent up to 90% of total seed protein in many plants. The seed storage proteins are strictly regulated, being expressed almost exclusively in seeds in a highly tissue-specific and stage-specific manner (Higgins et al., 1984 *Ann. Rev. Plant Physiol.* 35:191-221; Goldberg et al., 1989 *Cell* 56:149-160). Moreover, different seed storage proteins may be expressed at different stages of seed development Expression of seed-specific genes has been studied in great detail (see reviews by Goldberg et al. (1989) and Higgins et al. (1984). There are currently numerous examples of seed-specific expression of seed storage protein genes in transgenic dicotyledonous plants. These include genes from dicotyledonous plants for bean β-phaseolin (Sengupta-Gopalan et al., 1985; Hoffman et al., 1988 *Plant Mol. Biol.* 11:717-729), bean lectin (Voelker et al., 1987), soybean lectin (Okamuro et al., 1986 *Proc. Natl. Acad. Sci. USA* 83:8240-8244), soybean Kunitz trypsin inhibitor (Perez-Grau et al., 1989 *Plant Cell* 1:095-1109), soybean β-conglycinin (Beachy et al., 1985 *EMBO J.* 4:3047-3053; pea vicilin (Higgins et al., 1988), pea convicilin (Newbigin et al., 1990 *Planta* 180:461470), pea legumin (Shirsat et al., 1989 *Mol. Gen. Genetics* 215:326-331); rapeseed napin (Radke et al., 1988 *Theor. Appl. Genet.* 75:685-694) as well as genes from monocotyledonous plants such as for maize 15 kD zein (Hoffman et al., 1987 *EMBO J.* 6:3213-3221), maize 18 kD oleosin (Lee et al., 1991 *Proc. Natl. Acad. Sci. USA* 888:6181-6185), barley β-hordein (Marris et al., 1988 *Plant Mol. Biol.* 10:359-366) and wheat glutenin (Colot et al., 1987 *EMBO J.* 6:3559-3564). Moreover, promoters of seed-specific genes operably linked to heterologous coding sequences in chimeric gene constructs also maintain their temporal and spatial expression pattern in transgenic plants. Such examples include use of *Arabidopsis thaliana* 2S seed storage protein gene promoter to express enkephalin peptides in *Arabidopsis* and *B. napus* seeds (Vandekerckhove et al., 1989 *Bio/Technology* 7:929-932), bean lectin and bean β-phaseolin promoters to express luciferase (Riggs et al., 1989 *Plant Sci.* 63:47-57), and wheat glutenin promoters to express chloramphenicol acetyl transferase (Colot et al., 1987).

Also suitable for the expression of the nucleic acid fragment of the invention will be the heterologous promoters from several soybean seed storage protein genes such as those for the Kunitz trypsin inhibitor (Jofuku et al., 1989 *Plant Cell* 1:1079-1093; glycinin (Nielson et al., 1989 *Plant Cell* 1:313-328), and β-conglycinin (Harada et al., 1989 *Plant Cell* 1:415-425); promoters of genes for α- and β-subunits of soybean β-conglycinin storage protein for expressing the mRNA or the antisense RNA in the cotyledons at mid- to late-stages of seed development (Beachy et al., 1985 *EMBO J.* 4:3047-3053) in transgenic plants; *B. napus* isocitrate lyase and malate synthase (Comai et al., 1989 *Plant Cell* 1:293-300), delta-9 desaturase from safflower (Thompson et al. 1991 *Proc. Natl. Acad Sci. USA* 88:2578-2582) and castor (Shanklin et al., 1991 *Proc. Natl. Acad. Sci. USA* 88:2510-2514), acyl carrier protein (ACP) from *Arabidopsis* (Post-Beittenmiller et al., 1989 *Nucl. Acids Res.* 17:1777), *B. napus* (Safford et al., 1988 *Eur. J. Biochem.* 174:287-295), and *B. campestris* (Rose et al., 1987 *Nucl. Acids Res.* 15:7197), β-ketoacyl-ACP synthetase from barley (Siggaard-Andersen et al., 1991 *Proc. Natl. Acad. Sci. USA* 88:4114-4118), and oleosin from *Zea mays* (Lee et al., 1991 *Proc. Natl. Acad. Sci. USA* 88:6181-6185), soybean (Genbank Accession No: X60773) and *B. napus* (Lee et al., 1991 *Plant Physiol.* 96:1395-1397).

Attaining the proper level of expression of the nucleic acid fragments of the invention may require the use of different chimeric genes utilizing different promoters. Such chimeric genes can be transferred into host plants either together in a single expression vector or sequentially using more than one vector.

On the other hand, pollen specific promoter—i.e., promoters regulating temporal expression at a time prior to or soon after pollination so that fruit development and maturation is induced without significant seed development—are usually undesirable. Such undesired promoters include but are not limited to inducible promoters, microspore or megaspore promoters, pollen specific promoters, or maternal tissue promoters such as seed coat promoters or any other promoter associated with a gene involved in pollination or ovule maturation or development.

In addition, enhancers are often required or helpful to increase expression of the gene of the invention. It is necessary that these elements be operably linked to the sequence that encodes the desired proteins and that the regulatory elements are operable. Enhancers or enhancer-like elements may be either the native or chimeric nucleic acid fragments. This would include viral enhancers such as that found in the 35S promoter (Odell et al., 1988 *Plant Mol. Biol.* 10:263-272), enhancers from the opine genes (Fromm et al., 1989 *Plant Cell* 1:977-984), or enhancers from any other source that result in increased transcription when placed into a promoter operably linked to the nucleic acid fragment of the invention. For example, a construct may include the CaMV 35S promoter with dual transcriptional enhancer linked to the Tobacco Etch Virus (TEV) 5' nontranslated leader. The TEV leader acts as a translational enhancer to increase the amount of protein made.

The promoter elements described in Table 2 can be fused to the REVOLUTA sequences and a suitable terminator (polyadenylation region) according to well established procedure. Promoters specific for different tissue types are already available or can be isolated by well-established techniques (see for example U.S. Pat. Nos. 5,792,925; 5,783,393; 5,859,336; 5,866,793; 5,898,096; and 5,929,302).

"Digestion", "cutting" or "cleaving" of DNA refers to catalytic cleavage of the DNA with an enzyme that acts only at particular locations in the DNA. These enzymes are called restriction endonucleases, and the site along the DNA sequence where each enzyme cleaves is called a restriction site. The restriction enzymes used in this invention are commercially available and are used according to the instructions supplied by the manufacturers. (See also sections 1.60-1.61 and sections 3.38-3.39 of Sambrook et al., supra.)

"Recovery" or "isolation" of a given fragment of DNA from a restriction digest means separation of the resulting DNA fragment on a polyacrylamide or an agarose gel by electrophoresis, identification of the fragment of interest by comparison of its mobility versus that of marker DNA fragments of known molecular weight, removal of the gel section containing the desired fragment, and separation of the gel from DNA. This procedure is known generally. For example, see Lawn et al. (1982 *Nucleic Acids Res.* 9:6103-6114), and Goeddel et al. (1980).

The foregoing may be more fully understood in connection with the following representative examples, in which "Plasmids" are designated by a lower case p followed by an alphanumeric designation. The starting plasmids used in this invention are either commercially available, publicly available on an unrestricted basis, or can be constructed from such available plasmids using published procedures. In addition, other equivalent plasmids are known in the art and will be apparent to the ordinary artisan. The following examples are in no way intended to limit the scope of the present invention, but rather only illustrate the many possible ways of practicing the invention.

Example 1

Identification of REVOLUTA

Mapping the REVOLUTA Gene Using Polymorphic DNA Markers

To map a gene using small differences or polymorphisms in the DNA, a segregating population of *Arabidopsis* derived from two different ecotypes was screened. To generate this segregating population, a homozygous plant containing mutations in the revoluta gene (rev-1) of the Nossen (No) ecotype was crossed to a wild-type plant of the Landsberg erecta (Ler) ecotype. In the resulting F1 progeny, one chromosome of each pair was of the No ecotype, and the other was of the Ler ecotype. All the F1 progeny contained the rev-1 mutation from the No parent and a wild-type REVOLUTA gene from the Ler parent. One of these F1 progeny (called 21A) was allowed to self-fertilize and to produce F2 seeds in which recombination between the No and Ler chromosomes would have occurred. The F2 plants grown from these seeds were segregating for the different polymorphisms or markers and for the rev-1 mutation.

In order to detect polymorphisms between the different ecotypes, a technique called simple sequence length polymorphisms (SSLP) was used (Bell et al., 1994 *Genomics* 19:137-144). SSLP markers are a set of two primers that amplify a specific region of genomic DNA in a PCR reaction (polymerase chain reaction). The size of the genomic DNA amplified can vary in specific regions between different *Arabidopsis* ecotypes. This allows a determination of the region as being from the Ler or No ecotypes. Two SSLP markers, nga129 and MBK5, had already been identified in the region of chromosome 5 determined to contain the REVOLUTA gene (Talbert, et al., 1995). The nga129 primers (Table 3) amplify a 179 basepair (bp) fragment from the Ler ecotype and a 165 bp fragment from the No ecotype (Bell et al., 1994). The MBK5 primers were known to amplify an ~180 bp fragment from the Ler ecotype (http://genome.bio.upenn.edu/SSLP_info/coming-soon.html.). Experiments conducted with these primers on No ecotype DNA demonstrated that a ~207 bp fragment from the No ecotype was amplified with these primers.

Therefore, these SSLP markers were used to screen the segregating population of 21A progeny described above. First, F2 plants homozygous for the rev-1 mutation were identified by morphology (Talbert et al., 1995). Genome DNA was then prepared as follows. Approximately 50 mg of leaf material was ground in a microcentrifuge tube for 10 seconds with a blue pestle (Kontes Glass Co., Vineland, N.J.). Then, 100 µl of PEB (100 mM Tris, 8.0, 50 mM EDTA, 0.5M NaCl, 0.7% SDS, and 20 mg/ml freshly added proteinase K) was added and leaf material was ground 20 seconds more. Finally, 325 µl PEB was added and the material ground until no leaf chunks remain (15 seconds.) After heating at 65° C. for 1 hour, 260 µl saturated NaCl was added. The tubes were microfuged for 20 minutes at top speed. The supernatant was transferred to a new tube containing 850 µl of 85% isopropanol. This mixture was centrifuged for 10 minutes and the resulting pellet washed in 70% ethanol. The dried pellet was then resuspended in 200 µl TE buffer, then 133 µl LiCl was added and the tubes stored overnight at 4° C. RNA was pelleted for 10 min at room temperature. The supernatant was transferred into a new tube to which 2 volumes of ethanol was added. After 10 minutes centrifugation, the pellet was air dried and resuspended in 50 µl 10 mM Tris (pH 8.0). For PCR, either 1 µl or 1 µl of a 1:10 dilution of this DNA was used.

Genomic DNA was amplified in a PCR reaction using either the nga 129 primers or the MBK5 primers (Table 3) in 1× Buffer, 2 mM $MgCl_2$, 0.2 mM dNTPs 0.25 mM oligonucleotide, 2 U Taq polymerase (Life Technologies, Inc., Rockville, Md.). The PCR conditions included a 94° C. denaturation step for 3 minutes followed by 35 cycles at 94° C. for 30 seconds, 55° C. for 30 seconds, and 72° C. for 40 seconds. Each experiment included control DNA from No, Ler, and 21A plants. Out of the first 372 chromosomes screened (from 186 plants), 60 chromosomes had a Ler marker, indicating that recombination had occurred between the No chromosome and the Ler chromosome. Of the 360 chromosomes analyzed for MBK5, only 15 had the Ler marker.

Additional rev-1 plants were screened with an SSLP marker ~3.4 Mb south (towards the telomere) of nga129 F/R called K2L19. This SSLP marker and others were identified using the following protocol. First, a text file of the DNA sequences (FASTA format) was created from the known DNA sequences of chromosome 5 near the region where the rev-1 was mapped. The DNA sequence text file was saved as a text only document in Microsoft Word 98®, and used as a database for a BLOCKS search engine (Fred Hutchinson Cancer Research Center). The *Arabidopsis* database was searched for strings of repetitive DNA such as "GA" or "TA" repeats of at least 12 by long. Then PCR primers flanking the repetitive region were chosen using a primer program. Primer pairs were chosen to amplify regions of about 150-250 by in size. These primer pairs were then tested on DNA samples extracted from No, Ler, and 21A plants to determine if any polymorphisms could be detected. Primer pairs that amplified DNA fragments that were polymorphic between the No and Ler ecotypes were used to further map the REVOLUTA gene. These new SSLP markers (see Table 3) were named after the bacterial artificial chromosome clone (BAC) in which they were found (the *Arabidopsis* genome has been cloned into ~100 Kb pieces cloned in BACs or other similar vectors, which have been aligned contiguously along the chromosomes). If more than one marker was identified within a BAC, the primer pairs were given additional identification numbers.

TABLE 3

Oligonucleotides used for SSLP

| Primer Name (SEQ ID NO.) | Primer Sequence |
|---|---|
| nga129F (SEQ ID NO.: 13) | 5' TCAGGAGGAACTAAAGTGAGGG 3' |
| nga129R (SEQ ID NO.: 14) | 5' CACACTGAAGATGGTCTTGAGG 3' |
| MBK5-1 (SEQ ID NO.: 15) | 5' ATCACTGTTGTTTACCATTA 3' |
| MBK5-2 (SEQ ID NO.: 16) | 5' GAGCATTTCACAGAGACG 3' |
| K21L19L (SEQ ID NO.: 17) | 5' CTCCCTCCTTTCCAGACACA 3' |
| K21L19R (SEQ ID NO.: 18) | 5' TTCCACCAATTCACTCACCA 3' |
| MUP24-1 (SEQ ID NO.: 19) | 5' CGTAAAACGTCGTCGTTCATT 3' |
| MUP24-2 (SEQ ID NO.: 20) | 5' ATCGCTGGATTGTTTTGGAC 3' |
| MAP19L (SEQ ID NO.: 21) | 5' TTCTAAGAATGTTTTTACCACCAAAA 3' |
| MAF19R (SEQ ID NO.: 22) | 5' CCAACTGCGACTGCCAGATA 3' |
| MUP24-3 (SEQ ID NO.: 23) | 5' TCCGATTGGTCTAAAGTACGA 3' |
| MUP24-4 (SEQ ID NO.: 24) | 5' TGACCAAGGCCAAACATACT 3' |
| MUP24-13 (SEQ ID NO.: 25) | 5' GAAATCTCACCGGACACCAT 3' |
| MUP24-14 (SEQ ID NO.: 26) | 5' CGAATCCCCATTCGTCATAG 3' |
| MAE1-1 (SEQ ID NO.: 27) | 5' TTTCCAACAACAAAAGAATATGG 3' |
| MAE1-2 (SEQ ID NO.: 28) | 5' TGGTATGCGGATATGATCTTT 3' |
| MAE1-3 (SEQ ID NO.: 29) | 5' CACTCGTAGCATCCATGTCG 3' |
| MAE1-4 (SEQ ID NO.: 30) | 5' TCAGATTCAATCGAAAACGAAA 3' |
| MAE1-5 (SEQ ID NO.: 31) | 5' CCGTGGAGGCTCTACTGAAG 3' |
| MAE1-6 (SEQ ID NO.: 32) | 5' CGTTACCTTTTGGGTGGAAA 3' |

When DNA from the plants containing nga129 FIR/rev-1 recombinant chromosomes was screened using K21L19L and K21L19R primers (K21L19 L/R) (Table 3), 6 of the original 60 nga129 recombinant chromosomes were also recombinant for K21L19 L/R DNA region. In addition, 350 more chromosomes were analyzed for the K21L19 L/R polymorphic marker in which only 9 were recombinant for K21L19 L/R giving a total of 15 recombinants. The 350 recombinant chromosomes were also analyzed with the MBK5-1 and MBK5-1 PCR primers (MBK5 1/2) (Table 3). Eight new recombinants were identified at the MBK5 locus defined by the MBK5 1/2 primer pair for a total of 23 MBK5 1/2 recombinants. The K21L19 L/R and MBK5 1/2 loci define a region of 1.95 Mb in chromosome 5 of *Arabidopsis*.

Other SSLP primer/markers were generated in this region, of these the most informative were the primers MUP24-1 and 2 (MUP24 1/2) and MAF19 L and R MAF19 L/R (Table 3, FIG. 1). These markers were used to screen DNA isolated from the K21L19 and MBK5 1/2 recombinant plants. Of the 15 K21L19L/R recombinants, 3 were recombinant for the MUP24 1/2 marker, and none for the MAF19L/R marker. Of the 23 MBK5 1/2 recombinants, 6 were recombinant for MAF19 L/R, and none for MUP24 1/2. As shown in FIG. 1, these results placed the REVOLUTA gene in between MUP24 1/2 and MAF19 L/R in a region encompassing ~340 Kb.

Figure 2:
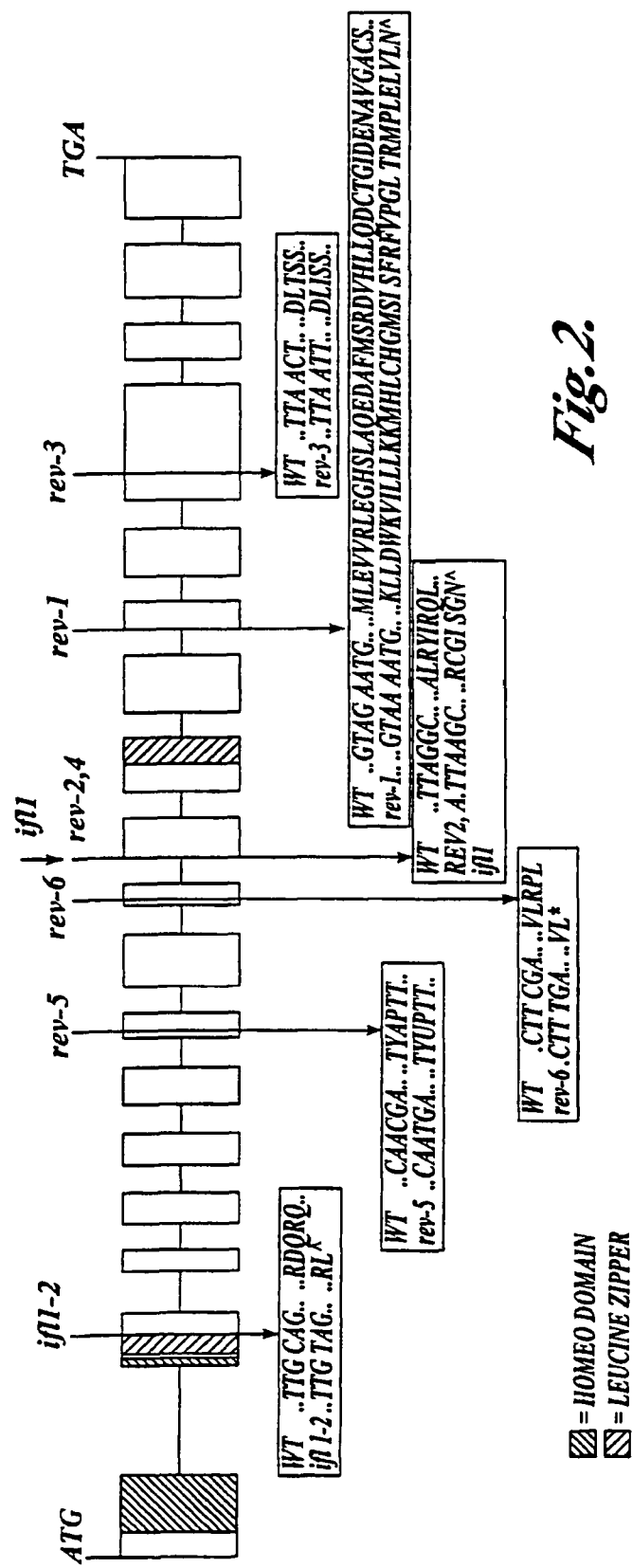
FIG. 2 shows an expanded region of the genetic map presented in FIG. 1 and the location of the REVOLUTA gene as determined by genetic crosses using simple sequence length polymorphism markers.

New SSLP markers were generated in this region, and used to further define where recombination occurred between the Ler and No (rev-1 containing) chromosomes. The markers are listed in FIG. 2 and include: MUP24 3/4, MUP24 13/14, MAE1 1/2, MAE 1 3/4, and MAE1 5/6.

REVOLUTA is Encoded by MUP24.4 and is a New HD-Zip III Subfamily Member

From the above-described mapping results, the smallest chromosome region containing the REVOLUTA gene was approximately 68,000 bp long. An examination of the translated open reading frames in this region revealed about 11 potential genes that could encode REVOLUTA. The MUP24.4—a homeodomain leucine zipper containing protein (HD-Zip) was determined to be the gene of interest. The DNA sequence encoding this HD-Zip protein was determined in DNA isolated from six different revoluta alleles (rev1-6). Genomic DNA from leaves of the different rev alleles was prepared as described above. The MUP24.4 gene was amplified using long distance PCR with the primers in Table 4 and the conditions described in (Henikoff et al., 1998, *Genetics* 149:307-318) except that denaturation steps were carried out at 94° C. and 20 second extensions were added to each cycle after 10 cycles for a total of 40 cycles of PCR amplification.

TABLE 4

Primers used to ampliFY MUP24.4 using LD-PCR

| Primer Name (SEQ ID NO.) | Primer Sequence |
|---|---|
| HDAL (SEQ ID NO: 33) | 5' AAAATGGAGATGGCGGTGGCTAAC 3' |
| HDAR (SEQ ID NO: 34) | 5' TGTCAATCGAATCACACAAAAGACCA 3' |

The resulting PCR products from each revoluta mutant and wild-type REVOLUTA genes were cloned into a TOPO II vector (Invitrogen, Carlsbad, Calif.) according to manufacturers instructions except that half the amount suggested for the TOPO vector and PCR products were used.

Plasmids containing inserts were purified using a spin miniprep kit (QIAGEN Inc., Valencia, Calif.), and sequenced using the oligonucleotides listed in Table 5 with the ABI PRISM Big Dye kit (Applied Biosystems, now PE Biosystems, Foster City, Calif.) according to manufacturer's instructions.

TABLE 5

Primers used to sequence the HD-Zip protein MUP24.4

| Primer Name (SEQ ID NO.) | Primer Sequence |
|---|---|
| Rev-1 (SEQ ID NO: 35) | 5' CAG ACT TTG ATC TGC TTA GGA TC 3' |
| Rev-2 (SEQ ID NO: 36) | 5' TGA GCC TAA GCA GAT CAA AGT C 3' |
| Rev-3 (SEQ ID NO: 37) | 5' ACC GGA AGC TCT CTG CGA TG 3' |
| Rev-4 (SEQ ID NO: 38) | 5' TCG CAG AGG AGA CTT TGG CAG 3' |
| Rev-5 (SEQ ID NO: 39) | 5' GGA GCC TTG AAG TTT TCA CTA TG 3' |
| Rev-6 (SEQ ID NO: 40) | 5' GGT ATT TAA TAA GGC CTT GTG ATG 3' |
| Rev-7 (SEQ ID NO: 41) | 5' AGA ACC TTT AGC CAA AGA TTA AGC 3' |
| Rev-8 (SEQ ID NO: 42) | 5' AGC ATC GAT CTG AGT GGG CTG 3' |
| Rev-9 (SEQ ID NO: 43) | 5' GTA CCG GGA TTG ACG AGA ATG 3' |
| Rev-10 (SEQ ID NO: 44) | 5' TGA GGA GCG TGA TCT CAT CAG 3' |
| Rev-11 (SEQ ID NO: 45) | 5' GCC AGT GTT CAT GTT TGC GAA C 3' |
| Rev-12 (SEQ ID NO: 46) | 5' ATG GCG GTG GCT AAC CAC CGT GAG 3' |
| M13 Forward (SEQ ID NO: 47) | 5' GTA AAA CGA CGG CCA G 3' |
| M13 Reverse (SEQ ID NO: 48) | 5' CAG GAA ACA GCT ATG AC 3' |

Sequence analysis of two independently generated clones per revoluta allele indicate that the REVOLUTA gene sequence [SEQ ID NO:1] is mutated in each of these six revoluta alleles. The observed mutations are found in both putative gene coding sequences (rev-3 [SEQ ID NO:5] and rev-5 [SEQ ID NO:9]) and at putative intron/exon splice junctions (rev-1 [SEQ ID NO:3], rev-2,4 [SEQ ID NO:7] and rev-6 [SEQ ID NO:11]) (See FIG. 3). Thus, DNA sequence analysis identified open reading frames in all six revoluta mutant genes that are capable of expressing a REV HD-Zip protein but the revoluta protein made in each cases has an altered amino acid sequence. The amino acid sequence predicted for the wild-type REVOLUTA protein is shown in FIG. 3 [SEQ ID NO:2] with the mutant amino acids and splice sites indicated. Translation of the rev-4 mutant DNA [SEQ ID NO:7] indicates that the mutation causes a translation frame shift at the beginning of exon 10 that results in a novel eight amino acid carboxy terminal sequence. The rev-4 protein terminates at an out of frame stop codon, thus translation of the rev-4 allele produces a truncated rev-4 polypeptide [SEQ ID NO:8]. SEQ ID NO:1 lists the complete wild-type DNA sequence for the genomic DNA region encoding the REVOLUTA gene. TABLE 6 lists the nucleotide positions mutated in each of the revoluta alleles and the nucleotide change associated with each mutant allele.

TABLE 6

Arabidopsis No-ecotype changes present in revoluta mutant alleles

| revoluta mutant | SEQ ID No.: | Base Change | Location |
|---|---|---|---|
| rev-1 | SEQ ID No.: 3 | G → A | nucleotide 2819 |
| rev-2 | SEQ ID No.: 7 | G → A | nucleotide 2093 |
| rev-3 | SEQ ID No.: 5 | C → T | nucleotide 3252 |
| rev-4 | SEQ ID No.: 7 | G → A | nucleotide 2093 |
| rev-5 | SEQ ID No.: 9 | T → C | nucleotide 2651 |
| rev-6 | SEQ ID No.: 11 | C → T | nucleotide 1962 |

Figure 4A:
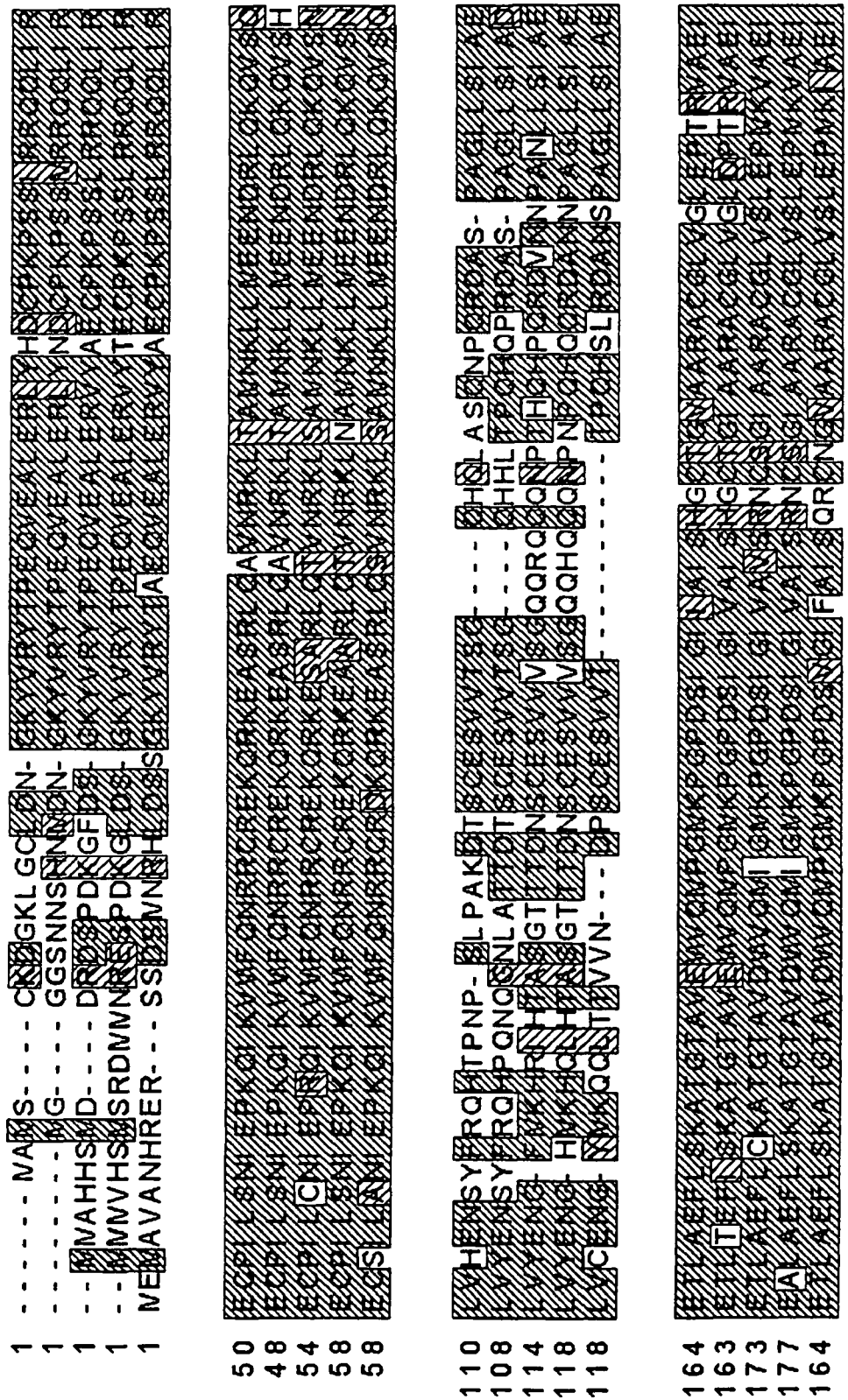
FIG. 4 shows an alignment of the HD-Zip III protein family of *Arabidopsis*. Protein sequences were aligned using a multiple sequence alignment program and boxshade. Residues highlighted in black are identical; conserved residues are highlighted in gray.
Figure 4B:
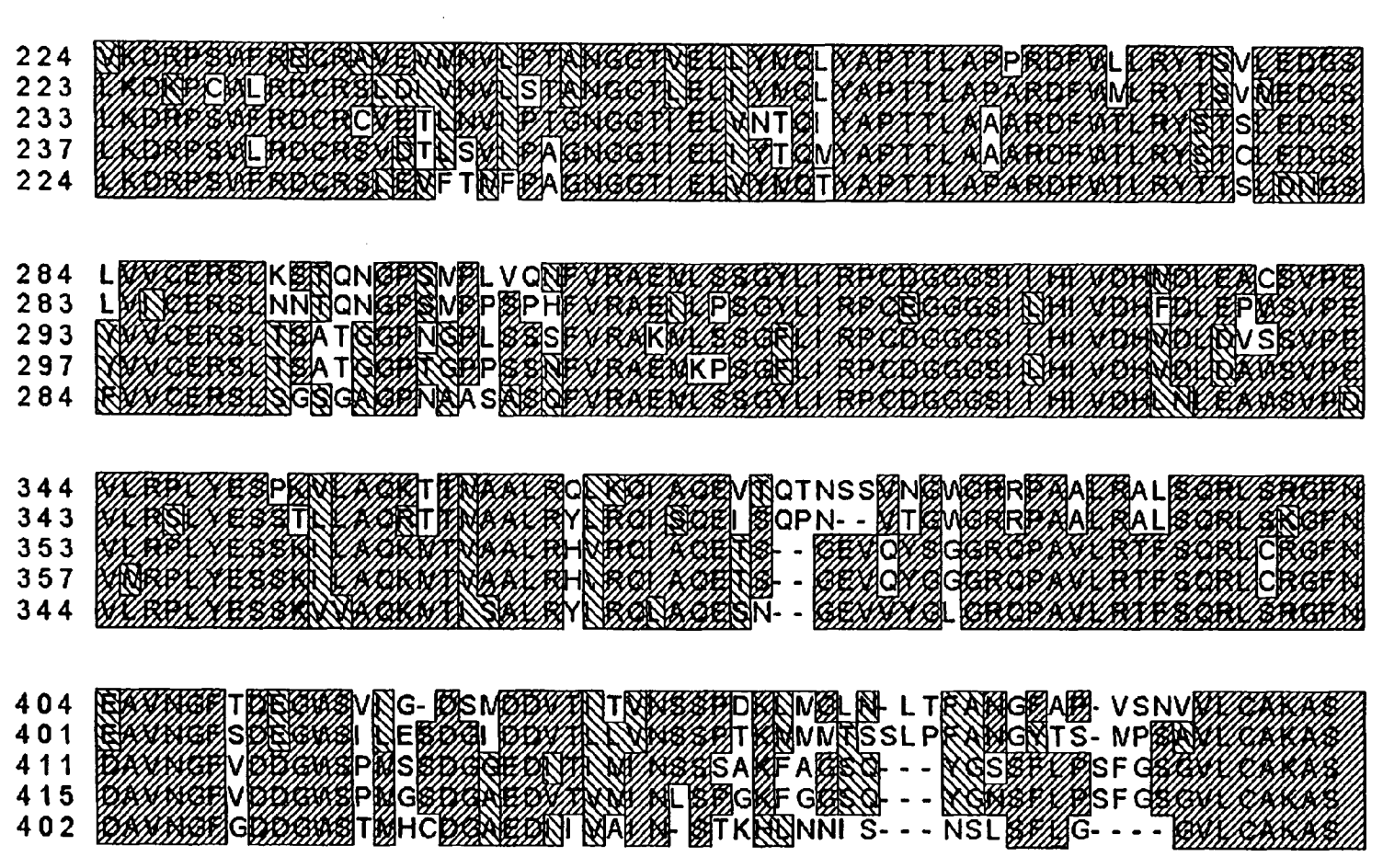
Figure 4C:
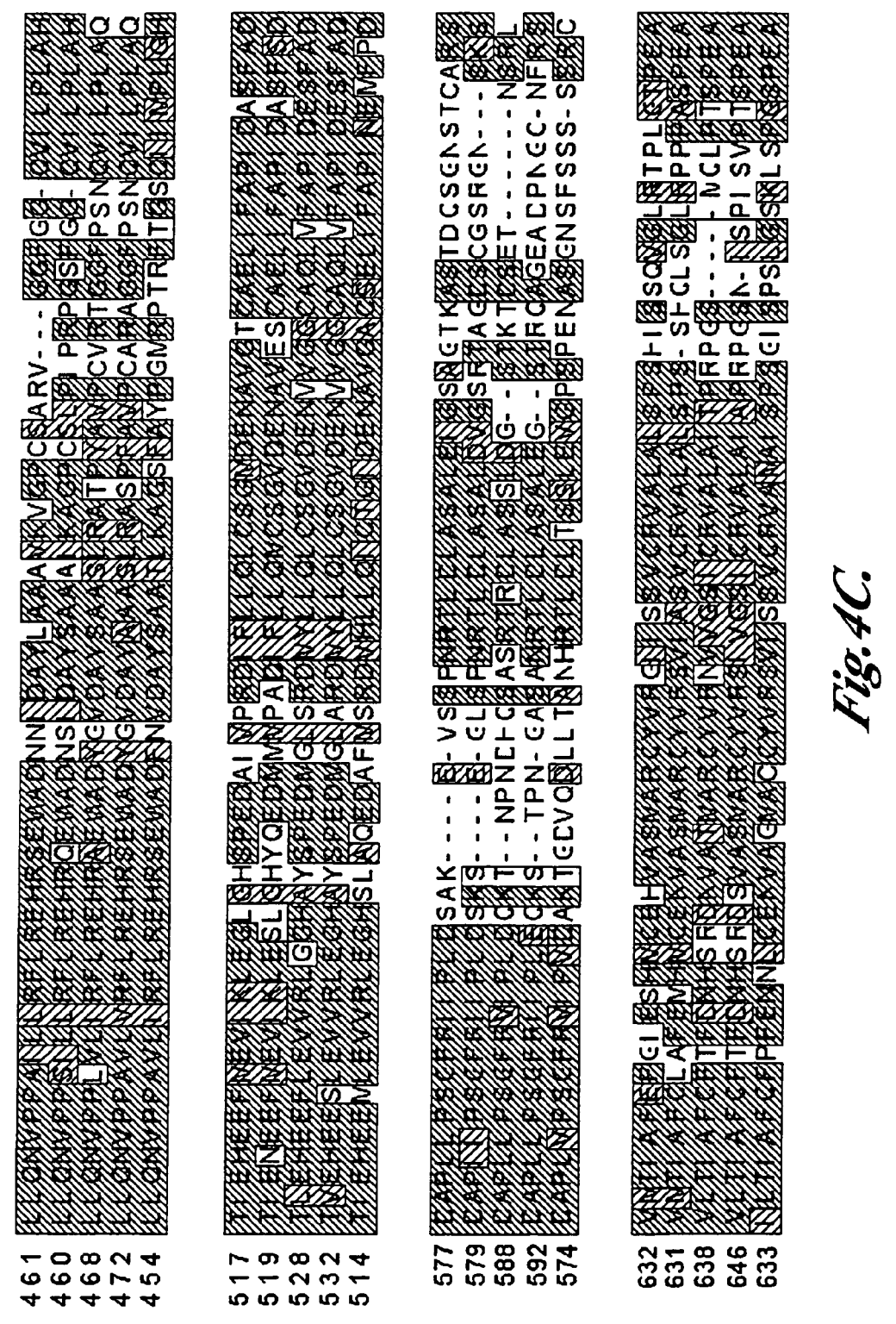
Figure 4D:
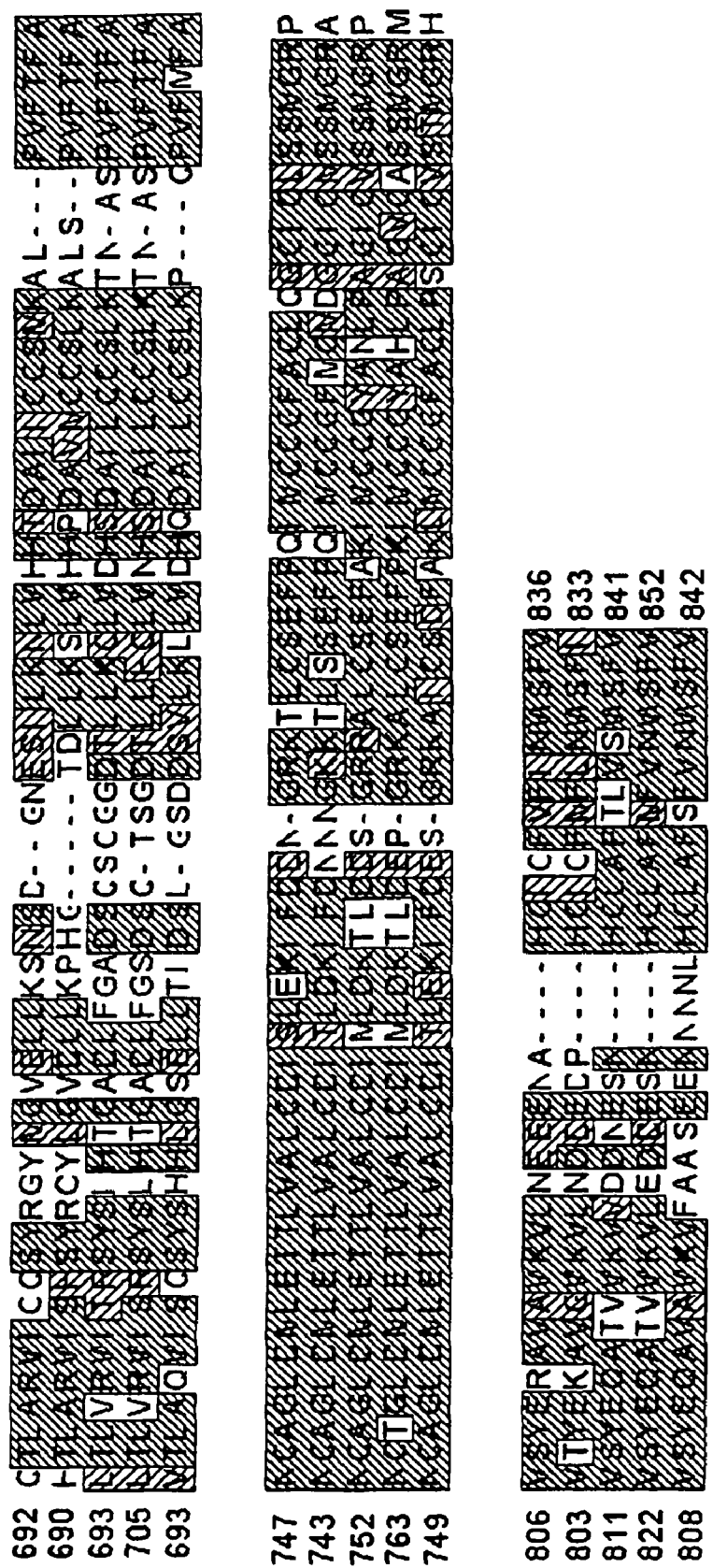

An alignment of the 842 amino acid REV protein sequence with previously identified members of the HD-Zip class III family is shown in FIG. 4. There was extensive homology between REV and the other four proteins over their entire lengths. REV (SEQ ID NO: 2) had 66% identity (78% similarity) to ATHB-9 (SEQ ID NO: 249) and ATHB-14 (SEQ ID NO: 250), 61% identity (75% similarity) to ATHB-8 (SEQ ID NO: 248). Comparison of REV to F5F19.21 (AAD12689.1, SEQ ID NO: 247), a putative new member of the family identified based on sequence similarity, yielded 64% identity and 77% similarity. F5F19.21 was expressed when analyzed using RT-PCR (not shown) and was represented by multiple Genbank EST database entries. When the N-terminal region of the protein, containing the homeobox and leucine zipper domains, was removed prior to alignment (leaving residues 114-832), the homology between the proteins was still quite high: REV showed 64% identity with ATHB-9 and ATHB-14, 61% with F5F19.21, and 58% with ATHB-8. Further analysis of the REV protein sequence indicated that it contained a second leucine zipper motif at residues 432 to 453. Amongst the Arabidopsis HD-ZipIII family members known, REV is the only protein that contained a second predicted leucine zipper.

Example 2

REVOLUTA Clones and Expression Vectors

A variety of recombinant DNA clones have been made that contain the wild-type REVOLUTA gene isolated from genomic DNA obtained from Arabidopsis the Columbia (Co) and Nossen (No) ecotypes. In addition, genomic DNA clones have been obtained from revoluta mutants: rev-1, rev-2, rev-3, rev-4, rev-5 and rev-6. Revoluta mutants rev-1, rev-2, and rev-4 are in the No ecotype background and the rev-3, rev-5, and rev-6 mutants are in Columbia. Overlapping regions of wild-type Columbia Revoluta cDNA were cloned separately into a vector for sequencing. The cDNA sequenced included approximately 350 nucleotides of untranslated 5' sequence, the entire Revoluta coding region and approximately 400 nucleotides of untranslated 3' sequence. The wild-type Columbia REV cDNA sequence was in agreement with the predicted spliced nucleotide sequence available on the Kazusa database site.

Expression of REVOLUTA from an Endogenous Promoter

A region of genomic DNA running from approximately 2.8 kb upstream of the Revoluta coding sequence (5' untranslated DNA) through 200 bp downstream of the initiating Methionine was amplified by PCR from Columbia genomic DNA and cloned into the pCRII-TOPO vector from Invitrogen (PCR primers used: forward primer (includes BamHI restriction site): 5' TTGGATCCGGGAACACTrAAAGTATAGT-GCAATTG 3' [SEQ ID NO:49], reverse primer: 5' CAGACTTTGATCTGCTTAGGCTC 3', [SEQ ID NO:50]). Clones from independent PCR reactions were sequenced to verify the accuracy of the PCR amplification. A clone whose sequence matched that in the Arabidopsis database, except for the apparent deletion of 1 T bp from a stretch of 12 Ts approximately 1.2 kb 5' of the Revoluta coding sequence, was chosen for use in cloning the endogenous Revoluta promoter region (nucleotides 1-2848 of SEQ ID NO:1). A clone, pNO84, containing the genomic DNA sequence of REVOLUTA was isolated from a No-ecotype plant. A 2.8 kb BamHI-SalI restriction digest DNA fragment, including approximately 2.6 kb of promoter and upstream sequence and 0.2 kb of REV coding sequence, was cloned into the BamHI and SalI sites of clone pNO84 to generate a REVOLUTA gene from ecotype No linked to its endogenous promoter. To clone a 3' polyadenylation signal onto the 3' end of the pNO84 Revoluta gene, approximately 0.7 kb of the 3' end of a Revoluta Co gene, starting immediately downstream of the REV stop codon was amplified using the polymerase chain reaction with the following oligonucleotides (5' primer includes a NotI site: 5'TTTGCGGCCGCTTCGATTGACAGAAAAA-GACTAATTT 3' [SEQ ID NO:51]; 3' primer includes ApaI and KpnI sites: 5' TTGGGCCCGGTACCCTCAACCAAC-CACATGGAC 3' [SEQ ID NO:52]). The amplified polyA addition site DNA fragment was cloned into the NotI and ApaI sites of pNO84 3' of the REVOLUTA coding sequence. REVOLUTA expression transgenes containing the expected 3' polyA addition sequence were verified by DNA sequencing. The resulting REVOLUTA transgene containing the REV promoter, coding, and 3' regions was cloned out of the original vector using KpnI and ligated into the pCGN1547 T-DNA binary vector (McBride et al., 1990 Plant Mol. Biol. 14:269-276).

REVOLUTA Expressed from the 35S Cauliflower Mosaic Virus Promoter

A DNA fragment encoding approximately 900 bp of the 35S cauliflower mosaic viral promoter (35S CaMV) was amplified from the pHomer 102 plasmid by PCR using primers 5'AAGGTACCAAGTrCGACGGAGAAGGTGA 3' [SEQ ID No.:53] and 5' AAGGATCCTGTA-GAGAGAGACTGGTGATTTCAG 3' [SEQ ID No.:54]. Clones containing amplified DNA fragments from independent PCR reactions were sequenced to verify the accuracy of the PCR amplification. Kpn1 and BamHI restriction sites were included in the PCR primers to allow for the isolation of a 900 bp Kpn1-BamH1 fragment that includes the amplified 35S CaMV promoter. This Kpn1-BamH1 35S CaMV fragment was inserted 5' of the REV genomic sequence in clone pNO84 at the Kpn1 and BamH1 sites to generate a No Revoluta transgene linked approximately 70 bp downstream of the 35S CaMV promoter transcription start site. The 3' end of the REV gene was placed downstream of the REV coding region following the same procedure described above. The entire 35S CaMV Revoluta transgene was cloned into T-DNA binary vector pCGN1547 using KpnI.

REV Inverted Repeat Constructs

REV cDNA was amplified using the following primers: REVIR-1 TTATCGATAGCTTTGCTTATCCGGGAAT [SEQ ID NO:138] and REVIR-2 TTGCGGCCGCCTGA-CAAGCCATACCAGCAA [SEQ ID NO:139]; REVIR-3 TTGCGGCCGCAGTTCAACGTGTTGCAATGG [SEQ ID NO:140] and REVIR-4 TTGCAT-GCGCTAGCGTCGTCGCTTCCAAGTGAAT [SEQ ID NO:141]; and REVIR-5 TTGTCGACCCGCG-GAGCTTTGCTTATCCGGGAAT [SEQ ID NO: 142] and REVIR-6 TTGATGCGCTAGCCTGACAAGCCATAC-CAGCAA [SEQ ID NO:143]. These PCR products were cloned behind the CaMV 35S promoter in the order 1/2 then 3/4 then 5/6, and then cloned into pCGN1547. All these IR primers have restriction sites on the end. REVIR-1 and REVIR-5 correspond to bp 5496-5515 (in exon 12) and REVIR-2 and REVIR-6 correspond to 6226-6245 (in exon 15). The linker sequence is made from the product of REVIR-3 corresponding to 6268-6288 (in exon 15) and REVIR-4 corresponding to 6509-6528 (in exon 16). The construct therefore consists of: CLAI restriction site 5496-5582; 5668-5748; 5834-5968; 6051-6245 NOTI restriction site 6268-6388; 6477-6528 NHEI SPHI restriction sites 6245-6051; 5968-5834; 5748-5668; 5582-5496 SAC II restriction site (SEQ ID NO: 144).

Additional inverted repeat constructs are made essentially as described above, and include the following: An inverted repeat construct is made from At REV comprising Exons 3-7, 3670 to 3743; 3822 to 3912; 4004 to 4099; 4187 to 4300; and 4383-4466 (SEQ ID NO:145); a linker of exon 15 (SEQ ID NO:146) and SEQ ID NO:147. Similarly, an inverted repeat construct is made from tomato REV comprising SEQ ID NO: 148 and SEQ ID NO: 150, with a linker of SEQ ID NO: 149. Inverted repeat constructs are made from rice, including an inverted repeat construct from rice Rev1, comprising SEQ ID NO:151 and SEQ ID NO:153, with a linker of SEQ ID NO: 152 and an inverted repeat construct from rice Rev2, comprising SEQ ID NO: 154 and SEQ ID NO: 156, with a linker of SEQ ID NO: 155.

Example 3

Complementation of Revoluta Mutants Using REVOLUTA Transgenes

Agrobacterium strain At503 was transformed with the above constructs and cocultivated with root explants from rev-1 and wild-type Nossen 2-3 week old seedlings (Valvekens et al., 1988 Proc. Nat. Acad. Sci. USA 85:5536-5540). Regenerated plants from this tissue are analyzed for complementation of the rev phenotype by comparing the transformed plants to the nontransformed rev mutant plants. Alternatively, Arabidopsis plants expressing a Revoluta transgene can be made using in planta transformation (Bechtold et al., 1998 Methods Mol. Biol. 82:259-266). Gene expression of the transgenes is determined by performing Northern blot hybridization assays using Revoluta transgene specific hybridization probes that do not hybridize significantly to endogenous Revoluta mRNA. Alternatively, Revoluta gene expression is measured by performing reverse transcriptase reactions on isolated mRNA samples and than using copy DNA from the reverse transcriptase reaction as substrate for PCR (see "PCR Strategies", M. A. Innis, D. H. Gelfand and J. J. Sninsky, eds., 1995, Academic Press, San Diego, Calif. (Chapter 14); "PCR Protocols: A Guide to Methods and Applications", M. A. Innis, D. H. Gelfand, J. J. Sninsky and T. J. White, eds., Academic Press, NY (1990)). The amount of PCR amplification product reflects the level of Revoluta gene expression in the plants at the time the tissue was collected for preparation of the mRNA sample.

Partial Complementation of the Rev-1 Mutant

Figure 5H:
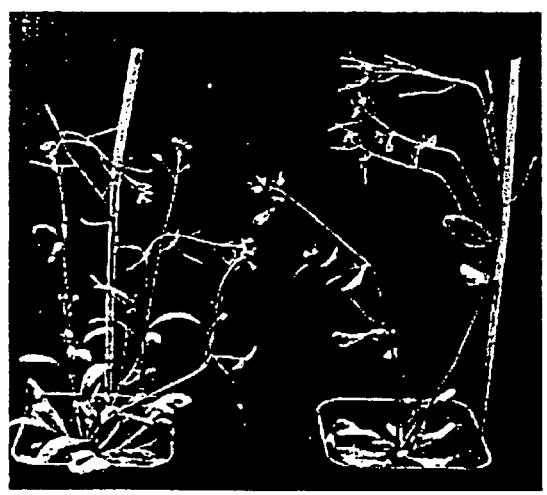
FIG. 5 shows the partial complementation of rev-1 mutants. Panel (A) shows a comparison of rev-1 transgenic plants transformed with either the empty vector (left) or with the 5' REV construct containing the wild-type REV gene under the control of the endogenous promoter (right). Panel (B) shows a close-up of the rev-1 vector-transformed plant showing empty axils and enlarged flowers characteristic of rev mutant plants. Panel (C) shows a close-up of the rev-1 plant transformed with the 5' REV construct. Many of the leaf axils have axillary shoots and the flowers are smaller, similar to wild type. Panel (D) shows a control plant (empty vector) for the inverted-repeat constructs, Columbia ecotype. Panels (E-G) show Columbia plants transformed with the 35S-REVIR construct, showing some characteristics of the Rev-phenotype including empty axils (arrowheads). The flowers are similar in size to wild-type flowers, not enlarged like rev flowers. Panel (H) shows a comparison of 35S-REVIR transgenic plant (left) to a parent Columbia plant (right).

We confirmed that the HD-Zip protein encoded by MUP24.4 was the REV gene product, by transforming constructs containing the wild-type coding region into homozygous rev-1 plants. Partial complementation was seen in one out of six fertile T2 lines transformed with the 5'REV construct. FIG. 5A shows two T2 rev-1 plants, one transformed with the vector alone (left) and one transformed with the 5'REV construct (right). Plants transformed with the 5'REV construct had an increased number of lateral shoots in the axils of the cauline leaves on the main inflorescence, relative to the rev-1 control plant transformed with the vector. They also had narrower leaf stalks, and smaller, less revolute leaves compared to the rev-1 control. Additionally the flowers in this transformed line, like wild-type flowers, are smaller than those on the rev-1 control plants (FIGS. 5B and 5C). Together these results supported the conclusion that the HD-Zip coding region was the REV gene, but suggested that a specific expression pattern may be necessary to complement the rev-1 mutation since no plants were complemented with a Cauliflower Mosaic Virus 35S promoter-Revoluta construct Suppression of REV with an Inverted Repeat Transgene Introduction of antisense RNA and inverted gene repeats into wild-type organisms has been shown to interfere with normal gene function in a variety of systems (reviewed in Sharp and Zamore, 2000). More recently, Waterhouse et al. (1998) showed that transformation of wild-type plants with a construct containing an inverted repeat of a wild-type gene under the control of a ubiquitous promoter, induces silencing of the endogenous gene. These results have been confirmed by Chuang and Meyerowitz (2000). Therefore, to further substantiate the conclusion that the HD-Zip protein identified was the REV gene, we transformed an inverted repeat construct of this ORF under the control of the CaMV 35S promoter into wild-type Columbia plants and determined the induction of a Rev$^-$ phenotype. Of 16 independent transformants examined, five showed a Rev$^-$ phenotype with similar or lesser intensity to that conferred by the weak alleles, rev-3 and -5. In particular, these plants, like rev mutant plants, had a large number of empty axils (FIG. 5E-H), compared to the wild-type Columbia plants (FIGS. 5D and H). FIG. 5H shows a control Columbia plant (right) and a transgenic Rev-like plant containing the inverted repeat construct (left).

Example 4

REV mRNA is Expressed in Proliferating and in Non-Dividing Tissue In Situ Hybridization Non-radioactive in situ hybridization was performed as follows. Either a 455 by central portion of REV, or a 779 by 3' portion of REV was amplified from cDNA as described above using the primers REVcentral-1 GGAGCCT-TGAAGTTTCACTATG [SEQ ID NO:175] and REVcentral-2 AGGCTGCCTTCCTAATCCAT [SEQ ID NO:176]; or the primers REVS'-1 TGAGGAGCGTGATCTCATCAG [SEQ ID NO: 177] and REV 3'-2 CAAAATTATCACATCAT-TCCCTTT [SEQ ID NO: 178] and cloned into the Topo II vector (Invitrogen, Carlsbad, Calif.). The central REV probe was used for FIG. 7 A-L, N-O, and the 3' REV probe for P-Q. A 622 by or FIL was amplified from cDNA using primers FIL-1 CGTCTATGTCCTCCCCTTCC [SEQ ID NO: 179]

and FIL-2 AACGTTAGCAGCTGCAGGA [SEQ ID NO: 180] and cloned into the Topo II vector. Histone H4 was amplified from cDNA using primers H4-1 TGGAAAGG-GAGGAAAAGGTT [SEQ ID NO: 181] and H4-2 GCCCAATCCGTAAAGAGTCC [SEQ ID NO: 182] and cloned into the TOPOII vector. Sense and antisense probes were generated as described in the protocol using a kit (Roche Biochemicals, Indianapolis, Ind.). Pictures were taken on a Nikon Microphot using a Nikon Coolpix digital camera and imported in Adobe Photoshop 4.01.

To determine the level of REV expression in different tissues, semi-quantitative RT-PCR was performed on RNA isolated from 3-4 week old plants (young cauline leaves, young rosette leaves) and 6-7 week old plants (buds, flowers, stems, older cauline leaves, older rosette leaves) using primers from the REV gene. Control reactions were performed simultaneously using primers from the actin gene (ACT2; Accession ATU41998).

REV and ACT2 were simultaneously amplified using RT-PCR on cDNA prepared from various plant tissues. The resulting products were blotted and probed with the respective genes. The blots were quantified using a Phosphorimager detection system and analyzed with NIH Image (1.60). The REV levels were corrected for loading differences using the ACT2 levels. For both genes, amplification of the genomic sequence yields a larger fragment than that derived from the cDNA with the same primers, as expected due to the absence of intronic sequences. Similar results were obtained from duplicate experiments. The tissue source for each lane are as follows: (A) bud, (B) flower, (C) stem, (D) young cauline leaves from 3-4 week plant, (E) older cauline leaves from 6-7 week plant, (F) young rosette leaves from 3-4 week plant, (G) older rosette leaves from 6-7 week plant, (H) no cDNA control, (I) 0.005 ng genomic DNA, (J) 0.05 ng genomic DNA, (K) 0.5 ng genomic DNA, (L) 5 ng genomic DNA.

Figure 6:
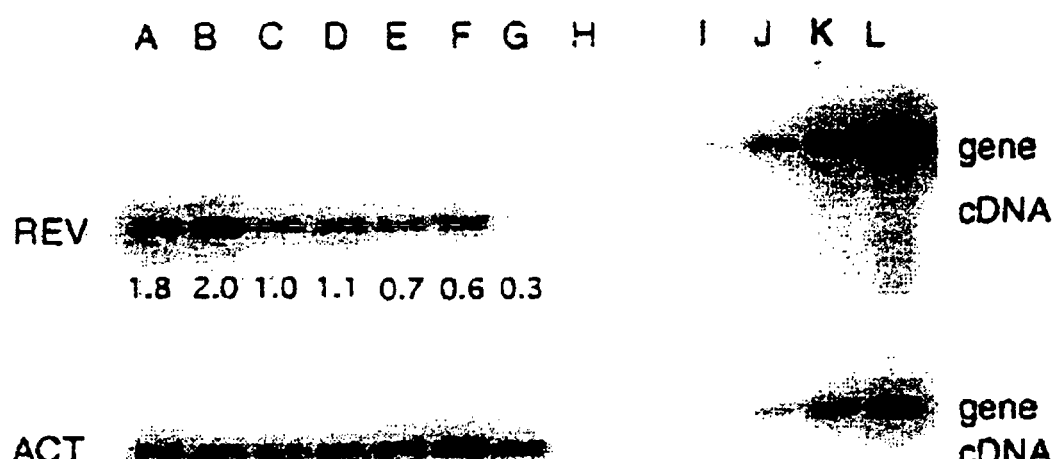
FIG. 6 shows a semi-quantitative RT-PCR analysis of REV mRNA levels.
Figure 7A:
FIG. 7 shows the expression pattern of REV mRNA. Panels (A-C) show longitudinal sections through inflorescence apices. Arrow indicates an axillary meristem in (A) showing REV expression. (B) is an axillary inflorescence meristem. The numbers indicate the stage of the developing flower primordia. im, inflorescence meristem; g, gynoecium; s, stamen; se, sepal. Panel (D) shows a longitudinal section of stage 10 gynoecium. op, ovule primordia; st, stigma. Panel (E) shows a longitudinal section of a young cauline leaf. Panel (F) shows a longitudinal section of a stage 4 flower showing highest expression in anthers and gynoecium. Panel (G) shows transverse section through a stage 9 flower showing highest expression in anthers and gynoecium. t, tapetum; PMC, pollen mother cells. Panel (H) shows a longitudinal section through a stage 8 flower showing REV expression in the stamens and petal. pe, petal primordia. Panel (I) shows a longitudinal section through a stage 9 flower showing REV expression in the stamens and petal. Panel (J) shows a longitudinal section through a developing seed, showing expression in the endosperm. Panel (K) shows a longitudinal section through a developing seed, showing REV expression in the endosperm. Arrow indicates the suspensor. Panel (L) shows a longitudinal section through a developing seed, showing expression in an early heart stage embryo. Panel (M) shows Histone H4 expression in a developing torpedo stage embryo. Panel (N) shows REV sense probe in a developing late heart stage embryo. Panel (O) shows a longitudinal section of an inflorescence apex with REV sense probe. Panel (P) shows a cross-section of a stein probed with REV antisense. co, cortex. Panel (Q) shows a cross-section of a stein with REV sense probe. Panel (R) shows a bright-field image of a cross-section of a rev-1 stem stained in safranin O and fast green FCF as described in Talbert et al., (1995). Panel (S) shows a bright-field image of a cross-section of a wild-type stem.
Figure 7B:
Figure 7C:
Figure 7D:
Figure 7E:
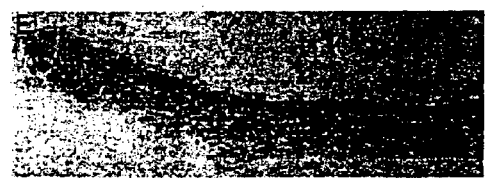
Figure 7F:
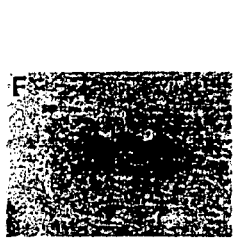
Figure 7G:
Figure 7H:

After PCR amplification, the reaction products were blotted and probed with the respective genes. Quantitation of the REV signal intensity, after normalization to the ACT2 signal, indicated that REV mRNA was detected in all tissues tested, as shown in FIG. 6. It was, however, most abundant in flowers and buds (FIG. 6, lanes A and B). The amount of REV mRNA dropped about twofold in stems and young cauline leaves (lanes C and D) and was further reduced in older cauline leaves and rosette leaves (lanes E, F and G).

In situ hybridization experiments with REV antisense probes showed results consistent with the RT-PCR experiments and are shown in FIG. 7. The REV mRNA was most abundant in apices and in regions of active cell division throughout the plant (FIG. 7A-L). REV was expressed in wild-type inflorescence meristems and its expression increased in floral primordia (FIG. 7A-C). In the floral meristem, an increased concentration of REV mRNA was apparent in sepals, stamen and carpel primordia, relative to the surrounding floral tissue (FIGS. 7C-D and 7F-I). However, REV expression decreased in the sepals of later stage flowers while expression remained strong in developing carpels and stamens at this stage (FIG. 7 A, C, F). REV mRNA was also abundant in axillary meristems (FIG. 7A). In the cauline leaves, expression was detected in two gradients simultaneously, one decreasing from the proximal to distal direction in the leaf, and the other decreasing in the adaxial to abaxial direction in the leaf (FIG. 7E). REV mRNA was detected in early embryos (FIG. 7K) and continued at high levels throughout the cell division phase of embryogenesis and in the endosperm (FIGS. 7L and J). Finally, REV mRNA was detected in mature non-dividing tissue of the stem, particularly in the cortical and vascular regions (FIG. 7P). This expression pattern correlates with the increased numbers of cell layers seen in the cortex of rev-1 stems (FIG. 7R) compared to wild-type stems (FIG. 7S).

Rev-1 Mutant Plants Display an Altered Pattern of the S-Phase Cells

Figure 8A:
FIG. 8 shows Histone H4 and FIL expression in rev-1 and wild-type tissue. Panel (A) shows Histone H4 expression in a longitudinal section of a wild-type inflorescence apex. Panel (B) shows Histone H4 expression in a longitudinal section of a rev-1 inflorescence apex. Panel (C) shows an enlarged view from A. Panel (D) shows an enlarged view from B, showing the increased number of H4 expressing cells in the adaxial side of the leaf. Panel (E) shows FIL expression in a transverse section of a wild-type inflorescence meristem (im), including stamen (st) and sepal (se) primordia of stage 3 and 5 flowers. Panel (F) shows transverse section through wild-type flower showing FIL expression in the abaxial sides of carpel valves (va) and petals (pe). Panel (G-H) shows FIL expression in a longitudinal section through rev-1 inflorescence apex, and developing stage 7 flower in the abaxial side of developing stamens (st). Panel (I) shows FIL expression in a transverse section through a rev-1 flower showing FIL expression in the abaxial sides of valves (va) and petal (pe).
Figure 8B:
Figure 8C:
Figure 8D:
Figure 8E:
Figure 8F:
Figure 8G:
Figure 8H:
Figure 8I:

The histone H4 gene is transcribed only in actively dividing cells and cells undergoing endoreduplication. Consequently, histone H4 mRNA can be used as a marker of cell cycle activity. To better understand how the REV gene influences cell division patterns in developing plants, histone H4 mRNA in situ hybridizations were performed on wild-type and rev-1 mutant plants. The number of cells expressing the H4 mRNA appeared increased in rev-1 mutant plants relative to wild type as shown in FIGS. 8A and 8B. This was particularly noticeable in the adaxial regions of cauline leaves and in the stem, both of which are regions that undergo excess growth in rev mutants. The striking localization of cell divisions to the adaxial compartment of rev cauline leaves affected the entire length of the leaf. In the thickened region proximal to the axil, clusters of cell divisions were common in the rev-1 mutant (FIG. 8D) compared to wild type (FIG. 8C).

Example 5

REV Double Mutants

FIL is Properly Expressed in Rev Mutants

REV Double Mutants lfy REV double mutants were obtained as described in Talbert et al., (1995). Briefly, REV F2 individuals from a rev-1 X lfy-6/+ cross were progeny tested for segregation of lfy rev F3 double mutants. The putative lfy rev-1 plants were tested using PCR to verify the presence of the lfy mutation because rev and lfy are tightly linked. The lfy-6 CAPS markers used were designed to take advantage of the single base pair change giving rise to the lfy-6 mutation: a CAA to UAA change at codon 32. The primers are AACGAGAGCATTG-GTTCAAG [SEQ ID NO:183] and CAACGAAAGATAT-GAGAGAG [SEQ ID NO:184]. Cutting the resulting PCR product with MaeIII distinguishes the lfy-6 mutant from the wild-type gene. For the rev fil mutant, pollen from homozygous rev-1 plants were crossed to homozygous fil-1 plants. The heterozygous progeny was crossed to rev-1 pollen and plants homozygous for both rev-1 and fil-1 identified.

Scanning Electron Microscopy

Samples were fixed in 3% glutaraldehyde in 0.02M sodium phosphate pH 7.0, and vacuum infiltrated for 15-30 minutes, then stored at 4° C. for 16 hours or greater. Samples were placed in 1% osmium tetroxide (Polysciences, Warrington, Pa.) for 2-4 hours before dehydration in an ethanol series. The samples were dried using a Denton DCP-1 Critical Point Drying Apparatus (Denton Vacuum Inc., Moorestown, N.J.). Samples were mounted on carbon conductive pads fixed to SEM specimen mounts and coated with Au/Pd. A Jeol JSM-840A scanning microscope was used. The images were taken using Polaroid Type 55 film, then scanned and imported into Adobe Photoshop 4.01

In fil mutants, flowers form earlier that in wild-type plants, tertiary shoots fail to form due to an apparent lack of meristem formation at the base of cauline leaves, and flowers show aberrant number, shape and arrangement of organs. Additionally severe fil alleles sometimes form flowerless pedicels or pedicels with single sepal structures on their distal end which resemble the filaments formed in rev plants (Chen et al., 1999; Sawa et al., 1999). In fil rev double mutants the primary inflorescence is severely shortened, and all floral primordia appear to terminate as flowerless pedicels. These structures, like pedicels on wild-type flowers, are smooth. However, because all floral primordia become flowerless pedicels, it has been suggested that REV and FIL have partially redundant functions to promote flower formation in floral primordia (Chen et al., 1999).

Given this strong double-mutant phenotype, it was helpful to determine the expression of FIL mRNA in rev plants. In wild-type plants, FIL mRNA expression occurs weakly throughout the SAM, but as the floral meristem becomes distinct from the SAM, FIL expression increases on the abaxial side of the meristem (Siegfried et al., 1999). FIL in situs on rev-1 tissue were indistinguishable from the wild-type controls, indicating that disruption of the rev gene product does not influence FIL expression (FIG. 7E-I).

Interactions of rev with Other Mutations

Figure 9A:
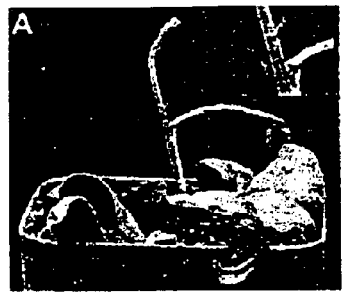
FIG. 9 shows rev double mutants. Panel (A) shows a rev lfy double mutant with severely shortened inflorescence terminating in a brush of filaments. The plant also has revolute leaves. Inset: an enlarged view of small filamentous appendages found on the stem of rev lfy plants. Panel (B) shows a rev lfy double mutant with severely shortened inflorescence and revolute leaves. Panel (C) shows small filamentous appendages present on the stem of rev lfy plants which resemble a structure frequently seen in axils of rev mutant plants. Panel (D) shows an axil of rev-1 mutant plant with small filamentous appendage. Panel (E) shows the inflorescence structure of a rev lfy plant with a cluster of flowerless filaments that can have stellate trichomes or carpelloid features. Panel (F) shows the inflorescence structure of a rev fil plant with a cluster of smooth flowerless filaments. Panel (G) shows an SEM of a rev fil inflorescence. Bar is 1 mm. Panel (H) shows an SEM of a rev lfy inflorescence with carpelloid features. Panel (I) shows an SEM of a rev lfy inflorescence.
Figure 9B:
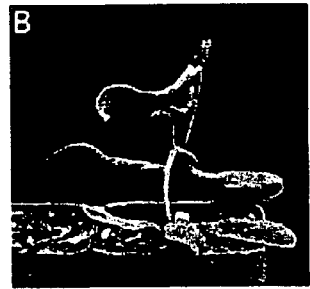
Figure 9C:
Figure 9D:
Figure 9E:
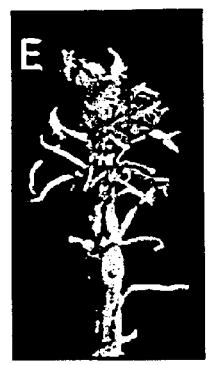
Figure 9F:
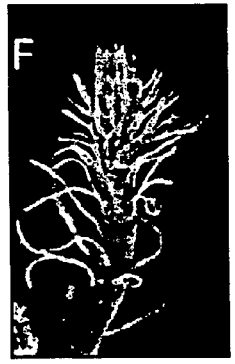
Figure 9G:
Figure 9H:

In order to better understand REV activity in floral meristems, we created rev-1 lfy-6 double mutant plants. LFY function is required for proper specification of floral meristem identity. As shown in FIG. 9, lfy rev double mutants, like rev fil double mutants, were short plants with a single inflorescence terminating in a bundle of filamentous structures. Unlike the filamentous structures formed in rev fil double mutants, which are usually smooth and resemble flowerless pedicels (FIGS. 9 B, F and G), the filamentous structures formed on rev lfy double mutants ranged from smooth to hairy acropetally, and were leaf-like in that they had stellate trichomes, although some were carpelloid (FIG. 9 A, E, H-D). A scale-like structure was visible at the base of each filament (FIGS. 9H and I) and may represent a rudimentary subtending organ (Long and Barton, 2000). Additionally rev lfy double mutants had one or more filamentous stem appendages, usually on the opposite side as the first cauline leaf (FIGS. 9 A and C). The appendages resembled the structures often detected in the axil of rev single mutants (FIG. 9D). As with the fil rev double mutant, the lfy rev double mutant indicates that REV has a role in floral meristem maintenance.

Figure 9I:

In concert with LFY, APETALA 1 is required to establish the floral meristem. Ectopic expression of either LFY or AP1 during vegetative development can result in precocious flower formation (Weigel and Nilsson (1995) Nature 377, 495; Mandel and Yanofsky (1995) Nature 377: 522). AP1 plays an additional role in determining the identity of sepal and petal organs in the first and second whorl. Specifically, in ap1-1 mutants, sepals are converted into cauline leaf or bract-like structures, and petals are absent having failed to be initiated. In addition, floral meristems are converted partially or completely into inflorescence meristems in the axil of the cauline leaf-like sepals, leading to the production of highly branched structures (Bowman 1993 Dev 119, 721-743 FIG. 9). Unlike the rev lfy double mutant, rev-1 ap1-1 double mutants produce normal size inflorescences with floral defects expected from the respective single mutant phenotypes (FIG. 9). The rev-1 ap1-1 mutant flowers resembled single ap1-1 mutant flowers, except that they had longer bract-like sepals than the ap1-1 mutant flowers (FIG. 9I). Although this phenotype of the rev-1 ap1-1 mutant is additive, the lack of axillary meristems of the rev-1 mutant is epistatic to the increased number of axillary meristems of the ap1-1 mutant which results in a non-branched structure (FIG. 9).

AGAMOUS is another multifunctional gene that regulates floral organ identity and is required for determinate growth of the flower. In ag-1 mutants, petals develop in place of the stamens in the third whorl, and a new flower is initiated in place of the carpels in the fourth whorl. The phenotype of the rev-1 ag-1 mutant is additive with the double mutant flowers producing enlarged petals as in rev-1 plants, but with petals in the third whorl as in ag-1 plants (FIG. 9). Also, rev-1 ag-1 double mutant flowers reiterate flower development in the fourth whorl as ag-1 single mutants.

The CLAVATA genes control the size of the apical meristem. Loss of function clv mutants have enlarged apical meristems due to the accumulation of undifferentiated stem cells in the central zone of the apical meristem. The strong clv1-4 mutant also has club shaped seed pods due to the presence of additional carpels. The double clv1-4 rev-1 mutant phenotype is synergistic because the have massive overgrowth of structures from within the floral bud. These callus-like tissues actually burst through the seed pod as they continue growing. This result is consistent with a role for REV in limiting cell divisions in the floral tissues that is partially redundant with CLV1 as revealed by the double mutant phenotype.

Example 6

Identification and Isolation of REVOLUTA from Other Plant Species

In one embodiment the present invention provides a method to identify and use REVOLUTA genes and proteins that function as modulators of cell division in the plant species from which they are isolated. REVOLUTA orthologs to the *Arabidopsis* REVOLUTA gene are isolated using a combination of a "sequence similar test" and a REVOLUTA "gene function test." First, a candidate REVOLUTA gene sequence is isolated from target plant DNA, such as for example, genomic DNA or DNA maintained in a gene library, by the polymerase chain reaction using "CODEHOP" PCR primers (Rose et al., 1998 *Nucleic Acids Res.* 26:1628-1635) that amplify subfamily III HD-Zip polynucleotides. The amplified DNA is then sequenced to determine that the PCR product encodes a region of protein that is at least about 70% identical, more preferably at least about 75% identical, and most preferably at least about 80% identical to the *Arabidopsis* REVOLUTA protein sequence corresponding to the PCR amplified region. The "gene function test" is then performed using a polynucleotide region from the candidate REVOLUTA coding sequence that has been transferred into a plant transformation vector and transformed back into the plant species from which the candidate REVOLUTA gene was derived. Actual REVOLUTA genes are those that modulate plant cell division when the REVOLUTA transgene is expressed in the transformed plant.

Identification of HD-Zip Subfamily III PCR Primers

To generate HD-Zip subfamily III CODEHOP primers, the known HD-Zip III amino acid sequences were entered into the blockmaker program located at the Fred Hutchinson Cancer Research Center website. The program compares the sequences and generates blocks of homology conserved between the different proteins. Table 8 lists the HD-Zip III amino acid block made from six HDZip III family members.

TABLE 8

HD-Zip III amino block identified using the
Fred Hutchinson Cancer Research Center "blocks"
computer program

| HD-Zip Block HD-Zip Protein | Amino Acid Sequence |
|---|---|

HD-ZipIII: Block A
(block width = 43)

REVOLUTA        24  GKYVRYTAEQVEALERVYAECPKPSSLRRQQLIRECSILANIE
SEQ ID NO.: 2

Athb-14         24  GKYVRYTPEQVEALERVYTECPKPSSLRRQQLIRECSILSNIE
SEQ ID NO.: 55

Athb-8          14  GKYVRYTPEQVEALERLYNDCPKPSSMRRQQLIRECSILSNIE
SEQ ID NO.: 56

Athb-9          20  GKYVRYTPEQVEALERVYAECPKPSSLRRQQLIRECPILMCNIE
SEQ ID NO.: 57

CRHB1           19  GKYVRYTSEQVQALEKLYCECPKPTLLQRQQLIRECSILRNVD
SEQ ID NO.: 58

F5F19.21        16  GKYVRYTPEQVEALERLYHDCPKPSSIRRQQLIRECPILSNIE
SEQ ID NO.: 59

HD-ZipIII: Block B
(block width = 42)

REVOLUTA        70  IKVWFQNRRCRDKQRKEASRLQSVNRKLSAMNKLLMEENDRL
SEQ ID NO.: 2

Athb-14         70  IKVWFQNRRCREKQRKEAARLQTVNRKLNAMNKLLMEENDRL
SEQ ID NO.: 197

Athb-8          60  IKVWFQNRRCREKQRKEASRLQAVNRKLTAMNKLLMEENDRL
SEQ ID NO.: 198

Athb-9          66  IKVWFQNRRCREKQRKESARLQTVNRKLSAMNKLLMEENDRL
SEQ ID NO.: 199

CRHB1           65  IKVWFQNRRCREKQRKEWCRLQSLNGKLTPINTMLMEENVQL
SEQ ID NO.: 200

F5F19.21        62  IKVWFQNRRCREKQRKEASRLQAVNRKLTAMNKLLMEENDRL
SEQ ID NO.: 201

HD-ZipIII: Block C
(block WIDTH = 29)

REVOLUTA        154 SPAGLLSIAEETLAEFLSKATGTAVDWVQ
SEQ ID NO.: 2

Athb-14         167 NPAGLLSIAEEALAEFLSKATGTAVDWVQ
SEQ ID NO.: 202

Athb-8          153 SPAGLLSIADETLTEFISKATGTAVEWVQ
SEQ ID NO.: 203

Athb-9          163 NPANLLSIAEETLAEFLCKATGTAVDWVQ
SEQ ID NO.: 204

CRHB1           109 KVAQLVTINHALRRQLSSTPSHFRFPTVS
SEQ ID NO.: 205

TABLE 8-continued

HD-Zip III amino block identified using the
Fred Hutchinson Cancer Research Center "blocks"
computer program

| HD-Zip Block HD-Zip Protein | Amino Acid Sequence |
|---|---|
| F5F19.21 SEQ ID NO.: 206 | 154 SPAGLLSIAEETLAEFLSKATGTAVEWVQ |

HD-ZipIII: Block D
(block width = 31)

| | |
|---|---|
| REVOLUTA SEQ ID No.:2 | 446 VLCAKASMLLQNVPPAVLIRFLREHRSEWAD |
| Athb-14 SEQ ID NO.: 207 | 464 VLCAKASMLLQNVPPAVLVRFLREHRSEWAD |
| Athb-8 SEQ ID NO.: 208 | 452 VLCAKASMLLQNVPPSILLRFLREHRQEWAD |
| Athb-9 SEQ ID NO.: 209 | 460 VLCAKASMLLQNVPPLVLIRFLREHRAEWAD |
| CRHB1 SEQ ID NO.: 210 | 138 LMNIYAIVRLQHVPIPECRS[2]XXXXXXXXXX |
| F5F19.21 SEQ ID NO.: 211 | 453 VLCAKASMLLQNVPPAILLRFLREHRSEWAD |

[1]The number denotes the amino acid position of the first amino acid in each block using the amino acid numbers in each protein sequence disclosed in the referenced SEQ ID Number.
[2]X means that no conesponding amino acid is found in the optimized computer alignment.

HD-Zip class III PCR primers were designed with the HD-Zip III "block" amino acid sequence data, presented in Table 8, by inputting the "block" sequence data into the CODEHOP program using either the gibbs algorithm or the motif algorithm. The PCR primer output was further refined by selecting a particular plant species, in this example rice, to which the PCR primer sequence was biased based upon the preferred codon usage compiled for rice (other plant codon biases can also be selected using the CODEHOP program). Table 9 presents a set of possible CODEHOP HD-Zip III PCR primers that can be compiled using the CODEHOP program to amplify HD-Zip genes from rice, barley and corn.

TABLE 9

HD-Zip III PCR primer designed using the
Fred Hutchinson Cancer Research Center
"CODEHOP" computer program.

| HD-Zip Block | Oligonucleotide Sequence[1] |
|---|---|

HD-ZipIII: Block A
Forward

| | |
|---|---|
| Rice A1F SEQ ID NO.: 60 | 5'-GGCGGCAGCAGCTGathmgngartg-3' |
| SEQ ID NO.: 213 | R Q Q L I R E C |
| | Degen[2]=48, temp[3]=62.4 |

TABLE 9-continued

HD-Zip III PCR primer designed using the
Fred Hutchinson Cancer Research Center
"CODEHOP" computer program.

| HD-Zip Block | Oligonucleotide Sequence[1] |
|---|---|
| Rice A2F SEQ ID NO.: 61 | 5'-GGAGAGGGTGTACTGCGAGtgyccnaarcc-3' |
| SEQ ID NO.: 214 | E R V Y C E C P K P |
| | Degen=16, temp=62.2 rice A2 |
| Rice A3F SEQ ID NO.: 62 | 5'-TGCGGTACACCCCgarcargtnsa-3' |
| SEQ ID NO.: 215 | R Y T P E Q V E |
| | Degen=32, temp=63.3 |
| Rice A4F SEQ ID NO.: 63 | 5'-TGCGGTACACCCCGArcargtnsarg-3' |
| SEQ ID NO.: 216 | R Y T P E Q V E A |
| | Degen=64, temp=63.3 |
| Rice A5F SEQ ID NO.: 64 | 5'-CGGTACACCCCCGAGcargtnsargc-3' |
| SEQ ID NO.: 216 | R Y T P E Q V E A |
| | Degen=32, temp=64.2 |

TABLE 9-continued

HD-Zip III PCR primer designed using the
Fred Hutchinson Cancer Research Center
"CODEHOP" computer program.

| HD-Zip Block | Oligonucleotide Sequence[1] |
|---|---|

Rice A6F
SEQ ID NO.: 65    5'-TGGAGAGGGTGTACTGCgantgyccnaa-3'
SEQ ID NO.: 217   E R V Y C E C P K
                  Degen=32, temp=60.4

Rice A7F
SEQ ID NO.: 66    5'-TGGAGAGGGTGTACTGCGAntgyccnaarc-3'
SEQ ID NO.: 218   E R V Y C E C P K P
                  Degen=64, temp=60.4

Rice A8F
SEQ ID NO.: 67    5'-CCGACCTCCATCGGmgncarcaryt-3'
SEQ ID NO.: 219   P S S L R R Q Q L
                  Degen=64 temp=60.8

Rice A9F
SEQ ID NO.: 68    5'-CCATGCGGCGGcarcarytnat-3'
SEQ ID NO.: 220   L R R Q Q L I
                  Degen=32, temp=62.4

HD-ZipIII: Block A
Reverse

Rice A1R
SEQ ID NO.: 69    5'-CGGGGGTGTACCGCacrtayttncc-3'
                  Degen=16, temp=62.1
                  [4]Complementary to:
SEQ ID NO.: 221   G K Y V R Y T P E
                  ccnttyatrcaCGCCATGTGGGGGC Rice A2R
SEQ ID NO.: 70    5'-CTGCTCGGGGGTGTACcknacrtaytt-3'
                  Degen=32, temp=60.1
                  Complementary to:
SEQ ID NO.: 222   K Y V R Y P E Q
                  ttyatrcabjcCATGTGGGGGCTCGTC Rice A3R
SEQ ID NO.: 71    5'-ACCTGCTCGGGGGTGtancknacrta-3'
                  Degen=64, temp=60.1
                  Complementary to:
SEQ ID NO.: 223   Y V R Y T P E Q V
                  atrcankcnatGTGGGGGCTCGTCCA Rice A4R
SEQ ID NO.: 72    5'-CCACCTGCTCGGGGftrtancknac-3'
                  Degan=64, temp=63.2
                  Complementary to:
SEQ ID NO.: 224   V R Y T P E Q V E
                  cankcnatrtgGGGGCTCGTCCACC Rice A5R
SEQ ID NO.: 73    5'-CACCCTCTCCAGGGCCtsnacytgytc-3'
                  Degen=32, temp=61.2
                  Complementary to:
SEQ ID NO.: 225   E Q V E A L E R V
                  ctygtycanstCCGGGACCTCTCCCAC TABLE 9-continued HD-Zip III PCR primer designed using the
Fred Hutchinson Cancer Research Center
"CODEHOP" computer program.

| HD-Zip Block | Oligonucleotide Sequence[1] |
|---|---|

Rice A6R
SEQ ID No: 74    5'-CAGTACACCCTCTCCAGGGcytsnacytgyt-3'
                 Degen=64 temp=62.0
                 Complementary to:
SEQ ID NO.: 226  Q V E A L E R V Y C
                 tygtycabstycGGGACCTCTCCCACATGAC Rice A7R
SEQ ID NO.: 75   5'-CAGTACACCCTCTCCAGGgcytsnacytg-3'
                 Degen=32, temp=62.0
                 Complementary to:
SEQ ID NO.: 226  Q V E A L E R V Y C
                 gtycanstycgGGACCTCTCCCACATGAC HD-ZipIII:
Block B
Forward Rice B1F
SEQ ID NO.: 76   5'-CCATGAACAAGATGCTGatggargaraa-3'
SEQ ID NO.: 227  M N K M L M E E N
                 Degen=4, temp=63.3

Rice B2F
SEQ ID NO.: 77   5'-CGGCTGCAGACCGTGaayvgnaaryt-3'
SEQ ID NO.: 228  R L Q S V N R K L
                 Degen=96, temp=63.3

Rice B3F
SEQ ID NO.: 78   5'-GACCGCCATGAACAAGATGytnatggarga-3'
SEQ ID NO.: 229  T A M N K M L M E E
                 Degen=16, temp=60.1

Rice B4F
SEQ ID NO.: 79   5'-CCGCCATGAACAAGAGCTnatggargara-3'
SEQ ID NO.: 230  A M N K M L M E E N
                 Degen=16, temp=62.2

Rice B5F
SEQ ID NO.: 80   5'-CCATGAACAAGATGCTGATggargaraayg-3'
SEQ ID NO.: 231  M N L M L M E E N D
                 Degen=8, temp=63.3

HD-ZipIII:
Block B
Reverse

Rice B1R
SEQ ID NO.: 81   5'-CGGCACCGCCGGttytgraacca-3'
                 Degen=4, temp=64.2
                 Complementary to:
SEQ ID NO.: 232  W F Q N R R C R
                 accaargtyttGGCCGCCACGGC Rice B2R
SEQ ID NO.: 82   5'-ATCTGGTTCATGGCGGTCaruttncbrtt-3'
                 Degen=96, temp=60.1
                 Complementary to:

TABLE 9-continued

HD-Zip III PCR primer designed using the Fred Hutchinson Cancer Research Center "CODEHOP" computer program.

| HD-Zip Block | Oligonucleotide Sequence[1] |
|---|---|
| SEQ ID NO.: 233 | N R K L T A M N K M<br>ttrbcnttyraCTGGCGGTACTTGTTCTA |
| Rice B3R | |
| SEQ ID NO.: 83 | 5'-CGCCGGTTCTGGAaaccanacytt-3'<br>degen=8, temp=64.3<br>Complementary to: |
| SEQ ID NO.: 234 | K V W F Q N R R<br>ttycanaccaaGGTCTTGGCCGC |
| Rice B4R | |
| SEQ ID NO.: 84 | 5'-GCACCGCCGGTTCtgraaccanac-3'<br>degen=8, temp=61.0<br>Complementary to: |
| SEQ ID NO.: 235 | V W F Q N R R C<br>canaccaargtCTTGGCCGCCACG |

HD-ZipIII: Block D Forward

| | |
|---|---|
| Rice D1F | |
| SEQ ID NO.: 85 | 5'-CCAAGGCCACCATGCTGytncarmaygt-3' |
| SEQ ID NO.: 236 | K A S M L L Q N V<br>Degen=64, temp=62.3 |
| Rice D2F | |
| SEQ ID NO.: 86 | 5'-AAGGCCACCATGCTGCTncarmaygtnc-3' |
| SEQ ID NO.: 237 | K A S M L L Q N V P<br>Degen=128, temp=60.4 |
| Rice D3F | |
| SEQ ID NO.: 87 | 5'-CCACCATGCTGCTGcarmaygtncc-3' |
| SEQ ID NO.: 238 | S M L L Q N V P<br>Degen=32, temp=60.1 |
| Rice D4F | |
| SEQ ID NO.: 88 | 5'-CCCGTCTGCATCCGGttyytnmgnga-3' |
| SEQ ID NO.: 239 | A V C I R F L R E<br>Degen=128, temp=63.1 |
| Rice D5F | |
| SEQ ID NO.: 89 | 5'-CCGTCTGCATCCGGTTCytnmgngarca-3' |
| SEQ ID NO.: 240 | V C I R F L R E H<br>Degen=128, temp=61.2 |
| Rice D6F | |
| SEQ ID NO.: 90 | 5'-GTCTGCATCCGGTTCCTGmgngarcaymg-3' |
| SEQ ID NO.: 241 | V C I R F L R E H R<br>Degen=64, temp=60.2 |
| Rice D7F | |
| SEQ ID NO.: 91 | 5'-TGCGGGAGCACCGGnvngartgggc-3' |
| SEQ ID NO.: 242 | R E H R S E W A<br>Degen=96, temp=62.9 |
| Rice D8F | |
| SEQ ID NO.: 92 | 5'-GCGGGAGCACCGGTCngartgggcng-3' |
| SEQ ID NO.: 243 | R E H R S E W A D<br>Degen=32, temp=62.6 |
| Rice D9F | |
| SEQ ID NO.: 93 | 5'-GGAGCACCGGTCGgartgggcnga-3' |
| SEQ ID NO.: 244 | E H R S E W A D<br>Degen=8, temp=60.3 |

HD-ZipIII: Block D Reverse

| | |
|---|---|
| Rice D1R | |
| SEQ ID NO.: 94 | 5'-GACGGGCGGCggnacrtkytg-3'<br>Degen=32, temp=60.4<br>Complementary to: |
| SEQ ID NO.: 245 | Q N V P P A V<br>gtyktrcanggCGGCGGGCAG |
| Rice D2R | |
| SEQ ID NO.: 95 | 5'-GACGGGCGGCggnacrtkytna-3'<br>Degen=128, temp=60.4<br>Complementary to: |
| SEQ ID NO.: 245 | Q N V P P A V<br>angtyktrcangGCGGCGGGCAG |
| Rice D3R | |
| SEQ ID NO.: 96 | 5'-CACTCCGACCGGTGCtcncknarraa-3'<br>Degen=128, temp=61.5<br>Complementary to: |
| SEQ ID NO.: 246 | F L R E H R S E W<br>aarrankcnctCGTGGCCAGCCTCAC |

[1]First line shows the oligonucleotide sequence of the CODEHOP designed primer. The degenerate nucleotide alphabet used by CODEHOP is: A → A, C → C, G → G, T → T, R → AG, Y → CT, M → AC, K → GT, W → AT, S → CG, B → CGT, D → AGT, H → ACT, V → ACG; and N → ACGT. The second line shows the amino acid sequence encoded by all of the redundant primers.
[2]"Degen" means the number of degenerate otigonucleotides within the primer pool that encode the designated amino acid sequence.
[3]"Temp." means the mean melting temperature of the degenerate oligonucleotide primer pool.
[4]"Complementary to" refer to the HD-Zip amino acid block that the designated reverse oligonuleotide is complementary to, i.e. the peptide encoding strand sequence region of the HD-Zip block.

Other HD-Zip III PCR primers can be selected by changing the primers sequences listed in Table 9 to reflect the appropriate codon usage bias of the target plant species. However, as shown below the CODEHOP HD-Zip III primers designed specifically for rice were also capable of amplifying HD-Zip fragments from the monocot plants maize and barley.

Isolation of Monocot HD-Zip Clones

Moncot HD-Zip III homologs were identified using CODEHOP primers Rice A2F [SEQ ID NO.:61] and Rice B2R [SEQ ID NO.:82] selected from Table 9. These primers were used in a 10 μL PCR reaction using 2 units AmpliTaq Gold (Perkin Elmer), the supplied buffer, 2 mM MgCl$_2$, 0.2 mM dNTPs, and 0.5 μM each primer. The template DNAs for PCR used were: 1.5 μL of a rice (Oryza sativa L. indicam var.IR36) cDNA library (Stratagene FL1041b); 1.5 μL of purified genomic rice (Oryza sativa) DNA (about 400 ng); 1.5

μL of purified genomic barley (*Hordeum vulgare*) DNA (about 400 ng); 1.5 μL of purified genomic maize (*Zea may*) DNA (about 400 ng). PCR conditions included a 95° C. incubation for 9 minutes, followed by 5 cycles of 95° C. (30 seconds); 60° C. to 55° C. (30 seconds) decreasing by 1° C. each cycle; 72° C. (2 minutes); then 35 cycles of 95° C. (30 seconds); 55° C. (30 seconds); and 72° C. (2 minutes). The resulting PCR DNA products were analyzed by gel electrophoresis, then cut out from a 0.8% low melt agarose gel (SeaPlaque, FMC Bioproducts, Rockland, Me.) in TAE buffer, and purified using a PCR clean up kit (Promega). The DNA fragments were cloned into a TOPO II vector kit (Invitrogen). DNA was purified from bacterial cells using a spin miniprep kit (Qiagen) and sequenced using BIG dye (Applied Biosystems). The rice, maize and barley DNA and protein sequences are disclosed in SEQ ID Nos.:97-126, respectively.

The BLAST2 computer program of Altschul et al. (1997) was used to compare the amplified monocot sequences with the corresponding protein region in *Arabidopsis* REVOLUTA. Computer aided sequence comparisons were performed using version BLAST2.0.9 at the National Institutes of Health webpage site. Each of the amplified sequences had a high degree of amino acid sequence identity or similarity to the *Arabidopsis* REVOLUTA protein (about 79% to 88% amino acid identity and about 87% to 97% amino acid similarity). These data demonstrate that genes can be isolated from distantly related monocot plant species using the HD-Zip CODEHOP primers disclosed in Table 9, that encode peptides regions that have a high degree of sequence homology to the corresponding amino acid region of the *Arabidopsis* Revoluta protein [SEQ ID NO: 2].

REVOLUTA Function Test

Plant genes isolated using the above-described methods are then tested for Revoluta function. Functional testing to identify actual Revoluta genes is done by cloning the polynucleotide sequences amplified using various combinations of the forward and reverse HD-Zip block PCR primers listed in Table 9 into plant transformation vectors. The putative Revoluta sequence is oriented in the plant transformation vector using one of the gene suppression strategies previously outlined, such as by making an inverted repeat transgene or an antisense transgene. Regenerated transgenic plants are examined and the number of cells contained in various tissues is compared to the number of cells in the corresponding tissues of untransformed plants. Plants that have been transformed with suppressor transgenes comprising Revoluta genes of the present invention have a statistically significant change in the number of cells within a representative cross sectional area of the tissue. Alternatively, the size of various plant organs such as leaves and shoots are significantly different as described for *Arabidopsis* by Taylor et al. (1995).

Alternatively, labeled DNA sequences are amplified using the forward and reverse HD-Zip CODEHOP PCR primers listed in Table 9, by using, for example, biotin or radiolabeled nucleotides in the PCR. The labeled HD-Zip III sequences are then used to screen a cDNA or genomic plant clone library via nucleic acid hybridization. Clones that positively hybridize to the labeled PCR amplified HD-Zip sequences are then isolated and the DNA inserts characterized by DNA sequencing to identify HD-Zip III coding and noncoding sequences. Regions of the isolated HD-Zip III genes are then manipulated in vitro to construct gene suppressive transgenes that are then tested in transgenic plants to identify HD-Zip III genes that have the same function as REVOLUTA, i.e. they modulate cell division.

Identification and Isolation of REVOLUTA from Tomato

The Tomato REV gene is identified using primers generated using the Codehops program as described above. Genomic DNA from 50 mg of young *Lycopersicum esculentum* leaves is isolated as described in Example 1 above. One microliter of DNA is PCR amplified using the conditions described in Example 3. The following primers are used: rice A2F; GGAGAGGGTGTACTGCGAGTGYCCNAARCC [SEQ ID NO:61] and tomato J1R; CAGCAGAATAAGCATCAACATTATAATCNGCCCAYT [SEQ ID NO:162]. The product is sequenced and a genomic clone (SEQ ID NO:163), encoding a protein having 84% identity and 90% similarity to the Rev-1 protein is identified. The coding region and amino acid sequence of the tomato Rev protein are presented as SEQ ID NO:164 and SEQ ID NO: 165, respectively.

Further analysis shows that there is significant identity at the amino acid level between the tomato REV and the other *Arabidopsis* HD-ZipIII family members (See Table 10).

TABLE 10

| TomatoREV | |
|---|---|
| REV | 84% |
| Athb-9 | 71% |
| Athb-8 | 66% |
| Athb-14 | 73% |
| F5F19.21 | 68% |

The tomato REV is then tested and shown to have REVOLUTA function, essentially as described above.

Identification and Isolation of REVOLUTA From Rice

Rice REV1:

Rice *Oryza sativa* leaf DNA, isolated essentially as described above, or cDNA from the library (Stratagene FL1041b) is used as a template for PCR essentially as described. The following primers are used for the rice genomic DNA REV1 clone: TG-cDNA; GTRAGTGCCCCATACTTGCT (SEQ ID NO.:4) R25AS-J; GCCGTTCACGGCSTCRTTRAANCC (SEQ ID NO.:166). To pull out the 5' end of the REV1cDNA, the following primers are used: one specific to the cloning vector, R22S; CGACGACTCCTGGAGTCCGTCAG (SEQ ID NO.: 167) and the other in the coding region of the gene, TGTATCATTTGCCAGCGGAG (SEQ ID NO.:168). The nucleic acid sequence of rice Rev1 gene is found in SEQ ID NO.: 169 (genomic) and SEQ ID NO.:170 (cDNA). The amino acid sequence of Rice Rev1 is set forth in SEQ ID NO.:171. the rice Rev1 is then tested and shown to have REVOLUTA function, essentially as described above.

Rice REV2:

Rice cDNA as described above was used as a template for PCR using the following oligos: Rice A2F [SEQ ID NO.:61]: GGAGAGGGTGTACTGCGAGTGYCCNAA RCC R10AS-K [SEQ ID NO.:161]: GCAGCAGCATGGAGGCYTTNGCRCA.

R10AS-K [SEQ ID NO:]: GCAGCAGCATGGAGGCYTTNGCRCA

PCR is performed, essentially as described above, to isolate the cDNA of rice Rev2. The nucleic acid sequence of rice Rev2 is set forth in SEQ ID NO:172. The amino acid sequence of rice Rev2 is set forth in SEQ ID NO:173. The rice Rev2 is then tested and shown to have REVOLUTA function, essentially as described above.

Example 7

Modulation of Cell Division in Maize

Zygotic immature embryos of about 0.5 to 1 mm are isolated from developing seeds of Zea mays using the methods disclosed in U.S. Pat. No. 5,712,135. The freshly isolated embryos are enzymatically treated for 1-2 minutes with an enzyme solution II (0.3% macerozyme (Kinki Yakult, Nishinomiya, Japan) in CPW salts (Powell et al., 1985 "Plant Cell Culture, A Practical Approach", R. A. Dixon ed., Chapter 3) with 10% mannitol and 5 mM 2-N-Morpholino-ethane sulfonic acid (MES), pH 5.6). After 1-2 minutes incubation in this enzyme solution, the embryos are carefully washed with N6aph solution (macro- and micro-elements of N6 medium (Chu et al., 1975 Sci. Sin. Peking 18:659) supplemented with 6 mM asparagine, 12 mM proline, 1 mg/l thiamine-HCl, 0.5 mg/l nicotinic acid, 100 mg/l casein hydrolysate, 100 mg/l inositol, 30 g/l sucrose and 54 g/l mannitol).

After washing, the embryos are incubated in the maize electroporation buffer, EPM-NaCl (150 mM NaCl, 5 mM $CaCl_2$, 10 mM HEPES (N-2-hydroxyethylpiperazine-N'-2-ethanesulfonic acid) and 0.425M mannitol, pH7.2). Approximately 100 embryos in 200 µl EPM-NaCl are loaded in each cuvette. About 20 µg of linearized maize HD-Zip protein-3 plasmid DNA, is added per cuvette. The maize HD-Zip protein-3 plasmid contains an inverted repeat of the entire maize protein-3 polynucleotide sequence as set forth in SEQ ID No.:107. Transcription of the inverted repeat maize protein-3 transgene is under the control of a maize 18 kD oleosin promoter (Qu et al., 1990 J. Biol. Chem. 265:2238-2243). In addition, the maize HD-Zip protein-3 plasmid also contains a chimaeric gene comprising the kanamycin resistance gene (neo) and 3' polyA addition region under the control of the CaMV 35S3 promoter (EP 359617).

After 1 hour DNA incubation with the explants, the cuvettes are transferred to an ice bath. After 10 minutes incubation on ice, the electroporation is carried out as follows: one pulse with a field strength of 375 V/cm is discharged from a 900 µF capacitor. The electroporation apparatus is as described by Dekeyser et al., (1990 Plant Cell 2:591). Immediately after electroporation, fresh liquid N6aph substrate is added to the explants in the cuvette, after which the explants are incubated for a further 10 minute period on ice.

Afterwards, the embryos are transferred to Mah1 VII substrate (macro- and micro-elements and vitamins of N6 medium supplemented with 100 mg/l casein hydrolysate, 6 mM proline, 0.5 g/l MES, 1 mg/l 2,4-dichlorophenoxyacetic acid (2,4-D) and 2% sucrose solidified with 0.75 g/l $MgCl_2$ and 1.6 g/l Phytagel (Sigma Chemical Company, St Louis, Mo.), pH 5.8) and supplemented with 0.2M mannitol. After 2-3 days the embryos are transferred to the same substrate supplemented with 200 mg/l kanamycin. After approximately 14 days, the embryos are transferred to Mah1 VII substrate without mannitol, supplemented with kanamycin (200 mg/A). The embryos are further subcultured on this selective substrate for approximately two months with subculturing intervals of about 3 weeks. The induced embryogenic tissue is then carefully isolated and transferred to MS medium (Murashige et al., 1962 Physicol. Plant 15:473-497) supplemented with 5 mg/l 6-benzylaminopurine or 5 mg/l zeatin. The embryogenic tissue is maintained on this medium for approximately 14 days and subsequently transferred to MS medium without hormones and 3-6% sucrose. Developing shoots are transferred to ½ MS medium with 1.5% sucrose for further development to normal plantlets. These plantlets are transferred to soil and cultivated in the greenhouse.

Modulation of plant cell division is determined by comparing the size of corn kernals in the transformed plants as compared to kernals obtained from untransformed control plants. More specifically, the embryos within the transgenic kernals are increased in size due to an increased number of cells. The size and development of maize embryos with specific attention to the number of cells, determined by reference to methods of Scott et al. (1998 Development 125:3329-41) and Ingram et al. (1999 Plant Mol. Biol. 40:343-54

Example 8

Modulation of Cell Division in Maize Shoots

An embryogenic maize callus line is prepared as described in U.S. Pat. No. 5,780,708. Maize callus is subcultured 7 to 12 days prior to microprojectile bombardment. Maize callus is prepared for bombardment as follows. Five clumps of callus, each approximately 50 mg in wet weight are arranged in a cross pattern in the center of a sterile 60×15 mm petri plate (Falcon 1007). Plates are stored in a closed container with moist paper towels, throughout the bombardment process.

Maize callus is transformed with a mixture of two plasmid DNA molecules. pHD-Zip-invp-1 contains a rice actin promoter and a 3' nos polyadenylation addition sequence region. An inverted repeat of polynucleotide sequence SEQ ID No.: 103 is inserted in between the rice actin promoter (Wang et al., 1992 Mol. Cell. Biol. 12:3399-3406) and the nopoline synthase (nos) polyA sequence (Chilton et al., 1983). pHYGI1 is a plasmid that contains the hygromycin coding sequence (Gritz et al. 1983 Gene 25:179-188) and a maize AdhIS intron sequence that enhances protein expression of transgenes in transgenic plants (U.S. Pat. No. 5,780,708).

pHD-Zip-invp-1 plasmid DNA and pHYGI1 is coated onto M-10 tungsten particles (Biolistics) exactly as described by Klein et al. (1988 Bio/Technology 6:559-563) except that, (i) twice the recommended quantity of DNA is used, (ii) the DNA precipitation onto the particles is performed at 0° C., and (iii) the tubes containing the DNA-coated tungsten particles are stored on ice throughout the bombardment process.

All of the tubes contain 25 µl of 50 mg/ml M-10 tungsten in water, 25 µl of 2.5M $CaCl_2$, and 10 µl of 100 mM spermidine along with a total of 5 µl of 1 mg/ml plasmid DNA. Each of the above plasmid DNAs are present in an amount of 2.5 µl.

All tubes are incubated on ice for 10 min., the particles are pelleted by centrifugation in an Eppendorf centrifuge at room temperature for 5 seconds, 25 µl of the supernatant is discarded. The tubes are stored on ice throughout the bombardment process. Each balistic preparation is used for no more than 5 bombardments.

Macroprojectiles and stopping plates are obtained from Biolistics, Inc. (Ithaca, N.Y.). They are sterilized as described by the supplier. The microprojectile bombardment instrument is obtained from Biolistics, Inc.

The sample plate tray is placed 5 cm below the bottom of the stopping plate tray of the microprojectile instrument, with the stopping plate in the slot nearest to the barrel. Plates of callus tissue prepared as described above are centered on the sample plate tray and the petri dish lid removed. A 7×7 cm square rigid wire mesh with 3×3 mm mesh and made of galvanized steel is placed over the open dish in order to retain the tissue during the bombardment. Tungsten/DNA preparations are sonicated as described by Biolistics, Inc. and 2.5 µl of the suspensions is pipetted onto the top of the macroprojectiles for each bombardment. The instrument is operated as described by the manufacturer.

Immediately after all samples are bombarded, callus from all of the plates treated with the pHYGI1 and pHD-Zip-invp-1 plasmid DNAs are transferred plate for plate onto F-medium containing 15 mg/l hygromycin B, (ten pieces of callus per plate). These are referred to as round 1 selection plates. Callus from the T.E. treated plate are transferred to F-medium without hygromycin. This tissue is subcultured every 2-3 weeks onto nonselective medium and is referred to as unselected control callus.

After about 14 days of selection, tissue appear essentially identical on both selective and nonselective media All callus from plates of the pHYGI1/pHD-Zip-invp-1 bombardment and one T.E. treated plate are transferred from round 1 selection plates to round 2 selection plates that contain 60 mg/l hygromycin. The round 2 selection plates each contained ten 30 mg pieces of callus per plate, resulting in an expansion of the total number of plates.

After about 21 days on the round 2 selection plates, all of the material is transferred to round 3 selection plates containing 60 mg/l hygromycin. After about 79 days post-bombardment, the Tound 3 sets of selection plates are checked for viable sectors of callus. Viable sectors of callus are dissected from a background of necrotic tissue on the plants treated with pHYGI1/pHD-Zip-invp-1 and transferred to F-medium without hygromycin.

After about 20 days on F-medium without hygromycin, the transformed callus is transferred to F-medium containing 60 mg/l hygromycin. The transformed callus is capable of sustained growth through multiple subcultures in the presence of 60 mg/l hygromycin.

Confirmation of Transformed Callus

To show that the pHYGI1/pHD-Zip-invp-1 treated callus has acquired the hygromycin resistance gene, genomic DNA is isolated from the callus that has sustained capacity to grow on 60 mg/l hygromycin and unselected control callus and analyzed by Southern blotting. DNA is isolated from tissue by freezing 2 g of callus in liquid nitrogen and grinding it to a fine powder which is transferred to a 30 ml Oak Ridge tube containing 6 ml extraction buffer (7M urea, 250 mM NaCl, 50 mM Tris-HCl pH 8.0 20 mM EDTA pH 8.0, 1% sarcosine). To this is added 7 ml of phenol:chloroform 1:1, the tubes shaken and incubated at 37° C. for 15 min. Samples are centrifuged at 8K for 10 min. at 4° C. The supernatant is pipetted through miracloth (Calbiochem 475855) into a disposable 15 ml tube (American Scientific Products, C3920-15A) containing 1 ml 4.4M ammonium acetate, pH 5.2. Isopropanol, 6 ml is added, the tubes shaken, and the samples incubated at −20° C. for 15 min. The DNA is pelleted in a Beckman TJ-6 centrifuge at the maximum speed for 5 min. at 4° C. The supernatant is discarded and the pellet is dissolved in 500 µl TE-10 (10 mM Tris-HCl pH 8.0, 10 mM EDTA pH 8.0) 15 min. at room temperature. The samples are transferred to a 1.5 ml Eppendorf tube and 100 µl 4.4M ammonium acetate, pH 5.2 and 700 µl isopropanol is added. This is incubated at −20° C. for 15 min. and the DNA pelleted 5 min. in an Eppendorf microcentrifuge (12,000 rpm). The pellet is washed with 70% ethanol, dried, and resuspended in TE-1 (10 mM Tris-HCl pH 8.0, 1 mM EDTA).

Ten µg of isolated DNA is digested with restriction endonuclease and analyzed by Southern Blot hybridization using a probes from both the pHD-Zip-invp-1 plasmid and pHYGI1 plasmid. Digested DNA is electrophoresed in a 0.8% w/v agarose gel at 15 V for 16 hrs in TAE buffer (40 mM Tris-acetate, pH 7.6, 1 mM EDTA). The DNA bands in the gel are transferred to a Nyaaan membrane (Schleicher and Schuell). Transfer, hybridization and washing conditions are carried out as per the manufacturer's recommendations. DNA samples extracted from the hygromycin resistant callus tissue that are transformed with the maize HD-Zip-invp-1 transgene have DNA fragments that hybridize specifically with the HD-Zip-invp-1 hybridization probe. No hybridization signal is observed in DNA samples from control callus.

Plant Regeneration and Production of Seed

Portions of the transformed callus are transferred directly from plates containing 60 mg/l hygromycin to RM5 medium which consists of MS basal salts (Murashige et al. 1962) supplemented with thiamine-HCl 0.5 mg/l, 2,4-D 0.75 mg/l, sucrose 50 µl, asparagine 150 mg/l, and Gelrite 2.5 g/l (Kelco Inc., San Diego).

After about 14 days on RM5 medium, the majority of transformed callus and unselected control callus are transferred to R5 medium (RM5 medium, except that 2,4-D is omitted). The plates are cultured in the dark for about 7 days at 26° C. and transferred to a light regime of 14 hrs light and 10 hrs dark for about 14 days at 26° C. At this point, plantlets that have formed are transferred to one quart canning jars (Ball) containing 100 ml of R5 medium. Plants are transferred from jars to vermiculite for about 7 or 8 days before transplanting them into soil and growing them to maturity. About 40 plants are produced from the transformed callus and about 10 plants are produced from control callus (untransformed hygromycin sensitive callus).

Controlled pollinations of mature transformed plants is conducted by standard techniques with inbred *Zea mays* lines MBS501 (Mike Brayton Seeds), and FR4326 (Illinois Foundation Research). Seed is harvested about 45 days post-pollination and allowed to dry further for 1-2 weeks.

Analysis of the R1 Progeny

R1 plants are tested for the presence of the HPT and pHD-Zip-invp-1 transgene sequences by PCR analysis. To conduct the PCR assay, 0.1 g samples are taken from plant tissues and frozen in liquid nitrogen. Samples are then ground with 120 grit carborundum in 200 µl 0.1M Tris-HCl, 0.1M NaCl, 20 mm EDTA, 1% Sarkosyl pH 8.5) at 40° C. Following phenol/chloroform extraction and ethanol and isopropanol precipitations, samples are suspended in T.E. and analyzed by polymerase chain reaction (K. B. Mullis, U.S. Pat. No. 4,683,202).

PCR is carried out in 100 µl volumes in 50 mM KCl, 10 mM Tris-HCl pH 8.4, 3 MM $MgCl_2$, 100 µg/ml gelatin, 0.25 µM each of the appropriate primers, 0.2 mM of each deoxynucleoside triphosphate (DATP, dCTP, dGTP, dTTP), 2.5 Units of Tag DNA polymerase (Cetus), and 10 µl of the DNA preparation. The mixture is overlaid with mineral oil, heated to 94° C. for 3 min, and amplified for 35 cycles of 55° C. for 1 min, 72° C. for 1 min, 94° C. for 1 min. The mixture is then incubated at 50° C. for 2 min and 72° C. for 5 min. 10 µl of the PCR product is electrophoresed in agarose gels and visualized by staining with ethidium bromide.

For analysis of the presence of the hygromycin-B phosphotransferase (HPT) gene, a PCR primer complementary to the CaMV 35S promoter, and one complementary to the HPT coding sequence is employed. Thus, in order to generate the appropriately sized PCR product, the HPT template DNA must contain contiguous CaMV 35S promoter region, Adhl intron, and 5' protein HPT coding sequence region. For analysis of the presence of the maize HD-Zip protein-1 inverted repeat transgene, PCR primers complementary to sequences within the HD-Zip protein-1 inverted repeat region are employed.

R₁ plants that are homozygous for the maize HD-Zip protein-1 inverted repeat transgene exhibit a plant morphology phenotype that is caused by a transgene suppression of endogenous HD-Zip protein-1 function. Loss of wild-type HD-Zip protein-1 function causes modulation of maize cell division. The modulated cell division phenotype results in transformed plants whose leaves are longer and contain more cells. Cell numbers in stem and leaves are determined as explained by Talbert et al. 1995 *Development* 121:2723-35.

Example 9

Modulation of Cell Division in Rice Seed

Dehusked mature seeds of the rice cultivar Nipponbare are surfaced-sterilized, placed on solid 2N6 medium (N6 medium (Chu et. al. 1975 *Sci. Sin. Peking* 18:659), supplemented with 0.5 mg/l nicotinic acid, 0.5 mg/l pyridoxine-HCl, 1.0 mg/l thiamine-HCl, 2.0 mg/l 2,4-D, 30 g/l sucrose, and 2.0 g/l Phytagel, pH 5.8), and cultured at 27° C. in the dark Callus develops from the scutella of the embryos within 3-4 weeks. Embryogenic portions of primary callus are transferred to N67 medium (N6 medium (Chu et al. 1975), supplemented with 0.5 mg/l nicotinic acid, 0.5 mg/l pyridoxine-HCl, 1.0 mg/l thiamine-HCl, 2.0 g/l casamino acids (vitamin assay, Difco), 1.0 mg/l 2,4-D, 0.5 mg/l 6-benzylaminopurine, 20 g/l sucrose, 30 g/l sorbitol, and 2.0 g/l Phytagel, pH 5.8) for propagation into compact embryogenic callus.

About three to four weeks after subculture, the embryogenic callus are used for transformation with rice genomic HD-Zip gp-1 plasmid DNA. The callus is cut into fragments with a maximum length of about 1.5 to 2 mm. The callus pieces are washed twice in EPM (5 mM CaCl₂, 10 mM HEPES and 0.425 M mannitol) and then preplasmolyzed in this buffer for 30 minutes to 3 hours at room temperature (25° C.). Then, the callus fragments are washed twice with EPM-KCl (EPM buffer with 80 mM Kcl) and transferred to electroporation cuvettes. Each cuvette is loaded with about 150 to 200 mg of callus fragments in 100 to 200 μl EPM-KCl. 10 to 20 μg of a plasmid DNA, either circular pHD-Zip-asgp-1 or linearized pHD-Zip-asgp-1, are added per cuvette. pHD-Zip-asgp-1 is a plasmid that contains an antisense HD-Zip protein-1 transgene that is under the transcriptional control of a rice actin promoter (Wang et al., 1992). The antisense HD-Zip-gp-1 transgene comprises a polynucleotide sequence cloned from rice genomic DNA (Example 3) that is set forth in SEQ ID No.:115. The pHD-Zip-asgp-1 plasmid also contains a chimaeric gene comprising the bar gene under the control of the CaMV 35S3 promoter (see European patent publication ("EP") 359617). The bar gene (see EP 242236) encodes phosphinothricin acetyl transferase which confers resistance to the herbicide phosphinothricin. The chimeric bar transgene comprises a phosphinothricin acetyl transferase coding sequence and a chloroplast targeting transit sequence.

The DNA is incubated with the callus fragments for about 1 hour at room temperature. Electroporation is then carried out as described in Example 4. After electroporation, liquid N67 medium without casamino acids is added to the callus fragments. The callus fragments are then plated on solid N67 medium without casamino acids but supplemented with 5, 10 or 20 mg/l phosphinothricin (PPT) and are cultured on this selective medium at 27° C. under a light/dark regime of 16/8 hours for about 4 weeks. Developing PPT-resistant calli are isolated and subcultured for about two to three weeks onto fresh N67 medium without casamino acids but containing 5 mg/l PPT. Thereafter, selected PPT-resistant calli are transferred to plant regeneration medium N6M25 (N6 medium (Chu et al. 1975), supplemented with 0.5 mg/l nicotinic acid, 0.5 mg/l pyridoxine-HCl, 1.0 mg/l thiamine-HCl, 288 mg/l aspartic acid, 174 mg/l arginine, 7.0 mg/l glycine, 1.0 mg/l O-naphthalenacetic acid (NAA), 5.0 mg/l kinetin, 20 g/l sucrose and 2.0 g/l Phytagel, pH 5.8) supplemented with 5 mg/l PPT. Plantlets develop within approximately 1 month and are then transferred to hormone-free N6 medium (Chu et al. 1975), supplemented with 0.5 mg/l nicotinic acid, 0.5 mg/l pyridoxin-HCl, 1.0 mg/l thiamine-HCl, 1.0 g/l casamino acids, 20 g/l sucrose, and 2.0 g/l Phytagel, pH 5.8) on which they are kept for another 2 to 3 weeks, after which they are transferred to soil and cultivated in the greenhouse.

Characterization of the Transformed Rice Plants

The above transformed rice plants are cultivated in soil until seed set and seed maturation. Seeds of the progeny of the transformants are sown in aqueous 400-fold Homai hydrate (Kumiai Kagaku Inc.) solution containing 70 mg/l of hygromycin and incubated therein at 25° C. for 10 days, thereby selecting for the resistance to hygromycin. Twenty seeds of each plant of the progeny of the transformants are sown and cultured for about 3 weeks. Leave are collected from the hygromycin resistant R₁ plants and compared to leaves collected from rice plants that were regenerated using the above described methods but do not contain an antisense HD-Zip-asgp-1 transgene. Leaves collected from the pHD-Zip-asgp-1 transformed plants exhibit modulated cell division as indicated by the increased size of the rice leaves.

Transformed and non transformed plants are analyzed by means of a Southern hybridization in which plant genomic DNA, is digested and probed with pRiceHD-Zip-gp-1 DNA. The hybridization data shows that the transgenic plants exhibiting modulation of cell division contain at least part of one copy of pRiceHD-Zip-gp-3 plasmid DNA that is integrated into the rice genome.

Example 10

Modulation of Cell Division in Rice Stems

Preparation of Sample Cultured Tissues

Scutellum callus from variety Koshihikari of japonica rice (*Oryza sativa* L.) is prepared for *Agrobacterium tumifaciens* mediated transformation using the method of Hiei et al. (1994; U.S. Pat. No. 5,591,616). Mature seeds of rice are sterilized by being immersed in 70% ethanol for 1 minute and then in 1% sodium hypochlorite solution for 30 minutes. The seeds are then placed on 2N6 solid medium (inorganic salts and vitamins of N6 (Chu, 1978 *Proc. Symp. Plant Tissue Culture*, Science Press Peking, pp. 43-50), 1 g/l of casamino acid, 2 mg/l of 2,4-D, 30 g/l of sucrose, 2 g/l of Gelrite). After culturing the mature seeds for about 3 weeks, callus growth forms that originates from scutella. This scutella callus is transferred to 2N6 medium and cultured therein for 4-7 days. The resulting calli are used as "scutellum callus" samples.

The calli originated from scutella are transferred to AA liquid medium (major inorganic salts of AA, amino acids of AA and vitamins of AA (Toriyama et al., 1985 *Plant Science* 41:179-183), MS minor salts (Murashige et al., 1962 *Physiol. Plant.* 15:473-497), 0.5 g/l of casamino acid, 1 mg/l of 2,4-D, 0.2 mg/l of kinetin, 0.1 mg/l of gibberellin and 20 g/l of sucrose) and the cells are cultured therein at 25° C. in the dark under shaking of 120 rpm to obtain suspended cultured cells. The medium is replaced with fresh medium every week.

Ti Plasmid (Binary Vector)

The T-DNA region of pTOK232 (Hiei et al., 1994) is altered by replacement of the CaMV 35S promoter/Gus/nos polyA transgene with the following inverted repeat rice HD-Zip protein-1 transgene construction. SEQ ID NO:121 discloses the DNA sequence of a rice cDNA insert obtained in Example 3. An inverted repeat of SEQ ID No.:121 is inserted between a rice actin promoter region and a nopaline synthase polyA addition sequence. This altered pTOK232 plasmid is a binary transformation vector called pTOKivr-HD-Zip-p1.

*Agrobacterium* strain LBA4404 has a Ti-plasmid from which the T-DNA region was deleted is used as the host bacteria for the rice transformation. Strain LBA4404 has a helper plasmid PAL4404 (having a complete vir region), and is available from American Type Culture Collection (ATCC 37349). Binary vector pTOKivr-HD-Zip-p1 is introduced into LBA4404 by the triple cross method of Ditta et al. (1980 Proc. Natl. Acad Sci. USA 77:7347-7351).

Colonies obtained by culturing the pTOKivr-HD-Zip-p1 Agrobacterium strains on AB medium (Drlica et al., 1974 Proc. Natl. Acad Sci. USA 71:3677-3681) containing hygromycin (50 µg/ml) and kanamycin (50 µg/ml) for about 3-10 days are collected with a platinum loop and suspended in modified AA medium (same as the composition of the above-described AA medium except that concentrations of sucrose and glucose are changed to 0.2 M and 0.2 M, respectively, and that 100 µM of acetosyringone is added, pH 5.2). The cell population is adjusted to $3\times10^9$–$5\times10^9$ cells/ml and the suspensions are used for inoculation of rice callus.

Inoculation Conditions

Rice scutellum callus tissues is washed with sterilized water and immersed in the above-described suspension of Agrobacterium for 3-10 minutes. Tissue is also incubated with LBA4404 that does not contain a binary vector as a negative control. The co-cultivating scutellum callus samples are cultured at 25° C. in the dark for 2-5 days on 2N6 solid medium containing acetosyringone, glucose and sucrose in the same concentrations as mentioned above. The resulting inoculated tissues are then washed with sterilized water containing 250 mg/l of cefotaxime and then continued to be cultured on the aforementioned 2N6 solid media containing 250 mg/l cefotaxime.

Selection of Transformed Cells and Tissues

Scutellum callus that has been cultured with the Agrobacterium strains for 3 days are cultured on 2N6 medium containing 250 mg/l of cefotaxiune for about 1 week. Hygromycin-resistant cultured tissues are selected by culturing the cultured tissues on 2N6 medium containing 50 mg/l of hygromycin for 3 weeks (primary selection). The obtained resistant tissues are further cultured on N6-12 medium (N6 inorganic salts, N6 vitamins, 2 g/l of casamino acid, 0.2 mg/l of 2,4-D, 0.5 mg/l of 6BA, 5 mg/l of ABA, 30 g/l of sorbitol, 20 g/l of sucrose and 2 g/l of Gelrite) containing 50 mg/l of hygromycin for about 2-3 weeks (secondary selection), and the calli grown on this medium are transferred to a plant regeneration medium N6S3 containing 0, 20 or 50 mg/l of hygromycin. In all of the media used after the co-cultivation with Agrobacterium, cefotaxime is added to 250 mg/l. Calli are incubated on N6S3 medium at 25° C. under continuous illumination (about 2000 lux). Regenerated plants ($R_0$ generation) are eventually transferred to soil in pots and grown to maturity in a greenhouse.

Seeds of the progeny of the transformants are sown in aqueous 400-fold Homai hydrate (Kumiai Kagaku Inc.) solution containing 70 mg/l of hygromycin and incubated therein at 25° C. for 10 days, thereby selecting for the resistance to hygromycin. Twenty seeds of each plant of the progeny of the transformants are sown and cultured for about 3 weeks. Leaves are collected from seedlings transformed with the HD-Zip protein-1 inverted repeat transgene and untransformed control plants. The transformed plants have an increased number of cells in their leaves due to transgene induced modulation of cell division Cell numbers in leaves are determined as explained by Talbert et al. 1995 Development 121:2723-35.

Transformed and non transformed plants are also analyzed by means of a Southern blot hybridization method in which plant genomic DNA, is digested and probed with pRiceHD-Zip-p-1 DNA. The hybridization data shows that the transgenic plants exhibiting modulation of cell division contain at least part of one copy of pRiceHD-Zip-p-1 plasmid DNA that is integrated into the rice genome.

Example 8

Sense Expression of the REVOLUTA Gene Driven from the 35S Cauliflower Mosaic Virus Promoter A DNA fragment encoding approximately 900 bp of the 35S Cauliflower Mosaic Virus promoter was amplified from the pHomer102 plasmid by PCR using primers AAGGTAC-CAAGTTCGACGGAGAAGGTGA [SEQ D NO:53] and AAGGATCCTGTAGAGAGAGACTGGTGATTTCAG [SEQ ID NO:54]. Clones from independent PCR reactions were sequenced to verify the accuracy of the PCR amplification. Kpn 1 and BamHI restriction sites were included in the PCR primers to allow for the isolation of a 900 bp Kpn1-BamH1 fragment that includes the amplified 35S promoter. This Kpn1-BamH1 fragment was inserted 5' of the REV genomic sequence in clone NO84 at KpnI and Bam H1 sites to generate a NO REV gene linked approximately 70 bp downstream of the 35S promoter transcription start site. The 3' end of the REV gene was placed downstream of the REV coding region as described below.

As described above, NO84 is a clone containing the genomic DNA sequence of REVOLUTA isolated from a NO-ecotype plant. The REV NO84 gene was amplified using long distance PCR with the primers HDAL: AAAATGGAGATG-GCGGTGGCTAAC [SEQ ID NO:33] and HDAR: TGT-CAATCGAATCACACAAAAGACCA [SEQ ID NO:34] and essentially the conditions described above, except that denaturation steps were carried out at 94° C. and 20 second extensions were added to each cycle after 10 cycles for a total of 40 cycles.

To clone the 3' polyadenylation signal onto the end of the gene, approximately 0.7 kb of the 3' end of Columbia REV starting immediately downstream of the stop codon was amplified using PCR using the following oligonucleotides (5' primer includes a NotI site: TTGCGGCCGCTTCGATTGA-CAGAAAAAGACTAATTT [SEQ ID NO:51]; 3' primer includes ApaI and KpnI sites: TTGGGCCCGGTACCCT-CAACCAACCACATGGAC [SEQ ID NO:52]). Clones were verified by sequencing, and the 3' region of REV placed downstream of the NO84REV coding region in the NotI and ApaI sites of the vector. The resulting gene containing the 35S promoter, REV coding, and REV 3' regions was cloned out of the original vector using KpnI and ligated to the pCGN1547 T-DNA binary vector.

Transformation of 35S-REV Gene

Agrobacterium strain At503 was transformed with the above constructs and used to transform wild-type No plants using in planta transformation.

Figure 10:
FIG. 10 shows a comparison of seed size produced by a typical plant transformed with the empty vector (C) and in a plant transformed with the 35S-REV gene (LS).
Figure 11:
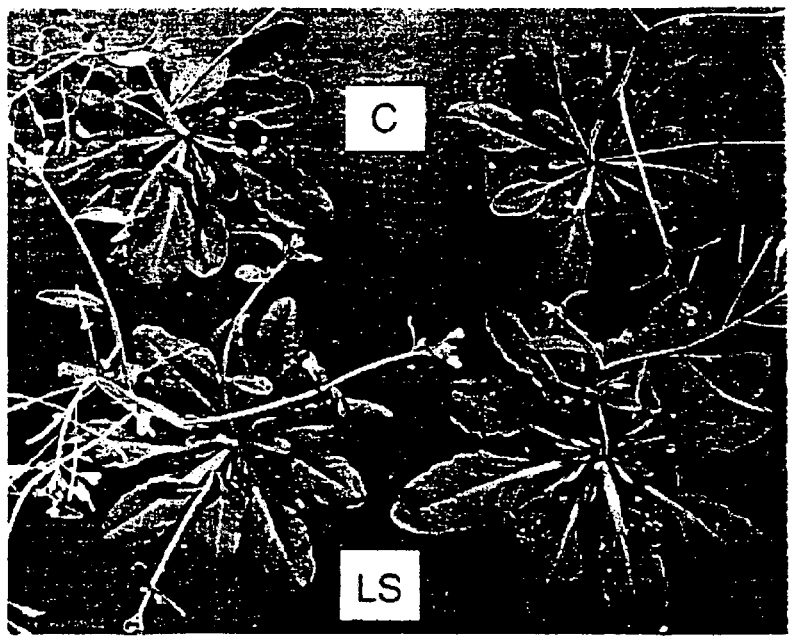
FIG. 11 provides examples of rosette and leaf sizes produced by plants transformed with the empty vector (C) and plants transformed with the 35S-REV gene (LS).
Figure 12:
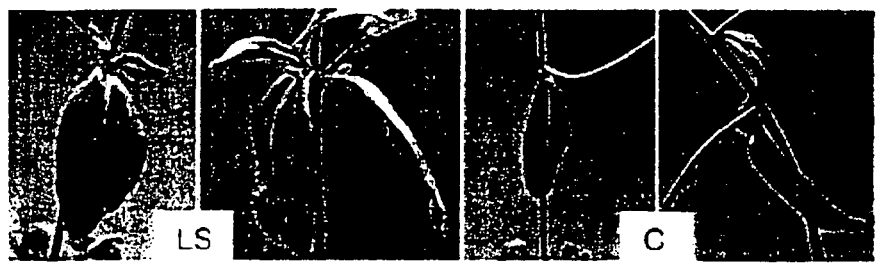
FIG. 12 provides examples of inflorescence stem and cauline leaf sizes produced by plants transformed with the empty vector (C) and plants transformed with the 35S-REV gene (LS).

Five independently transformed lines were characterized for their growth phenotype. We found increases in leaf, stem and seed size (see FIGS. 10-12, and Table 11). Increased size was displayed to different extent by the different lines. The line that showed the largest increase in seed size produced seed that was nearly twice as heavy as the control seed.

The production of independent transgenic lines displaying large organs and seeds indicate that expression of the CaMV35S-REV gene in plants results in increased growth. Notably, the phenotype of CaMV35S-REV plants does not show any of the abnormalities displayed by rev mutants: abnormal flower, empty axils and contorted leaves. Thus, sense expression of REV is useful in obtaining crop plants with valuable characteristics.

All publications and patents mentioned in the above specification are herein incorporated by reference. While the preferred embodiment of the invention has been illustrated and described, it will be appreciated that various changes can be made therein without departing from the spirit and scope of the invention.

The embodiments of the invention in which an exclusive property or privilege is claimed are defined as follows:

1. A transformed plant cell comprising a transgene, wherein the transgene comprises a polynucleotide encoding a polypeptide comprising the amino acid sequence of SEQ ID NO: 159 or SEQ ID NO: 171.

2. The transformed plant cell of claim 1 wherein said transgene comprises SEQ ID NO: 157.

3. A transgenic plant comprising a transgene, wherein the transgene comprises a polynucleotide sequence encoding a polypeptide comprising the amino acid sequence of SEQ ID NO: 159 or SEQ ID NO: 171.

4. The transgenic plant of claim 3 wherein said transgene comprises the polynucleotide of SEQ ID NO: 157.

5. The transformed plant cell of claim 1 wherein said transgene comprises the polynucleotide of SEQ ID NO: 170.

6. The transgenic plant of claim 3 wherein said transgene comprises SEQ ID NO: 170.

7. The transgenic plant cell of claim 1, wherein the transgene is operably linked to a promoter that functions in the plant cell.

8. The transgenic plant cell of claim 7, wherein the promoter is heterologous.

9. The transgenic plant cell of claim 7, wherein the promoter is an inducible promoter, a tissue-specific promoter, a developmentally regulated promoter, or a constitutive promoter.

10. The transgenic plant cell of claim 9, wherein the tissue-specific promoter is a seed specific promoter, a seed storage protein specific promoter, or an embryo specific promoter.

* * * * *